(12) United States Patent
Breidenthal et al.

(10) Patent No.: US 8,480,976 B2
(45) Date of Patent: **\*Jul. 9, 2013**

(54) INSTRUMENTS AND METHODS FOR MIXING THE CONTENTS OF A DETECTION CHAMBER

(75) Inventors: Scott S. Breidenthal, Oceanside, CA (US); Sara H. Fan, San Diego, CA (US); Richard S. Lee, San Diego, CA (US); Norman C. Nelson, San Diego, CA (US); Matthew J. Scott, Oceanside, CA (US); Jason A. Taylor, Windham, NH (US)

(73) Assignees: Gen-Probe Incorporated, San Diego, CA (US); Qualigen, Inc., Carlsbad, CA (US)

(\*) Notice: Subject to any disclaimer, the term of this patent is extended or adjusted under 35 U.S.C. 154(b) by 0 days.

This patent is subject to a terminal disclaimer.

(21) Appl. No.: 13/181,850

(22) Filed: Jul. 13, 2011

(65) Prior Publication Data

US 2011/0275087 A1 Nov. 10, 2011

Related U.S. Application Data

(63) Continuation of application No. 12/333,335, filed on Dec. 12, 2008, now Pat. No. 8,048,375, which is a continuation of application No. PCT/US2008/007685, filed on Jun. 20, 2008.

(60) Provisional application No. 60/945,520, filed on Jun. 21, 2007.

(51) Int. Cl.
*B01L 3/00* (2006.01)

(52) U.S. Cl.
USPC ........... 422/504; 366/142; 366/143; 366/144; 422/68.1; 436/172

(58) Field of Classification Search
USPC ... 422/68.1, 504; 366/142, 143, 144; 436/172
See application file for complete search history.

(56) References Cited

U.S. PATENT DOCUMENTS

| 2,487,236 A | 11/1949 | Greenberg |
| 2,534,229 A | 12/1950 | Carhart et al. |

(Continued)

FOREIGN PATENT DOCUMENTS

| DE | 102005049976 A1 | 4/2006 |
| EP | 0295526 A1 | 12/1988 |

(Continued)

OTHER PUBLICATIONS

Office Action in Canadian Patent Application No. 2,691,197, 3 pages (Oct. 11, 2011).

(Continued)

*Primary Examiner* — Michael Marcheschi
*Assistant Examiner* — Johnathan Hurst
(74) *Attorney, Agent, or Firm* — Rothwell, Figg, Ernst & Manbeck PC; Charles B. Cappellari, Esq.

(57) ABSTRACT

A receptacle having a plurality of interconnected chambers arranged to permit multiple process steps or processes to be performed independently or simultaneously. The receptacles are manufactured to separate liquid from dried reagents and to maintain the stability of the dried reagents. An immiscible liquid, such as an oil, is included to control loading of process materials, facilitate mixing and reconstitution of dried reagents, limit evaporation, control heating of reaction materials, concentrate solid support materials to prevent clogging of fluid connections, provide minimum volumes for fluid transfers, and to prevent process materials from sticking to chamber surfaces. The receptacles can be adapted for use in systems having a processing instrument that includes an actuator system for selectively moving fluid substances between chambers and a detector. The actuator system can be arranged to concentrate an analyte present in a sample. The detector can be used to detect an optical signal emitted by the contents of the receptacle.

12 Claims, 35 Drawing Sheets

U.S. PATENT DOCUMENTS

| | | | |
|---|---|---|---|
| 2,785,057 A | 3/1957 | Schwab et al. |
| 3,028,000 A | 4/1962 | Clements et al. |
| 3,036,894 A | 5/1962 | Forestiere |
| 3,064,802 A | 11/1962 | Jess et al. |
| 3,074,544 A | 1/1963 | Bollmeier et al. |
| 3,311,303 A | 3/1967 | Noyes |
| 3,367,785 A | 2/1968 | Finucane et al. |
| 3,380,888 A | 4/1968 | Numerof et al. |
| 3,419,719 A | 12/1968 | Goffe et al. |
| 3,476,515 A | 11/1969 | Johnson et al. |
| 3,477,821 A | 11/1969 | Hamilton |
| 3,477,822 A | 11/1969 | Hamilton |
| 3,480,398 A | 11/1969 | Hamilton |
| 3,491,935 A | 1/1970 | Trotter, Jr. et al. |
| 3,496,061 A | 2/1970 | Freshour et al. |
| 3,497,320 A | 2/1970 | Balckburn et al. |
| 3,504,376 A | 3/1970 | Bednar et al. |
| 3,540,857 A | 11/1970 | Martin |
| 3,552,928 A | 1/1971 | Fetter |
| 3,554,705 A | 1/1971 | Johnston et al. |
| 3,582,283 A | 6/1971 | Mirasol, Jr. |
| 3,596,828 A | 8/1971 | Foster et al. |
| 3,647,227 A | 3/1972 | Lojkutz et al. |
| 3,647,386 A | 3/1972 | Gilford |
| 3,660,033 A | 5/1972 | Schwartz |
| 3,666,631 A | 5/1972 | Rich et al. |
| 3,689,224 A | 9/1972 | Agnew et al. |
| 3,690,836 A | 9/1972 | Buissiere et al. |
| 3,691,017 A | 9/1972 | Brown et al. |
| 3,697,227 A | 10/1972 | Goldstein et al. |
| 3,698,822 A | 10/1972 | Polanyi |
| 3,713,779 A | 1/1973 | Sirago et al. |
| 3,713,780 A | 1/1973 | Shapiro |
| 3,715,189 A | 2/1973 | Nighohossian et al. |
| 3,726,645 A | 4/1973 | Kaczmarek |
| 3,740,196 A | 6/1973 | Stroterhoff |
| 3,748,098 A | 7/1973 | Dutch |
| 3,756,920 A | 9/1973 | Kelbaugh et al. |
| 3,785,771 A | 1/1974 | Luchsinger et al. |
| 3,794,490 A | 2/1974 | Nerwin |
| 3,799,742 A | 3/1974 | Coleman |
| 3,807,467 A | 4/1974 | Tascher et al. |
| 3,825,410 A | 7/1974 | Bagshawe |
| 3,833,381 A | 9/1974 | Chen et al. |
| 3,862,302 A | 1/1975 | Price et al. |
| 3,891,089 A | 6/1975 | Goodwin et al. |
| 3,898,457 A | 8/1975 | Packard et al. |
| 3,904,369 A | 9/1975 | Adler et al. |
| 3,917,453 A | 11/1975 | Milligan et al. |
| 3,918,910 A | 11/1975 | Soya et al. |
| 3,933,594 A | 1/1976 | Milligan et al. |
| 3,964,604 A | 6/1976 | Prenntzell |
| 3,981,981 A | 9/1976 | Reunanen |
| 3,994,594 A | 11/1976 | Sandrock et al. |
| 4,007,010 A | 2/1977 | Woodbridge, III |
| 4,038,030 A | 7/1977 | Albright et al. |
| 4,038,150 A | 7/1977 | Dorn et al. |
| 4,065,263 A | 12/1977 | Woodbridge, III |
| 4,066,412 A | 1/1978 | Johnson et al. |
| RE29,725 E | 8/1978 | Johnson et al. |
| 4,110,079 A | 8/1978 | Schaeffer et al. |
| 4,119,407 A | 10/1978 | Goldstein et al. |
| 4,135,883 A | 1/1979 | McNeil et al. |
| 4,198,972 A | 4/1980 | Herb |
| 4,210,623 A | 7/1980 | Breno et al. |
| 4,269,212 A | 5/1981 | Kaartinen |
| 4,365,716 A | 12/1982 | Watt |
| 4,390,499 A | 6/1983 | Curtis et al. |
| 4,458,811 A | 7/1984 | Wilkinson |
| 4,474,015 A | 10/1984 | Christmas et al. |
| 4,477,575 A | 10/1984 | Vogel et al. |
| 4,539,793 A | 9/1985 | Malek |
| 4,581,333 A | 4/1986 | Kourilsky et al. |
| 4,585,623 A | 4/1986 | Chandler |
| 4,588,554 A | 5/1986 | Kaartinen et al. |
| 4,647,541 A | 3/1987 | Guadagno et al. |
| 4,654,127 A | 3/1987 | Baker et al. |
| 4,655,047 A | 4/1987 | Temple et al. |
| 4,657,869 A | 4/1987 | Richards et al. |
| 4,665,034 A | 5/1987 | Chandler |
| 4,673,657 A | 6/1987 | Christian |
| 4,683,195 A | 7/1987 | Mullis et al. |
| 4,690,801 A | 9/1987 | Anderson |
| 4,753,775 A | 6/1988 | Ebersole et al. |
| 4,756,884 A | 7/1988 | Hillman et al. |
| 4,770,853 A | 9/1988 | Bernstein |
| 4,786,600 A | 11/1988 | Kramer et al. |
| 4,795,265 A | 1/1989 | Dahlberg et al. |
| 4,806,313 A | 2/1989 | Ebersole et al. |
| 4,806,316 A | 2/1989 | Johnson et al. |
| 4,810,653 A | 3/1989 | Helfer et al. |
| 4,859,421 A | 8/1989 | Apicella |
| 4,865,986 A | 9/1989 | Coy et al. |
| 4,902,624 A | 2/1990 | Columbus et al. |
| 4,916,078 A | 4/1990 | Klose et al. |
| 4,922,092 A | 5/1990 | Rushbrooke et al. |
| 4,937,457 A | 6/1990 | Mitchell |
| 4,952,068 A | 8/1990 | Flint |
| 4,952,373 A | 8/1990 | Sugarman et al. |
| 4,961,495 A | 10/1990 | Yoshida et al. |
| 4,963,498 A | 10/1990 | Hillman et al. |
| 4,963,663 A | 10/1990 | White et al. |
| 4,965,047 A | 10/1990 | Hammond |
| 4,978,502 A | 12/1990 | Dole et al. |
| 4,982,577 A | 1/1991 | Milankov et al. |
| 5,031,797 A | 7/1991 | Boris et al. |
| 5,038,852 A | 8/1991 | Johnson et al. |
| 5,057,285 A | 10/1991 | Belt et al. |
| 5,061,446 A | 10/1991 | Guigan |
| 5,077,010 A | 12/1991 | Ishizaka et al. |
| 5,089,232 A | 2/1992 | May |
| 5,089,233 A | 2/1992 | DeVaney, Jr. et al. |
| 5,098,660 A | 3/1992 | Devaney, Jr. |
| 5,116,576 A | 5/1992 | Stanley |
| 5,124,246 A | 6/1992 | Urdea et al. |
| 5,125,919 A | 6/1992 | Miller et al. |
| 5,128,104 A | 7/1992 | Murphy et al. |
| 5,130,238 A | 7/1992 | Malek et al. |
| 5,131,760 A | 7/1992 | Farmer |
| 5,132,087 A | 7/1992 | Manion et al. |
| 5,133,938 A | 7/1992 | Glanville et al. |
| 5,133,940 A | 7/1992 | Kalkkinen et al. |
| 5,154,888 A | 10/1992 | Zander et al. |
| 5,160,702 A | 11/1992 | Kopf-Sill et al. |
| 5,173,260 A | 12/1992 | Zander et al. |
| 5,176,203 A | 1/1993 | Larzul |
| 5,188,455 A | 2/1993 | Hammerstedt |
| 5,200,152 A | 4/1993 | Brown |
| 5,219,762 A | 6/1993 | Katamine et al. |
| 5,223,219 A | 6/1993 | Subramanian et al. |
| 5,225,163 A | 7/1993 | Andrews |
| 5,229,297 A | 7/1993 | Schnipelsky et al. |
| 5,230,866 A | 7/1993 | Shartle et al. |
| 5,254,479 A | 10/1993 | Chemilli |
| 5,258,314 A | 11/1993 | Skerratt |
| 5,270,183 A | 12/1993 | Corbett et al. |
| 5,279,797 A | 1/1994 | Burns et al. |
| 5,283,174 A | 2/1994 | Arnold, Jr. et al. |
| 5,287,961 A | 2/1994 | Herran |
| 5,288,463 A | 2/1994 | Chemelli |
| 5,288,611 A | 2/1994 | Kohne |
| 5,290,518 A | 3/1994 | Johnson |
| 5,294,404 A | 3/1994 | Grandone et al. |
| 5,304,487 A | 4/1994 | Wilding et al. |
| 5,320,808 A | 6/1994 | Holen et al. |
| 5,333,675 A | 8/1994 | Mullis et al. |
| 5,364,591 A | 11/1994 | Green et al. |
| 5,374,395 A | 12/1994 | Robinson et al. |
| D354,220 S | 1/1995 | Mahan et al. |
| 5,380,489 A | 1/1995 | Sutton et al. |
| 5,387,510 A | 2/1995 | Wu |
| 5,399,491 A | 3/1995 | Kacian et al. |
| 5,415,839 A | 5/1995 | Zaun et al. |
| 5,422,271 A | 6/1995 | Chen et al. |
| 5,424,413 A | 6/1995 | Hogan et al. |
| 5,425,917 A | 6/1995 | Schmid |
| 5,427,930 A | 6/1995 | Birkenmeyer et al. |

| | | |
|---|---|---|
| 5,443,959 A | 8/1995 | Kikuchi et al. |
| 5,447,841 A | 9/1995 | Gray et al. |
| 5,455,166 A | 10/1995 | Walker |
| 5,455,175 A | 10/1995 | Wittwer et al. |
| 5,460,780 A | 10/1995 | Devaney, Jr. et al. |
| 5,476,774 A | 12/1995 | Wang et al. |
| 5,498,392 A | 3/1996 | Wilding et al. |
| 5,545,528 A | 8/1996 | Mitsuhashi et al. |
| 5,547,842 A | 8/1996 | Hogan et al. |
| 5,554,502 A | 9/1996 | Mitsuhashi et al. |
| 5,565,339 A | 10/1996 | Bloch et al. |
| 5,567,617 A | 10/1996 | Caprio et al. |
| 5,577,369 A | 11/1996 | Becker et al. |
| 5,591,578 A | 1/1997 | Meade et al. |
| 5,593,804 A | 1/1997 | Chemelli et al. |
| 5,593,867 A | 1/1997 | Walker et al. |
| 5,605,796 A | 2/1997 | Chen et al. |
| 5,609,828 A | 3/1997 | O'Bear et al. |
| 5,639,423 A | 6/1997 | Northrup et al. |
| 5,639,428 A | 6/1997 | Cottingham |
| 5,641,658 A | 6/1997 | Adams et al. |
| 5,645,801 A | 7/1997 | Bouma et al. |
| 5,646,039 A | 7/1997 | Northrup et al. |
| 5,652,149 A | 7/1997 | Mileaf et al. |
| 5,655,562 A | 8/1997 | Palmer |
| 5,656,207 A | 8/1997 | Woodhead et al. |
| 5,656,493 A | 8/1997 | Mullis et al. |
| 5,658,737 A | 8/1997 | Nelson et al. |
| 5,674,653 A | 10/1997 | Chemelli et al. |
| 5,674,742 A | 10/1997 | Northrup et al. |
| 5,691,145 A | 11/1997 | Pitner et al. |
| 5,705,628 A | 1/1998 | Hawkins |
| 5,710,029 A | 1/1998 | Ryder et al. |
| 5,714,380 A | 2/1998 | Neri et al. |
| 5,716,842 A | 2/1998 | Baier et al. |
| 5,720,923 A | 2/1998 | Haff et al. |
| 5,725,831 A | 3/1998 | Reichler et al. |
| 5,731,148 A | 3/1998 | Becker et al. |
| 5,736,314 A | 4/1998 | Hayes et al. |
| 5,746,978 A | 5/1998 | Bienhaus et al. |
| 5,766,849 A | 6/1998 | McDonough et al. |
| 5,779,977 A | 7/1998 | Haff et al. |
| 5,783,148 A | 7/1998 | Cottingham et al. |
| 5,786,208 A | 7/1998 | Clark et al. |
| 5,800,784 A | 9/1998 | Horn |
| 5,804,375 A | 9/1998 | Gelfand et al. |
| 5,819,842 A | 10/1998 | Potter et al. |
| 5,824,518 A | 10/1998 | Kacian et al. |
| 5,827,653 A | 10/1998 | Sammes et al. |
| 5,834,254 A | 11/1998 | Shen et al. |
| 5,837,860 A | 11/1998 | Anderson et al. |
| 5,840,488 A | 11/1998 | Hogan |
| 5,840,573 A | 11/1998 | Fields |
| 5,849,478 A | 12/1998 | Cashman |
| 5,849,544 A | 12/1998 | Harris et al. |
| 5,863,801 A | 1/1999 | Southgate et al. |
| 5,869,321 A | 2/1999 | Franklin |
| 5,871,908 A | 2/1999 | Henco et al. |
| 5,888,723 A | 3/1999 | Sutton et al. |
| 5,897,842 A | 4/1999 | Dunn et al. |
| 5,916,522 A | 6/1999 | Boyd et al. |
| 5,919,711 A | 7/1999 | Boyd et al. |
| 5,922,288 A | 7/1999 | Herst |
| 5,925,517 A | 7/1999 | Tyagi et al. |
| 5,928,862 A | 7/1999 | Morrison |
| 5,932,100 A | 8/1999 | Yager et al. |
| 5,948,673 A | 9/1999 | Cottingham |
| 5,948,684 A | 9/1999 | Weigl et al. |
| 5,955,029 A | 9/1999 | Wilding et al. |
| 5,955,351 A | 9/1999 | Gerdes et al. |
| 5,971,158 A | 10/1999 | Yager et al. |
| 5,972,710 A | 10/1999 | Weigl et al. |
| 6,002,475 A | 12/1999 | Boyd et al. |
| 6,013,170 A | 1/2000 | Meade |
| 6,033,880 A | 3/2000 | Haff et al. |
| 6,033,914 A | 3/2000 | Boyd et al. |
| 6,043,506 A | 3/2000 | Heffelfinger et al. |
| 6,054,277 A | 4/2000 | Furcht et al. |
| 6,077,669 A | 6/2000 | Little et al. |
| 6,102,289 A | 8/2000 | Gabrielson |
| 6,103,476 A | 8/2000 | Tyagi et al. |
| 6,124,138 A | 9/2000 | Woudenberg et al. |
| 6,126,899 A | 10/2000 | Woudenberg et al. |
| 6,132,996 A | 10/2000 | Hunicke-Smith |
| 6,144,448 A | 11/2000 | Mitoma |
| 6,150,097 A | 11/2000 | Tyagi et al. |
| 6,171,865 B1 | 1/2001 | Weigl et al. |
| 6,180,372 B1 | 1/2001 | Franzen |
| 6,221,677 B1 | 4/2001 | Wu et al. |
| 6,231,559 B1 | 5/2001 | Loretti |
| 6,232,079 B1 | 5/2001 | Wittwer et al. |
| 6,245,176 B1 | 6/2001 | Greenland |
| 6,251,660 B1 | 6/2001 | Muir et al. |
| 6,251,684 B1 | 6/2001 | Buhl et al. |
| 6,258,323 B1 | 7/2001 | Hormann et al. |
| 6,263,743 B1 | 7/2001 | Colin et al. |
| 6,297,365 B1 | 10/2001 | Adams et al. |
| 6,300,068 B1 | 10/2001 | Burg et al. |
| 6,300,124 B1 | 10/2001 | Blumenfeld et al. |
| 6,300,138 B1 | 10/2001 | Gleason et al. |
| 6,312,886 B1 | 11/2001 | Lee et al. |
| 6,312,906 B1 | 11/2001 | Cass et al. |
| 6,318,191 B1 | 11/2001 | Chen |
| 6,334,980 B1 | 1/2002 | Hayes et al. |
| 6,342,123 B1 | 1/2002 | Rees et al. |
| 6,344,326 B1 | 2/2002 | Nelson et al. |
| 6,361,945 B1 | 3/2002 | Becker et al. |
| 6,372,484 B1 | 4/2002 | Ronchi et al. |
| 6,379,929 B1 | 4/2002 | Burns et al. |
| 6,410,275 B1 | 6/2002 | Kluttz et al. |
| 6,410,278 B1 | 6/2002 | Notomi et al. |
| 6,426,230 B1 | 7/2002 | Feistel |
| 6,428,987 B2 | 8/2002 | Franzen |
| 6,454,945 B1 | 9/2002 | Weigl et al. |
| 6,534,273 B2 | 3/2003 | Weisburg et al. |
| 6,534,274 B2 | 3/2003 | Becker et al. |
| 6,537,501 B1 | 3/2003 | Holl et al. |
| 6,541,213 B1 | 4/2003 | Weigl et al. |
| 6,576,194 B1 | 6/2003 | Holl et al. |
| 6,576,459 B2 | 6/2003 | Miles et al. |
| 6,582,963 B1 | 6/2003 | Weigl et al. |
| 6,605,813 B1 | 8/2003 | Kovalsky et al. |
| 6,629,820 B2 | 10/2003 | Kornelsen |
| 6,645,758 B1 | 11/2003 | Schnipelsky et al. |
| 6,649,378 B1 | 11/2003 | Kozwich et al. |
| 6,656,431 B2 | 12/2003 | Holl et al. |
| 6,663,743 B1 | 12/2003 | Becker et al. |
| 6,691,041 B2 | 2/2004 | Sagner et al. |
| 6,695,147 B1 | 2/2004 | Yager et al. |
| 6,712,925 B1 | 3/2004 | Holl et al. |
| 6,743,399 B1 | 6/2004 | Weigl et al. |
| 6,748,332 B2 | 6/2004 | Chen |
| 6,780,617 B2 | 8/2004 | Chen |
| 6,830,729 B1 | 12/2004 | Holl et al. |
| 6,849,412 B2 | 2/2005 | Becker et al. |
| 6,852,284 B1 | 2/2005 | Holl et al. |
| 6,880,576 B2 | 4/2005 | Karp et al. |
| 6,911,327 B2 | 6/2005 | McMillan et al. |
| 6,913,931 B2 | 7/2005 | Halverson et al. |
| 6,919,058 B2 | 7/2005 | Andersson et al. |
| 6,936,476 B1 | 8/2005 | Anderson et al. |
| 6,964,862 B2 | 11/2005 | Chen |
| 6,985,672 B2 | 1/2006 | Kylberg et al. |
| 7,067,783 B2 | 6/2006 | Curry et al. |
| 7,156,803 B2 | 1/2007 | Voellmicke et al. |
| 7,169,138 B2 | 1/2007 | Becker et al. |
| 7,198,755 B2 | 4/2007 | Tokhtuev et al. |
| 7,201,881 B2 | 4/2007 | Cox et al. |
| 7,214,544 B2 | 5/2007 | Poirier et al. |
| 7,226,562 B2 | 6/2007 | Holl et al. |
| 7,261,859 B2 | 8/2007 | Anderson et al. |
| 7,282,328 B2 | 10/2007 | Kong et al. |
| 7,306,095 B1 | 12/2007 | Bourque et al. |
| 7,337,072 B2 | 2/2008 | Chen |
| 7,374,885 B2 | 5/2008 | Becker et al. |
| 7,384,409 B2 | 6/2008 | Fischer et al. |
| 7,541,178 B2 | 6/2009 | Takagi et al. |
| 2002/0049557 A1 | 4/2002 | Chen |

| | | |
|---|---|---|
| 2002/0076825 A1 | 6/2002 | Cheng et al. |
| 2002/0086417 A1 | 7/2002 | Chen |
| 2003/0049833 A1 | 3/2003 | Chen et al. |
| 2003/0087292 A1 | 5/2003 | Chen et al. |
| 2003/0175947 A1 | 9/2003 | Liu et al. |
| 2004/0058407 A1 | 3/2004 | Miller et al. |
| 2004/0086872 A1 | 5/2004 | Childers et al. |
| 2004/0161788 A1 | 8/2004 | Chen et al. |
| 2004/0171170 A1 | 9/2004 | Sandell |
| 2004/0209266 A1 | 10/2004 | Squirrell |
| 2004/0223878 A1 | 11/2004 | Chen |
| 2004/0254559 A1 | 12/2004 | Tanaami et al. |
| 2005/0019898 A1 | 1/2005 | Adey |
| 2005/0026134 A1 | 2/2005 | Miller et al. |
| 2005/0142664 A1 | 6/2005 | Loney |
| 2005/0176026 A1 | 8/2005 | Franck et al. |
| 2005/0189109 A1 | 9/2005 | Eagland et al. |
| 2005/0194060 A1 | 9/2005 | Houwaert et al. |
| 2005/0221034 A1 | 10/2005 | Iwasaki et al. |
| 2005/0244308 A1 | 11/2005 | Tanaami et al. |
| 2005/0287591 A1 | 12/2005 | Browne |
| 2006/0014494 A1 | 1/2006 | Vanderperren et al. |
| 2006/0019333 A1 | 1/2006 | Rodgers et al. |
| 2006/0019379 A1 | 1/2006 | Taylor et al. |
| 2006/0024201 A1 | 2/2006 | Bell |
| 2006/0030038 A1 | 2/2006 | Taylor et al. |
| 2006/0068398 A1 | 3/2006 | McMillan |
| 2006/0088931 A1 | 4/2006 | Ririe |
| 2006/0090800 A1 | 5/2006 | Banerjee et al. |
| 2006/0093528 A1 | 5/2006 | Banerjee et al. |
| 2006/0105453 A1 | 5/2006 | Brenan et al. |
| 2006/0114296 A1 | 6/2006 | Gascoyne et al. |
| 2006/0141539 A1 | 6/2006 | Taylor |
| 2006/0154341 A1 | 7/2006 | Chen |
| 2006/0166233 A1 | 7/2006 | Wu et al. |
| 2006/0241550 A1 | 10/2006 | Kamen et al. |
| 2006/0264779 A1 | 11/2006 | Kemp et al. |
| 2006/0264783 A1 | 11/2006 | Holmes et al. |
| 2006/0275813 A1 | 12/2006 | Tanaami et al. |
| 2006/0275852 A1 | 12/2006 | Montagu et al. |
| 2006/0276972 A1 | 12/2006 | Light, II et al. |
| 2006/0292619 A1 | 12/2006 | Carrick et al. |
| 2007/0014698 A1 | 1/2007 | Tanaami |
| 2007/0026439 A1 | 2/2007 | Faulstich et al. |
| 2007/0062583 A1 | 3/2007 | Cox et al. |
| 2007/0068964 A1 | 3/2007 | Tanaami et al. |
| 2007/0077170 A1 | 4/2007 | Tanaami et al. |
| 2007/0082331 A1 | 4/2007 | Tanaami et al. |
| 2007/0087362 A1 | 4/2007 | Church et al. |
| 2007/0127309 A1 | 6/2007 | Nitta et al. |
| 2007/0217971 A1 | 9/2007 | Michalsky et al. |
| 2007/0224084 A1 | 9/2007 | Holmes et al. |
| 2007/0248958 A1 | 10/2007 | Jovanovich et al. |
| 2007/0259348 A1 | 11/2007 | Phadke et al. |
| 2007/0264629 A1 | 11/2007 | Holmes et al. |
| 2008/0004594 A1 | 1/2008 | Pahlberg et al. |
| 2008/0026373 A1 | 1/2008 | Rodionova |
| 2008/0026451 A1 | 1/2008 | Braman et al. |
| 2008/0032391 A1 | 2/2008 | Araragi et al. |
| 2008/0035576 A1 | 2/2008 | Satou et al. |
| 2008/0038164 A1 | 2/2008 | Satou et al. |
| 2008/0038810 A1 | 2/2008 | Pollack et al. |
| 2008/0038813 A1 | 2/2008 | Chen |
| 2008/0038837 A1 | 2/2008 | Satou et al. |
| 2008/0050287 A1 | 2/2008 | Araragi et al. |
| 2008/0069732 A1 | 3/2008 | Yi et al. |
| 2008/0081004 A1 | 4/2008 | Daniel et al. |
| 2008/0113391 A1 | 5/2008 | Gibbons et al. |
| 2008/0286775 A1 | 11/2008 | Becker et al. |
| 2009/0134046 A1 | 5/2009 | Breidenthal et al. |
| 2009/0136913 A1 | 5/2009 | Breidenthal et al. |
| 2009/0136963 A1 | 5/2009 | Breidenthal et al. |
| 2009/0137029 A1 | 5/2009 | Breidenthal et al. |
| 2009/0139992 A1 | 6/2009 | Breidenthal et al. |
| 2009/0142745 A1 | 6/2009 | Breidenthal et al. |
| 2009/0142771 A1 | 6/2009 | Breidenthal et al. |

FOREIGN PATENT DOCUMENTS

| | | |
|---|---|---|
| EP | 0318255 A2 | 5/1989 |
| EP | 0402994 A2 | 12/1990 |
| EP | 0504772 A2 | 9/1992 |
| EP | 0594260 A1 | 4/1994 |
| EP | 0281201 A1 | 7/1998 |
| EP | 1004870 A1 | 5/2000 |
| EP | 1179585 A2 | 2/2002 |
| EP | 1547686 A1 | 6/2005 |
| EP | 1605264 A1 | 12/2005 |
| FR | 1513306 | 2/1968 |
| FR | 2612295 | 12/1988 |
| GB | 1428306 | 3/1976 |
| JP | 2002-519642 A | 2/2002 |
| JP | 2007078490 A2 | 3/2007 |
| KR | 1020040039571 A | 5/2004 |
| WO | WO 85/00890 A1 | 2/1985 |
| WO | WO 86/00704 A1 | 1/1986 |
| WO | WO 96/05510 A2 | 2/1996 |
| WO | WO 96/41864 A1 | 12/1996 |
| WO | WO 97/16561 A1 | 5/1997 |
| WO | WO 9727324 A1 | 7/1997 |
| WO | WO 98/16183 A1 | 4/1998 |
| WO | WO 98/50147 A1 | 11/1998 |
| WO | WO 9900655 A2 | 1/1999 |
| WO | WO 99/15622 A1 | 4/1999 |
| WO | WO 99/26724 A2 | 6/1999 |
| WO | WO 99/67646 A1 | 12/1999 |
| WO | WO 00/13014 A1 | 3/2000 |
| WO | WO 0013014 A1 | 3/2000 |
| WO | WO 01/55704 A1 | 8/2001 |
| WO | WO 2004073486 A2 | 9/2004 |
| WO | WO 2004/108287 A1 | 12/2004 |
| WO | WO 2005029041 A2 | 3/2005 |
| WO | WO 2005121963 A2 | 12/2005 |
| WO | WO 2006121997 A2 | 11/2006 |
| WO | WO 2007076023 A2 | 7/2007 |
| WO | WO 2007/094758 A2 | 8/2007 |
| WO | WO 2007093939 A1 | 8/2007 |
| WO | WO 2007120816 A2 | 10/2007 |
| WO | WO 2008/006500 A1 | 1/2008 |
| WO | WO 2008/006502 A1 | 1/2008 |
| WO | WO 2008055915 A2 | 5/2008 |

OTHER PUBLICATIONS

PCT Search Report, International Application No. PCT/US2008/0077685, Feb. 12, 2008.

PCT Written Opinion, International Application No. PCT/US2008/0077685, Feb. 12, 2008.

Notice of Allowance in co-pending U.S. Appl. No. 12/333,335, (mailed Jun. 27, 2011), 20 pgs.

Notice of Allowance in co-pending Application U.S. Appl. No. 13/078,348, (mailed Jun. 30, 2011), 44 pgs.

Final Office Action in co-pending U.S. Appl. No. 12/333,455, (mailed Jun. 3, 2011), 18 pgs.

Non-final Office Action in co-pending U.S. Appl. No. 12/337,108, (mailed Jun. 23, 2011), 25 pgs.

Non-final Office Action in co-pending U.S. Appl. No. 12/333,334, (mailed Jun. 23, 2011), 48 pgs.

Adessi et al., "Solid phase DNA amplification: characterisation of primer attachment and amplification mechanisms," Nucleic Acids Res., 2000, 28(20):e87, 1-8, Oxford University Press, UK.

Alm et al., "Critical factors influencing the recovery and integrity of rRNA extracted from environmental samples: use of an optimized protocol to measure depth-related biomass distribution in freshwater sediments," J. Microbiol Methods, 2000, 40:153-162, Elsevier Biomedical, The Netherlands.

Andreadis et al., "Use of immobilized PCR primers to generate covalently immobilized DNAs for in vitro transcription/translation reactions," Nucleic Acids Res., 2000, 28(2):e5, i-viii, Oxford University Press, UK.

Burke, "Vapor Barrier Films," Graphs and Illustrations, 1992, 14(2):13-17.

Carmon et al., "Solid-Phase PCR in Microwells: Effects of Linker Length and Composition on Tethering, Hybridization, and Extension," BioTechniques, 2002, 32(2):410-420, Informa Healthcare USA, Inc. USA.

Caruthers et al., "Chemical Synthesis of Deoxyoligonucleotides by the Phosphoramidite Method," Methods Enzymol., 1987, 154:287-313, Academic Press, USA.

Chayen et al., "Microbatch crystallization under oil—a new technique allowing many small-volume crystallizations trials," J. Cryst. Growth, 1992, 122(1-4):176-180, North-Holland Pub. Co., The Netherlands.

Dinkel et al., "Detection of *Echinococcus multilocularis* in the Definitive Host: Coprodiagnosis by PCR as an Alternative to Necropsy," J. Clin. Microbiol., 1998, 36(7):1871-1876, American Society for Microbiology, USA.

Duffy et al., "Rapid Prototyping of Microfluidic Systems in Poly(dimethylsiloxane)," Anal. Chem., 1998, 70(23):4974-4984, American Chemical Society, USA.

Findlay et al, "Automated Closed-Vessel System for In Vitro Diagnostics Based on Polymerase Chain Reaction," Clin. Chem., 1993, 39(9):1927-1933, American Association for Clinical Chemistry, USA.

Friedenberg et al., "Developing a fully automated instrument for molecular diagnostic assays," IVD Technology, 2005, 11(6):47-53, Canon Communications LLC., USA.

Guy et al., "Real-Time PCR for Quantification of *Giardia* and *Cryptosporidium* in Environmental Water Samples and Sewage," Appl. Environ. Microbiol., 2003, 69(9):5178-5185, American Society for Microbiology, USA.

Hill, "Automating nucleic acid amplication tests," IVD Technology, 2000, 6(7):36-45, Canon Communications LLC., USA.

Hori et al., "Uniform amplification of multiple DNAs by emulsion PCR," 2007, Biochem. Biophys. Res. Commun. 2007, 352(2):323-328, Academic Press, USA.

Jo et al., "Prevalence and characteristics of *Escherichia coli* O157 from major food animals in Korea," Int. J. Food Microbiol., 2004, 95:41-49, Elsevier Science Publishers, The Netherlands.

Jung et al., "Labels and Detection Formats in Amplification Assays," Nucleic Acid Amplification Technologies, Lee et al., eds., 1997, pp. 135-150, BioTechnique Books, Natick, MA, USA.

Kelly et al., "Miniaturizing chemistry and biology in microdroplets," Chem. Comm. (Camb), 2007, 14(18):1773-1788. Royal Society of Chemistry, UK.

Koch et al., "Photochemical Immobilization of Anthraquinone Conjugated Oligonucleotides and PCR Amplicons on Solid Surfaces," Bioconjug. Chem., 2000, 11:474-483, American Chemical Society, USA.

Kojima et al., "PCR amplification from single DNA molecules on magnetic beads in emulsion: application for high-throughput screening of transcription factor targets," Nucleic Acids Res., 2005, 33(17):e150, 1-9, Oxford University Press, UK.

Kwiatkowski et al., "Clinical, Genetic, and Pharmacogenetic Applications of the Invader Assay," Mol. Diagn., 1999, 4(4):353-64, Adis International, USA.

Liu et al., "DNA probe attachment on plastic surfaces and microfluidic hybridization array channel devices with sample oscillation," Anal. Biochem., 2003, 317:76-84, Academic Press, USA.

Lizardi et al., "Exponential Amplification of Recombinant—RNA Hybridization Probe," BioTechnology, 1988, 6:1197-1202, Informa Healthcare USA, Inc. USA.

Matsubara et al., "Microchamber array based DNA quantification and specific sequence detection from a single copy via PCR in nanoliter volumes," Biosens Bioelectron, 2005, 20:1482-1490, Oxford Elsevier Advanced Technology, UK.

Nakano et al., "Single-molecule PCR using water-in-oil emulsion," J Biotechnol., 2003, 102:117-124, Elsevier Science Publishers, The Netherlands.

Nakayama et al., "Circumventing air bubbles in microfluidic systems and quantitative continuous-flow PCR applications," Anal. Bioanal. Chem., 2006, 386:1327-1333, Springer-Verlag, Germany.

Nazarenko et al., "A closed tube format for amplification and detection of DNA based on energy transfer," Nucleic Acids Res., 1997, 25(12):2516-2521, Oxford University Press, UK.

Nazarenko, Homogeneous Detection of Nucleic Acids Using Self-Quenched Polymerase Chain Reaction Primers Labeled With a Single Fluorophore (LUX™ Primers), Methods Mol. Biol., 2006, 335:95-114, Humana Press, USA.

Ng et al., "Multiplex Real-Time PCR Assay Using Scorpion Probes and DNA Capture for Genotype-Specific Detection of *Giardia lamblia* on Fecal Samples," J. Clin. Microbiol., 2005, 43(3):1256-1260, American Society for Microbiology, USA.

Northrup et al., "DNA Amplification with a Microfabricated Reaction Chamber," The 7th Int'l Conference on Solid-State Sensors and Actuators, Transducers, Digest of Technical Papers, pp. 924-926, Jun. 7-10,1993, Pacifico, Yokohama, Japan.

Packard et al., "Profluorescent protease substrates: Intramolecular dimers described by the exciton model," Proc. Natl. Acad. Sci. USA., 1996, 93:11640-11645, National Academy of Sciences, USA.

Selvakumar et al., "Evaluation of the Phenol Ammonium Sulfate Sedimentation Smear Microscopy Method for Diagnosis of Pulmonary Tuberculosis," J. Clin. Microbiol., 2002, 40(8):3017-3020, American Society for Microbiology, USA.

Sloutsky et al., "Practical Strategies for Performance Optimization of the Enhanced Gen-Probe Amplified Mycobacterium Tuberculosis Direct Test," J. Clin. Microbiol., 2004, 42(4):1547-1551, American Society for Microbiology, USA.

Stroock et al., "Chaotic Mixer for Microchannels," Science, 2002, 295:647-651, American Assn. For the Advancement of Science, USA.

Strother et al., "Covalent attachment of oligodeoxyribonucleotides to amine-modified Si (001) surfaces," Nucleic Acids Res., 2000, 28(18)3535-3541, Oxford University Press, UK.

Täpp et al., "Homogeneous Scoring of Single-Nucleotide Polymorphisms: Comparison of the 5'-Nuclease TaqMan® Assay and Molecular Beacon Probes," BioTechniques, 2000, 28(4):732-738, Informa Healthcare USA, Inc., UK.

Tice et al., "Effects of viscosity on droplet formation and mixing in microfluidic channels," Anal. Chim. Acta., 2004, 507:73-77, Elsevier, The Netherlands.

Tyagi et al., "Molecular Beacons: Probes that Fluoresce upon Hybridization," Nat. Biotechnol., 1996, 14(3):303-308, Nature America Publishing, USA.

Tyagi et al., "Multicolor molecular beacons for allele discrimination," Nat. Biotechnol., 1998, 16:49-53, Nature America Publishing, USA.

Van De Pol et al., "Micro Liquid-Handling Devices—A Review," 1st Int'l Conference on Micro Electro, Opto, Mechanic Systems and Components, Micro Systems Technologies 90, Berlin, Sep. 10-13, 1990, pp. 799-805, Germany.

Wittwer et al, "Minimizing the Time Required for DNA Amplification by Efficient Heat Transfer to Small Samples," Anal. Biochem., 1990, 186:328-331, Academic Press, USA.

Wittwer et al., "Rapid Cycle DNA Amplification: Time and Temperature Optimization," BioTechniques, 1991, 10(1):76-83, Informa Healthcare USA, Inc., USA.

Wu et al., "Time-resolved multichannel imaging of fluorescent objects embedded in turbid media," Optic Letters, 1995, 20(5):489-491, Optical Society of America, USA.

Zheng et al., "Formation of Droplets of Alternating Composition in Microfluidic Channels and Applications to Indexing of Concentrations in Droplet-Based Assays", Anal Chem., 2004, 76(17):4977-4982, American Chemical Society, USA.

Extended European Search Report, European Application No. 12159759.5, mailed May 15, 2012.

Notice of Reasons of Rejection with English translation in Japanese Patent Application No. 2011-071146, 5 pages (mailed Aug. 31, 2012).

Office Action issued in U.S. Appl. No. 13/414,195, 60 pages (mailed Nov. 9, 2012).

Notice of Allowance issued in U.S. Appl. No. 13/414,195, 30 pages (Mar. 22, 2013).

US 8,480,976 B2

INSTRUMENTS AND METHODS FOR MIXING THE CONTENTS OF A DETECTION CHAMBER

PRIORITY CLAIM/CROSS REFERENCE TO RELATED APPLICATION

This application is a continuation under 35 U.S.C. 120 of U.S. patent application Ser. No. 12/333,335, now U.S. Pat. No. 8,048,375, filed Dec. 12, 2008, which is a continuation of International Application No. PCT/US2008/007685, filed Jun. 20, 2008 and designating the United States, which claims the benefit under 35 U.S.C. 119(e) of U.S. Provisional Application No. 60/945,520, filed Jun. 21, 2007, the respective disclosures of which are hereby incorporated by reference.

FIELD OF THE INVENTION

The present invention relates to multi-chambered receptacles and associated instruments and detection devices for use in performing complex processes.

BACKGROUND OF THE INVENTION

All documents referred to herein, or the indicated portions, are hereby incorporated by reference herein. No document, however, is admitted to be prior art to the claimed subject matter.

Highly sophisticated instruments have been developed for performing complex assays requiring multiple process steps to be performed simultaneously and independent of each other. Such instruments can be used to perform chemical analyses, immunoassays, molecular-based tests, and the like. The most advanced of these instruments are capable of performing sample-to-result, nucleic acid-based amplification tests ("NAAT") that allow for walk-away testing. See Friedenberg et al., "Developing a Fully Automated Instrument for Molecular Diagnostic Assays," *IVD Technology* (2005) 11(6):47-53; Hill, "Automating Nucleic Acid Amplification Tests," *IVD Technology* (2000) 6(7):36-45. Fully automated NAAT testing reduces the chances for contamination or user error and is increasingly important because of a national shortage of medical technologists trained to conduct more complex assays, such as NAAT tests. With full automation, the instrument performs all the necessary steps of an assay with minimal human intervention. For NAAT assays, these steps include processing of raw samples to extract one or more nucleic acids of interest and to separate the nucleic acids from potentially interfering materials; performing an amplification reaction, such as polymerase-based extension reaction, to increase the sensitivity of the assay (e.g., TMA, SDA or PCR); and detection of the nucleic acids of interest. In general, however, instruments used to perform NAAT assays are not easily portable and their usefulness is typically limited to large-scale testing in controlled environments. Therefore, a need currently exists for a compact system capable of performing sample-to-result, NAAT assays in point-of-use testing, such as in field testing or bedside medical applications.

SUMMARY OF THE INVENTION

The present invention provides compact instruments, detectors and associated receptacles and processes for performing complex procedures, such as sample-to-result NAAT assays, that permit point-of-use testing at substantial cost savings to conventional, large-scale instrument systems. The receptacles include interconnected chambers that can be pre-packaged in unit dose form with all of the reagents needed to perform an assay. The receptacles are closed systems that minimize opportunities for contamination.

In a first embodiment, a multi-chambered receptacle is provided that permits multiple process steps or processes to be performed independently and/or simultaneously. In one embodiment, the receptacle comprises: (i) a first linear path of chambers interconnected by a plurality of openable connections that includes: first and second chambers connected by a first openable connection, where the first and second chambers and the first openable connection are configured to permit substance movement from the first chamber to the second chamber when a substance-moving force is applied to the contents of the first chamber and the first openable connection has been altered from a closed state to an open state; third and fourth chambers connected by a second openable connection, where the third and fourth chambers and the second openable connection are configured to permit substance movement from the third chamber to the fourth chamber when a substance-moving force is applied to the contents of the third chamber and the second openable connection has been altered from a closed state to an open state; and an intermediate chamber between the second and fourth chambers; and (ii) a sample inlet port for receiving sample into a sample receiving chamber, provided that if the sample receiving chamber is a chamber of the first linear path, then the sample receiving chamber is between the second and fourth chambers. The sample inlet port may be closed with, for example, a Luer connection. The intermediate chamber is directly or indirectly connected to the second chamber by a third openable connection, and the second and intermediate chambers and the third openable connection are configured to permit substance movement from the second chamber to or toward the intermediate chamber when a substance-moving force is applied to the contents of the second chamber and the third openable connection has been altered from a closed state to an open state. The intermediate chamber is also directly or indirectly connected to the fourth chamber by a fourth openable connection, and the fourth and intermediate chambers and the fourth openable connection are configured to permit substance movement from the fourth chamber to or toward the intermediate chamber when a substance-moving force is applied to the contents of the fourth chamber and the fourth openable connection has been altered from a closed state to an open state. The first linear path of chambers is configured so that if a substance-moving force is applied to the contents of the first chamber, then the third openable connection is not altered from a closed state to an open state. The first linear path of chambers is also configured so that if a substance-moving force is applied to the contents of the third chamber, then the fourth openable connection is not altered from a closed state to an open state. The second and fourth chambers are not interconnected by any arrangement of chambers that does not include the intermediate chamber. In a preferred aspect, each of the plurality of interconnected chambers is adjacent to at least one other chamber of the receptacle (seals alone separate chambers). Additionally, the chambers of the receptacle may have a radial arrangement, where the end chambers (i.e., outermost chambers of a linear path of chambers) have a non-circular arrangement.

In one aspect, the receptacle comprises second and third linear paths of chambers, where the chambers of each of the second and third linear paths are interconnected by a plurality of openable connections and comprise a sixth chamber connected to a first process chamber by a fifth openable connection, where the first process chamber is any chamber of the first linear path that is located between the first and third chambers, and where the sixth and first process chambers and the fifth openable connection are configured to permit substance movement from the sixth chamber to the first process chamber when a substance-moving force is applied to the contents of the sixth chamber and the fifth openable connection has been altered from a closed state to an open state. The second linear path of this aspect comprises the first chamber but not the third chamber of the first linear path, and the third linear path comprises the third chamber but not the first chamber of the first linear path. The intermediate chamber may be the first process chamber or the sample receiving chamber. Alternatively, the sixth chamber may be the sample receiving chamber.

In another aspect, the receptacle comprises a seventh chamber connected to the sixth chamber by a sixth openable connection, where the sixth and seventh chambers and the sixth openable connection are configured to permit substance movement from the seventh chamber to the sixth chamber when a substance-moving force is applied to the contents of the seventh chamber and the sixth openable connection has been altered from a closed state to an open state. For this aspect, the sixth chamber may be the sample receiving chamber.

One or more chambers of the second and third linear paths may comprise a solid support for immobilizing an analyte in the sample. The solid support may be any material, in a natural or modified form, which is capable of immobilizing an analyte of interest. A preferred solid support is a magnetically-responsive particle or bead that can be manipulated by an applied magnetic field. The solid support may be provided to, for example, any of the sixth, seventh and first process chambers. To concentrate the solid support within a chamber (i.e., increase the density of solid support material within a region of a chamber without increasing the total amount of solid support material provided to the chamber), the solid support can be provided to the chamber with an immiscible liquid which is non-reactive with the other components of the chamber (i.e., inert). The immiscible liquid may be an oil, preferably a mineral oil.

In yet another aspect, the receptacle comprises a fourth linear path of chambers interconnected by a plurality of openable connections and includes: an eighth chamber connected to a second process chamber of at least one of the second and third linear paths by a seventh openable connection, where the eighth and second process chambers and the seventh openable connection are configured to permit substance movement from the eighth chamber to the second process chamber when a substance-moving force is applied to the contents of the eighth chamber and the seventh openable connection has been altered from a closed state to an open state; and a ninth chamber connected to the second process chamber by an eighth openable connection, where the ninth and second process chambers and the eighth openable connection are configured to permit substance movement from the second process chamber to the ninth chamber when a substance-moving force is applied to the contents of the second process chamber and the eighth openable connection has been altered from a closed state to an open state, and where the fourth linear path does not include a chamber of the second or third linear paths other than the second process chamber. The second process chamber may be adjacent the sample receiving chamber or it may be the sample receiving chamber. To purify one or more analytes in the sample, the eighth chamber may contain a wash solution for removing unwanted material from the sample and the ninth chamber may be substantially void, so that it can function as a waste chamber for spent wash solution.

In a further aspect, the receptacle includes a tenth chamber connected to the intermediate chamber by a ninth openable connection, where the tenth and intermediate chambers and the ninth openable connection are configured to permit substance movement from the tenth chamber to the intermediate chamber when a substance-moving force is applied to the contents of the tenth chamber and the ninth openable connection has been altered from a closed state to an open state. The first linear path of this aspect does not include the tenth chamber.

Substance movement between chambers can be facilitated by chambers having flexible portions that yield to moderate external forces (i.e., forces that do not rupture chamber-defining members or otherwise damage a receptacle in a way that renders it inoperative for its intended purpose). Thus, the receptacle may include top and bottom or opposed members, with at least one of the members being a flexible sheet. The flexible sheet may have a plurality of layers (including one or a plurality of plastic layers selected to have desired bonding characteristics) which exhibit acceptable light, water and/or oxygen transmission properties. Each of the opposed members may be formed from flexible sheets. At least one of the flexible sheets may include a foil layer.

Depending on the types of materials being bonded, the boundaries of the interconnected chambers may be defined by any sealing means, including adhesive or heat sealing, ultrasonic welding or radio frequency ("RF") welding. When one of the members of a receptacle is a flexible sheet having an exposed plastic layer, heat seals may be used to define the boundaries of the interconnected chambers. Each openable connection may be blocked with one or a combination of barriers, including a seal, valve, or external force (e.g., actuator) applied to the connection, when in a closed state to prevent substance movement between chambers. The seal may be a burstable seal (e.g., peelable heat seal, such as chevron or V-shaped seal). Seals blocking the connections between chambers and chamber-defining seals are preferably formed under different conditions so that the chamber-defining seals resist peeling or rupturing when forces are applied to the openable connections to alter them from closed states to open states. In this respect, the chamber-defining seals are referred to as "permanent seals."

At least one of the openable connections of the receptacle may be configured so that it can be altered from the closed state to the open state by a substance-moving force applied to an adjacent chamber. The substance-moving force may be in the form of, for example, an internal compressor, vacuum, or a roller or actuator that presses against a flexible, at least partially compressible portion of the adjacent chamber. An example of an external actuator is a pneumatic actuator or group of actuators having compression pads that are shaped to generally conform to the shape of the chamber or a flexible portion thereof. Alternatively, the substance-moving force may be a manual, digital force To process large samples, the volume capacity of the sample receiving chamber may be greater than the volume capacity of any chamber directly connected to the sample receiving chamber that is other than an end chamber. By sequentially processing portions of the sample, unwanted sample and process materials can be removed to a waste chamber or to a chamber that has already been vacated of a process material, and analyte in the sample can be concentrated to a more manageable size for analyzing. Being able to concentrate the analyte will limit the required dimensions of the receptacle, which is particularly advantageous for field applications since larger receptacles require larger and heavier instruments for processing samples. Analyte concentration may be carried out using a receptacle having a flexible member and a cooperating array of actuators which allows aliquots of sample to be incrementally moved and processed.

For processes having a detection component, at least one of the chambers may be configured to enable detection of a characteristic of a sample. What is detected may be, for example, the existence of an analyte, a chemical reaction, or a change in a property of a sample or sample component. In one aspect, detection may include determining the existence or amount of a signal indicative of the characteristic of the sample. Examples of such signals include light (e.g., luminescence or fluorescence), turbidity, radioactivity, and electrical currents. For light detection, at least a portion of a detection chamber needs to be formed of optically transmissive materials (e.g., transparent or translucent).

A process material for use in preparing, modifying, reacting with or otherwise affecting a sample or component of a sample may be provided to any chamber of the receptacle. The process material may be provided to at least one of the first and second chambers. The same or different process materials may be provided to the first and second chambers, such as a dried reagent (e.g., lyophilized or tabletted reagent) provided to the second chamber and a reconstitution reagent provided to the first chamber for reconstituting the dried reagent. With this particular combination of process materials, it may be desirable to further include an immiscible liquid (e.g., an oil, such as a mineral oil) to the first chamber in an amount sufficient to facilitate reconstitution of the dried reagent. (The reconstitution reagent and the immiscible liquid may be provided together from the second chamber or they may be provided to the first chamber from different chambers.) In this aspect, the ratio of the immiscible liquid to the reconstitution reagent is preferably from about 1:10 to about 10:1, and more preferably from about 1:3 to about 10:1. The immiscible liquid should not be reactive with the dried reagent or the reconstitution reagent. Similarly, the third and fourth chambers may be provided with a reconstitution reagent and dried reagent, respectively, where the reconstituted forms of the dried reagents can be united to achieve a combined effect. For example, the dried reagents of the second and fourth chambers may be amplification and enzyme reagents, respectively, having components needed for a nucleic acid-based amplification reaction. An immiscible liquid may also be combined with the reconstitution reagent of the third chamber to facilitate reconstitution of the dried reagent contained in the fourth chamber.

One of the dried reagents present in the second and fourth chambers may include a binding agent, such as a probe for forming a probe:target complex with a product of the nucleic acid-based amplification reaction. The probe may have an oligonucleotide component that hybridizes with specificity (i.e., does not detectably hybridize to non-target nucleic acid in a sample) to an amplification product of the nucleic acid-based amplification reaction. For detection, the probe may be associated with a label, such as a fluorescent, luminescent or radioactive moiety. Alternatively, the reaction may include a label which recognizes the formation of the probe:target complex, such as an intercalating dye (e.g., ethidium bromide or SYBR® Green), or detection may occur without the aid of a label, such as by detecting electrical signals or mass changes associated with the formation of the probe:target complex. To enable real-time detection in a nucleic acid-based amplification reaction, the probe may assume a different and detectable conformation when it is in a hybridized state than when it is in an unhybridized state. Such probes may include interacting labels that undergo a detectable signal change when the probe complexes with an amplification product.

For chambers containing dried reagents, all or a portion of the materials used to construct the chambers may exhibit a greater water vapor transmission rate ("WVTR") than the materials used to construct at least one other chamber of the receptacle, particularly a directly connected chamber containing a liquid. By way of example, the directly connected chambers may be formed with one or more flexible plastic layers and the liquid-containing chamber may further include a foil layer or layers which have a lower water vapor transmission rate than the plastic layers used to form each of the directly connected chambers. In one aspect, at least a portion of a chamber containing a dried reagent is constructed of optically transmissive materials so that the contents of the chamber can be interrogated by an optical sensor (e.g., fluorometer or luminometer).

To further control the moisture level in chambers containing dried reagents, the receptacle may be stored in a sealed container until use. The sealed container may include a desiccant for drawing moisture from the receptacle and maximizing the stability of the dried reagents.

The receptacles of this embodiment may be used or adapted for use in any of the other embodiments described herein.

In another embodiment, a first method of processing a sample in a receptacle having a plurality of interconnected chambers is provided, where the method includes the steps of: providing a sample to a first chamber of the receptacle; independently combining the following in separate chambers of the receptacle: (i) at least a portion of the sample contained in the first chamber and at least a portion of a sample processing reagent contained in a second chamber of the receptacle; (ii) at least a portion of a substance contained in a third chamber and at least a portion of a substance contained in a fourth chamber; and (iii) at least a portion of a substance contained in a fifth chamber and at least a portion of a substance contained in a sixth chamber; and, after performing substeps (i)-(iii), combining in a chamber of the receptacle a component of the sample with at least a portion of each of the resulting combinations of substeps (ii) and (iii). In a preferred aspect, each of the plurality of interconnected chambers is adjacent to at least one other chamber of the receptacle (seals alone separate chambers). Additionally, the chambers of the receptacle may have a radial arrangement, where the end chambers (i.e., the outermost chambers of a linear path of chambers) of the receptacle have a non-circular arrangement.

In one aspect, the first and second chambers are directly connected to each other, the third and fourth chambers are directly connected to each other, and the fifth and sixth chambers are directly connected to each other. In another aspect, the method further includes the step of mixing the resulting combination of at least one of substeps (i)-(iii) by alternately moving the combination between a pair of directly connected chambers in the receptacle. In still another aspect, the first chamber is intermediate between the fourth and sixth chambers, and the receptacle comprises a sample inlet port for receiving the sample into the first chamber. In yet another aspect, the resulting combination of substep (i) is moved to a seventh chamber intermediate between the first chamber and at least one of the fourth and sixth chambers prior to combining a component of the sample with at least a portion of each of the resulting combinations of substeps (ii) and (iii). In a further aspect, the fourth and sixth chambers are each directly connected to the first chamber but not to each other. In a still further aspect, no component of the sample is moved into the third or fourth chamber or, alternatively, the fifth or sixth chamber during the method. The sample processing chamber may be the first chamber or it may be directly connected to the first chamber.

A solid support may be included in the sample processing reagent for immobilizing an analyte present in the sample. While immobilized on the solid support and contained in the sample processing chamber, one or more non-analyte components of the sample may be removed to a waste chamber of the receptacle, which may be an eighth chamber directly connected to the sample processing chamber. Preferred solid supports are dispersible in a liquid medium, such as magnetically-responsive particles or beads that are exposed to magnetic forces during removal of the non-analyte components.

In another aspect, the method further includes the steps of: providing a wash solution to the sample processing chamber; mixing the solid support and the wash solution in the sample processing chamber; and removing the wash solution from the sample processing chamber to the eighth chamber while the analyte remains immobilized by the solid support in the sample processing chamber. The wash solution may be a buffered, non-reactive solution that is provided from a ninth chamber directly connected to the sample processing chamber. Additionally, a rinse solution may be provided from a tenth chamber directly connected to the sample processing chamber when it is needed or useful for removing residual wash solution in the sample processing chamber, such as when the wash solution contains one or more components known to be inhibitory to a desired reaction in the receptacle (e.g., detergents that inhibit nucleic acid-based amplification reactions).

A dried reagent may be reconstituted in at least one of substeps (ii) and (iii), where at least one of the chambers of these two substeps includes a solution formulated for reconstituting a corresponding dried reagent. The dried reagent may be in, for example, a lyophilized or tabbed form.

In still another aspect, the method of this embodiment further includes, after combining a component of the sample with at least portions of the resulting combinations of substeps (ii) and (iii), the step of detecting a characteristic of the contents of a detection chamber of the receptacle. The detecting step may include determining the existence or amount of a signal indicative of the presence or amount of a component of the sample. At least a portion of the detection chamber may be constructed of optically transmissive materials, thereby permitting the contents of the detection chamber to be interrogated by an optical sensor located or moved to a position adjacent the detection chamber. The detection chamber may be the third, fourth, fifth or sixth chamber.

What is detected in the detection chamber may be a product of an amplification reaction. The amplification reaction may be a nucleic acid-based amplification reaction (e.g., target or signal amplification). For this use, a dried enzyme reagent may be reconstituted in substep (ii). In addition to reconstituting a dried enzyme reagent in substep (ii), a dried amplification reagent may be reconstituted in substep (iii). At least one of the amplification and enzyme reagents may include a probe capable of forming a detectable probe:target complex with a product of the nucleic acid-based amplification reaction (e.g., a hybridizing probe). The probe may include one or more labels to facilitate detection. The product of the nucleic acid-based amplification reaction may be detected at the conclusion of the amplification reaction or in real-time using, for example, a probe that assumes a differently detectable conformation when it is hybridized to a product of the reaction.

Receptacles of this embodiment may include a flexible portion that yields to a compressive force, thereby facilitating substance movement between chambers. The receptacle may include opposed members, where at least one of the members includes a flexible sheet. The chambers, and any associated interconnections, may be defined by a sealing engagement between the opposed members, which, depending on the materials being joined, may be formed by any sealing means, including, as described above, adhesives or heat sealing, ultrasonic welding or RF welding. Each of the opposed members may include a flexible sheet. The flexible sheet may have a plurality of layers (including one or a plurality of plastic layers selected to have desired bonding characteristics) which exhibit acceptable light, water and/or oxygen transmission properties. At least one of the flexible sheets may include a foil layer.

The chambers of the receptacle may be connected by a plurality of openable connections, and each openable connection is configured to permit substance movement between directly connected chambers when a substance-moving force is applied to the contents of at least one of the directly connected chambers and the openable connection has been altered from a closed state to an open state. Connections in the closed state may be blocked by one or a combination of obstructions, including a seal, valve, or external force (e.g., actuator) applied to the connection. The seal may be a burstable seal (e.g., peelable heat seal, such as a chevron or V-shaped seal).

In yet another aspect, the method of this embodiment further includes the step of applying a substance-moving force to each of a plurality of the chambers, where the substance-moving force includes one or more actuators, and where each of the plurality of chambers is adapted to cooperate with the actuators in substance movement between the plurality of chambers. The actuators may include compression pads generally conforming to the shapes of the flexible portions of the chambers. The one or more actuators may be pneumatic actuators. Alternatively, the substance-moving force may include an external roller or a positive or negative force applied within the receptacle.

In still another embodiment, a second method is provided for processing a sample in a receptacle having a plurality of interconnected chambers, where the method includes the steps of: providing a sample to a first chamber of the receptacle; independently combining the following in separate chambers of the receptacle: (i) at least a portion of the sample contained in the first chamber and at least a portion of a sample processing reagent contained in a second chamber of the receptacle; and (ii) at least a portion of a substance contained in a third chamber and at least a portion of a substance contained in a fourth chamber; and, after performing substeps (i) and (ii), combining in a chamber of the receptacle a component of the sample with at least a portion of the resulting combination of substep (ii) and at least a portion of a substance or combination of substances contained in a fifth chamber, provided that no component of the sample is moved into at least one of the third and fifth chambers during the method if the fifth chamber is directly connected to the fourth chamber, also provided that no component of the sample is moved into at least one of the third and fifth chambers during the method if the fifth chamber is not directly connected to either of the third and fourth chambers, and further provided that no component of the sample is moved into the fifth chamber during the method if the fifth chamber is directly connected to the third chamber but not to the fourth chamber. The chambers of the receptacle may have a radial arrangement, where the end chambers of the receptacle have a non-circular arrangement.

In one aspect, the first and second chambers are directly connected to each other and the third and fourth chambers are directly connected to each other. In another aspect, the method of this embodiment further includes the step of mixing the resulting combination of at least one of substeps (i) and (ii) by alternately moving the combination between a pair of directly connected chambers in the receptacle. In still another aspect, the first chamber is intermediate between the fourth and fifth chambers, and the receptacle includes a sample inlet port for receiving the sample into the first chamber. In yet another aspect, the fourth and fifth chambers are each directly connected to the first chamber. In a further aspect, the resulting combination of substep (i) is moved to a sixth chamber intermediate between the first and fourth chambers. In a still further aspect, the fourth and fifth chambers are directly connected to the seventh chamber. In another aspect, the fifth chamber is directly connected to the third chamber but not to the fourth chamber. In still another aspect, each of the third and fifth chambers is directly connected to the fourth chamber. The sample processing chamber may be the first chamber or directly connected to the first chamber.

In another aspect, the method of this embodiment further includes the step of removing one or more non-analyte components of the sample to a waste chamber of the receptacle while an analyte present in the sample remains immobilized by a solid support contained in a sample processing chamber of the receptacle. The solid support may be provided to the receptacle in the sample processing reagent. The solid support is preferably dispersible in a liquid medium, such as magnetically-responsive particles or beads that are exposed to a magnetic field during removal of the non-analyte components. The waste chamber may be a seventh chamber that is directly connected to the sample processing chamber.

In yet another aspect, the method of this embodiment further includes the steps of: providing a wash solution to the sample processing chamber; mixing the solid support and the wash solution in the sample processing chamber; and removing the wash solution from the sample processing chamber to the seventh chamber while the analyte remains immobilized by the solid support in the sample processing chamber. The wash solution may be provided from an eighth chamber that is directly connected to the sample processing chamber.

A first dried reagent may be reconstituted in substep (ii), and the fifth chamber may contain a reconstituted form of a second dried reagent. The first dried reagent may contain a probe capable of forming a detectable probe:target complex with a product of a nucleic acid-based amplification reaction. The first dried reagent may be an enzyme reagent and the fifth chamber may contain an amplification reagent. The dried reagents may be in lyophilized forms.

Other process steps and particulars of the receptacles that may be used in the method of this embodiment are set forth above in the description of the first embodiment of a method of processing a sample in a receptacle having a plurality of interconnected chambers.

In yet another embodiment, an instrument programmed to process a sample in accordance with any of the methods described herein is provided. The instrument is adapted to receive and align a receptacle having a non-linear arrangement of interconnected chambers in a stationary receptacle-receiving area associated with the instrument. The instrument comprises an actuator system operatively positioned with respect to the receptacle-receiving area that includes a plurality of actuators arrayed to conform to the arrangement of at least a portion of the chambers and to selectively apply pressure to flexible portions of the chambers, thereby forcing fluid substances to move between directly connected chambers. The instrument also comprises a detector operatively positioned adjacent the receptacle-receiving area so as to be in operative proximity to a detection chamber contained in a receptacle provided to the instrument, where the detector is capable of detecting a characteristic of the contents of the detection chamber. The instrument further comprises a controller programmed to control the operation of the instrument, including the actuator system, the detector, and thermal elements.

In further embodiment, a system is provided that comprises the above-described instrument for processing samples and a receptacle positioned in the receptacle-receiving area. In a preferred aspect, the receptacle is formed from first and second opposed members joined to each other so as to define the plurality of interconnected chambers. For certain applications, the receptacle includes a linear path having a minimum of five chambers. At least one of the opposed members comprises flexible portions, and at least a portion of the passages include fluid barriers.

In a still further embodiment, a detector for detecting an optical signal that may be indicative of the presence, amount, or state of one or more analytes in a sample, includes one or more excitation channels, each adapted to direct an excitation signal of a prescribed excitation optical characteristic toward the sample. Each excitation channel includes a light emitting element adapted to emit excitation light and excitation optical elements defining an excitation optical path having an excitation optic axis. The excitation optical elements are constructed and arranged to transmit at least a portion of the light emitted by the light-emitting element having the prescribed excitation optical characteristic toward the sample. The detector further comprises one or more emission channels, each adapted to receive an emission signal from the sample. Each emission channel comprises emission optical elements defining an emission optical path having an emission optic axis, and the emission optical elements are constructed and arranged to transmit at least a portion of any light emitted by the sample having a prescribed emission optical characteristic. Each emission channel further includes a light-detecting element and associated circuitry adapted to detect light transmitted by the emission optical elements and to convert the detected light to an electronic signal indicative of at least one of the presence and strength of the detected light. The light-emitting and light detecting elements are operably connected to a single circuit board. The detector further includes one or more optic elements constructed and arranged to receive an excitation signal from each excitation channel and direct at least a portion of each excitation signal at a prescribed location and to receive emission signals emitted from the sample at the prescribed location and to direct at least a portion of the received emission signals into each emission channel. The detector does not include a reflective element for redirecting all light impinging on the reflective element in a direction different from an incidence direction of the impinging light, and the detector does not include a light characteristic separating element for redirecting a portion of the light impinging on the separating element having a first light characteristic in a direction different from an incidence direction of the impinging light and for transmitting a portion of the light impinging on the separating element having a second light characteristic.

In another aspect, the excitation optic axis of each excitation channel and the emission optic axis of each emission channel are parallel to one another throughout their extents.

In a further aspect, the one or more optic elements are constructed and arranged to (1) receive an excitation signal from each excitation channel and direct at least a portion of the excitation signal at a prescribed location on a container within which the sample is processed, and (2) receive an emission signal emitted from the sample within the container and to direct at least a portion of the received emission signals into each emission channel.

In a further aspect, the detector comprises two or more excitation channels and two or more emission channels.

In a further aspect, the one or more optic elements consist of a single, undivided lens.

In a still further embodiment, a detector for detecting an optical signal from a sample that may be indicative of the presence, amount, or state of one or more analytes in the sample comprises one or more excitation channels, each adapted to direct an excitation signal of a prescribed excitation wavelength or range of excitation wavelengths toward the sample and one or more emission channels, each adapted to receive an emission signal from the sample and detect an emission signal having a prescribed emission wavelength or range of emission wavelengths. Each excitation channel comprises a light emitting element adapted to emit excitation light and excitation optical elements defining an excitation optical path having an excitation optic axis. The excitation optical elements are constructed and arranged to transmit at least a portion of the light emitted by the light-emitting element having the prescribed excitation wavelength or range of excitation wavelengths toward the sample. Each emission channel comprises emission optical elements defining an emission optical path having an emission optic axis. The emission optical elements are constructed and arranged to transmit at least a portion of any light emitted by the sample having the prescribed emission wavelength or range of emission wavelengths. Each emission channel further includes a light-detecting element adapted to detect light transmitted by the emission optical elements and to convert the detected light to an electronic signal indicative of at least one of the presence and strength of the detected light. The excitation and emission optic axes are parallel to one another throughout their extents. And the detector further includes an optic lens constructed and arranged with respect to the excitation and emission channels to (1) direct excitation light transmitted by each excitation channel and impinging on a different portion of the optic lens at a prescribed location and (2) receive emission signals emitted by the sample at the prescribed location and to direct at least a portion of the received emission signals into each emission channel.

In another aspect, the light emitting element comprises a light-emitting diode.

In a further aspect, the excitation optical elements of each excitation channel comprise a lens and an excitation filter constructed and arranged to transmit only light having the prescribed excitation wavelength or range of excitation wavelengths.

In a further aspect, the light-detecting element comprises a photodiode.

In a further aspect, the emission optical elements of each emission channel comprise a lens and an emission filter constructed and arranged to transmit only light having the prescribed emission wavelength or range of emission wavelengths.

In a further aspect, the light emitting elements of the excitation channels and the light detecting elements of the emission channels are mounted on the same plane.

In a further aspect, the detector further comprises a housing, wherein each of the excitation and emission channels is disposed within a different conduit defined within the housing.

In a further aspect, the detector comprises two excitation channels and two emission channels, and the conduits of the excitation channels and the emission channels are disposed in a circular pattern, with the conduits being spaced by approximately 90°.

In a further aspect, the detector further comprises a base including at least one printed circuit board, the housing is mounted to the base, and the light emitting elements of the excitation channels and the light detecting elements of the emission channels are operatively connected to the printed circuit board.

In a further aspect, the detector further comprises ambient light filtering circuitry comprising excitation modulation circuitry and detection circuitry. The excitation modulation circuitry is constructed and arranged to modulate the excitation signal of each excitation channel at a predefined excitation frequency, and the detection circuitry is constructed and arranged to identify that portion of the detected light that is substantially at the excitation frequency.

In a further aspect, the detector comprises two or more excitation channels, and the excitation frequency is different for the excitation signal of each excitation channel.

In a further aspect, the detector comprises two or more excitation channels, and the excitation frequency is the same for the excitation signal of each excitation channel.

In a further aspect, the excitation optical elements and the emission optical elements do not include optic fibers.

In a still further embodiment, a detector is provided that detects optical emissions of two or more different wavelengths or ranges of wavelengths from a sample, wherein emissions of two or more different wavelengths may be indicative of the presence, amount, or state of two or more analytes of interest in the sample, and wherein the emissions are detected without moving components of the detector with respect to the sample. The detector comprises two or more excitation channels fixed with respect to the sample and each other and two or more emission channels fixed with respect to the sample, the excitation channels, and each other. Each excitation channel is adapted to direct an excitation signal of a different prescribed excitation wavelength or range of excitation wavelengths toward the sample, and each excitation channel comprises a light emitting element adapted to emit excitation light and excitation optical elements defining an excitation optical path having an excitation optic axis. The excitation optical elements are constructed and arranged to transmit at least a portion of the light emitted by the light-emitting element having the prescribed excitation wavelength or range of excitation wavelengths toward the sample. Each emission channel is adapted to receive and detect an emission signal of a different prescribed emission wavelength or range of emission wavelengths from the sample, and each emission channel comprises emission optical elements defining an emission optical path having an emission optic axis, and the emission optical elements are constructed and arranged to transmit at least a portion of any light emitted by the sample having the prescribed emission wavelength or range of emission wavelengths. Each emission channel further includes a light-detecting element adapted to detect light transmitted by the emission optical elements and to convert the detected light to an electronic signal indicative of at least one of the presence and strength of the detected light. The detector is adapted to direct light having a unique excitation wavelength or range of excitation wavelengths at the sample with each of the excitation channels and detect light having a unique emission wavelength or range of emission wavelengths emitted from the sample with each of the emission channels without moving the excitation channels or the emission channels with respect to the sample or each other.

In another aspect the excitation optical elements are constructed and arranged to transmit at least a portion of the light emitted by the light-emitting element having the prescribed excitation wavelength or range of excitation wavelengths toward a container within which the sample is processed. The emission optical elements are constructed and arranged to transmit at least a portion of any light having the prescribed emission wavelength or range of emission wavelengths emitted by the sample from within the container. The detector is adapted to direct light having a unique excitation wavelength or range of excitation wavelengths at the container with each of the excitation channels and detect light having a unique emission wavelength or range of emission wavelengths emitted from the container with each of the emission channels without moving the excitation channels or the emission channels with respect to the container or each other.

In a still further embodiment, a method for detecting an optical signal that may be indicative of the presence, amount, or state of one or more analytes in a sample comprises generating a first excitation signal and transmitting a portion of the first excitation signal having a first excitation wavelength or range of excitation wavelengths along a first excitation path, focusing the first excitation signal at the sample with a first portion of an optic lens, and directing a portion of a signal emitted by the sample, if any, into a first emission path using a second portion of the optic lens, transmitting light having a first emission wavelength or range of emission wavelengths along the first emission path, and detecting light having the first emission wavelength or range of emission wavelengths. The first excitation path and the first emission path are parallel to each other throughout their extents.

In another aspect, the method further comprises generating a second excitation signal and transmitting a portion of the second excitation signal having a second excitation wavelength or range of excitation wavelengths along a second excitation path, focusing the second excitation signal at the sample with a third portion of the optic lens, and directing a portion of a signal emitted by the sample, if any, into a second emission path using a fourth portion of the optic lens, transmitting light having a second emission wavelength or range of emission wavelengths along the second emission path, and detecting light having the second emission wavelength or range of emission wavelengths. The first and second excitation paths and the first and second emission paths are parallel to each other throughout their extents.

In a further aspect, focusing the first excitation signal at the sample comprises focusing the first excitation signal at the contents of a container within which the sample is being processed.

In a further aspect, directing a portion of a signal emitted by the sample into a first emission path comprises directing a signal emitted by the sample within the container.

In a further aspect, the optic lens comprises a solid, undivided lens.

In a further aspect, the method comprises transmitting the first excitation signal along the first excitation path and transmitting light along the first emission path without the use of (1) a reflective element for redirecting all light impinging on the reflective element in a direction different from an incidence direction of the impinging light or (2) a light characteristic separating element for redirecting a portion of the light impinging on the separating element having a first light characteristic in a direction different from an incidence direction of the impinging light and for transmitting a portion of the light impinging on the separating element having a second light characteristic.

In a further aspect, the focusing and directing steps are accomplished without any optic element other than the single lens outside the first excitation path and the first emission path.

In a further aspect, the generating step is performed by a light emitting diode.

In a further aspect, transmitting the portion of the first excitation signal having the first excitation wavelength or range of excitation wavelengths along the first excitation path comprises filtering the first excitation signal to remove wavelengths of the first excitation signal other than the first excitation wavelength or range of excitation wavelengths, and transmitting light having the first emission wavelength or range of emission wavelengths along the first emission path comprises filtering the portion of the emission signal directed into the first emission path to remove wavelengths of the first emission signal other than the first emission wavelength or range of emission wavelengths.

In a further aspect, the method further comprises modulating the excitation signal at a predefined excitation frequency and identifying that portion of the detected light that is substantially at the excitation frequency.

Transmitting the portion of the first excitation signal having the first excitation wavelength and transmitting light having the first emission wavelength along the first emission path do not include transmitting light along an optic fiber.

The manufacture and special uses of receptacles in accordance with the present invention will now be described. For the described embodiments, the receptacles may include opposed members that are configured to define a plurality of interconnected chambers, where the chambers are joined by passages or openings, as between adjacently positioned chambers, or by channels or passageways, as between separated chambers. The plurality of interconnected chambers may be defined by seals formed between the opposed members by any sealing means, such as, for example, adhesives or heat sealing, ultrasonic welding or RF welding. At least one of the opposed members may include a flexible sheet that includes a flexible, at least partially compressible portion of a chamber. The flexible sheet may have a plurality of layers, including one or more plastic layers selected to have desired bonding characteristics, as well as acceptable light, water and/or oxygen transmission properties. Both opposed members may be formed from flexible sheets, at least one of which may include a foil layer.

The connections between directly connected chambers of these receptacles may be blocked by openable connections that can be altered from closed states to open states when substance-moving forces are applied to the contents of the chambers. Each substance-moving force may include, for example, an externally applied force pressing on a chamber, such as one or more actuators (e.g., pneumatic actuators) or a roller, or it may include a positive or negative force applied within the receptacle. If the substance-moving force is one or more actuators, the actuators may include compression pads generally conforming to the shape of the flexible portion of a chamber, such as a chamber wall. The connection may be blocked in the closed state by one or a combination of obstructions, including a seal, valve, or external force (e.g., actuator) applied to the connection. The seal may be a burstable seal, such as a peelable heat seal (e.g., chevron or V-shaped seal).

In another embodiment, a method is provided for loading liquid substances into a receptacle having a plurality of interconnected chambers, where the method includes the steps of: sequentially providing an immiscible liquid and a liquid substance (the liquid substance following the immiscible liquid)

to an open chamber of the receptacle, where the immiscible liquid has a lower density than the liquid substance, and where the immiscible liquid is provided to the open chamber in an amount sufficient to control wicking of the liquid substance within the open chamber; and closing the open chamber to provide a substantially fluid-tight seal. The open chamber may be one of a plurality of chambers opened to a side of the receptacle and adapted to receive substances for use in performing an assay. The lower density immiscible liquid floats on the liquid substance, which was found to control wicking in an open chamber that can lead to contamination of the contents of an adjacent chamber or affect the concentration of a process material used in a reaction or other process. The immiscible liquid is preferably non-reactive with the liquid substance, and the amount of the immiscible liquid provided to an open chamber will depend, at least in part, on the volume capacity of the chamber and the volume of the liquid substance provided to the open chamber. Notwithstanding, the ratio of the immiscible liquid to the liquid substance is preferably up to about 10:1. Any immiscible liquid is contemplated, but oils (e.g., mineral oils) are especially suitable.

The receptacle may be comprised of opposed members, at least one of which includes a flexible sheet. The flexible sheet may include a flexible portion of the open chamber that is drawn away from the opposed member during the providing step, when the immiscible liquid and the liquid substance are delivered to the open chamber. The opposed members may comprise opposed flexible sheets, where the opposed flexible sheets include opposed flexible portions of the open chamber that are drawn away from each other during the providing step. After delivering the immiscible liquid and the liquid substance to the open chamber, the open chamber may be closed by any means sufficient to provide a fluid-tight seal, such as a heat seal formed between opposed members of the open chamber. The steps of the method are preferably automated.

In still another embodiment, a method of manufacturing a receptacle having a plurality of interconnected chambers to separately contain liquid and dried substances is provided, where the method includes the steps of: providing at least one liquid substance to one or more first chambers opened to a first side of the receptacle; closing the first chambers to provide substantially fluid-tight enclosures; providing at least one dried substance to one or more second chambers opened to a second side of the receptacle; and closing the second chambers to provide substantially fluid-tight enclosures, where the chambers of the receptacle are separated from each other by fluid barriers, and where dried substances are not provided to chambers opened to the first side and liquid substances are not provided to chambers opened to the second side. The liquid substances may be provided to one or more chambers of the receptacle that are then closed off prior to providing the dried substances to one or more chambers or vice versa. The first and second sides of the receptacle are positioned adjacent to each other or, preferably, opposite each other.

An immiscible liquid may be provided to one or more of the first chambers of the receptacle prior to providing the liquid substances, where the immiscible liquid is selected to have a lower density than any of the liquid substances provided to the receptacle. The immiscible liquid is preferably non-reactive with any of the liquid substances and may be, for example, an oil (e.g., a mineral oil). The ratio of the immiscible liquid to any of the liquid substances is preferably up to about 10:1.

The liquid and dried substances may be used to perform an assay. At least a portion of the liquid substances may be used to reconstitute, dissolve or rehydrate the dried substances. In a particularly preferred embodiment, the dried substances include amplification and enzyme reagents for performing a nucleic acid-based amplification reaction, and the liquid substances include corresponding reconstitution reagents.

The receptacle may be comprised of opposed members, at least one of which includes a flexible sheet. The flexible sheet may include flexible portions of the open chambers that are drawn away from the opposed member during the providing steps. The opposed members may comprise opposed flexible sheets, where the opposed flexible sheets include opposed flexible portions, such as chamber walls, of the open chambers that are drawn away from each other during the providing steps. Following each of the providing steps, the first chambers and or the second chambers are closed by any means sufficient to provide a fluid-tight seal, such as a heat seal formed between opposed members of the open chamber. The steps of the method are preferably automated.

In yet another embodiment, a method is provided for concentrating an analyte contained in a sample delivered to a receptacle having a plurality of interconnected chambers. The method includes the steps of: forming a first volume in a first chamber of the receptacle, where the first volume comprises the sample and a solid support; immobilizing the analyte on the solid support; removing non-analyte components of the sample from the analyte; and moving a second volume comprising the analyte to a partitioned section of the first chamber or to a second chamber of the receptacle, where the second volume and the volume capacity of the partitioned section of the first chamber or the second chamber are each less than the first volume. The first chamber may be a sample receiving chamber having a sample addition port.

The solid support of the first volume may be present in the first chamber when the method of this embodiment is initiated or it may be moved to the first chamber from a third chamber prior to or during the forming step. Non-analyte components of the sample may be removed from the analyte while the analyte is immobilized on the solid support in the first chamber or in a chamber other than the first chamber. To facilitate movement of the second volume between chambers or to prevent the solid support from obstructing connections between chambers, the first volume may further include a non-reactive, immiscible liquid. The immiscible liquid may be, for example, an oil (e.g., a mineral oil). The ratio of the immiscible liquid to the remainder of the first volume in the first chamber is preferably about 1:10 to about 10:1, and more preferably about 1:3 to about 10:1.

Moving the second volume to the second chamber may be accomplished by applying a substance-moving force to a flexible portion of the first chamber, such as a compressible chamber wall, thereby forcing the second volume through a connection to the second chamber. The connection may be an openable connection, such as a seal, that can be altered from a closed state to an open state when the substance-moving force is applied to the flexible portion of the first chamber.

Alternatively, or in combination with a seal, the first and second chambers may be isolated from each other by an external and retractable force applied to the connection prior to the moving step. The external closing force, alone or in combination with a seal, provides a substantially fluid-tight seal and may include one or more actuators, such as pneumatic actuators, having compression pads that extend across the connection.

A solid support of this embodiment may be in the form of a particle or bead. The solid support may be a magnetically-responsive material that is exposed to a magnetic field when non-analyte components of a sample are removed from the analyte.

The immobilizing step may be specific, partially specific, or non-specific for the analyte. For example, if the analyte is a target nucleic acid, the solid support may be used to immobilize essentially any nucleic acid present in the sample, a group of nucleic acids—such as obtained from a phylogenetic grouping of organisms—to which the target nucleic acid belongs, or the target nucleic acid but not other nucleic acids present in the sample. The analyte may remain immobilized by the solid support during the moving step, or it may be eluted first and then moved independent of the solid support. In the latter case, the solid support may remain in the first chamber while the analyte is being moved to the second chamber.

In a further embodiment, a method is provided for concentrating an analyte contained in a sample delivered to a receptacle having a plurality of interconnected chambers. The method includes the steps of: forming a first volume in a first chamber of the receptacle, where the first volume comprises the sample and a solid support; immobilizing the analyte on the solid support; moving an aliquot of the first volume from the first chamber to a second chamber of the receptacle directly connected to the first chamber, where the volume capacity of the second chamber is less than the first volume; isolating the solid support in the second chamber; removing non-analyte components of the sample to a waste chamber of the receptacle, where the waste chamber is directly connected to the second chamber; and repeating the moving, isolating and removing steps one or more times. Aliquots of the first volume may be moved to the second chamber by applying substance-moving forces to a flexible portion of the first chamber, such as a compressible chamber wall, so that the aliquots move through a connection to the second chamber. The above-described receptacles for use in concentrating an analyte present in a sample may be adapted for use in the method of this embodiment.

In a still further embodiment, a receptacle having a plurality of interconnected chambers is provided, where the chambers of the receptacle include a first chamber directly connected to a second chamber and containing a sample processing reagent which includes dispersible solid supports in a liquid medium. Also contained in the first chamber is an immiscible liquid in an amount sufficient to hinder the solid supports from obstructing the connection. The immiscible liquid is preferably non-reactive with the other components of the sample processing reagent and may be, for example, an oil (e.g., a mineral oil). The solid supports may be particles or beads, such as magnetically-responsive particles or beads that can be isolated in the presence of a magnetic force. When the sample processing reagent is contacted with a fluid sample in the first chamber, the ratio of the immiscible liquid to the liquid medium/fluid sample combination is preferably about 1:10 to about 10:1, and more preferably about 1:3 to about 10:1.

Where the receptacle is comprised of opposed members, the sides of the receptacle are formed by the joining of the opposed members. One of the sides, indicated to a top end because of its orientation during use, may have a sample receiving chamber with a sample addition port for receiving a sample into the sample receiving chamber. At least a portion of the second chamber may be positioned closer to a bottom end of the receptacle than the first chamber. With this configuration, the connection from the first chamber to the second chamber preferably has a generally downward orientation relative to the top end (i.e., the connection joins a lower half of the first chamber to an upper half of the second chamber). The sample receiving chamber may be first chamber.

The solid supports of this embodiment are small relative to the volume capacities of corresponding holding chambers. As such, the solid supports are dispersible in the liquid contents of the chambers, such that they are susceptible to manipulation in the receptacle, as with charged solid supports that are influenced by magnetic forces. The solid supports are preferably adapted to immobilize one or more analytes of interest that are suspected of being present in a sample so that the analytes can be isolated and non-analyte components can removed from the sample, especially interfering materials that can affect the results or performance of a procedure. The solid supports may be used in combination with capture agents, such as capture probes, to immobilize analytes.

In another embodiment, a method of using the above receptacle is provided to effect movement of a fluid substance between chambers of the receptacle. In a first step of this method, a fluid sample is combined with the sample processing reagent and the immiscible liquid in a first process chamber of the receptacle, the immiscible liquid being provided in an amount sufficient to concentrate the solid supports in the first process chamber. Concentrating the solid supports limits their dispersion within a chamber, such that they are less disperse than they would be in the absence of the immiscible liquid. This, in turn, minimizes the presence of the solid supports at peripheral portions of the chamber, especially portions adjacent connections between chambers. In a second step, a fluid substance is moved from the first process chamber to a second chamber of the receptacle through a connection, such as a passage or channel between the chambers. The fluid substance may be the resulting combination of the first step or it may be, for example, a buffered solution containing a purified form of the analyte, if present in the sample. The presence of the immiscible liquid in the first step hinders the solid supports from obstructing movement of the fluid substance through the connection.

In still another embodiment, a receptacle is provided for improving the stability of dried substances stored in the same receptacle as liquid substances. The receptacle has a plurality of interconnected chambers that include first and second chambers which are directly connected to each other. The first chamber contains a dried substance and the second chamber contains a liquid substance capable of altering the state or a characteristic of the dried substance. The liquid substance may be formulated to reconstitute, dissolve or rehydrate the dried substance upon contact. The dried substance may be, for example, a lyophilized or tabletted reagent. To prevent the dried and liquid substances from prematurely coming into contact with each other, the connection between the first and second chambers is usually blocked by, for example, a seal, valve or other obstruction, including external forces. The connection may be blocked by an openable connection that can be altered from a closed state to an open state when a substance-moving force is applied to the contents of the second chamber. The substance-moving force may be one or more compressive forces, such as one or more pneumatic actuators, applied to a flexible portion of the second chamber.

The first and second chambers are constructed so that water vapor passes from the first chamber at a faster rate than it passes from the second chamber. In this way, it is believed that water vapor is drawn from the second chamber, through the first chamber and into the ambient environment without substantially hydrating the dried substance, which might affect its stability and performance in an assay. Where multiple chambers are directly connected to the first chamber, water vapor passes from the first chamber faster than it passes from any directly connected, liquid-holding chamber, and preferably from any directly connected chamber. To achieve this effect, the first chamber preferably includes at least one chamber wall having a greater water vapor transmission rate than any chamber wall of a directly connected, liquid-holding chamber of the receptacle.

In one aspect, each of the first and second chambers includes a flexible chamber wall. The flexible walls may include a plurality of layers, one or more of which may be a plastic layer. To limit light, vapor and/or oxygen transmission through a chamber wall, at least one of the layers may include a foil layer. In another aspect, the flexible wall of the second chamber fully comprises a foil layer and the flexible wall of the first chamber does not fully comprise a foil layer. The flexible wall of the first chamber may include one or more but less than all of the layers of the flexible wall of the second chamber. To facilitate detection of a light signal from the contents of the first chamber, the chamber wall of the first chamber may include an optically transmissive region. In a further aspect, the second chamber is constructed so that it does not include a chamber wall having an optically transmissive region, which could affect the water vapor transmission rate of the chamber wall and the stability of the dried substance.

To limit exposure to ambient conditions (e.g., light, water and/or oxygen) which could affect the stability of the dried substance, the receptacle may be contained within a sealed container. A desiccant is preferably included in the sealed container.

In yet another embodiment, a method is provided for mixing substances contained in first and second chambers of a receptacle having a plurality of interconnected chambers that relies upon gravity to move the contents of one of the chambers. In this method, the receptacle is first oriented in an analyzer so that the first chamber is positioned substantially above the second chamber, thus permitting the contents of the first chamber to be drawn by gravity (or negative pressure) into the second chamber when a fluid communication is established between the first and second chambers. In a preferred embodiment, the fluid communication is established when an openable connection between the first and second chambers is altered from a closed state to an open state by a substance-moving force applied to the contents of the second chamber, such as one or more compressive forces applied to a flexible portion of the second chamber. The same force used to establish fluid communication between the first and second chambers may also be used to move the contents of the second chamber to the first chamber. After moving the contents of the second chamber into the first chamber, the substance-moving force is removed so that the contents of the first chamber can be drawn into the second chamber. This process may be repeated one or more times to achieve complete mixing of substances stored in the first and second chambers prior to the initiation of this procedure.

The first and second chambers may each contain a fluid substance or the first chamber may contain a dried substance, such as a lyophilized or tableted reagent. If a dried substance is contained in the first chamber, then the fluid substance of the second chamber is provided to reconstitute, dissolve or rehydrate the dried substance. It was discovered that including a non-reactive, immiscible liquid with the fluid substance of the second chamber facilitates more complete mixing of the substances to be combined, especially when a dried substance is being hydrated. The immiscible liquid may be an oil, such as a mineral oil, and the ratio of the immiscible liquid to the fluid substance is preferably about 1:10 to about 10:1, and more preferably about 1:3 to about 10:1.

In a further embodiment, a system is provided for performing gravity-assisted mixing of substances contained in first and second chambers of a receptacle having a plurality of interconnected chambers. The system includes one of the above-described receptacles and an analyzer which supports the receptacle in an operative position. The analyzer includes one or more actuators for applying a compressive force to the second chamber to thereby displace at least a portion of the contents of the second chamber into the first chamber. Removing the compressive force from the second chamber allows the contents of the first chamber to flow by gravity into the second chamber without applying a compressive force to the contents of the first chamber. The analyzer is programmed to control operation of the actuators and to cause the contents of the second chamber to move between the first and second chambers multiple times, thus mixing the combined contents of the first and second chambers. The actuators may be pneumatic actuators and preferably have compression pads that are arranged to generally conform to the shape of the second chamber, or at least a flexible portion of the second chamber.

In a preferred aspect, each of the chambers of the receptacle is an at least partially compressible chamber to facilitate substance movement between chambers. According to this aspect, the analyzer includes a plurality of actuators, each of which is associated with at least one of the chambers of the receptacle, and the controller is programmed to control the operation of the actuators and to cause the actuators to move substances among the various chambers by selective application of external force by the actuators. The controller is not programmed to cause the analyzer to apply a compressive force to the contents of the first chamber or, alternatively, the analyzer does not include an actuator associated with the first chamber. In certain aspects, an actuator plate provided to house the actuators includes an opening adjacent the first chamber to permit a detector to detect a characteristic of the contents of the first chamber, such as an optical signal.

In a still further embodiment, a receptacle having a plurality of interconnected chambers is provided that includes at least one chamber treated to limit evaporation of a contained liquid substance. The chamber has a flexible portion, such as a compressible chamber wall, and contains, in addition to a liquid substance, an immiscible liquid. The immiscible liquid coats an inner surface of the chamber, thereby, limiting evaporation of the liquid substance from the chamber. The immiscible liquid is preferably non-reactive with the other contents of the chamber and may be, for example, an oil (e.g., a mineral oil). The ratio of the immiscible liquid to the other liquid contents of the chamber is preferably about 1:10 to about 10:1, and more preferably about 1:3 to about 10:1.

In another embodiment, a method of mixing substances contained in a receptacle having a plurality of interconnected chambers is provided. In a first aspect of this embodiment, the method includes the steps of: forming a volume in a first chamber of the receptacle, where the volume comprises first and second substances and an immiscible liquid that is preferably non-reactive with the first and second substances; and moving the volume through a connection between the first chamber and a second chamber of the receptacle one or more times to facilitate mixing of the first and second substances in the presence of the immiscible liquid. The first and second chambers of this aspect may include flexible portions that yield to substance-moving forces. In a second aspect of this embodiment, the method includes the steps of: forming a volume in a closed chamber of the receptacle, where the volume comprises first and second substances and a preferably non-reactive, immiscible liquid, and where the closed chamber comprises a flexible portion that yields to substance-moving forces; closing the chamber to provide a substantially fluid-tight seal; and applying the substance-moving forces to different portions of the flexible portion in an alternating manner to mix the first and second substances in the presence of the immiscible liquid within the closed chamber. In preferred aspects, immiscible liquids were found to improve mixing by, among other things, generally concentrating the substances to be mixed toward the centers of chambers. The ratio of the immiscible liquid to other liquid substances in the chambers is preferably from about 1:10 to about 10:1, and more preferably from about 1:3 to about 10:1.

To effect mixing in the first aspect of this embodiment, it is preferred that substance-moving forces are alternately applied to the flexible portions of the first and second chambers during the moving step. (The connection and/or second chamber may also be configured to facilitate a turbulent flow and mixing of the substances when moved from the first chamber.) In this aspect, the substance-moving forces are compressive forces that may be applied by one or more actuators having compression pads generally conforming to the shape of the flexible portions, such as chamber walls, of each of the first and second chambers. In the second aspect of this embodiment, the substance-moving forces are compressive forces that may include two or more actuators having compression pads that are arranged to generally conform to the shape of the flexible portion of the closed chamber. The actuators are preferably pneumatic actuators.

Alternatively, or in combination with an internal barrier (e.g., seal), the first and second chambers may be isolated from each other by an external and retractable compressive force applied to the connection prior to the moving step. The external closing force, alone or together with an internal obstruction, provides a substantially fluid-tight seal and may include one or more actuators having compression pads that extend across the connection. Pneumatic actuators are particularly preferred.

The substances used to form the volume of this method of mixing are typically liquids, and the immiscible liquid may be, for example, an oil (e.g., a mineral oil).

In still another embodiment, a receptacle having a plurality of interconnected chambers is provided, where one of the chambers is a first chamber containing a process material and a preferably non-reactive, immiscible liquid in an amount sufficient to substantially coat an interior surface of the first chamber, thereby hindering the process material from sticking to the interior surface. The process material is preferably a liquid, such as a reconstitution reagent, and the immiscible liquid is preferably an oil (e.g., a mineral oil). The ratio of the immiscible liquid to the process material is preferably about 1:10 to about 10:1, and more preferably about 1:3 to about 10:1. The first chamber is directly connected to a second chamber of the receptacle and may comprise a flexible portion, such as a compressible chamber wall, that yields to a substance-moving force.

In yet another embodiment, a method of moving a process material in a receptacle having a plurality of interconnected chambers is provided, where the method includes the steps of: forming a volume in a first chamber of the receptacle, where the volume comprises a process material and an immiscible liquid in an amount sufficient to substantially coat an interior surface of the first chamber, thereby hindering the process material from sticking to the interior surface of the first chamber; and moving the volume from the first chamber to a second chamber of the receptacle through a connection between the first and second chambers. The above-described receptacles for use in coating the interior surface of a chamber may be used in this method.

In a further embodiment, a method of moving a liquid substance from a first chamber to a second chamber of a receptacle is provided, where the first and second chambers are directly connected to each other by an openable connection. The method includes the steps of: forming a volume in the first chamber comprising the liquid substance and a preferably non-reactive, immiscible liquid; and applying a substance-moving force to the volume of the first chamber sufficient to alter the openable connection from a closed state to an open state and to move the volume of the first chamber to the second chamber, where the volume in the first chamber is insufficient to alter the openable connection from the closed state to the open state in the absence of the immiscible liquid. The immiscible liquid may be, for example, an oil (e.g., a mineral oil).

In a still further embodiment, a method of altering the temperature of a liquid substance contained in a chamber of a receptacle is provided. The method includes a first step of forming a volume in a first chamber of the receptacle so that a flexible portion of a first chamber wall expands to contact a stationary thermal element positioned adjacent the first chamber. The volume in the first chamber comprises a liquid substance and a corresponding immiscible liquid, where the presence of the immiscible liquid causes the flexible portion of the first chamber to contact the thermal element to a greater extent than if the immiscible liquid was absent from the first chamber. In a second step, the temperature of the liquid substance in the first chamber is altered by transmitting thermal energy between the thermal element and the volume. The liquid substance of this method may be a reagent for performing an assay, and the immiscible liquid is preferably inert, such that is does not react with any components of the assay. The ratio of the immiscible liquid to the remaining volume in the first chamber is preferably up to about 10:1. Suitable immiscible liquids include, for example, oils (e.g., a mineral oil).

One or more connections may be included for joining the first chamber to one or more other chambers of the receptacle, where the connections remain blocked at least until a predetermined temperature of the fluid volume is reached during the altering step. At least one of the connections may be an openable connection that can be altered from a closed state to an open state when a substance-moving force is applied to the contents of the process chamber. In the closed state, at least one connection may be blocked by an internal barrier and/or an externally applied closing force, such as an actuator.

The first chamber may also include a flexible portion of a second chamber wall that yields to a substance-moving force. The second flexible portion may be positioned adjacent the substance-moving force, which is located opposite the thermal element. The substance-moving force may include one or more actuators having compression pads generally conforming to the shape of the second flexible portion. The one or more actuators may be pneumatic actuators. In this aspect, the substance-moving force contacts the second flexible portion during the method. The second flexible portion may, but need not, expand during the fluid volume forming step.

The thermal element may function alone or it may cooperate with the substance-moving force to alter the temperature of the fluid volume during the altering step (e.g., the substance-moving force can also function as a thermal conducting medium). See, e.g., Devaney et al., "Temperature Control Device and Reaction Vessel," U.S. Pat. No. 5,460,780. The thermal element may include a heat transfer element formed from a thermally conductive material, such as aluminum or other metals or combinations of metals. The heat transfer element may be placed in thermal contact with a thermoelectric device to effect temperature changes. To raise or lower the temperature of the heat transfer element, the thermoelectric device may operate on the Peltier effect. The temperature of the fluid volume will generally be elevated during the temperature altering step and, for certain applications, may be cycled between different temperatures (e.g., PCR thermal cycling to effect binding and extension of primers in the presence of single-stranded nucleic acid templates and melting of double-stranded extension products).

In a still further embodiment, an instrument for processing a sample in a receptacle having a plurality of interconnected chambers is constructed and arranged to support the receptacle in an operative position during the processing. The instrument comprises one or more thermal elements defining one or more multiple chamber thermal zones. The multiple chamber thermal zones are in thermal communication with the receptacle and are constructed and arranged to transmit thermal energy between each multiple chamber thermal zone and an associated region of the receptacle, wherein the associated region of the receptacle encompasses all or a portion of each of two or more but less than all chambers of the receptacle. The instrument also includes a controller programmed to control operation of the one or more thermal elements defining the multiple chamber thermal zones to selectively heat or cool the chambers encompassed within the regions associated with the multiple chamber thermal zones.

In anther aspect, the instrument further comprises one or more thermal elements defining one or more single chamber thermal zones disposed to be in thermal communication with the receptacle and constructed and arranged to transmit thermal energy between each single chamber thermal zone and an associated region of the receptacle encompassing all or a portion of one chamber of the receptacle. The controller is also programmed to control operation of the thermal elements defining the single chamber thermal zones to selectively heat or cool the chambers encompassed within the regions associated with the single chamber thermal zones.

The instrument may have anywhere from one to five thermal zones including all multiple chamber thermal zones or a combination of multiple chamber and single chamber thermal zones.

In anther aspect, the thermal elements comprise one or more Peltier' devices controlled by the controller to selectively heat or cool a body with which the Peltier' device is in thermal contact.

In a further aspect, the thermal elements comprise a heat transfer element formed from a thermally conductive material and having a peripheral shape corresponding to a predetermined shape of a multiple chamber thermal zone defined by the heat transfer element. The heat transfer element may be formed from aluminum.

In another aspect, the instrument further comprises a temperature sensor in thermal communication with the heat transfer element. The sensor is adapted to sense the temperature of the heat transfer element and communicate the sensed temperature to the controller.

The heat transfer element may be held within the instrument in a fixed position with respect to the receptacle.

In another aspect, the thermal elements comprise one or more Peltier' devices controlled by the controller to selectively heat or cool a body with which the Peltier' devices are in thermal contact and a heat transfer element associated with each multiple chamber thermal zone. The heat transfer element is formed from a thermally conductive material and has a generally flat surface and a peripheral shape corresponding to a predetermined shape of a multiple chamber thermal zone defined by the heat transfer element, and the Peltier' devices are in thermal contact with the heat transfer element.

In another aspect, each multiple chamber thermal zone is separated from other multiple chamber thermal zones by isolating structure comprising a thermally non-conductive material. The heat transfer element and the isolating structure may be held within the instrument in fixed positions with respect to the receptacle.

The instrument may further include a heat dissipation element constructed and arranged to dissipate heat from the Peltier' devices. And the heat dissipation element may comprise a heat sink formed from a conductive material and including a block having one side in thermal communication with at least one Peltier' device and an opposite side from which heat dissipation fins extend from the block. In one embodiment, the heat sink may be made from aluminum.

In another aspect, the heat dissipation element may further comprises a fan disposed adjacent the heat sink and configured to generate an air flow over the heat dissipation fins of the heat sink. Operation of the fan may be controlled by the controller.

In another aspect, the instrument may comprise one or more temperature sensors for sensing the temperature of each thermal zone and communicating the sensed temperature to the controller.

In another aspect, the controller is configured to control the operation of the thermal elements to establish an ambient temperature within a prescribed temperature range. The prescribed temperature range may be about 20° C. to 40° C. or about 25° C. to 37° C.

In another aspect, the controller is configured to control operation of the thermal elements to heat one or more chambers to temperatures within a prescribed temperature range. The prescribed temperature range of the chambers may encompass temperatures required to perform a process requiring thermal cycling. The prescribed temperature range may be about 5° C. to 95° C.

In another aspect, the process may be a PCR amplification reaction.

In another aspect, the controller may be configured to control operation of the thermal elements to heat or cool the contents of chambers encompassed within a region associated with the multiple chamber thermal zone to a predetermined temperature for a predetermined period of time.

In a further aspect, the when a receptacle is supported in the operative position within the instrument, filling a chamber encompassed within the region associated with the multiple chamber thermal zone with fluid will increase thermal communication between the chamber and the multiple chamber thermal zone.

In a still further embodiment, a method for heating or cooling substances within a receptacle having a plurality of interconnected chambers comprises the steps of positioning the receptacle in thermal communication with one or more multiple chamber thermal zones contained in an analyzer. Each multiple chamber thermal zone is associated with a region of the receptacle encompassing all or a portion of each of two or more but less than all chambers of the receptacle. The method further includes transmitting thermal energy between each multiple chamber thermal zone and the chambers encompassed by the region associated with the multiple chamber thermal zone to selectively heat or cool substances contained within the encompassed chambers to a temperature different than the temperature of the chambers encompassed by at least one other region.

In another aspect, the method further comprising positioning the receptacle in thermal communication with one or more single chamber thermal zones contained in the analyzer, each single chamber thermal zone being associated with a region of the receptacle encompassing all or a portion of one chamber of the receptacle.

In another aspect, the transmitting step comprises heating or cooling the thermal zone with one or more Peltier' devices.

In another aspect, the ambient temperature of the analyzer is different than the temperature of substances contained within chambers encompassed by the regions of the receptacle associated with each thermal zone during the method.

In another aspect, the transmitting step comprises alternately heating and cooling at least one of the multiple chamber thermal zones.

In another aspect, the method further comprises thermally separating each thermal zone from other thermal zones.

In another aspect, the method further comprises dissipating heat from the thermal zone.

In another aspect, the method further comprises sensing the temperature of each thermal zone.

In another aspect, the method further comprises expanding a chamber encompassed by the region of the receptacle associated with a multiple chamber thermal zone to increase the thermal communication between the expanded chamber and the associated multiple chamber thermal zone.

In another aspect, the analyzer contains at least three multiple chamber thermal zones.

In another aspect, each of the plurality of interconnected chambers is adjacent to at least one other chamber of the receptacle.

These and other features, aspects, and advantages of the present invention will become apparent to those skilled in the art after considering the following detailed description, appended claims and accompanying drawings.

GENERAL OVERVIEW OF THE INVENTION

Figure 1A:
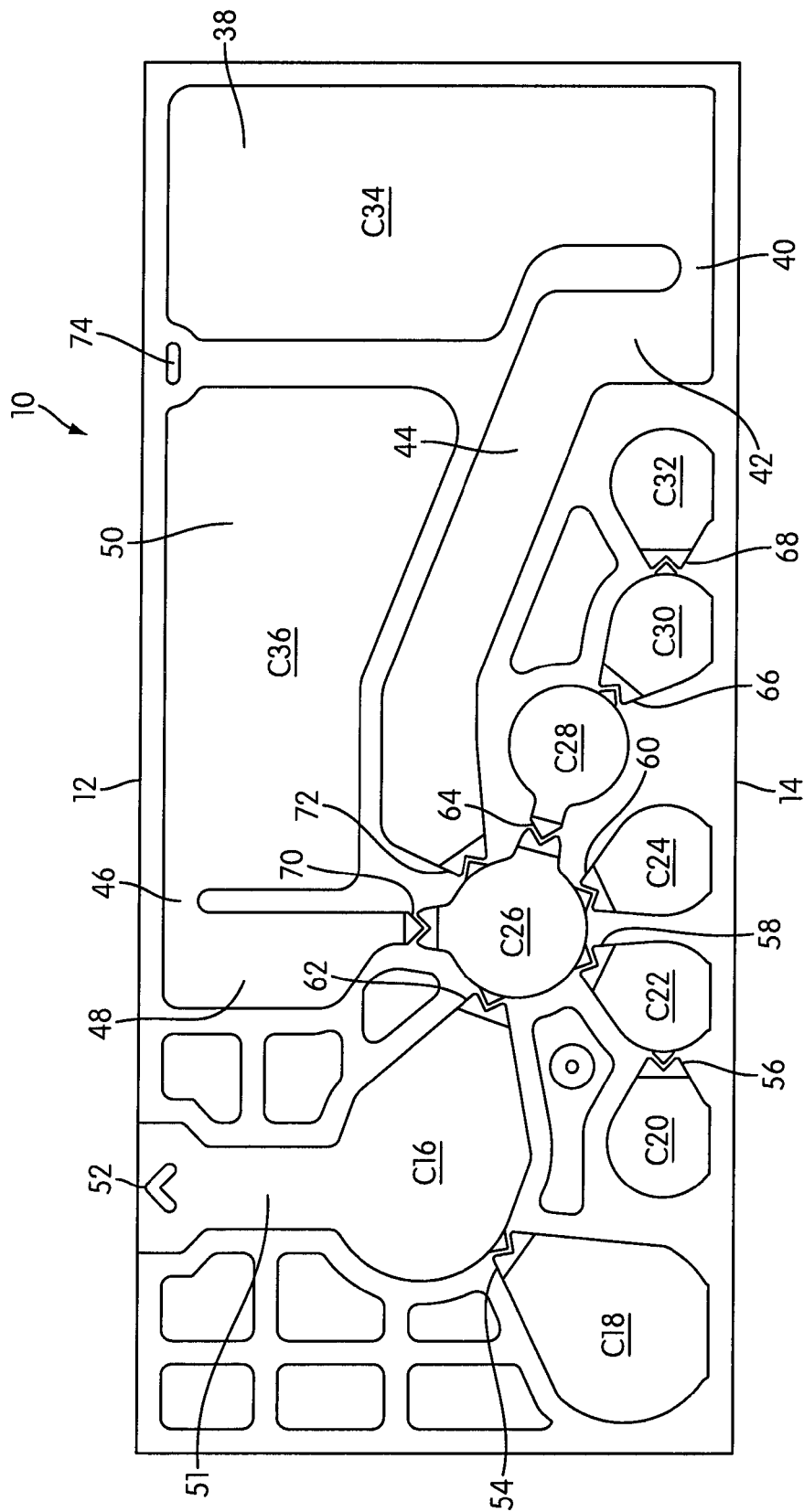
FIGS. 1A-1C are plan views illustrating a multi-chambered receptacle embodying aspects of the current invention.

The present invention relates to multi-chambered receptacles that can be used to perform one or more manual or automated processes with a sample of interest, such as determining the chemical composition of a substance, measuring the activity of a group of metabolic enzymes, or testing for the presence of one or more analytes in a sample. Some or all of the chambers of the receptacles are interconnected by means of blocked or sealed passages that can be permanently or temporarily opened to permit the movement of substances between chambers. The arrangement of chambers within the receptacles permits complex processes to be performed by allowing different steps of a process or multiple processes to be performed non-sequentially and/or simultaneously.

Receptacles of the present invention may be constructed of flexible or rigid materials, as well as combinations thereof, provided the receptacles permit substances to be forced or drawn between chambers. At least some of the chambers can be pre-loaded with process materials (e.g., reagents) and then enclosed or sealed off from the environment prior to loading sample material. The process and sample materials may be comprised of liquids, solids, gases, or combinations thereof. Once sample material is loaded into a chamber or chambers, the receptacle may be sealed or otherwise closed to maintain all materials within the receptacle during a procedure. Alternatively, a sample chamber may remain open after a procedure has been initiated so that some or all of the sample material is added to the receptacle after the procedure has begun.

The passages interconnecting the chambers are sized and arranged to permit substances to pass between adjacent chambers. The substances are preferably fluids or fluidized substances and may include, for example, gels, emulsions, suspensions and solids, where the solids may be transported through the passages alone or using, for example, a fluid carrier, such as an inert oil. Barriers are provided to block the movement of substances through the passages until such movement is desired. The receptacles, or the receptacles in cooperation with an automated instrument, can include one or multiple types of barriers. Such barriers may be constructed from the materials of the receptacle (e.g., openable seals), or they may be fixed, movable or alterable components or substances positioned adjacent to or inserted into the passages (e.g., valves, magnetically-responsive particles, or heat-sensitive wax plugs), or they may be components of the automated instrument that apply a reversible, compressive force to the passages (e.g., actuators).

Altering or removing a barrier between adjacent chambers allows a substance present in one chamber to be forced or drawn into an adjacent chamber. This movement may be achieved by, for example, the action of a pressure source, such as an actuator or a group of actuators that are adapted to apply pressure to the exterior of the chamber to thereby collapse or partially collapse the chamber to force all or a portion of the material between chambers. The material may be moved unidirectionally or bidirectionally between chambers where, for example, a mixing of combined materials is desired.

The chambers are arranged in the receptacle so that there are at least two non-linear paths that allow for steps of a process to be performed independent of each other. This provides a tremendous advantage in that the substances of two or more sets of chambers can be mixed or combined before the resulting mixtures or combinations, or the underlying substances of the separate sets of chambers, are contacted with each other. By permitting process steps to be performed independent of each other, complex procedures having a series of steps that cannot or are preferably not performed linearly (i.e., steps are performed sequentially) can be performed with the receptacles of the present invention.

The compact design of the receptacles and systems of the present invention makes them especially suitable for use in point-of-care and field applications. By sealing off chambers pre-loaded with the process materials needed to carry out a process, contamination and user error issues are substantially minimized. The receptacles of the present invention are also ideal for unit dose testing, where chambers of the receptacles are pre-loaded with the precise amounts of process materials required to conduct a test.

DETAILED DESCRIPTION OF THE INVENTION

While the present invention may be embodied in a variety of forms, the following description and accompanying figures are merely intended to disclose some of these forms as specific examples of the present invention. Accordingly, the present invention is not intended to be limited to the forms or embodiments so described and illustrated.

DEFINITIONS

The following terms have the following meanings unless expressly stated to the contrary. It is noted that the term "a" or "an" entity refers to one or more of that entity; for example, "an analyte," is understood to represent one or more analytes. As such, the terms "a" or "an," "one or more," and "at least one" can be used interchangeably herein.

Adjacent/Adjacently. With reference to chambers, the term "adjacent" or "adjacently" means that the referred to chambers adjoin each other (i.e., the chambers are positioned directly next to each other in a receptacle). The only structure separating adjacent chambers of a receptacle when a process is initiated is a seal. Thus, adjacently positioned chambers are not connected to each other by channels or passageways.

Amplification/Amplification Reaction. By "amplification" or "amplification reaction" is meant a procedure for increasing the amount, concentration or detectability of a substance that is indicative of the presence of an analyte in a sample.

Amplification Conditions. By "amplification conditions" is meant temperature conditions adequate to effect an amplification reaction.

Amplification Oligonucleotide. By "amplification oligonucleotide" is meant an oligonucleotide that binds to a target nucleic acid, or its complement, and participates in a nucleic acid-based amplification reaction.

Amplification Product. By "amplification product" is meant a nucleic acid generated in a nucleic acid-based amplification reaction that contains a target sequence for detection.

Amplification Reagent. By "amplification reagent" is meant a material containing one or more components needed for an amplification reaction. In a nucleic acid-based amplification reaction, such components may include amplification oligonucleotides (e.g., primers and/or promoter-primers), nucleoside triphosphates, and/or cofactors needed for amplification of a target nucleic acid sequence (e.g., divalent cations such as $Mg^{++}$).

Analyte. By "analyte" is meant a sample, or a component of a sample, that is undergoing analysis.

Assay. By "assay" is meant a qualitative or quantitative analysis of one or more analytes.

Barrier. By "barrier" is meant a structure or material that impedes or prevents the movement of substances between spaces.

Blocked. By "blocked" is meant closed to the movement of a substance.

Binding Agent. By "binding agent" is meant a molecule or molecular complex capable of binding to a component of a sample or reaction mixture. The binding agent may be, for example, an antibody, antigen, peptide, protein, nucleic acid or analog thereof, organic molecule, or complex of any of the foregoing (e.g., antibody:nucleic acid complex).

Burstable Seal. By "burstable seal" is meant a seal that ruptures or peels when sufficient pressure is applied to the seal.

Capture Agent. By "capture agent" is meant a binding agent capable of binding to an analyte and of being directly or indirectly bound to a solid support.

Capture Probe. By "capture probe" is meant a binding agent capable of binding to a nucleic acid analyte.

Chamber. By "chamber" is meant a distinct section or space within a receptacle.

Chamber-Defining Member. By "chamber-defining member" is meant the whole (e.g., bladder) or a part (e.g., wall) of what determines the volume of a chamber. The chamber-defining member may consist of a single component (e.g., one layer) or multiple components (e.g., a plurality of layers bonded together).

Closed/Closing. With reference to a chamber, "closed" or "closing" means that a chamber of a receptacle is not in fluid communication, or the chamber is placed in a condition in which it is not in fluid communication, with any other chamber of the receptacle. With reference to a sample-holding receptacle, "closed" means that all chambers of a receptacle are maintained in a substantially airtight environment relative to the ambient environment. With reference to a receptacle prior to sample addition, "closed" means that all chambers of a receptacle except a sample-receiving chamber are maintained in a substantially airtight environment relative to the ambient environment.

Concentrate. By "concentrate" is meant to limit dispersion of one or more components within a chamber.

Contiguous Path of Chambers. By "contiguous path of chambers" is meant a series of adjacently connected chambers.

Directly Connected. By "directly connected" is meant that there are no intervening chambers in the connection between two referred to chambers.

Distinct Connection. By "distinct connection" is meant a connection that is separate from and non-overlapping with any other connection of a receptacle.

End Chambers. By "end chambers" is meant the outermost chambers of a linear path of chambers.

Enzyme Reagent. The phrase "enzyme reagent" refers to a material that contains at least one enzyme that participates in a process. In a nucleic acid-based amplification reaction, the enzyme reagent may contain one or more enzymes that catalyze the synthesis of DNA and/or RNA polynucleotides using an existing strand of DNA or RNA as a template. Examples of such enzymes include DNA-dependent DNA polymerases (e.g., DNA polymerase I from *E. coli* and bacteriophage T7 DNA polymerase), DNA-dependent RNA polymerases or transcriptases (e.g., DNA-dependent RNA polymerases from *E. coli* and bacteriophages T7, T3 and SP6), RNA-dependent DNA polymerases or reverse transcriptases, and RNA-dependent RNA polymerases (e.g., an RNA replicase).

Flexible. By "flexible" is meant a property of a material that allows it yield to a reasonable force without tearing or breaking.

Fluid. By "fluid" is meant a substance that tends to flow or to conform to the shape of its receptacle (e.g., a liquid or gas). The fluid may be a fluidized substance or mixture of liquids or gases, such as an emulsion. As used herein, the term "fluid" also refers to a substance, such as a paste, that yields to pressure by changing its shape.

Fluidized. By "fluidized" is meant a substance that has been altered so that it is in a form or medium that has fluid characteristics.

Immiscible Fluid. By "immiscible fluid" is meant a fluid that does not mix with one or more liquids contained in a receptacle.

Immunoassay. By "immunoassay" is meant an assay which involves an antibody-antigen interaction.

Independently Combining. The phrase "independently combining" means separately combining two or more sets of substances in distinct chambers of a receptacle, where the separate combinations of substances do not come into contact with each other.

Indirectly Connected. By "indirectly connected" is meant that there are one or more intervening chambers in the connection between two referred to chambers.

Interconnected. The term "interconnected" refers to chambers that are fluidly connected or connectable, as in the case of an openable connection.

Intermediate Between. The phrase "intermediate between" means that the referenced chamber is located between and in the same linear path as each of two other identified chambers, or that the referenced chamber is located between and in a different linear path with each of two other identified chambers.

Intermediate Chamber. By "intermediate chamber" is meant a chamber that is connected by openable connections to at least two other chambers.

Isolated. By "isolated" is meant that one or more components of a sample are sequestered from one or more other components of the sample.

Label. By "label" is meant any substance having a detectable property.

Linear Path. By "linear path" is meant a contiguous path of consecutively ordered chambers interconnected by a plurality of openable connections and defined by a first end chamber, a last end chamber, and one or more intermediate chambers disposed between the first and last end chambers.

Non-Circular Arrangement. The phrase "non-circular arrangement" refers to an arrangement of interconnected chambers that includes two or more linear paths, where the end chambers of the linear paths are not circularly arranged about a central chamber.

Non-linear. By "non-linear" is meant at least two contiguous paths of consecutively ordered chambers that share less than all chambers in common.

Non-sequential. By "non-sequential" is meant that certain steps of a process are performed independent of each other rather than in sequence.

Nucleic Acid-Based Amplification. By "nucleic acid-based amplification" is meant an amplification reaction that is dependent upon the presence of a nucleic acid.

Oligonucleotide. By "oligonucleotide" is meant a polymeric chain of at least two, generally between about five and about 100, chemical subunits, each subunit comprising a nucleotide base moiety, a sugar moiety, and a linking moiety that joins the subunits in a linear spatial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present invention range in size from about 10 to about 100 residues. Oligonucleotides may be purified from naturally occurring sources, but preferably are synthesized using any of a variety of well-known enzymatic or chemical methods.

Openable Connection. By "openable connection" is meant a passage that can be temporarily or permanently altered from a "closed" state in which the connection is blocked by a barrier to an "open" state in which the barrier has been modified or moved so that a substance can pass through an opening in the passage.

Optically Transmissive. The phrase "optically transmissive" is a reference to materials permitting the passage of light, so that light emitted on one side of the materials is detectable by an optical device positioned on the opposite side of the materials.

Primer. By "primer" is meant an amplification oligonucleotide capable of being extended at its 3'-end in the presence of a polymerase in a template-dependent manner.

Probe. By "probe" is meant a binding agent that binds to an analyte or other substance in a reaction mixture to form a detectable probe:target complex indicative of the presence of the analyte in a sample under the conditions of a process. For nucleic acid-based reactions, the probe comprises an oligonucleotide having a base sequence sufficiently complementary to a nucleic acid sequence indicative of the presence of a target nucleic acid to form a detectable probe:target complex therewith. A probe may also include non-complementary sequences, such as a sequence for immobilizing the probe on a solid support, a promotor sequence, a binding site for RNA transcription, a restriction endonuclease recognition site, or sequences which will confer a desired secondary or tertiary structure, such as a catalytic active site or a hairpin structure, which can be used to facilitate detection and/or amplification. Probes of a defined sequence may be produced by techniques known to those of ordinary skill in the art, such as by chemical synthesis, and by in vitro or in vivo expression from recombinant nucleic acid molecules.

Process. By "process" is meant a series of actions, changes or functions performed on or with a substance to bring about a result.

Purified. By "purified" is meant that one or more components of a sample are removed from one or more other components of the sample.

Reagent. By "reagent" is meant any non-sample substance used in a process, including reactants in a chemical, biochemical or biological reaction, diluents, solvents, wash materials, rinse materials, buffers and the like.

Real-Time. The phrase "real-time" means that a characteristic of a reaction is or is capable of being detected as the reaction is occurring.

Receptacle. By "receptacle" is meant a device having a plurality of interconnected chambers capable of receiving and/or holding substances.

Reconstitution Reagent. By "reconstitution reagent" is meant a reagent used to alter a non-fluid process material to a fluid or fluidized state.

Sample. By "sample" is meant a substance capable of being subjected, in whole or in part, to a process.

Sample Processing Reagent. By "sample processing reagent" is meant a reagent that alters or is useful for altering the original state of a sample.

Sample Receiving Chamber. By "sample receiving chamber" is meant a chamber of a receptacle that is open or openable for receiving a sample to be processed.

Seal. By "seal" is meant a barrier formed between adjacent chambers. The seal may be, for example, a heat seal formed between opposed thermoplastic sheets.

Target Nucleic Acid. By "target nucleic acid" is meant a nucleic acid analyte.

Target Sequence. By "target sequence" is meant a nucleic acid sequence contained within a target nucleic acid or its complement that is amplified and/or detected in a detection assay.

Water Vapor Transmission Rate. By "water vapor transmission rate" or "WVTR" is meant the steady state rate at which water vapor permeates through a material at specified conditions of temperature and relative humidity. Water vapor transmission rate values are expressed in $g/m^2/24$ hrs. A PERMATRAN-W® water vapor permeation instrument available from MOCON, Inc. of Minneapolis, Minn. (Model 3/33) can be used to measure WVTR in accordance with ASTM F 1249.

Multi-Chambered Receptacles

Receptacles in accordance with the present invention include a plurality of interconnected, non-linearly arranged chambers arrayed to perform one or more processes. The precise dimensions of the receptacles will depend upon the number and arrangement of the chambers, as well as the volume of substances to be loaded or moved into the chambers. The receptacles preferably have relatively broad surface dimensions in relation to their thicknesses, although this is not a requirement. The receptacles are preferably formed from top and bottom portions, each of which may be made with rigid and/or flexible materials. In a preferred mode, at least one of the top and bottom portions of the preferred receptacles is at least partially flexible.

The non-linear arrangement of chambers allows for non-sequential processing of samples in the receptacles. The exact number, configuration, sizes and arrangement of chambers will depend on the particular process or processes to be performed. Distinct from the surrounding receptacle materials, the chambers may be constructed of rigid or flexible materials or combinations thereof. Material selection will depend in part on whether the chambers must yield to an external pressure in order to move substances between chambers. The chambers may be of any shape that does not interfere with the movement of substances between chambers, which includes generally planar or bubble-like shapes, including hemispherical and spherical shapes. In a preferred embodiment, the chambers are generally flat and have a tear-drop shape that funnels substances through an open connecting passage and into an adjacent chamber. Tear-drop shaped chambers also advantageously focus pressure on connecting passages, thereby more readily opening barriers such as seals and valves used to temporarily block access to adjacent chambers. The chambers may have the same or different shapes and/or sizes.

Passages used to connect the chambers of a receptacle may be, for example, portals or passageways that are dimensioned to permit substances used in a process to move between chambers. In the case of a portal, a seal or other barrier may be substantially all that separates adjacent chambers. A passageway on the other hand comprises a conduit extending between chambers. Portals are preferred because they permit a more compact receptacle design and require materials to travel shorter distances between the various chambers. Some of the passages may remain open throughout a process, such as a passage leading to a waste chamber, while others are blocked by barriers until it is desired to move a substance between chambers. The barriers can be selectively altered from "closed" to "open" states to create substance-transferring connections, which are preferably fluid-transferring connections for moving fluids and substances in a fluidized form. A barrier may be an external force, such as a compressive force provided by, for example, a clamping device (e.g. pneumatically driven actuator having a clamping pad), or it may be a seal or valve that yields to pressure, is mechanically operated, or is altered by, for example, heat, laser ablation, or a chemical or biochemical reaction to provide an opening between chambers, or it may be an external force/seal combination. In a preferred embodiment, the passages are blocked with a heat seal, such as a V-shaped or chevron seal, that is reinforced with a compressive force during use. While the blocking properties of some barriers are designed to be affected by conditions such as heat (e.g., wax plugs), or may be affected by a chemical agent moved into or formed in a chamber, barriers formed or positioned in a receptacle should not otherwise be influenced by environmental conditions or substances that are contained within the chambers.

Once a barrier separating adjacent chambers has been removed or altered to create an opening, a substance may be pushed, pressed, drawn or otherwise moved, such as by gravity, into a neighboring chamber. If the chambers are to be acted upon by a pressing force, such as a roller or an actuator-driven compression pad, to move substances between chambers, then the chambers are formed to have at least one flexible surface that yields to the pressure of the pressing force. Otherwise, the chambers may be constructed of a rigid material, as in the case of pads or vacuums used to push or draw substances into adjacent chambers. This is also true where gravity draws a substance from a chamber that is positioned above a receiving chamber, although in some applications it is desirable for both chambers to have at least one flexible surface so that substances can be moved back-and-forth between chambers in order to mix two substances.

The chambers are arranged in the receptacles so that there are at least two distinct linear paths. Each of the paths includes at least three contiguously connected chambers, with at least one of the paths preferably including five or more contiguously connected chambers. As used herein, the phrase "contiguously connected chambers" refers to a series of directly connected chambers in which the chambers are successively arranged, with one chamber coming after another. Each of the paths may share at least one but less than all chambers in common with any other path in the receptacle. This arrangement of chambers allows certain steps of a process to be performed independently and/or simultaneously. In this way, substances used in a complex process can be prepared and kept segregated until it desirable to combine them. Such independent activities may include, for example, dissolving, diluting, mixing, combining or reacting substances. By way of example only, one set of adjacent chambers may contain a dried, primer-containing amplification reagent for use in amplifying a target nucleic acid sequence present in a sample and a reagent for reconstituting the amplification reagent, while another set of adjacent chambers may contain a dried enzyme/probe reagent for use in amplifying and detecting the target nucleic acid sequence and a reagent for reconstituting the enzyme reagent. If, in this particular example, the amplification and enzyme/probe reagents are prematurely combined in their reconstituted forms, there is some risk of target-independent amplification that could interfere with the amplification of the target or consume scarce reagents for amplification. See, e.g., Adams et al., "Decoy Probes," U.S. Pat. No. 6,297,365. Therefore, it is desirable to separately reconstitute these reagents and then to combine them in the presence of the target nucleic acid.

Figure 1B:
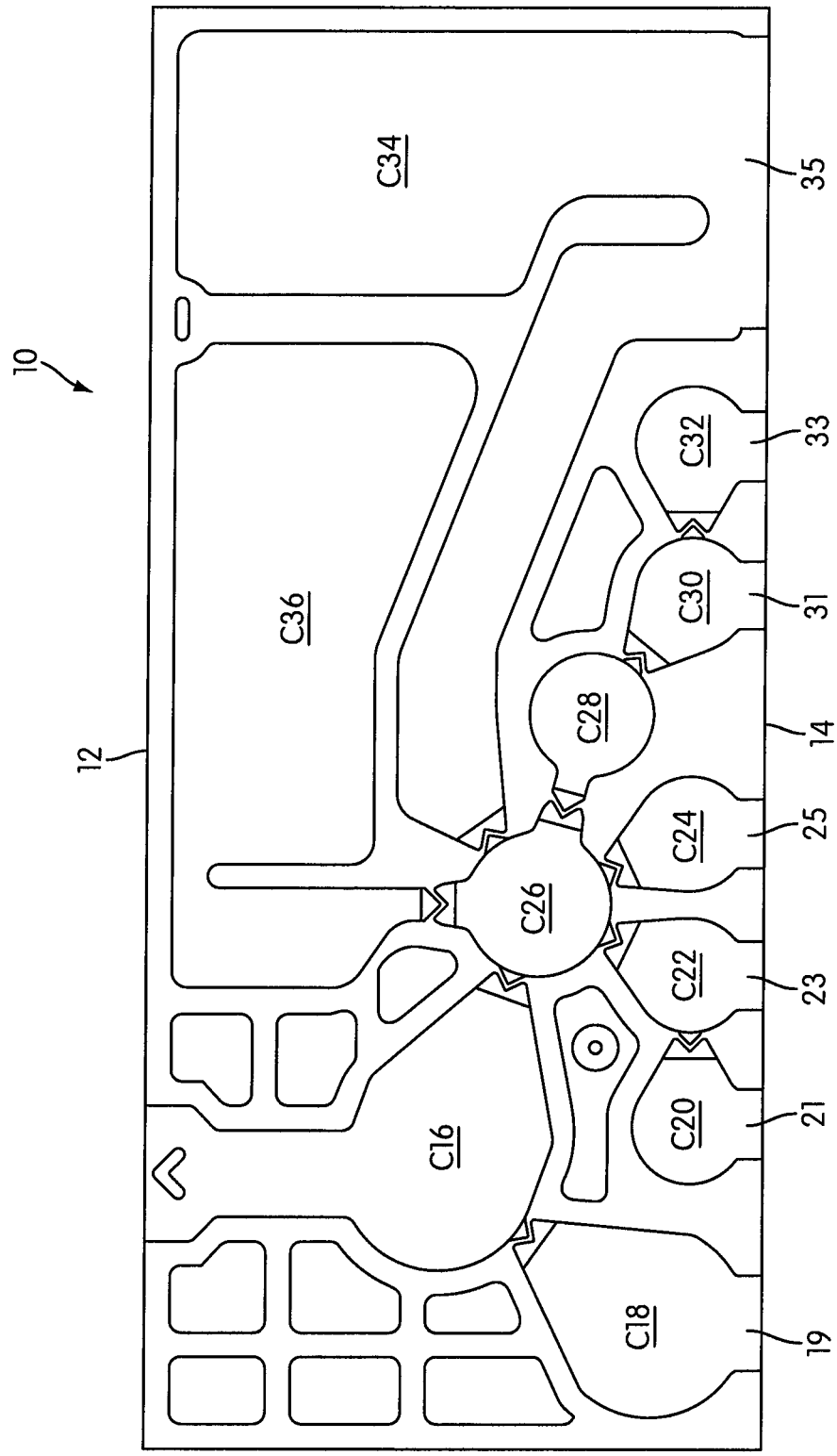
Figure 1C:
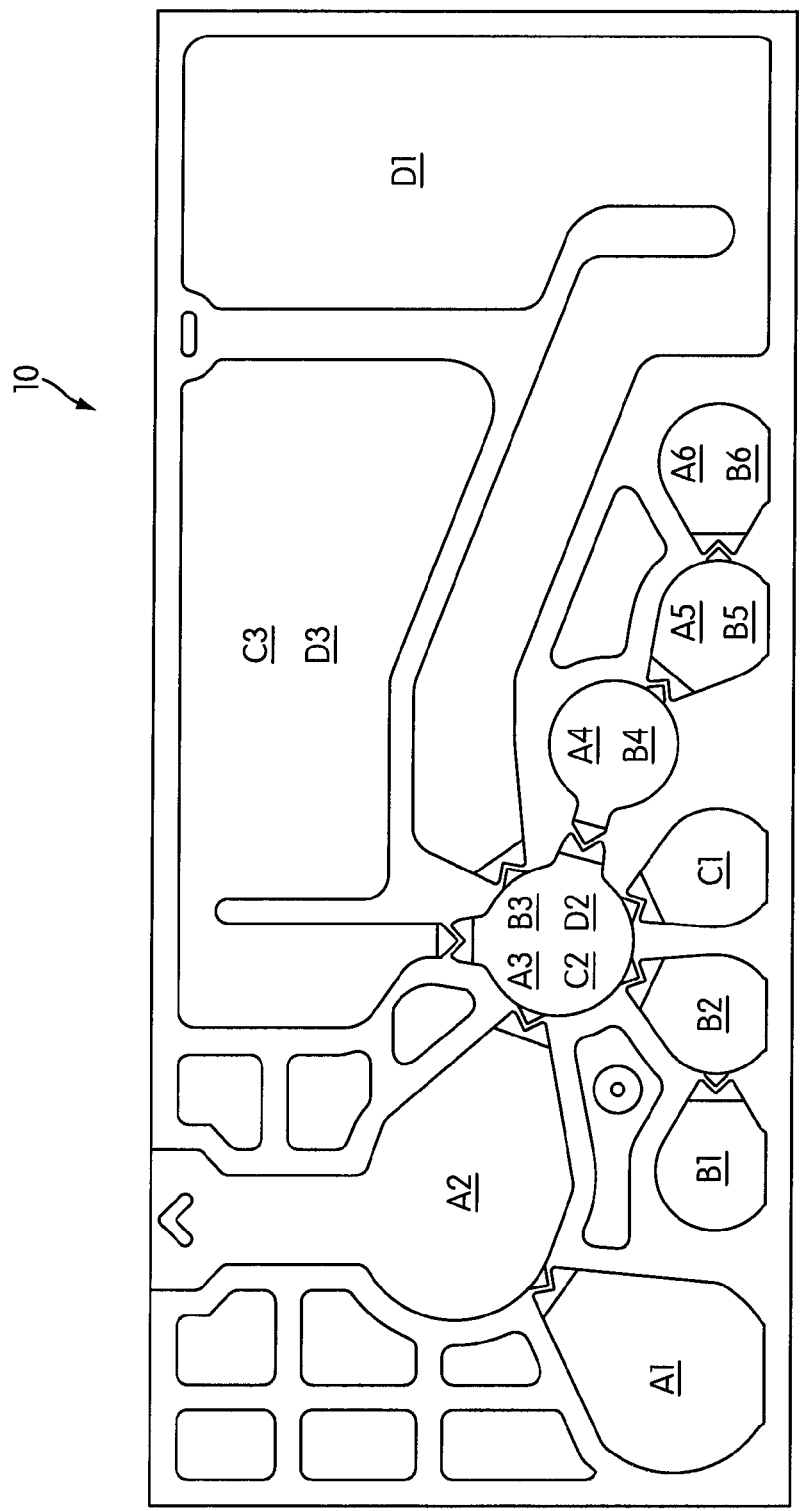

For illustration purposes only, FIG. 1C shows a receptacle 10 having a non-linear arrangement of chambers that defines a number of distinct linear paths. Some of the possible linear paths of this receptacle are identified with letter designations, each chamber of a linear path having the same letter designation (i.e., A, B, C or D), and each chamber of a linear path being assigned a distinct number. The arrangement of the paths is such that the steps of a process can be performed non-sequentially. For example, a sample material can be added to chamber A2 and mixed with a binding agent provided from chamber A1 before isolating and purifying an analyte in chamber A3. At the same time or different times, a first dried or solid process material in chamber B2 can be reconstituted with a first reconstitution reagent (e.g., a first solvent) provided from chamber B1. Also, at the same or different times, a second dried or solid process material in chamber B4 can be reconstituted with a second reconstitution reagent (e.g., a second solvent) provided from chamber B5. Finally, the purified analyte and the reconstituted first and second process materials can be combined in chamber B3 or B4 for detection of the analyte. While there are only four distinct linear paths identified in FIG. 1C, it is readily apparent that other possible linear paths and combinations of linear paths could be utilized.

The non-linear arrangement of chambers in the receptacles can facilitate their use in performing multiple processes of the same or different kind. This is because the chambers can be arranged so that substances and/or chambers that are not shared between processes remain isolated during a process. Thus, the present invention also relates to "universal" receptacles, where a single receptacle can be designed and manufactured, including pre-loading of process materials, for multiple applications. In this way, the end-user does not need to have a different receptacle for each process to be performed or to predict the volume requirements for any particular process in advance. Materials used to form the chambers and barriers of the present invention should be selected to maintain acceptable stability and reactivity levels of the various substances used to perform a process. Such materials may provide, for example, a moisture barrier for substances that are altered, degraded or otherwise affected by moisture. In an alternative or complementary approach, a desiccant, such as calcium oxide, may be loaded with a dried process material to minimize the affects of moisture in a chamber. When a process is being performed in a receptacle, it may be desirable to sequester the desiccant to prevent it from interfering with or altering a reaction involving the dried process material. The desiccant can be sequestered by, for example, locating it in a section of a chamber containing the dried process material or by placing the desiccant in an adjacent chamber having an open connection with the chamber holding the dried process material. It may be desirable to block this open connection after reconstituting the dried process material to prevent unwanted interactions with the reconstituted process material. Yet another approach would be to store the receptacle in a vessel formed from a material or materials that provide a moisture barrier and/or which includes a desiccant. Common desiccants include clay, silica gels, calcium oxide and synthetic molecular sieves. An example of a molecular sieve is a Type 4A Molecular Sieve Multiform™ Tablet having a 0.45" diameter and a 0.125" height, where "Type 4A" indicates a pore size of 4 angstroms (Multisorb Technologies, Inc., Buffalo, N.Y.; Product No. 02-00674AH01).

Similarly, receptacle materials may be selected to protect substances from the environmental affects of exposure to oxygen or electromagnetic radiation. Alternatively, the materials used to form the receptacles may be selected to prevent stored substances from adversely interacting with each other by selecting materials that provide a barrier against transmission of any liquid, solid or gas intended for use in the receptacle. It may also be desirable to use materials in constructing the receptacles that protect against evaporation of substances to prevent the activity of those substances from being altered. Further, the materials selected for use should not significantly alter the intended functions of the stored substances, nor should they adhere to or otherwise bind reactants in a manner that significantly affects their ability to participate in a process or processes.

Where a procedure involves sample manipulations that require concentrating or moving magnetic particles within or between chambers, at least a portion of the receptacle will need to be constructed of materials that do not substantially interfere with the influence of magnetic fields generated by adjacently positioned magnets. For processes requiring heating and/or cooling of all or some of the chambers, either continuously or for precise periods of time, the receptacles must be capable of an energy transfer on at least one side of the receptacles that is capable of affecting the thermal conditions of the contents of chambers requiring heating and/or cooling. Additionally, the receptacles may include optically transparent portions capable of transmitting light of the visible, infrared and/or ultraviolet spectrum to detect changes in the physical characteristics of a sample, such as color or turbidity, or to enable the detection of labels that are indicative of the presence of analytes of interest.

Receptacles of the present invention may be constructed from such materials as polymers, glass, silicon, metals, ceramics and combinations thereof. The materials used will depend, in part, on the means selected for moving substances between chambers, whether a physical change in the sample must be visualized or a light signal detected, and the manner in which substances present in the receptacles, such as magnetic particles, are to be manipulated. The materials used to construct receptacles should be stable under the expected transportation, storage and use conditions. Such conditions include temperature, pressure, humidity and duration of storage. Also, materials used to form flexible chambers of the receptacles should yield to the selected pressure forces for moving substances between chambers without being torn, punctured or ruptured.

In a preferred embodiment, the receptacles are formed from flexible top and bottom sheets that are of the same or different materials and may be multilaminates. Each sheet preferably has at least one liquid-impervious layer, and the sheets preferably have a relatively uniform thickness, which may be between about 0.05 mm and 2.0 mm. Also, select regions of one of the multilaminates are preferably optically transparent or translucent. The sheets may be formed from, for example, foils—with one or more holes cut in the foil to provide detection windows as necessary—and/or thermoplastic materials such as polypropylene (e.g., Reflex® polyolefins available from the Rexene Corporation, Dallas, Tex.), polyester, polyethylene (e.g., polyethylene teraphtalate ("PET") and polyethylene naphtalate ("PAN")), polyvinyl chloride, polyvinylidene chloride, polycarbonate resins (e.g., polyvinyl fluoride films) and polyurethane. In a particularly preferred embodiment, the top and bottom sheets are each multilaminates, an example of which is a Scotchpak® film layer (3M Corporation, St. Paul, Minn.; Cat. No. ES-48) bonded to a Perflex® foil layer (Perfecseal, Oshkosh, Wis.; Product No. 35786). Other suitable materials for forming the flexible sheets of this embodiment will be appreciated by those skilled in the art. See, e.g., Burke (1992) WAAC Newsletter 14(2):13-17.

Exemplary laminates include: foil coated PET with Surlyn® blend peel layer (4.5 mils), clear double AlOx coated PET on low-density polyethylene ("LPDE") with coextruded peel layer (4.5 mils), foil coated LDPE with coextruded peel layer (4.5 mils), foil coated LDPE seal layer (3.5 mils), clear single AlOx coated PET on Biaxial Oriented Polyamide with peel layer (4 mils), clear AlOx coated PET on LDPE seal layer with zone coat defined frangible seal (2.5 mil), foil barrier with peel sealant. (3.5 mil), clear AlOx coated PET on LDPE seal layer (2.5 mil), clear AlOx coated PET on LDPE seal layer, (4 mil), PET coated Foil with HDPE seal layer, clear AlOx coated PET with EVA based peel layer, (3 mil), and foil coated PET with Surlyn® blend peel layer (4.5 mils), as well as laminates of opaque polyethylene terephthalate ("OPET"), ink, white LDPE, aluminum foil, polyethylene ("PE"), linear low-density polyethylene ("LLDPE"), and nylon and OPET, white PE, foil, adhesive, and EZ Peel® Sealant.

Opposed inner heat sealing layers of the top and bottom sheets in the preferred receptacles are bonded to form the walls of the chambers and openable seals (e.g., chevron seals) that separate adjoining chambers using heat sealing techniques well known in the art. The bonds defining the walls of the chambers are stronger than the openable seals separating chambers so that when pressing forces are applied to the chambers, materials are forced between chambers rather than peeling apart the walls of the chambers. Target seal strengths for chamber seals may be on the order of about 9-10 lb/inch, and target seal strengths for peelable seals may be on the order of 2.2-2.3 lb/inch.

More specifically, flexible or semi-rigid receptacles, or pouches—including features of the receptacles, such as chambers, passages, permanent and semi-permanent (e.g., ruptureable, burstable, peelable, frangible, etc.) seals—can be formed by welding two films together using heated filaments, a heat sealing die, impulse welder, or ultrasonic welder or other known techniques. Alternatively, adhesives, or other bonding techniques, capable of forming bonds of differential seal strengths, can be used.

A receptacle constructed for implementation within the present invention preferably includes chambers defined by permanent inter-film bonds formed around the peripheries of the chambers to avoid peeling or creep of the bonds. Semi-permanent seals which are used to initially block passages or portals interconnecting adjacent chambers are constructed and arranged to rupture, or burst, when subject to a predetermined, preferably consistent force to provide fluid communication between the adjacent chambers. Application of a compression force to the chamber causes lateral expansion of the fluid or other substance contained within the chamber in a direction that is transverse to the direction of the force. The permanent and semi-permanent inter-film bonds defining the chamber preferably have bursting pressures, or seal strengths, such that the expanding fluid will generate a sufficient force to hydraulically peel, or rupture, the semi-permanent seal, but will not generate force sufficient to peel the permanent bond defining the remainder of the periphery of the chamber. As well known in the art, the burst pressure, or seal strength, of a seal or bond formed by known techniques is a function of a number of factors, including, the nature of the materials being bonded together, the temperature at the interface of the materials, the pressure applied to the materials, and the dwell time or period of time during which the assembled films are exposed to elevated temperatures and pressures.

Methods for forming such receptacles having bonds of differential seal strengths are well-known in the art. Exemplary disclosures can be found in Johnson et al., "Analytical Test Pack and Process for Analysis," U.S. Pat. No. 3,476,515 at col. 3, lines 36-56; Freshour et al., "Flexible Packages Containing Nonfusible High Peel Strength Heat Seals," U.S. Pat. No. 3,496,061 at col. 2, lines 6-52, and col. 7, lines 50-59; Farmer, "Packaging Device," U.S. Pat. No. 5,131,760 at col. 4, lines 25-34; Robinson et al., "Diagnostics Instrument,"

U.S. Pat. No. 5,374,395 at col. 31, lines 27-58; and Rees et al., "Method and Apparatus for Forming Heat Seals with Films," U.S. Pat. No. 6,342,123 (disclosure is directed to the formation of differential seals with a single die).

Surprisingly, it was discovered that there are advantages to constructing chambers designated for holding moisture-sensitive materials, such as dried process materials, to include regions that permit a greater degree of moisture transmission than surrounding portions of the receptacles. For example, the sheets of the flexible receptacle described above may include thermoplastic and foil layers, where at least one of the sheets includes cut-outs in the foil layer around the chambers containing moisture-sensitive materials. (Cut-outs may also be needed for chambers requiring light transmission for detection or other purposes.) To keep the moisture-sensitive materials dry, the receptacles are placed in sealed, desiccant-containing vessels, where moisture is drawn from chambers holding moisture-sensitive materials and into the vessels where it is absorbed by the desiccants. The desiccant-containing vessels should be constructed of materials having low moisture vapor transmission rates, such as a Mylar® OB12 polyester packaging film available from Dupont Packaging and Industrial Polymers of Wilmington, Del.

To register the receptacles in an instrument, the receptacles may be provided with attachment holes that are aligned with corresponding mounting posts in the instrument. Alternatively, the receptacles may be precisely positioned in an instrument using hooks, loops, adhesives and other like attachment materials. Where an instrument includes a slot for receiving and registering receptacles, those receptacles constructed of flexible materials are preferably supported by a rigid frame about their peripheries for precisely positioning the receptacles within the instrument. It is also contemplated that in some embodiments no positioning structures will be required.

One or more labels or devices providing information that is human and/or machine readable or recognizable may be affixed to or otherwise associated with the receptacles in regions that do not interfere with the processing of samples. The labels and/or devices may provide information relating to the sample type or source and/or the testing protocol or other process to be run. Markings on labels preferably include scannable barcodes. Such labels may be, for example, peel-off labels that can be transferred to an associated chart or file. Alternatively, the information may be printed on or formed in a material used to construct the receptacles.

Substances Used in the Receptacles

The chambers can be loaded with reagents, compounds, compositions or other substances for use in a single process, multiple applications of the same process, or multiple processes of the same or different kind (e.g., nucleic acid-based tests and/or immunoassays). The types of substances that can be loaded into the chambers include liquids, solids, gases, and various combinations thereof. For some processes, it may also be desirable to leave one or more chambers initially empty so that they may serve as, for example, sample, waste, venting, mixing or detection chambers within a receptacle. Receptacles having arrangements of chambers that can be used to perform any of multiple different procedures may have additional empty chambers depending on the number of process materials loaded to perform any particular procedure. Liquids that may be loaded and moved between chambers include aqueous and non-aqueous substances, combinations of liquid substances, such as mixtures of liquid substances and emulsions (with and without an emulsifier or emulsifiers), and liquefied substances, such as solids melted by heating or gases condensed by cooling. Solids that may be loaded and moved between chambers include waxes, mixtures of solids, and solids in liquids, such as suspensions (e.g., colloids, including gels) and slurries. Solids can be in a wide variety of forms, including their natural elemental or molecular forms.

Liquid, partially liquid and/or solid substances can be prepared so that they are in a dried or altered solid form when loaded into a chamber. Such substances may be the product of, for example, encapsulation, lyophilization, pelletizing, powderizing, tabletization, drying, spotting, including spotting of the same or different substances within a chamber (including multiple spots of the same and/or different substances in array patterns), the formation of particles, fibers, networks or meshes, and absorption and/or drying onto a carrier, including an inner surface of a chamber. These substances may provide advantages, such as improved stability or durability, enhanced effectiveness, convenience of manufacturing and handling, precise amounts of substances, protection against environmental and other stresses, including temperature, moisture, oxygen and electromagnetic radiation, loading into spatially separated sections of a chamber, and protection against premature and adverse interactions of different substances within a receptacle, including unintended interactions between a sample and process materials.

Solids loaded in the chambers could be useful for such functions as filtration, immobilization, collection, drying, detection (e.g., probe reagents, chromatography, electrophoresis, etc.), and amplification (e.g., amplification oligonucleotides and enzyme reagents). A solid may remain unchanged during a process or it may be altered prior to or after initiating a process. Types of alterations may include dissolution, the formation of a suspension, slurry or gel, melting, or a chemical, biochemical or biological reaction. Such alterations may be caused by, for example, an interaction with a fluid loaded or formed in an adjacent chamber, heating, cooling, irradiating, sonicating and/or subjecting the solid or solids of a chamber to an electrical current or magnetic field.

Substances may be loaded into the receptacles using manual, semi-automated or automated methods. Particular process materials that may be loaded into the receptacles include, for example, dried and/or liquid reagents, including binding reagents (e.g., nucleic acids, antibodies, antigens, receptors and/or ligands) and signal generators, solvents, diluents, suspensions, solutions, including wash and rinse reagents, and solid supports, including particles, beads and filters. Loading may be accomplished by such means as pouring, pipetting, injecting, spotting, drawing (e.g., applied vacuum or syringe), evacuating, exchanging atmospheres, and the like. Keeping the amount of air present in a chamber to a minimum is generally preferred and, for reproducibility, the air/material ratios in like chambers should be kept substantially constant across receptacles prepared for identical uses. When loading substances into a flexible receptacle, the substances are preferably loaded from access openings extending from an edge or edges of the receptacle into the chambers to be loaded. FIG. 1B provides an illustration of access openings 19, 21, 23, 25, 31, 33, 35 in an exemplary receptacle 10 described more fully below. The opposed sides of the receptacle are preferably drawn apart by suctioning to facilitate loading of substances and to control wicking of liquid substances up the sides of partially sealed chambers. Dried or solid substances are preferably loaded first, and the chambers so loaded are temporarily sealed with a tack seal, which provides a substantially fluid-tight seal to protect substances that are sensitive to or altered by the presence of moisture. Liquid substances are then loaded, and all openings leading to chambers with loaded substances are sealed with a heat seal.

Some process materials exhibit a strong tendency to wick up the sides of the chambers during loading and, in some instances, migrate into adjacent chambers where they can alter the nature, concentration and/or performance of other process materials. By way of example, if amplification and enzyme reagents co-mingle prematurely, unintended interactions could occur which consume a portion of these reagents prior to contacting them with a target nucleic acid. To address this problem, it was discovered that providing oil (e.g., light mineral oil) to the chambers prior to loading process materials significantly reduces the wicking effect and improves the performance of processes. Also, when a light mineral oil is included in chambers filled near their capacities, any loss of material during the sealing or closing process is typically limited to the inert, inactive oil rather than active process materials. Further, an oil layer situated above a heat-labile process material (e.g., enzyme reagents) will insulate the process material from the high temperatures used in sealing closed the receptacle.

The use of oil was found to have other benefits as well. For example, if a process material contains particles or beads (e.g., magnetically-responsive particles) that tend to settle along the sides of a chamber, or adjacent passages between chambers, the use of oil helps to concentrate the particles or beads toward the center of the chamber. Otherwise, it might be difficult to fully re-suspend the particles or beads or they could clog a passage, thereby preventing or interfering with the movement of substances between chambers. Additionally, oil can be used to increase the fluid volume of a chamber that otherwise has an insufficient amount of a process material to fully or adequately open a barrier in an adjoining passage when pressure is applied to the chamber. And, because oil is inert, it will not affect the relative concentrations of combined process materials. Another benefit of oil is that it interferes with the evaporation of liquid substances from the chambers. For receptacles including rigid portions, substances may be provided to cavities formed in the rigid portions by such means as spraying, spotting or otherwise bonding or adhering substances to surfaces of the cavities, or by pouring or pipetting. Alternatively, process materials are provided to the receptacles, in whole or in part, through resealable openings, such as Luer connections, septums or valves. In this latter embodiment, substances may be added to receptacles while procedures are in progress.

All substances, except sample material, are preferably provided to the receptacle and sealed to the environment prior to shipping for use. By doing so, processes carried out with the receptacles are easier to perform, opportunities for operator error are minimized, and there is less risk that a receptacle or associated process materials will become contaminated. Substances loaded in advance must be provided in a form and kept under conditions such that the substances remain stable prior to use. Among other things, this means that the materials used to construct a chamber cannot adversely affect a loaded substance, thereby altering its intended function or performance. Likewise, a loaded substance should not substantially affect the function or performance of the chamber it is stored in.

Types of sample materials that can be tested with the receptacles of the present invention include both fluid and solid samples. Fluid samples that may be tested with the receptacles include, for example, urine, blood, saliva, mucus, seminal fluid, amniotic fluid, cerebrospinal fluid, synovial fluid, cultures, liquid chemicals, condensed gases and water. Solid samples that can be tested with the receptacles include, for example, tissues, stool, soil, plants, powders, crystals, food and filters. Sample materials may be provided to the receptacles in a raw or processed form. A processed sample is one that has been modified in any manner, such as by removing components of a raw sample or by otherwise altering the material from its original state. For example, with a solid sample, it may be necessary to alter the sample either prior to or after adding the solid material to a sample chamber so that an analyte of interest is free to move between chambers of the receptacle. In an altered state, the solid sample may form part of, for example, a suspension, slurry or homogenate or it may be a liquefied or dissolved form of the solid sample.

Sample materials are preferably introduced into one or more sample chambers of a receptacle through an inlet port immediately prior to initiating a process, although some of the steps of a process may be initiated or completed prior to adding sample material to the receptacle. The inlet port may be an access opening or it may include, for example, the female portion of a Luer connection for insertion of a syringe or other having a male Luer connection. If the sample material is stable in the receptacle, then the sample material may not need to be added to the receptacle immediately prior to use. For automated uses of the receptacles, it is generally preferable to load sample material into the sample chamber or chambers of a receptacle manually or in a separate loading device. If sample material is directly loaded into receptacles being held by an associated instrument, there is an increased chance of carry-over contamination between receptacles that could lead to a false positive or altered result. One such loading device that can be used or adapted for use with flexible receptacles of the present invention is the FastPack® Sample Dispenser (Qualigen, Inc., Carlsbad, Calif.). For some applications, a relatively large volume of sample material may be required to ensure that there is a detectable amount of an analyte, if present in the sample. Receptacles of the present invention can be designed to include sample chambers that are larger than subsequent chambers that are employed to process a sample. Using manually or automatically activated pressure means, aliquots of a sample can be sequentially treated in a neighboring chamber or chambers to remove unwanted components of the sample and to reduce the volume or size of the sample being moved between chambers. The unwanted components can be transferred to a designated waste chamber in the receptacle. Separating an analyte from other components of a sample will generally involve immobilizing the analyte within a chamber, removing unbound material, and further purifying the immobilized analyte by washing it one or more times with a wash reagent.

Instruments for Manipulating the Contents of the Receptacles

Receptacles of the present invention are preferably adapted for use with an automated instrument capable of acting on all or a portion of the chambers of a receptacle to affect the location or state of substances contained therein. Such actions may include moving substances between or within chambers, opening and closing interconnections between chambers, reinforcing barriers between chambers, localized or generalized heating or cooling, and screening for one or multiple signals or other physical, chemical, biochemical or biological events that may be indicative of, for example, the presence, amount or state of one or more analytes of interest. Other effects of such actions may be to mix, combine, dissolve, reconstitute, suspend, isolate, wash or rinse substances of a process, to manipulate dried or solid substances, to remove waste substances, and/or to reduce the volume of a substance, such as a sample substance, to facilitate processing in a receptacle. The instrument may be used to process substances in a single receptacle or it may be adapted to process substances in multiple receptacles independently and in any desired order, including simultaneously (i.e., parallel processing). The instrument, alone or as part of an overall system, preferably has the capability of collecting, analyzing, and/or presenting data during and/or after a process has been performed. All or a portion of the actions of the instrument are governed by a controller.

The instrument is designed to cooperate with a receptacle to move substances between and/or within chambers. Substances may be moved in a receptacle by applying an external pressing force or forces to a flexible surface or surfaces of a chamber, such as by the use of linear actuators or rollers, or by applying an internal pressing force, such as by the use of pistons contained in piston chambers that are in air and/or fluid communication with the contents of selected chambers. Alternatively, a vacuum may be created to draw substances between chambers or to different regions of a chamber. Magnetic fields may be used to direct the movement of magnetized substances within and between chambers, as well as substances associated therewith. Other means for moving substances between or within chambers may include centrifugal forces, gravitational forces, electrical forces, capillarity, convection, sonication, irradiation and the like. In a particularly preferred embodiment, one or a combination of actuator pads are used to press substances into adjacent chambers or to move substances within chambers. The use of a combination of actuators can facilitate serial movement of substances into adjacent chambers or the mixing of substances within a chamber.

In a preferred mode, burstable heat seals interrupt connecting passages between at least a portion of the adjacent chambers of a receptacle and provide a barrier against the movement of substances between chambers. Actuator-driven compression pads of a cooperating instrument may be used to apply pressure to the chambers, thereby peeling the seals apart (e.g., bursting) and allowing some or all of the substances of the chambers to pass into adjacent chambers. Where an opened seal allows for a bidirectional flow of substances, it may be desirable to use at least one actuator as a clamping device to prevent a backflow of substances. The actuators can also be used as clamps to prevent seals from prematurely opening. As an example, a chamber may be directly connected to multiple other chambers. To focus the flow of a substance into a desired chamber, those chambers that are not being utilized are sealed-off by using the actuators as clamps to reinforce sealed interconnections with the undesired chambers. Actuators may also be used to control the flow of substances when no seals are provided.

Substances in a chamber, or in multiple chambers, can be mixed in an instrument by various active and passive means. "Active" methods of mixing substances involve the application of a mechanical force, such as a pressing force, whereas "passive" methods of mixing substances do not involve the application of a mechanical force, such as by gravitation. In one method, substances are mixed by force of flow as a substance of one chamber is moved into and contacts a substance of a second chamber. By another method, substances are mixed by turbulence when one of the substances is forced through the restricted space of a passage joining two chambers. Alternatively, the substances of two chambers can be mixed by forcing the combined substances back-and-forth between the two chambers. Yet another method of mixing involves the use of multiple actuators adjacent a chamber to force combined substances between different regions of a chamber. In one application of this embodiment, the actuator is a movable optical element of a light detecting device (e.g., fluorometer) that is in sliding engagement with a corresponding ring member, where the optical element and the ring member generally conform to the shape of an associated chamber and move into engagement with the chamber in an alternating fashion to achieve mixing. In another approach, mixing is carried out by forcing a first substance upward from a first chamber into a second chamber, where it is combined with a second substance, and then allowing for gravity assisted movement of the combined substances back into the first chamber. This procedure can be repeated until the desired degree of mixing is achieved. Other procedures for mixing may involve, for example, heating and/or cooling to produce convection mixing or sonication, with or without solid particles.

The instrument and receptacle can also cooperate to manipulate components of a substance. For example, one or more chambers of the receptacle may include a filter, or series of filters, for removing constituents of a substance as the instrument actively or passively causes the substance to pass through the filter. The constituents removed from a substance may include components of a sample material that can interfere with a process or solid supports that are used for processing a sample material, such as beads, particles, rods, fibers and the like. These solid supports may be used, for example, to bind an analyte, either directly or indirectly, or components of a sample. In another approach, the instrument may be adapted to cause solid supports or solid substances in a material to be concentrated in a chamber by imposing a centrifugal force on the receptacle. In an alternative approach, magnetically responsive particles present in a chamber can be manipulated by magnetic forces exerted by a component of the instrument. By isolating the magnetic particles in a specific chamber, substances bound to the particles remain in the chamber while unbound substances can be removed from the chamber. In addition to separating wanted from unwanted materials, solid supports, such as beads and particles, can also be used in the receptacles of the present invention to facilitate a reduction in the volume of a sample material. The initial volume of the sample material may be relatively large to ensure that there is an adequate quantity of the analyte of interest for detection and/or quantification. However, in some cases this initial volume is too large for practical processing of the sample material in the receptacle. Instruments and receptacles in accordance with the present invention can address this problem by immobilizing the analyte on a solid support (e.g., magnetically-responsive particle) in, for example, a sample receiving chamber, isolating the solid support within the chamber (e.g., exposing the particles to a magnetic field), and then generating forces that remove the remainder of the sample material from the sample receiving chamber and dispose of it in a designated waste chamber. Alternatively, this same procedure can be performed in an adjoining chamber of a receptacle having a smaller volume capacity than the sample receiving chamber by incrementally moving, isolating and separately processing aliquots of a sample material. By having or moving the solid support into a smaller chamber, processing of the sample material may be more efficient and the consumption of process materials lower.

To purify an analyte, the solid support can be washed one or more times with a wash reagent in a designated sample processing chamber. When performing a wash procedure, a force or forces may be imposed by the instrument which cause the solid support to remain isolated or otherwise concentrated in the sample processing chamber or which cause it to be resuspended in the wash reagent. Resuspending the solid support in the wash reagent may be accompanied by mixing, such as by agitating the receptacle, a turbulent movement of wash reagent from the wash reagent chamber into the sample processing chamber, or the use of pressing forces to mix the contents of the sample processing chamber. After an appropriate dwell time, the solid support can again be isolated or otherwise concentrated and the wash reagent moved from the sample processing chamber into a waste chamber. This process can be repeated as needed.

The instrument may include elements for controlling the thermal conditions of one or more chambers or for providing a uniform temperature within the instrument. Factors to be considered in selecting thermal control elements for use in performing a particular process include determining the desired temperature range, the rate of change of temperature, the accuracy, precision and stability of temperature, whether zonal heating and/or cooling or a uniform temperature is required, and the effect of external conditions, as well as heat-producing components of the instrument (e.g., motors), on temperature control capabilities. The heating and/or cooling of the chambers or subsets of chambers may be accomplished with thermal control elements that use, for example, electrical changes, radiation, microwaves, sonication, convection, conduction, forced air, chemical reactions (e.g., exothermic and endothermic reactions), biological activities (e.g., heat-generating growth), circulating fluids (e.g., heated water or freon), and the like to alter the thermal conditions of a chamber or chambers. Alternatively, the instrument may be placed in a temperature-controlled environment, such as an incubator or refrigerator, to maintain a uniform temperature.

A preferred instrument includes thermal conducting plates, such as copper or aluminum plates, that align with a collection of chambers, or a particular chamber or region of a chamber, when the receptacle is properly loaded in the instrument. The temperature of each plate can be controlled by, for example, the use of a thermoelectric device. Depending on the direction of current flow in a thermoelectric device, the junction of dissimilar conductors in the thermoelectric device will either absorb or release heat. Thus, thermoelectric devices can be used for the heating and/or cooling of chambers or regions of chambers. Other advantages of thermoelectric devices include their size, the absence of any moving parts or vibration, rapid temperature changes, precision temperature control, and no CFCs or moving fluids.

In practice, the thermal conducting plates are positioned in the instrument so that they will be in the general proximity of, and preferably contacting, the chambers or regions of chambers to be heated or cooled in a properly loaded receptacle. The plates are separated from each other using a non-conductive material, such as Ultem® polyimde thermoplastic resin or Delrin® acetyl resin. Using the thermoelectric devices, heat is transferred by conduction, convection or radiation.

In an alternative embodiment, all or a portion of the thermal control elements may be associated with actuators which provide localized heating or cooling of chambers.

The instrument preferably includes at least one detector for detecting a signal or other physical, chemical, biochemical or biological event. The detector may be used to detect whether an analyte or multiple analytes are present in a sample material, or present in an altered state. The detector, in cooperation with a microprocessor, may also provide information about the quantity of an analyte or analytes present in a sample material. Detectors contemplated by the present invention include fluorometers, luminometers, spectrophotometers, infrared detectors and charged-coupled devices. Each of these types of detectors, or signal receiving components associated with these detectors, can be positioned adjacent a detection chamber for detecting a wide variety of signal types. A detector may be mounted on a movable platform so that the detector can be positioned adjacent different chambers of a stationary receptacle. Alternatively, multiple types of detectors may be movably mounted on a platform to facilitate different detection methods for different processes. The instrument may also include multiple detectors of the same or different types for detecting signals emitted from different chambers simultaneously. Fiber optics may also be used to collect signals from different locations and transmit this information to a detector or detectors at stationary sites removed from the receptacle. Also contemplated is a fiber optic arrangement in combination with a movable detector. Other possible detectors might be used to detect, for example, radioactive, magnetic or electronic labels, Raman scattering, Surface Plasmon Resonance, gas, turbidity, or a mass, density, temperature, electronic or color change.

Uses of the Receptacles

The receptacles of the present invention can be used, alone or in combination with a cooperating instrument, to perform a variety of processes. Such processes may include, for example, separating or isolating an analyte of interest from other components of a sample, exposing a sample or component of a sample to reagents and conditions needed to analyze the sample, and/or performing a chemical, biochemical or biological reaction which effects a detectable change, such as a change in composition, sequence, volume, quantity, mass, conductivity, turbidity, color, temperature or the like. As discussed above, the receptacles are particularly suited for use in applications requiring or benefiting from actions that are performed non-sequentially. These types of applications include, but are not limited to, complex tests or assays involving detectable binding interactions such as antigen-antibody, nucleic acid-nucleic acid, and receptor-ligand interactions.

Nucleic acid based assays that can be performed in the receptacles of the present invention may rely upon direct detection of a target nucleic acid or detection of an amplification product indicative of the presence of the target nucleic acid in a sample. Direct detection requires that there be a sufficient quantity of the target nucleic acid in a sample to sensitively determine the presence of a target sequence associated with, for example, gene expression, a chromosomal abnormality or a pathogenic organism. Because of the large cellular quantities of ribosomal RNA (rRNA) in non-viral organisms, and the sequence conservation that enables phylogenetically coherent groupings of organisms to be distinguished from each other, rRNA is an ideal target for a direct detection assay designed to determine the presence of a pathogenic organism (e.g., bacterium, fungus or yeast). See, e.g., Kohne, "Method for Detecting, Identifying, and Quantitating Organisms and Viruses," U.S. Pat. No. 5,288,611; and Hogan et al., "Nucleic Acid Probes for Detection and/or Quantitation of Non-Viral Organisms," U.S. Pat. No. 5,840,488. Regardless of the type of nucleic acid being targeted, the sensitivity of a direct detection assay can be improved by a signal amplification procedure in which a probe or probe complex binding to a target nucleic acid has multiple labels for detection, thereby increasing the signal of an assay without affecting the amount of target in the sample. See, e.g., Hogan et al., "Branched Nucleic Acids," U.S. Pat. No. 5,424,413; and Urdea et al., "Nucleic Acid Multimers and Amplified Nucleic Acid Hybridization Assays Using the Same," U.S. Pat. No. 5,124,246. Another form of amplification that does not require increasing the copy number of a target nucleic acid sequence is probe amplification, which includes procedures such as the Ligase Chain Reaction (LCR). LCR relies upon repeated cycles of probe hybridization and ligation to generate multiple copies of a nucleic acid sequence.

See, e.g., Birkenmeyer et al., "Amplification of Target Nucleic Acid Using Gap Filling Ligase Chain Reaction," U.S. Pat. No. 5,427,930. Other contemplated signal amplification procedures include those utilizing Third Wave Technology's Invader® chemistry. See, e.g., Kwiatkowski et al., "Clinical, Genetic, and Pharmacogenetic Applications of the Invader Assay," Mol. Diagn. (1999) 4(4):353-64.

Target nucleic acid amplification involves the use of amplification oligonucleotides (e.g., primers) and polymerases to enzymatically synthesize nucleic acid amplification products (copies) containing a sequence that is either complementary or homologous to the template nucleic acid sequence being amplified. The amplification products may be either extension products or transcripts generated in a transcription-based amplification procedure. The amplification oligonucleotides may be provided to a reaction mixture free in solution or one or more of the amplification oligonucleotides may be immobilized on a solid support, including the inner surface of a chamber or chambers within a receptacle. See, e.g., Adams et al., "Method for Performing Amplification of Nucleic Acid with Two Primers Bound to a Single Solid Support," U.S. Pat. No. 5,641,658; and Browne, "Nucleic Acid Amplification and Detection Method," U.S. Patent Application Publication No. US 2005-0287591 A1. Examples of nucleic acid amplification procedures practiced in the art include the polymerase chain reaction (PCR), strand displacement amplification (SDA), helicase dependent amplification (HDA), loop-mediated isothermal amplification (LAMP), and a variety of transcription-based amplification procedures, including transcription-mediated amplification (TMA), nucleic acid sequence based amplification (NASBA), and self-sustained sequence replication (3SR). See, e.g., Mullis, "Process for Amplifying, Detecting, and/or Cloning Nucleic Acid Sequences," U.S. Pat. No. 4,683,195; Walker, "Strand Displacement Amplification," U.S. Pat. No. 5,455,166; Kong et al., "Helicase Dependent Amplification of Nucleic Acids," U.S. Pat. No. 7,282,328, Notomi et al., "Process for Synthesizing Nucleic Acid," U.S. Pat. No. 6,410,278; Kacian et al., "Nucleic Acid Sequence Amplification Methods," U.S. Pat. No. 5,399,491; Becker et al., Single-Primer Nucleic Acid Amplification Methods," U.S. Pat. No. 7,374,885; Malek et al., "Enhanced Nucleic Acid Amplification Process," U.S. Pat. No. 5,130,238; and Lizardi et al. (1988) BioTechnology 6:1197. With some procedures, the formation of detectable amplification products depends on an initial antibody/antigen interaction. See, e.g., Cashman, "Blocked-Polymerase Polynucleotide Immunoassay Method and Kit," U.S. Pat. No. 5,849,478. Nucleic acid amplification is especially beneficial when the amount of analyte (e.g., targeted nucleic acid, antigen or antibody) present in a sample is very low. By amplifying a target sequence associated with the analyte and detecting the synthesized amplification product, the sensitivity of an assay can be vastly improved, since less analyte is needed at the beginning of the assay to ensure detection of the analyte.

The conditions of a target nucleic acid amplification reaction may be substantially isothermal or they may require periodic temperature changes, as with PCR thermal cycling. The instrument described supra may provide a constant or ambient temperature or it may be modified and programmed to fluctuate the overall temperature within the instrument or, alternatively, particular zones of the instrument which affect specific chambers of a receptacle. Target nucleic acid amplification reactions may be either "real-time" or "end-point" assays. A compact, lightweight, multi-channel fluorometer that is particularly suited for use in performing real-time assays in an instrument of the present invention is described below. Real-time amplification assays involve periodically determining the amount of targeted amplification products as the amplification reaction is taking place, thereby making it easier to provide quantitative information about an analyte (e.g. target nucleic acid) present in a sample, whereas end-point amplifications determine the amount of targeted amplification products after the amplification reaction has occurred, generally making them more useful for providing qualitative information about an analyte present in a sample. Algorithms for calculating the quantity of target nucleic acid or other analyte originally present in a sample based on signal information collected during or at the completion of an amplification reaction include those disclosed by Wittwer et al., "PCR Method for Nucleic Acid Quantification Utilizing Second or Third Order Rate Constants," U.S. Pat. No. 6,232,079; Sagner et al., "Method for the Efficiency-Corrected Real-Time Quantification of Nucleic Acids," U.S. Pat. No. 6,691,041; McMillan et al., "Methods for Quantitative Analysis of a Nucleic Acid Amplification Reaction," U.S. Pat. No. 6,911,327; Light et al., "Method for Determining the Amount of an Analyte in a Sample," U.S. Patent Application Publication No. US 2006-0276972 A1; Chismar et al., "Method and Algorithm for Quantifying Polynucleotides," U.S. Patent Application Publication No. US 2006-0292619 A1; and Ryder et al., "Methods for Determining Pre-Amplification Levels of a Nucleic Acid Target Sequence from Post-Amplification Levels of Product," U.S. Pat. No. 5,710,029. Also, to confirm that the amplification conditions and reagents were appropriate for amplification, it is generally desirable to provide an internal control sequence at the start of a nucleic acid amplification reaction. See, e.g., Wang et al., "Quantitation of Nucleic Acids Using the Polymerase Chain Reaction," U.S. Pat. No. 5,476,774.

Detection of a target nucleic acid may be in situ or in vitro. See, e.g., Gray et al., "Methods for Chromosome-Specific Staining," U.S. Pat. No. 5,447,841. For in vitro assays, it may be necessary to lyse or permeabilize cells to first release the targeted nucleic acid and make it available for hybridization with a detection probe. See, e.g., Clark et al., "Method for Extracting Nucleic Acids from a Wide Range of Organisms," U.S. Pat. No. 5,786,208. If the cells are lysed, the contents of the resulting lysate may include, in addition to nucleic acids, organelles, proteins (including enzymes such as proteases and nucleases), carbohydrates, and lipids, which may necessitate further purification of the nucleic acids. Additionally, for pathogenic organisms, chemical or thermal inactivation of the organisms may be desirable. The cells may be lysed or permeabilized prior to loading sample into a receptacle of the present invention, or a sample or other chamber of the receptacle may be pre-loaded with an agent for performing this function. Cells may be lysed or permeabilized by a variety of means well known to those skilled in the art, including by chemical, mechanical (e.g., sonication) and/or thermal means. One preferred lytic agent in described in the Examples section below.

Released nucleic acids can be isolated or separated in the receptacles from other sample components that may act as inhibitors which interfere with the detection and/or amplification of a target sequence. The presence of potentially interfering components will vary depending on the sample type and may include components of the cell lysate, such as nucleases that can digest the released and targeted nucleic acids. Some unwanted sample components may be separated from the target nucleic acid through precipitation or solid phase capture by providing to a chamber such materials as filters, beads, fibers, membranes, glass wool, filter paper, polymers or gels. Suitable filters include glass, fiberglass, nylon, nylon derivatives, cellulose, cellulose derivatives, and other polymers. Alternatively, a solid phase material may be used to capture sample components for lysing, such as cells, spores or microorganisms, where the components may be captured by physical retention (e.g., size exclusion, affinity retention, or chemical selection).

Various solid phase methods for capturing nucleic acids are known in the art and can be readily adapted for use in the receptacles of the present invention. These methods may be specific or non-specific for the targeted nucleic acid. One such method is Solid Phase Reversible Immobilization, which is based on the selective immobilization of nucleic acids onto magnetic microparticles having carboxyl group-coated surfaces. See Hawkins, "DNA Purification and Isolation Using Magnetic Particles," U.S. Pat. No. 5,705,628. In another method, magnetic particles having poly(dT) sequences derivatized thereon bind to capture probes having 5' poly(dA) tails and 3' target binding sequences. See, e.g., Weisburg et al., "Two-Step Hybridization and Capture of a Polynucleotide," U.S. Pat. No. 6,534,273. Yet another commonly used method binds nucleic acids to silica or glass particles in the presence of guanidinium thiocyanate, which is a known agent for lysing cells and inactivating nucleases. Still another approach is based on the ChargeSwitch® Technology, which is a magnetic bead-based technology that provides a switchable surface that is charge dependent on the surrounding buffer pH to facilitate nucleic acid purification (Invitrogen Corporation, Carlsbad, Calif.; Cat. No. CS12000). In low pH conditions, the ChargeSwitch® Magnetic Beads have a positive charge that binds the negatively charged nucleic acid backbone. Proteins and other contaminants that are not bound can be washed away. By raising the pH to 8.5, the charge on the surface is neutralized and the bound nucleic acids are eluted.

In another approach, capture probes that are capable of binding to the targeted nucleic acid (or to intermediate oligonucleotides that also bind to the targeted nucleic acids) are covalently or non-covalently attached to an inner surface of a designated sample processing chamber during manufacture of the receptacle. Attachment chemistries are well known to skilled artisans and include amine and carboxylic acid modified surfaces for covalent attachment of oligonucleotides and biotin-labeled oligonucleotides and avidin- or streptavidin-coated surfaces for non-covalent attachments. With this approach, targeted nucleic acids introduced into the sample processing chamber can be immobilized on the surface of the chamber and liquid and other unbound materials can be removed without having to immobilize or trap particles or beads. Following separation from other materials of the sample, the targeted nucleic acids may remain immobilized on the surface for amplification and detection or they may be first eluted from the capture probes. Alternatively, the capture probes could be immobilized on a porous solid support, such as a sponge, that is located in the sample processing chamber.

Capture probes suitable for use in the present invention may be specific or non-specific for the targeted nucleic acids. A specific capture probe will include a target binding region that is selected to bind to a target nucleic acid under a predetermined set of conditions and not to non-target nucleic acids which may be present in a sample. A non-specific capture probe does not discriminate between target and non-target nucleic acids under the conditions of use. Wobble capture probes are an example of a non-specific capture probe and may include at least one random or non-random poly(K) sequence, where "K" can represent a guanine, thymine or uracil base. See Becker et al., "Methods of Nonspecific Target Capture of Nucleic Acids," U.S. patent application Ser. No. 11/832,367, which enjoys common ownership herewith. In addition to hydrogen bonding with cytosine, its pyrimidine complement, guanine will also hydrogen bond with thymine and uracil. Each "K" may also represent a degenerate nucleoside such as inosine or nebularine, a universal base such as 3-nitropyrrole, 5-nitroindole or 4-methylindone, or a pyrimidine or purine base analog such as dP or dK. The poly(K) sequence of a wobble capture probe is of sufficient length to non-specifically bind the target nucleic acid, and is preferably 6 to 25 bases in length.

Formats for detecting a target nucleic acid or related amplification product can be divided into two basic categories: heterogeneous and homogeneous. Both of these detection formats can be adapted for use in the receptacles of the present invention. Heterogeneous assays include a step to separate bound from unbound probe, while no such physical separation step is used in homogeneous assays. Numerous heterogeneous and homogeneous detection methods are known in the art. See, e.g., Jung, P. et al. 1997. "Labels and Detection Formats in Amplification Assays." In Nucleic Acid Amplification Technologies, eds. Lee, H. et al., 135-150. Natick, Mass.: BioTechnique Books.

Assay methods utilizing a physical separation step include methods employing a solid-phase matrix, such as glass, minerals or polymeric materials, in the separation process. The separation may involve preferentially binding the probe:analyte complex to the solid phase matrix, while allowing the unassociated probe molecules to remain in a liquid phase. Such binding may be non-specific, as, for example, in the case of hydroxyapatite, or specific, for example, through sequence-specific interaction of the target nucleic acid with a capture probe that is directly or indirectly immobilized on the solid support. In any such case, the amount of probe remaining bound to the solid phase support after a washing step is proportional to the amount of analyte in the sample.

Alternatively, the assay may involve preferentially binding the unhybridized probe while probe:analyte complexes remain in the liquid phase. In this case the amount of probe in the liquid phase after a washing step is proportional to the amount of analyte in the original sample. When the probe is a nucleic acid or oligonucleotide, the solid support can include, without limitation, an adsorbent such as hydroxyapatite, a polycationic moiety, a hydrophobic or "reverse phase" material, an ion-exchange matrix, such as DEAE, a gel filtration matrix, or a combination of one or more of these solid phase materials. The solid support may contain one or more oligonucleotides, or other specific binding moiety, to capture, directly or indirectly, probe, target, or both. In the case of media, such as gel filtration, polyacrylamide gel or agarose gel, the separation is not due to binding of the oligonucleotide but is caused by molecular sieving of differently sized or shaped molecules. In the latter two cases, separation may be driven electrophoretically by application of an electrical current through the gel causing the differential migration through the gel of nucleic acids of different sizes or shapes, such as double-stranded and single-stranded nucleic acids.

A heterogeneous assay method may also involve binding the probe to a solid-phase matrix prior to addition of a sample suspected of containing the analyte of interest. The sample can be contacted with the label under conditions that would cause the desired nucleic acid to be labeled, if present in the sample mixture. The solid phase matrix may be derivatized or activated so that a covalent bond is formed between the probe and the matrix. Alternatively, the probe may be bound to the matrix through strong non-covalent interactions, including, without limitation, the following interactions: ionic, hydrophobic, reverse-phase, immunobinding, chelating, and enzyme-substrate. After the matrix-bound probe is exposed to the labeled nucleic acid under conditions allowing the formation of a hybrid, the separation step is accomplished by washing the solid-phase matrix free of any unbound, labeled analyte. Conversely, the analyte can be bound to the solid phase matrix and contacted with labeled probe, with the excess free probe washed from the matrix before detection of the label.

As noted above, homogenous assays take place in solution, without a solid phase separation step, and commonly exploit chemical differences between free probe and probe:analyte complexes. An example of an assay system that can be used in a homogenous or heterogeneous format is the hybridization protection assay (HPA). See Arnold et al., "Homogenous Protection Assay," U.S. Pat. No. 5,283,174. In HPA, a probe is linked to a chemiluminescent moiety, contacted with a sample and then subjected to selective chemical degradation or a detectable change in stability under conditions which alter the chemiluminescent reagent linked to unhybridized probe without altering the chemiluminescent reagent linked to a probe:analyte complex. Subsequent initiation of a chemiluminescent reaction causes the hybrid-associated label to emit light.

Other homogeneous assays rely upon a physical alteration to a detection probe or amplification primer to provide a detectable signal change indicative of the presence of a target nucleic acid. Probes and primers capable of undergoing detectable physical alterations include, but are not limited to, self-hybridizing probes, such as molecular beacons or molecular torches, bi-molecular probes, TaqMan® probes that are commercially available from Applied Biosystems, Lux™ primers that are commercially available from Invitrogen Corporation, and signal primers. See, e.g., Tyagi et al. (1996) Nature Biotechnology 14(3):303-308; Becker et al., "Molecular Torches," U.S. Pat. No. 6,849,412; Morrison, "Competitive Homogeneous Assay," U.S. Pat. No. 5,928,862; Tapp et al. (2000) BioTechniques 28(4):732-738; Nazarenko (2006) Methods Mol. Biol. 335:95-114; and Nazarenko (1997) Nucleic Acids Res. 25(12):2516-2521. Each of these probes and primers relies upon a conformational change in the probe or primer upon hybridization to a target nucleic acid to render a detectable change in an associated reporter moiety (e.g., fluorescent molecule). Prior to hybridization, signal from the reporter moiety may be altered by an associated quencher moiety which, in the case of Lux™ primers, is a guinine located near the 3' end of the primer sequence.

Particularly preferred detection probes for use in real-time amplification reactions are self-hybridizing probes that emit differentially detectable signals, depending on whether the probes remain self-hybridized or bind to amplification products. The probes may be provided to a reaction mixture free in solution or immobilized on solid supports. See, e.g., Cass et al., "Immobilized Nucleic Acid Hybridization Reagent and Method," U.S. Pat. No. 6,312,906. Advantageously, they may also be provided to a reaction mixture before, after or at the time an amplification reaction has been initiated. If the probes are provided on a solid support, then the solid support may additionally include one or more immobilized amplification oligonucleotides for amplifying a target nucleic acid sequence. Preferred self-hybridizing probes include molecular beacons and molecular torches.

Molecular beacons comprise nucleic acid molecules or analogs thereof having a target complementary sequence, an affinity pair (or nucleic acid or nucleic acid analog arms or stems) holding the probe in a closed conformation in the absence of a target nucleic acid sequence, and a label pair that interacts when the probe is in a closed conformation. See Tyagi et al., "Detectably Labeled Dual Conformation Oligonucleotide Probes, Assays and Kits," U.S. Pat. No. 5,925,517. Hybridization of the target nucleic acid and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS).

Molecular torches have distinct regions of self-complementarity, described as the "target binding" and "target closing" domains. These domains are linked by a joining region and are sufficiently complementary to hybridize to each other under predetermined hybridization assay conditions. When exposed to denaturing conditions, the complementary regions melt, leaving the target binding domain available for hybridization to a target sequence when the predetermined hybridization assay conditions are restored. And when exposed to strand displacement conditions, a portion of the target sequence binds to the target binding domain, thereby displacing the target closing domain from the target binding domain. Molecular torches are designed so that the target binding domain favors hybridization to the target sequence over the target closing domain. The target binding domain and the target closing domain of a molecular torch include interacting labels positioned so that a different signal is produced when the molecular torch is self-hybridized than when it is hybridized to a target nucleic acid, thereby permitting detection of probe:target complexes in a test sample in the presence of unhybridized probe having a viable label or labels associated therewith.

Different types of interacting moieties can be used to determine whether a probe has undergone a conformational change. For example, the interacting moieties may be a luminescent/quencher pair, a luminescent/adduct pair, a Förrester energy transfer pair or a dye dimer. More than one type of label may be present on a particular molecule.

A luminescent/quencher pair is made up of one or more luminescent moieties, such as chemiluminescent or fluorescent moieties, and one or more quenchers. Preferably, a fluorescent/quencher pair is used to detect a probe that has undergone a conformational change. A fluorescent moiety absorbs light of a particular wavelength, or wavelength range, and emits light with a particular emission wavelength, or wavelength range. A quencher moiety dampens, partially or completely, signal emitted from an excited fluorescent moiety. Quencher moieties can dampen signal production from different fluorophores. For example, DABCLY ([4-(4'-dimethylaminophenylazo) benzoic acid]) can quench about 95% of the signal produced from EDANS (5-(2'-aminoethyl)aminoaphthaline-1-sulfonic acid), rhodamine and fluorescein.

Different numbers and types of fluorescent and quencher moieties can be used. For example, multiple fluorescent moieties can be used to increase signal production from an opened molecular beacon or torch, and multiple quencher moieties can be used to help ensure that, in the absence of a target sequence, an excited fluorescent molecule produces little or no signal. Examples of fluorophores include acridine, fluorescein, sulforhodamine 101, rhodamine, EDANS, Texas Red, Eosine, Bodipy and lucifer yellow. See, e.g., Tyagi et al. (1998) Nature Biotechnology 16:49-53. Examples of quenchers include DABCYL, Thallium, Cesium, and p-xylene-bis-pyridinium bromide.

A luminescent/adduct pair is made up of one or more luminescent moieties and one or more molecules able to form an adduct with the luminescent molecule(s) and, thereby, diminish signal production from the luminescent molecule(s). The use of adduct formation to alter signals from a luminescent molecule using ligands free in solution is disclosed by Becker et al., "Adduct Protection Assay," U.S. Pat. No. 5,731,148.

Förrester energy transfer pairs are made up of two moieties, where the emission spectra of a first moiety overlaps with the excitation spectra of a second moiety. The first moiety can be excited and emission characteristic of the second moiety can be measured to determine if the moieties are interacting. Examples of Förrester energy transfer pairs include pairs involving fluorescein and rhodamine; nitrobenz-2-oxa-1,3-diazole and rhodamine; fluorescein and tetramethylrhodamine; fluorescein and fluorescein; IAEDANS and fluorescein; and BODIPYFL and BIODIPYFL.

Dye dimers comprise two dyes that interact upon the formation of a dimer to produce a different signal than when the dyes are not in a dimer conformation. See, e.g., Packard et al. (1996) Proc. Natl. Acad. Sci. USA 93:11640-11645.

While homogeneous assays are generally preferred, essentially any labeling and detection system that can be used for monitoring specific nucleic acid hybridization can be used in conjunction with the receptacles of the present invention. Included among the collection of useful labels are radiolabels, intercalating dyes, enzymes, haptens, linked oligonucleotides, chemiluminescent molecules and redox-active moieties that are amenable to electronic detection methods. Preferred chemiluminescent molecules include acridinium esters of the type disclosed by Arnold et al. in "Homogeneous Protection Assay," U.S. Pat. No. 5,283,174 for use in connection with hybridization protection assays (HPA), and of the type disclosed by Woodhead et al. in "Detecting or Quantifying Multiple Analytes Using Labeling Techniques," U.S. Pat. No. 5,656,207 for use in connection with assays that quantify multiple targets in a single reaction. Preferred electronic labeling and detection approaches are disclosed by Meade et al., "Nucleic Acid Mediated Electron Transfer," U.S. Pat. Nos. 5,591,578, and Meade, "Detection of Analytes Using Reorganization Energy," U.S. Pat. No. 6,013,170. Redox active moieties useful as labels include transition metals such as Cd, Mg, Cu, Co, Pd, Zn, Fe and Ru.

Synthetic techniques and methods of bonding reporter moieties to nucleic acids and detecting reporter moieties are well known in the art. See, e.g., J. SAMBROOK ET AL., MOLECULAR CLONING: A LABORATORY MANUAL, Chapter 10 (2d ed. 1989); Becker et al., U.S. Pat. No. 6,361,945; Tyagi et al., U.S. Pat. No. 5,925,517, Tyagi et al., "Nucleic Acid Detection Probes Having Non-FRET Fluorescence Quenching and Kits and Assays Including Such Probes," U.S. Pat. No. 6,150,097; Nelson et al., U.S. Pat. No. 5,658,737; Woodhead et al., U.S. Pat. No. 5,656,207; Hogan et al., "Nucleic Acid Probes for Detection and/or Quantitation of Non-Viral Organisms," U.S. Pat. No. 5,547,842; Arnold et al., U.S. Pat. No. 5,283,174; Kourilsky et al., "Method of Detecting and Characterizing a Nucleic Acid or Reactant for the Application of this Method," U.S. Pat. No. 4,581,333; and Becker et al., U.S. Pat. No. 5,731,148.

Process materials may be provided to the chambers of a receptacle in a dried or liquid form. Providing process materials in a dried form can be especially beneficial where the process materials are, in their liquid form, unstable, biologically or chemically active, temperature sensitive or chemically reactive with each other. Drying inhibits the activity of microorganisms and enzymes and can improve the shelf-life and storage conditions of process materials (room temperature as opposed to cold storage). Dried process materials, in addition to their reactive components, may include a cryoprotectant (e.g., disaccharides such as sucrose, maltose, lactose or trehalose) to help preserve the biological activity of a material as it is being frozen, dried and/or reconstituted and a stabilizing agent (e.g., various sugars including sucrose and trehalose, sugar alcohols and proteins) to prevent or delay the loss of a material s biological activity over time. The suitability of any given cryoprotectant or stabilizing agent will depend on the nature of the material being dried. After drying, the process materials should be sealed to prevent reabsorption of moisture. Methods and devices for drying process materials are well known in the art and include lyophilization or freeze-drying. See, e.g., Price et al., "Pelletized Pregnancy Test Reagents," U.S. Pat. No. 3,862,302; Temple et al, "Process for Freezing or Chilling," U.S. Pat. No. 4,655,047; Milankov et al., "Cryogenic Apparatus," U.S. Pat. No. 4,982,577; Shen et al., "Stabilized Enzyme Compositions for Nucleic Acid Amplification," U.S. Pat. No. 5,834,254; Buhl et al., "Dried Chemical Compositions," U.S. Pat. No. 6,251,684; and McMillan, "Universal and Target Specific Reagent Beads for Nucleic Acid Amplification," U.S. Patent Application Publication No. US 2006-0068398 A1.

Illustrative Embodiments

An exemplary embodiment of a multi-chambered receptacle embodying aspects of the invention is designated by reference number 10 in FIG. 1A. In this embodiment, the receptacle 10 is a generally planar vessel having flexible top and bottom sheets formed from thin flexible materials, such as foils and/or plastics, and an upper edge 12 and a lower edge 14 that indicate the preferred orientation of the receptacle during use and define an upper direction and a lower direction. The exemplary receptacle 10 has dimensions of about 7.5 inches by about 3.2 inches and is less than about ¼ inch thick (when filled with sample and process materials), but may be of any dimensions suitable for manual manipulation or for use with an automated system, such as the one described herein. In general, the dimensions of the receptacle must accommodate the substances needed to conduct a process or set of processes. Persons of skill will recognize that a wide variety of sizes, conformations, shapes, and the like are compatible with various processes and are contemplated for use.

The receptacle may include one or more attachment or alignment holes 74 that register with structures, such as hooks or pins, of an automated instrument for mounting and/or alignment of the receptacle with respect to the instrument. One or more labels for identification of the sample, patient or any other information of interest, including test conditions and parameters optionally may be provided on a receptacle surface or embedded in material used to construct the receptacle. Such labels can include indicia that are human readable, machine readable (e.g., barcodes), Optical Character Recognition (OCR), Radio Frequency Identification (RFID), or some combination thereof. Referring to FIG. 1A, receptacle 10 comprises a number of chambers that form part of an integrated system, where the chambers collectively define a plurality of non-linear pathways punctuated with selectively openable connections. Inlet port 52 and neck portion 51 serve as a channel for receiving a sample or other material for processing, testing or subjecting to reactants and may have any suitable configuration for admission of the sample or other material. Sample material may be transferred to the receptacle 10 by any suitable means, for example, by using a syringe with needle that punctures the inlet port 52. The inlet port 52 alternatively may comprise the female portion of a Luer connection for insertion of a syringe or other container having a male Luer connection or an unsealed opening in the top of the receptacle through which the sample material may be poured, pipetted or otherwise inserted. The inlet port 52 is preferably located at or near the upper edge 12 of the receptacle 10 to reduce the potential for spillage of sample material upon its transfer or prior to placement of the receptacle into an automated instrument. However, the inlet port 52 may be located at any edge of the receptacle 10 or located more centrally, as is convenient, for example as a slot or other opening, which optionally is reversibly sealed. For example, the inlet port may be closed by heat sealing the opposed sheets of the receptacle 10 after admission of sample material.

The integrated chamber system of the illustrated receptacle 10 includes eleven chambers C16, C18, C20, C22, C24, C26, C28, C30, C32, C34 and C36. The chambers are generally enclosed compartments that may be connected (selectively, temporarily, or permanently) with one or more adjacent chambers so as to permit substances to flow between at least a portion of the adjacent chambers, as well as between various chambers of the integrated system. Each chamber may contain a substance used to perform a process within the receptacle 10 such as, for example, sample material, sample processing reagents for preparing a sample material for further analysis, reactants, solvents, diluents, wash reagents and the like. Furthermore, chambers may function, either through manual manipulation or in cooperation with various elements of an instrument, as the locus for performing one or more process steps, such as an analyte purification procedure, mixing, heating/cooling, detection of a signal or visual characteristic (e.g. color change), waste storage and removal, etc. Some chambers may be pre-loaded with substances, e.g., sample, reaction reagents, buffers, etc., when the receptacle 10 is placed in an instrument and other chambers may be initially empty, but one or more substances may be moved into or through the initially-empty chamber when performing a process. Some chambers may not be used at all, depending on the requirements of the particular process being performed within the receptacle 10.

In an exemplary use of the receptacle 10, the chambers can be filled with substances needed to perform a binding reaction, such as an immunoassay or a nucleic acid-based reaction. In such an application of the receptacle 10, chamber C16 may be loaded with sample material, chamber C18 may be loaded with a sample processing reagent for binding and immobilizing an analyte present in the sample material on a solid support, chamber C26 may function as a sample processing chamber for separating the immobilized analyte from other components of the sample material, chamber C22 may be loaded with a dried, first process material, chamber C20 may be loaded with a reagent for reconstituting the first process material, chamber C28 may be loaded with a dried, second process material, chamber C30 may be loaded with a reagent for reconstituting the second process material, chamber C34 may be loaded with a wash reagent, and chamber C36 may function as a waste chamber into which waste substances are moved when performing a process and in which those waste substances are stored in relative isolation from other aspects of the process. In addition to containing the second process material, chamber C28 may also function as a detection chamber for detecting a signal or change in a reaction mixture that is indicative of the presence of the analyte in the sample material. In an alternative implementation of the receptacle 10, chamber C32 could contain a reagent for reconstituting a dried, second process material contained in chamber C30, which then could be used to reconstitute a dried, third process material contained in chamber C28. Alternatively, a dried, second process material could be loaded in chamber C30 and a reagent for reconstituting the second process material could be loaded in chamber C32, where reconstituted forms of the first and second process materials could be combined with the separated analyte in chamber C28.

Other non-limiting uses of the receptacle 10 will be described in the Examples section of the disclosure.

In the illustrated embodiment, chamber C34 is specially designed to contain a wash reagent and includes an upper portion 38, a lower neck 40, a vertical section 42, and a lateral section 44 extending toward chamber C26.

Also, in the illustrated embodiment of the receptacle 10, chamber C36 is advantageously configured to function as a waste chamber for receiving waste materials from chamber C26 and includes an initial vertical inlet 48 extending from chamber C26, an upper neck 46, and a collection region 50. Vertical inlet 48 is positioned above chamber C26 and is connected to chamber C26 by means of portal 70 positioned at the top of chamber C26. When an analyte separation procedure, such as a magnetic separation procedure, is performed in chamber C26, bubbles may be formed in or moved into chamber C26 by, for example, a detergent present in the reaction mixture (e.g., a detergent-based lytic agent provided to the sample or detergent present in a sample processing reagent).

As illustrated in FIG. 1A, the chambers of the receptacle 10 are interconnected as follows: chamber C18 is connected to chamber C16 by portal 54; chamber C16 is connected to chamber C26 by portal 62; chamber C20 is connected to chamber C22 by portal 56; chamber C22 is connected to chamber C26 by portal 58; chamber C24 is connected to chamber C26 by portal 60; chamber C32 is connected to chamber C30 by portal 68; chamber C30 is connected to chamber C28 by portal 66; chamber C28 is connected to chamber C26 by portal 64; chamber C34 is separately connected to chamber C26 by portal 72; and, as noted above, chamber C26 is connected to chamber C36 by portal 70. In some embodiments, one or more of portals 54, 56, 58, 60, 62, 64, 66, 68, 70, and 72 is temporarily closed to prevent fluid flow therethrough by an openable seal, such as a heat seal that peels open when pressure is applied to a connected chamber.

In the embodiment of FIG. 1A, chamber C16 of the receptacle 10 is configured to hold a suitable sample volume. Generally, the sample will be a fluid or fluidized sample, such as a fluid sample taken from a human or other animal, which may include blood or a blood product (i.e., plasma or serum), cerebral spinal fluid, a conjunctiva specimen, a respiratory specimen, a nasopharyngeal specimen, or a genitourinary tract specimen, or it may be, for example, an environmental, industrial, food, beverage or water sample. Solid or viscous sample materials (e.g., food, fecal matter and sputum) will generally need to be at least partially solubilized prior to adding the sample material to chamber C16 (although it is also possible to solubilize such sample materials directly in the receptacle as well). The sample material may be organic or inorganic, and it may be a material for processing or analysis or a reactant in a chemical, biochemical or biological reaction.

The volume capacity of chamber C16 is preferably from about 10 µL to about 1 mL, more preferably up to about 850 µL, and most preferably about 625 µL. This volume capacity is intended to accommodate the total volume of substance expected to be placed in chamber C16, which in the exemplary application described herein, includes a volume of sample material combined with the sample processing reagent from chamber C18. At the most preferred volume amounts, this would be a 500 µL sample combined with 125 µL of a sample processing reagent. At the low end of the expected volume range there needs to be enough fluid in the chamber C16 to force open the seal at portal 62 upon the application of external pressure to chamber C16. At the upper end of the expected volume range, the volume placed in chamber C16 cannot be so great that there is stretching of the receptacle and perhaps peeling or rupturing of a wall of the chamber.

Portal 54 connects chamber C18 to chamber C16 and is temporarily closed by a selectively openable seal. Upon application of sufficient compressive force to chamber C18 by a pressure application mechanism, an example of which is described below, the seal closing portal 54 is opened and the sample processing reagent is moved from chamber C18 to chamber C16, where it is mixed with the sample material provided to chamber C16. The sample processing reagent preferably includes a binding agent and a solid support, such as magnetically-responsive particles, for immobilizing the analyte.

The first process material is contained in chamber C22, and the reconstitution reagent for the first process material is contained in chamber C20. In one embodiment, the first process material is an amplification reagent. Dried or solid amplification reagents are preferred because they are more stable than liquid amplification reagents. Suitable carriers for the amplification reagent include any chemically inert or compatible material and may optionally include, for example, diluents, binding agents, lubricants, dissolution aids, preservatives and the like. In one embodiment, amplification reagents are frozen in a cryogenic fluid to form uniformly sized pellets, which are then lyophilized for use in unit dose applications. Solid forms of the amplification reagents can also be compressed into pellets or tablets, but may be in the form of powders, granules, or any other convenient and stable solid form. Dried amplification reagents are also preferred because there is less chance of an accidental rupture with dried reagents than with liquid reagents, and solid materials provide for very precise dosing of reagents.

If the first process material is an amplification reagent, then the amplification reagent may contain at least one amplification oligonucleotide, such as a primer, a promoter-primer, and/or a non-extendable promoter-provider oligonucleotide, nucleoside triphosphates, and cofactors, such as magnesium ions, in a suitable buffer. The specific components of the amplification reagent will depend on the amplification procedure to be practiced. An exemplary amplification reagent for performing a transcription-based amplification reaction is described in the examples portion of this disclosure.

In some embodiments, chamber C20 is left empty or is omitted altogether if the first process material is omitted or is provided in a fluid form in chamber C22. Alternatively, chamber C22 could be left empty and liquid loaded in chamber C20.

Upon application of a sufficient compressive force to chamber C20 by a pressure application mechanism, such as the one described below, the seal closing portal 56 is opened and the reconstitution reagent contained in chamber C20 is transferred to the first process material contained in chamber C22.

In embodiments in which the reconstitution reagent is not provided (e.g., chamber C20 is empty or omitted in the illustrated receptacle 10), the first process material may be a liquid or a solid that is pre-dissolved prior to loading in chamber C22. If the first process material is an amplification reagent, then the amplification oligonucleotides are preferably present in great excess. Appropriate amounts of these and other reagents can be determined by the skilled artisan and will depend on the assay parameters and the amount and type of target to be detected.

After the reconstitution reagent is transferred from chamber C20 to chamber C22, a pressure application mechanism applies an external pressure to chamber C22 that opens the seal closing portal 58 between chamber C22 and chamber C26, thereby causing a reconstituted form of the first process material to flow from chamber C22 to chamber C26. In some embodiments, the contents of chambers C20 and C22 are mixed, such as by moving the combined materials between chambers C20 and C22 several times, prior to transferring the reconstituted form of the first process material to chamber C26.

A rinse, if used, follows a wash step and is intended to remove substances present in the wash reagent that might interfere with processing of the analyte. The rinse reagent is contained in chamber C24 and preferably comprises an aqueous buffered solution containing detergent or functionally similar material. The rinse reagent could be a reconstituted form of the first process material (e.g., an amplification reagent without nucleoside triphosphates). Alternatively, the rinse reagent may be a buffer containing no detergents, no anionic detergents, a lower concentration of anionic detergents than the wash reagent, or a nonionic detergent to counteract the effect of an anionic detergent present in the wash reagent. The volume of rinse reagent contained in chamber C24 in preferred embodiments is from about 150 µL to about 500 µL. At the appropriate time, a pressure application mechanism applies pressure on chamber C24 and produces fluid pressure that opens the seal closing the portal 60 between chamber C24 and chamber C26, allowing the rinse reagent to flow from chamber C24 to chamber C26.

Chamber C30 contains a reagent for reconstituting the second process material. In preferred embodiments, the volume of the reconstitution reagent contained in chamber C30 is from about 20 to about 125 µL, and more preferably from about 25 to about 100 µL. If the receptacle is used to perform a nucleic acid-based amplification reaction, then the second process material may contain one or more enzymes, such as polymerases for effecting extension and/or transcription of a target sequence and, optionally, a probe that specifically and detectably binds to an amplification product containing the target sequence or its complement. Suitable carriers for solid enzyme and/or probe reagents include any chemically inert or compatible material and may optionally include, for example, diluents, binding agents, lubricants, dissolution aids, preservatives and the like. The enzyme and/or probe reagents can be frozen in a cryogenic fluid to form uniformly sized pellets, which are then lyophilized for use in unit dose applications. Solid forms of the enzyme and probe reagents can also be compressed into pellets or tablets with suitable carriers for ease of handling, but may be in the form of a powder, granules, or any convenient and stable solid form. The two solid compositions may be formulated as separate pellets or combined as a single solid form. Furthermore, a dried probe reagent may be loaded into a chamber, such as chamber C28, in, for example, pellet or granule form, or it may be sprayed, printed or otherwise applied to the walls of a chamber.

In reconstituting dried process materials, it was observed that the reconstitution reagents have a tendency to concentrate along the perimeters of the chambers (e.g., heat sealed regions defining the chamber walls), such that dried process materials that are more centrally located in the chambers either do not dissolve or do not fully dissolve. To overcome this problem, the inventors discovered that by providing a light oil, such as a mineral oil (e.g., silicon oil), with reconstitution reagents, they were able to direct the reconstitution reagents toward the centers of chambers, thus improving reconstitution of dried process materials. The oil was also found to have a "squeegee" effect, in which the oil essentially sweeps along the walls of a chamber, thereby causing all or substantially all of a substance to be moved into an adjacent chamber. This is particularly critical in unit dose applications that are sensitive to changes in the amounts or concentrations of process materials. Oil was also found to contribute to better mixing of substances by concentrating aqueous substances near the centers of chambers, which, in combination with the squeegee effect, ensures that more of the substances being mixed are transferred between chambers. An additional benefit of oil is its coating ability, which prevents or interferes with substances sticking to the surfaces of chambers. As an alternative to oil, other inert, immiscible liquids having similar advantages may be used.

It should be mentioned here that an advantage of the receptacle 10 embodying aspects of the present invention is the ability, due to the non-linear arrangement of the chambers, to reconstitute process materials in a non-sequential manner. That is, it is not necessary for the first process material to be fully reconstituted before reconstituting the second process material. The first process material can be reconstituted in chamber C22 and the second process material can be reconstituted in chamber C28 at any time that is required or convenient for performing a process, including simultaneously.

A pressure application mechanism physically presses upon chamber C30 to produce fluid pressure that opens the seal closing portal 66 between chamber C30 and chamber C28, allowing fluid flow between the chambers and transferring the reconstitution reagent from chamber C30 to chamber C28 to dissolve the second process material contained therein. If the process material contained in chamber C28 is already in a liquid form—for example, if the enzyme reagent and detection probe are prepared in a liquid form or are reconstituted prior to loading them into the receptacle—chamber C30 may be empty. For certain liquid process materials, it may be desirable to include a detergent, such as TRITON® X-100 (octylphenolpoly(ethyleneglycolether)$_n$), to prevent components of the process materials from sticking to the walls of the chamber. Furthermore, if the process materials provided in a liquid or reconstituted form are sensitive to electromagnetic radiation, then the chamber holding these process materials (e.g., chamber C28) may be constructed using light-shielding materials.

It is often desirable and necessary to effect a mixing between substances moved from one chamber into an adjacent chamber. For example, when moving a reconstitution reagent from chamber C30 into chamber C28 to reconstitute a dried process material contained in chamber C28, it is desirable to mix the reconstitution reagent and dried process material. In the illustrated embodiment, chamber C30 and chamber C28 are positioned and oriented with respect to each other to facilitate gravity assisted mixing of the combined contents of the two chambers. With gravity assisted mixing, a pressure mechanism is used to force a substance (e.g., reconstitution reagent) from a lower chamber (e.g., chamber C30) to an upper chamber (e.g., chamber C28). Gravity assisted mixing generally depends on at least one of the following mechanisms: (i) turbulence generated when a substance is forced through a relatively narrow passage connecting adjacently positioned upper and lower chambers (or upper and lower regions of a chamber connected by a restricted section), where the substances in both the upper and lower chambers (or sections of a chamber) contain liquids; (ii) movement of the combined liquids about the periphery of the upper chamber; and (iii) gravitational movement of the substance through the passage connecting the upper and lower chambers. One advantage of gravity assisted mixing is that a pressure mechanism does not have to be associated with the upper chamber (or upper region of a chamber).

Chamber C34 contains a wash reagent which is used to remove unwanted materials from the sample processing procedure performed in chamber C26. The volume of wash reagent contained in chamber C34 in preferred embodiments is from about 400 µL to about 5,000 µL and most preferably is from about 700 µL to about 2,000 µL. A pressure application mechanism presses selected portions of chamber C34, thereby producing a fluid pressure that opens the seal closing portal 72, and forces wash reagent into chamber C26, the sample processing chamber. As described above, chamber C34 includes an upper portion 38, a lower neck 40, a vertical section 42, and a lateral section 44 extending toward chamber C26. Due to the arrangement of chamber C34, it is believed that gravitational forces assist in moving the wash reagent from the upper portion 38 through the lower neck 40. In some embodiments, the instrument may include passive means, such as a sponge or other compressible body positioned adjacent upper portion 38, to apply a continuous and relatively mild pressure to the upper portion to further assist in forcing substance toward the lower neck 40. From the lower neck, pressure mechanisms, examples of which are described below, are used to force the wash reagent—usually a portion at a time—through the vertical and lateral sections 42, 44 and then through portal 72 into chamber C26. Another pressure mechanism, an example of which is described below, is positioned at lower neck 40 to function as a clamp for selectively stopping further movement of wash reagent.

Chamber C36, when used for waste collection, is empty prior to performing a procedure and is designed to contain the total waste material volume required by a procedure, including, for example, waste materials containing sample material, wash reagent, rinse reagent, and other expended process materials (e.g., reagents). In general, the preferred capacity for chamber C36 is about 2 mL when used as a waste chamber.

As explained above, portal 70 connects chamber C26 and chamber C36 and has an upper orientation relative to chamber C26. This orientation was discovered to be advantageous because bubbles which may be formed in chamber C26 during a separation procedure, possibly due to the presence of detergent-based solutions, will naturally tend to rise and accumulate adjacent to portal 70 near the top of chamber C26. Thus, bubble-containing waste materials are more easily and efficiently transferred to chamber C36 and, therefore, less likely to interfere with subsequent signal detection steps. The location of portal 70 adjacent the top of chamber C26 also helps to retain solid support particles in chamber C26 when waste material is removed during a sample processing procedure, especially one involving the use of magnetically-responsive particles. As discussed more fully below, during a preferred sample processing procedure, magnetically-responsive particles used to bind analyte are immobilized when a magnetic field is applied to the contents of chamber C26. Bubbles that form in chamber C26 during sample processing will tend to collect near the top of chamber C26 and will generally not come into contact with the more centrally located magnetically-responsive particles when the waste material is moved from chamber C26 to chamber C36. If the connection between a sample processing chamber and a waste chamber is other than at the top of sample processing chamber, then at least some bubbles will remain in the sample processing chamber when the waste materials are moved from the sample processing chamber to the waste chamber. Additionally, at least some of the bubbles that form will likely pass over the immobilized particles and could impart a force strong enough to dislodge some particles, thereby causing some of the particles to be transferred to the waste chamber with the waste materials. The sensitivity and repeatability of processes are thereby improved by the design of the chambers in the exemplified receptacle 10 because solid support particles are more likely to be retained in the designated sample processing chamber during a separation procedure.

In the illustrated embodiment employing receptacle 10, chamber C26 (the sample processing chamber) is connected to six chambers, including chamber C16 (the sample chamber), chamber C22 (a first process material chamber), chamber C24 (the rinse reagent chamber), chamber C28 (a second process material chamber), chamber C34 (the wash reagent chamber), and chamber C36 (the waste chamber). Prior to performing an assay or other process in the receptacle, chamber C26 can be empty.

When receptacle 10 is placed in an automated instrument (described below), chamber C26 is oriented so that a removable magnetic field can be applied to the area of chamber C26. In one embodiment, the magnetic field is applied by an actuator which moves a permanent magnet to a position adjacent to the chamber C26. Suitable magnets are those having a holding force of about 4.0 lbs. each, such as those available from Bunting Magnets Co. of Newton, Kans. as Catalog No. N50P250250. In a preferred aspect of this embodiment, the magnet is moved into position by a magnet actuation mechanism (described in more detail below) along the plane of the receptacle when the receptacle is placed into the automated instrument. The magnet may be moved from any direction relative to the receptacle. The magnet applies a magnetic field to chamber C26 and its contents of sufficient strength to retain magnetic particles in chamber C26 while the field is being applied. As will be appreciated by the person of ordinary skill in the art, when a permanent magnet is used, the magnet must be movable to a location sufficiently distant from chamber C26 to remove the effect of the magnetic field from the sample processing chamber, when desired. Thus, the magnet is located on a movable magnet actuation means which can be moved to at least two positions: (1) an "on" position in which the magnet is adjacent to chamber C26 and sufficiently close to apply a particle-retaining magnetic field to the chamber and its contents, and (2) an "off" position in which the magnet is positioned sufficiently distant from chamber C26 such that no magnetic field of substantial strength is applied to the chamber or its contents and any magnetic particles present in the chamber are not appreciably affected thereby.

Alternative means for applying the magnetic field to the desired location may include selective activation of an electromagnet, which is either located adjacent to chamber C26 during an assay or process by an automated instrument or which is moved into such position prior to activation. Still further means for selectively applying a magnetic field include a permanent magnet mounted on a platen that is movable transversely with respect to the plane of the receptacle 10 into and out of magnetically affecting proximity to chamber C26. Any suitable actuating mechanism can be used to move the platen, such as a threaded rod operatively coupled to a suitable motor, an electronic linear actuator, or a solenoid. Such magnetic separation means are known per se in the art and can easily be modified by the skilled artisan to any conformation or orientation of receptacle chambers.

As mentioned above, opening the seals blocking passages between chambers and then transferring substances between adjacently connected chambers can be effected by pressure application mechanisms. The pressure application mechanisms of the automated instrument deliver a physical force to the outside of the receptacle at select locations and, in particular, to the outside of individual chambers of the receptacle at predefined instances as governed by a computer controller. In the context of the present invention, the term pressure application mechanism refers to any means for delivering a physical pressing force to the external surface(s) of the receptacle. Preferably each pressure application mechanism comprises a compression pad with a receptacle-contacting surface. The compression pad is coupled to an actuator that moves the pad relative to the receptacle, generally perpendicularly with respect to the face of the receptacle, selectively into and out of pressing contact with the receptacle. Alternatively, roller bars or wheels may provide the physical force. The pressure application mechanisms may also have an additional function, such as to provide a thermal change to the area adjacent to the actuator. When an actuator comprises a compression pad, the pad can be made of any material suitable for exerting an appropriate force to the surface of the receptacle without damaging the receptacle. Typically, the compression pad applies a pressure to either side of the receptacle, while the opposite side of the receptacle, when in the automated instrument, is supported against a wall. Thus, application of external force by the compression pad of the pressure application mechanism pinches the receptacle at a selected location to compress the receptacle at that location and force fluid movement in a chamber and/or effect a temporary separation of one chamber from another (or one portion of a single chamber from another portion) by bringing the two sides of the receptacle into fluid sealing contact with each other. Alternatively, a pair of compression pads placed on opposing sides of the receptacle and both moveable toward and away from the receptacle can pinch the receptacle and its contents between them.

Figure 2:
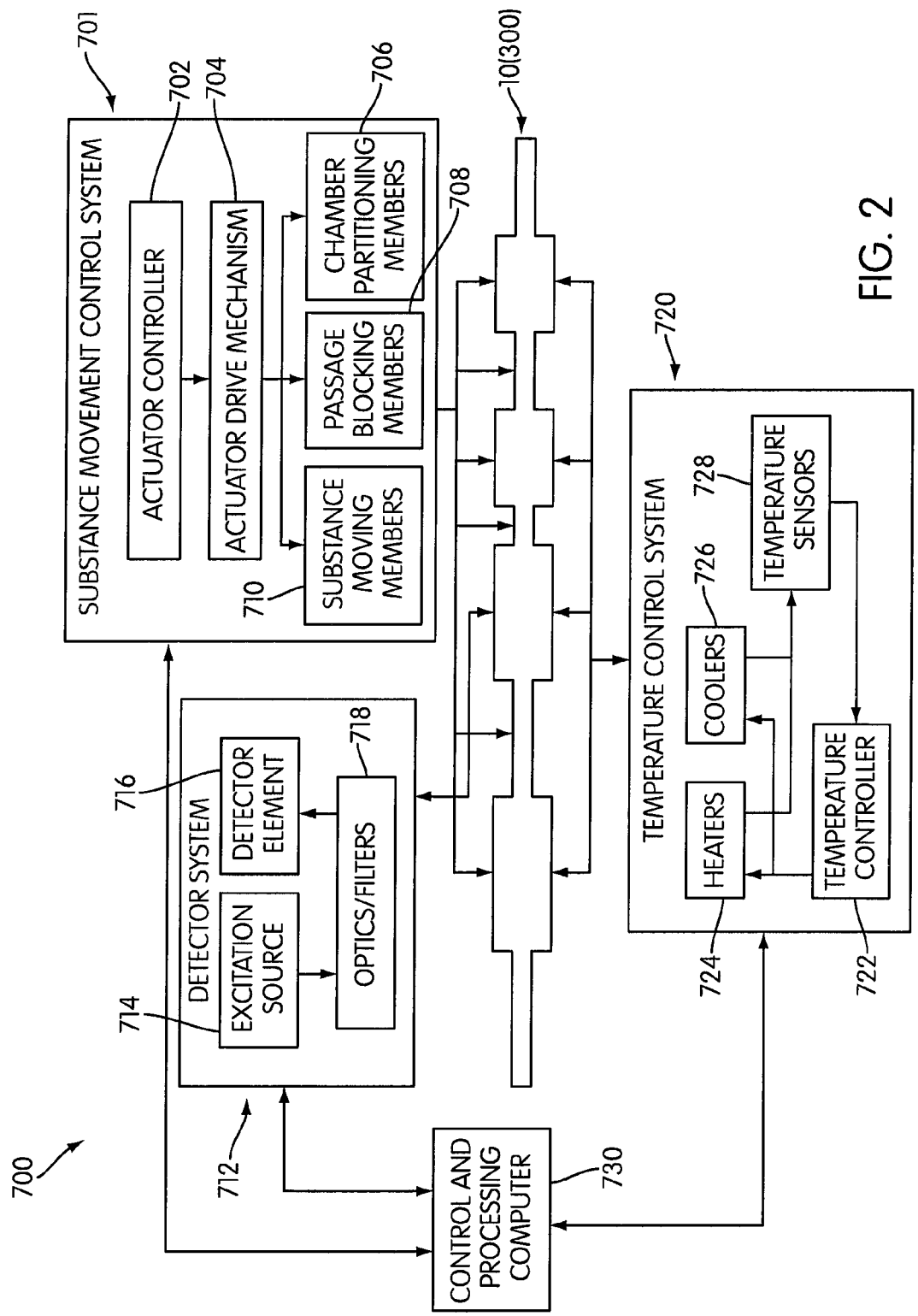
FIG. 2 is schematic block diagram of the functional architecture of a system embodying aspects of the present invention.

The functional architecture 700 of a system embodying aspects of the present invention is shown schematically in FIG. 2. The system operates on a reaction receptacle, or container, 10 (300, described below, See FIGS. 12A and 12B) which is schematically represented in FIG. 2 as a series of interconnected rectangles (i.e., chambers) as if the container were shown in a transverse cross-section. Operation of the system is controlled by a computer or other microprocessor, represented in FIG. 2 as the control and processing computer 730, which is programmed to control operation of the system and processing of data. The system shown is a schematic representation; overall system operation may be controlled by more than one computer. The control and processing computer 730 may reside within an instrument for processing the receptacle, or it may be a separate, stand-alone computer operably connected—e.g., by serial cable, by network connection, or wirelessly—to the instrument.

A first element of the system 700 is the substance movement control system 701. Substance movement control system 701 both causes and controls movements of substances from chamber to chamber within the system. More specifically, the substance movement control system 701 may include substance moving members 710, which apply a substance moving force to individual chambers or to the contents of the chamber, passage blocking members 708, which selectively block and unblock portals or passageways between individual chambers, and chamber partitioning members 706 which selectively divide individual chambers into two or more sub-chambers by, for example, pressing against a flexible chamber with a narrow-edged partitioning member to collapse a narrow portion of the chamber thereby forming two sub-chambers on opposite sides of the narrow collapsed portion. Substance moving member 710, passage blocking member 708, and chamber partitioning member 706 are moved, or actuated, by an actuator drive mechanism 704 which may comprise pneumatics, pneumatic pistons, hydraulics, motors, solenoids, etc. The actuator drive mechanism 704 is controlled by an actuator controller 702, comprising a computer or other microprocessor device programmed to control operation of the actuator drive mechanism 704 to regulate movement, sequence, and timing of substance moving member 710, passage blocking member 708, and chamber partitioning member 706. The actuator controller 702, in combination with the control and processing computer 730, selectively activates the substance moving members 710, passage blocking member 708, and chamber partitioning members 706 in selected sequences to control movement of fluids throughout the receptacle during the performance of an assay or other process performed in the receptacle. In an alternate configuration, control of the actuator drive mechanism 704 may reside in the control and processing computer 730.

The architecture 700 may further include a temperature control system 720, which may include heaters 724 and coolers 726 for selectively heating and/or cooling the contents of one or more chambers of the receptacle that are in proximity to the heaters or coolers. It should be understood that the heaters 724 and coolers 726 may comprise a single thermal element, such as a Peltier' chip. Operation of the heaters 724 and coolers 726 is controlled by a temperature controller 722, which may comprise a computer or other microprocessor device programmed to control operation (temperature, timing, and sequence) of the heaters 724 and coolers 726, e.g., by regulating power to the heaters 724 and coolers 726. Temperature sensors 728 detect the temperature of the heaters 724 and coolers 726 and feed the temperature data to the temperature controller 722 to control operation of the heaters 724 and coolers 726 to achieve the desired temperatures. The temperature controller 722, in combination with the control and processing computer 730, control operation of the heaters 724 and coolers 726 to provide the desired temperatures and sequences of temperature variations (e.g., thermal cycling) to perform an assay or other process within the receptacle. In an alternate configuration, control of the heaters 724 and coolers 726 may reside in the control and processing computer 730.

A detector system 712 is provided to detect an output signal from the contents of one or more chambers, which signal may be indicative of the presence and/or quantity of an analyte of interest. The detector system 712 may comprise a fluorometric detector, or fluorometer, comprising an excitation source 714 for generating an excitation signal. The excitation signal passes through optics and filters 718, and a resulting excitation signal having a prescribed wavelength or other optic characteristic is directed at one or more of the chambers. Emissions from the contents of the chamber pass through the optics and filters 718 (which are not necessarily the same optic elements through which the excitation signal passes) to a detector element 716, wherein the optics and filters 718 may pass only an emission signal of a prescribed wavelength to be detected by the detector element 716. Control of the operation of the detector system 712, as well as processing of the data collected by the detector system, may be performed by the control and processing computer 730.

Figure 3:
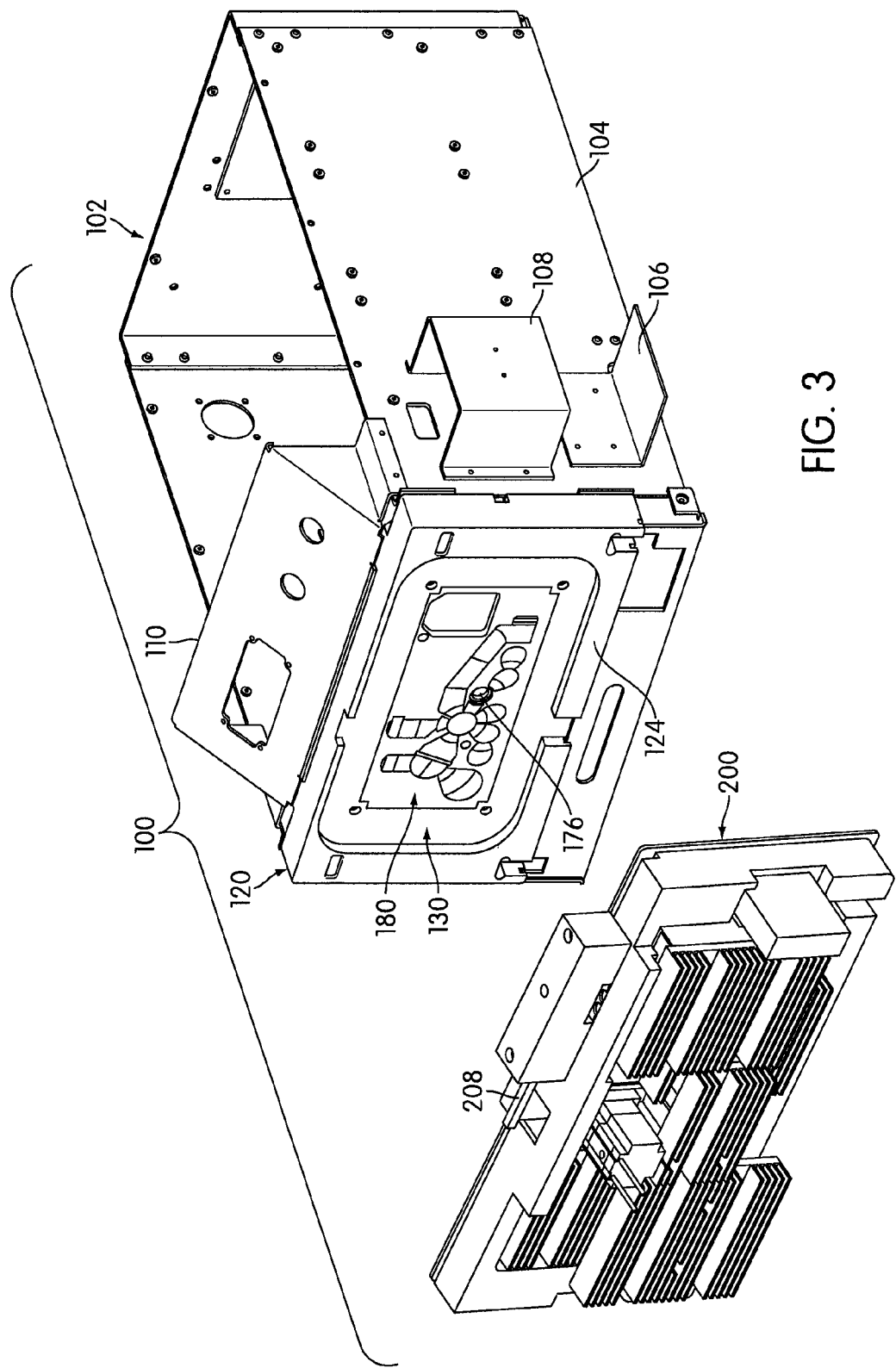
FIG. 3 is an exploded perspective view of an automated instrument embodying aspects of the present invention.

An automated instrument for performing a procedure on a sample in cooperation with a multi-chambered receptacle, such as receptacle 10, and which embodies aspects of the present invention, is designated by reference number 100 in FIG. 3. The automated instrument 100 can be used to perform all or a portion of the steps of a process in a single, multi-chambered receptacle, without the need for interaction by a technician during the operation of the process or steps of the process. The instrument shown in FIG. 3 includes a processing unit 102 and a door assembly 200. Certain components and surface panels are omitted from the processing unit 102, and a covering shroud is omitted from the door assembly 200 in the illustrated embodiment so that the underlying components and features can be more readily observed.

Processing unit 102 includes a housing 104. It is noted that the top panel of the housing is omitted in the figure. Housing 104 contains electronics, circuitry, and pneumatics for the operation of the instrument 100. Barcode reader brackets 106 and 108 hold a barcode reader (not shown). In one embodiment, a barcode label is placed on the receptacle 10, and the barcode reader situated on the instrument will read this barcode and provide information such as process instructions, expiration information, calibration information, and sample identification. Brackets 106 and 108 hold the barcode reader for hand-held reading of the receptacle barcode label.

A display panel 110 projects upwardly from the housing 104 and is positioned and oriented to permit a user ready access to any control switches mounted on the panel and to readily view any displays mounted on the panel.

The housing 104 further includes a front portion 120 which carries many of the functional components of the processing unit 102. The front portion 120 of the housing 104 includes a pressure mechanism cluster 180 (described in more detail below) mounted with an actuator plate 124, which may be formed (e.g., machined) from Delrin® or aluminum, which may be coated with Teflon® (PTFE). A recess 130 formed in the actuator plate 124 forms an opening for receiving and holding a receptacle 10 placed in the instrument unit 100 prior to closing the door assembly 200. The door assembly is hinged or otherwise mounted with respect to the front portion 120 of the housing so as to permit movement of the door assembly 200 between a receptacle-receiving, open position and a closed position. Latches or other similar mechanism (not shown) may be provided to releasably hold the door assembly 200 in the closed position with respect to the housing 104. More specifically, the latch or other mechanism may be provided to hold the door assembly 200 in the closed position but be adapted to release the door and permit its movement to the open position upon application of a moderate amount of door opening force.

To begin a process, the receptacle 10 is placed in the instrument 100, and the door assembly 200 is then closed. The receptacle 10 may include one or more registration features, such as alignment holes 74 and 75, which cooperate with mating features within the instrument, such as hooks or alignment pins (not shown) provided within the instrument 100 for properly positioning and orienting the receptacle with the receptacle-receiving opening of the instrument. As an alternative to the exemplary embodiment shown, an instrument incorporating aspects of the present invention may include a slot or other opening into which the receptacle is operatively placed, and a pivoting door assembly may be omitted. Sample material is preferably transferred to the receptacle prior to its placement in the instrument. Adding sample material to the receptacle before positioning the receptacle in the instrument minimizes opportunities for the instrument to be contaminated with spilled sample material.

Figure 5:
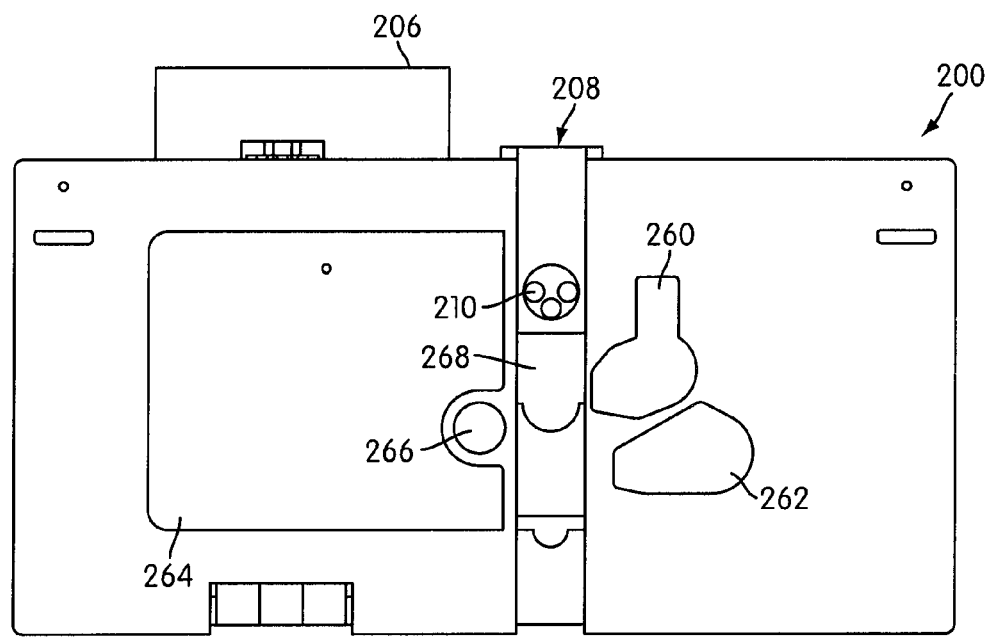
FIG. 5 is a plan view of a front side of a door assembly of the instrument.

Details of the door assembly 200 are shown in FIGS. 3 and 5. In the figures, a shroud, or housing, preferably covering portions of the door assembly is not shown so as to permit the underlying components of the door assembly to be seen.

FIG. 5 shows the front side of the door assembly 200, i.e., the side of the door assembly 200 that faces the processing unit 102 and the receptacle when the door assembly is closed. The door assembly 200 may include one or more thermal zones for heating and/or cooling regions of the receptacle that are in proximity to the thermal zones. The exemplary door assembly 200 shown in FIG. 4 includes five thermal zones 260, 262, 264, 266, and 268. The thermal zones are specifically located to provide heating and/or cooling to one or more specific chambers of the receptacle. In the illustrated embodiment, thermal zone 260 covers chamber C16 and neck portion 51. Thermal zone 262 covers chambers C18 and C20. Thermal zone 264 covers chambers C34, C32, C30, and most of C36. Thermal zone 266 covers chamber C28. Thermal zone 268 is located on the magnet translation mechanism 208 (described in more detail below) and covers chamber C26 and parts of chambers C22 and C24.

One or more thermal zones may be used to provide localized heating and/or cooling to one or more specific chambers of the receptacle or to provide controlled and stable ambient temperatures within the instrument. The ambient temperature may be any convenient temperature for optimal performance of a process or particular steps of a process, as described above. For example, the ambient temperature may be in the range of about 20° C. to about 40° or in the range of about 25° C. to about 37° C.

The thermal zones are preferably designed to rapidly heat (and/or optionally rapidly cool) an area of the receptacle and its contents to any desired temperature. Rapid temperature changes may be needed for processes requiring thermal cycling, such as PCR amplification reactions. Ideally, the thermal zones will have a high temperature range to accommodate variations between processes to be performed. Therefore, the temperature range of the thermal zones is preferably from about 5° C. to about 95° C. for water-based fluids, and may be much greater for non-aqueous fluids, such as those containing oil.

The portions of thermal zones 260, 262, 264, 266 and 268 visible in FIG. 5 are conductor plates made from a thermally conductive material, such as copper or aluminum, for conducting thermal energy (heating and/or cooling) from a thermal energy source, such as a Peltier thermoelectric device, to the receptacle 10. The exposed surface of each conductor plate, as shown in FIG. 5, has a size and shape conforming to the area of the receptacle intended to be affected by the thermal zone. Each conductor plate is mounted within a conforming opening formed in blocks of non-conductive material, which provide thermal separation between the conductor plates. Preferably, the exposed surfaces of each of the conductor plates for thermal zones 260, 262, 264, 266, and 268 and the exposed surfaces of the separating blocks are coplanar, together forming a flat surface that contacts the side of the receptacle 10 when the door assembly 200 is in the closed position.

The conductor plate of each thermal zone is in thermal contact with a source of thermal energy for conducting heating or cooling energy from the source to the exposed surface of the plate and then to the receptacle. In one embodiment, the source is a thermoelectric module, otherwise known as a Peltier device. In a preferred embodiment, thermoelectric units are mounted within the door assembly 200 in thermal contact with the thermal zones. Suitable Peltier devices include TEC1-12708T125 for thermal zone 264, TEC1-12705T125 for thermal zones 260 and 262, and TES1-12704T125 for thermal zones 266 and 268, all available from Pacific Supercool Ltd., Bangkok, Thailand.

Thermal insulation, such as foam insulation, may be provided around the thermoelectric modules and between portions of the conductor plates. As is generally known by persons of ordinary skill in the art, means may be provided within the door assembly 200 for dissipating excess heat away from the source of thermal energy, such as one or more thermally-conductive heat sinks which may be combined with one or more fan mechanisms for generating a convective airflow with respect to the heat sink(s).

The thermal zones 260, 262, 264, 266, and 268 are under microprocessor control for controlling the magnitude and duration of the thermal conditions, including thermal cycling where indicated, affected by the thermal zones. And one or more of the thermal zones can be deactivated during a test in which heating and/or cooling in the area(s) of the inactive thermal zone(s) is not required. Accordingly, control of the thermal zones can be configured to accommodate a variety of different process requirements.

To improve heat transfer to particular chambers, it was found that the use of oil or other inert substance can reduce the volume of air (a very poor thermal conductor) in a chamber and, simultaneously, increase chamber pressure. Increased chamber pressure can facilitate greater contact between chambers and corresponding conductor plates, so that the contents of the chambers are more completely and rapidly heated.

The magnet translation mechanism 208 is constructed and arranged to move a magnet—including a single permanent magnet, a cluster of permanent magnets, and/or one or more electromagnets—relative to a chamber in which a magnetic separation procedure is being performed (e.g., chamber C26), referred to, for the purposes of this explanation, as the magnetic separation chamber. More specifically, the magnet translation assembly 208 is constructed and arranged to move the magnet with respect to the magnetic separation chamber between: (1) an "on" position in which the magnet is sufficiently close to the magnetic separation chamber so that the magnetic field generated by the magnet will have a sufficient effect on the contents of the magnetic separation chamber to substantially immobilize any magnetically-responsive materials within the magnetic separation chamber; and (2) an "off" position in which the magnet is sufficiently removed from the magnetic separation chamber so that the magnetic field generated by the magnet will have an insufficient effect on the contents of the magnetic separation chamber to substantially immobilize any magnetically-responsive materials within the magnetic separation chamber.

In the embodiment shown in FIG. 5, the magnet translation mechanism 208 includes a magnet carrier which supports a magnet or cluster of magnets and an actuator coupled to the carrier for moving the carrier up and down relative to the door assembly 200 between the on and off positions. In the illustrated embodiment, the magnet translation mechanism 208 caries a cluster of three magnets 210, with a magnet being omitted from the top or "12 o'clock" position on the mechanism 208. The 12 o'clock position is closest to the portal 70 connecting the magnetic separation chamber 210 with the inlet 48 of the waste chamber C36. By omitting a magnet from this position, an accumulation of magnetic particles at this position is avoided. This helps minimize the number of magnetic particles inadvertently carried into the waste chamber C36 during the rinse and wash steps of the magnetic separation procedure.

Figure 4:
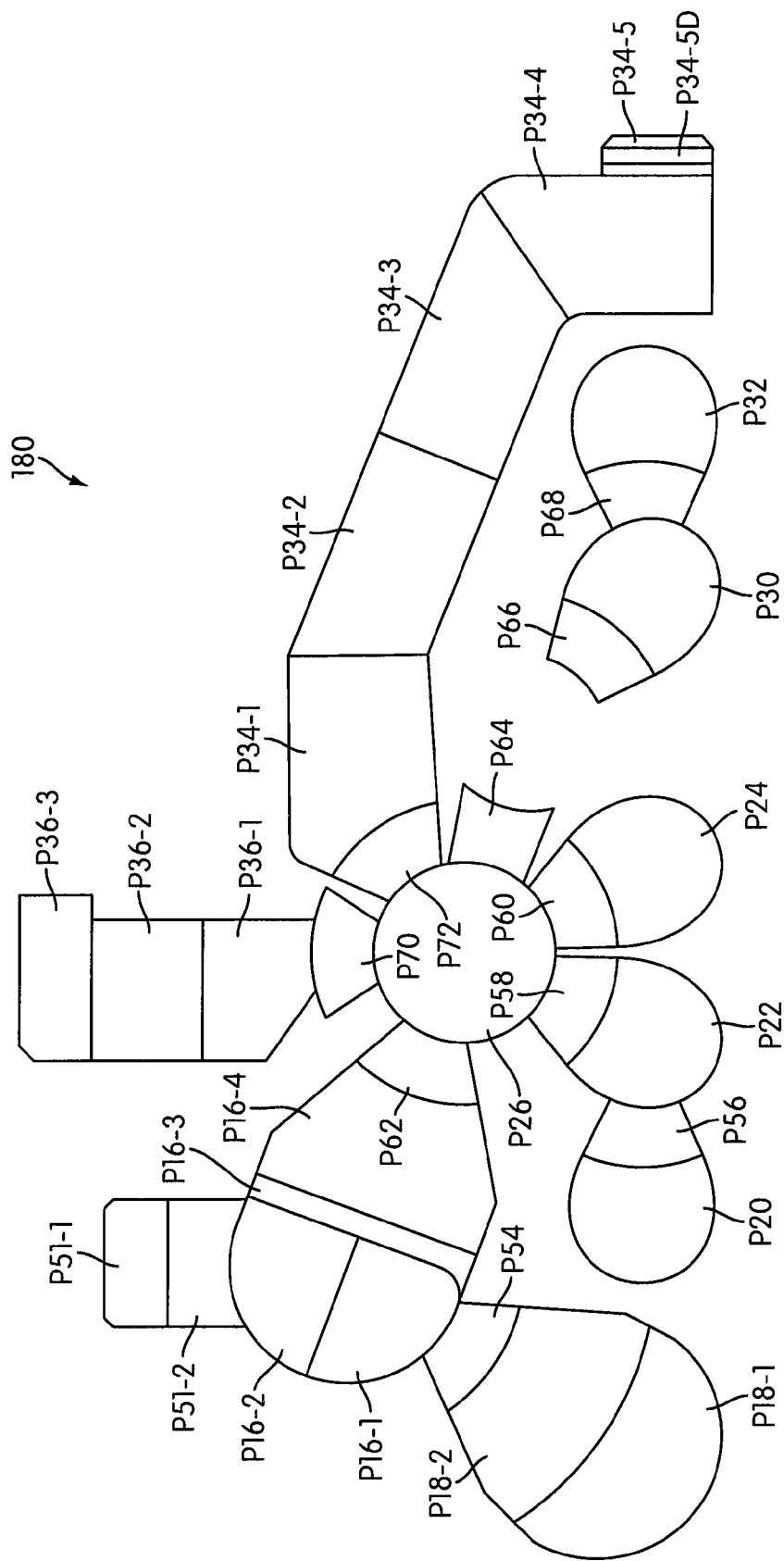
FIG. 4 is a schematic view illustrating an arrangement of compression pads of a pressure mechanism cluster of the instrument.

Referring to FIG. 4, the compression pads of pressure mechanism cluster 180 are positioned in a pattern conforming to the location of the chambers and fluid pathways of the exemplary receptacle 10 shown in FIG. 1 and are shaped to perform various of the process-related functions described herein. The automated instrument activates appropriate pressure mechanisms, magnets, and/or thermal zones in appropriate sequences, as controlled by an internal microprocessor controller.

The pressure mechanism cluster 180 is installed within the actuator plate 124 and is shown schematically in FIG. 4. The cluster 180 includes a plurality of individual compression pads constructed and arranged for reciprocal movement transversely to the outer surface actuator plate 124 to selectively apply pressure to selected portions of the receptacle 10. The pressure mechanism cluster 180 includes a plurality of compression pads sized and arranged to align with various chambers and portals of the receptacle 10. Each compression pad includes a head operatively attached to a reciprocating pneumatic actuator, a magnetic actuator, solenoid, or other suitable mechanical, electro-mechanical or other actuator (not shown) for moving the pad out into compressing engagement with a corresponding portion of the receptacle 10 and back into its stowed position.

Compression pad P51-1 is positioned so as to align with a top portion of the neck 51 of the receptacle 10. Compression pad P51-2 is positioned so as to align with a lower portion of the neck 51 of the receptacle 10 where the neck 51 enters chamber C16 Compression pads P16-1, P16-2, P16-3 and P16-4 are all positioned so as to align with different portions of chamber C16 of the receptacle 10. Compression pad P16-1 is the bottom compression pad for chamber C16, compression pad P16-2 is the top compression pad for chamber C16, compression pad P16-3 is the divider for chamber C16, and compression pad P16-4 is the front compression pad for chamber C16.

Having multiple pads P16-1, P16-2, P16-3 and P16-4 combined with a large chamber C16, which may be employed as the sample chamber, allows flexibility in the size of the sample to be assayed. Divider pad P16-3 can be used to partition the chamber C16 into two smaller chambers. Note that chambers C26 and C28 are much smaller than chamber C16 and, thus, it is self-evident that the entire contents of chamber C16, if filled substantially to capacity, would not fit within chamber C26 and/or chamber C28. For some applications, a relatively large volume of sample material may be required to ensure that there is a detectable amount of an analyte, if present in the sample, but subsequent chambers, such as chambers C26 and C28, for processing the sample cannot accommodate such a large volume of sample material. The multiple pads adapted to compress different portions of chamber C16 allows the sample to be moved from chamber C16 to chamber C26 one portion, or aliquot, at a time.

Compression pads P18-1 and P18-2 are positioned so as to align with the chamber C18. Compression pad P18-1 is the rear compression pad for chamber C18 and compression pad P18-2 is the front compression pad for chamber C18.

Compression pad P20 is positioned so as to align with chamber C20. Compression pad P22 is positioned so as to align with chamber C22. Compression pad P24 is positioned so as to align with chamber C24. Compression pad P30 is positioned so as to align with chamber C30. Compression pad P32 is positioned so as to align with chamber C32.

Note that in the illustrated embodiment, there are no compression pads associated with chamber C28 or with region 50 of chamber C36 or region 38 of chamber C34. The instrument may, however, include other mechanisms for imparting forces onto the chambers, or portions thereof, as described in more detail below. Moreover, the illustrated embodiment is exemplary, and other embodiments encompassing aspects of the present invention may provide compression pads for chamber C28 as well as regions 50 and/or 38 or may omit compression pads for other chambers and/or regions thereof.

Compression pads P34-1, P34-2, and P34-3 align with the lateral section 44 of chamber C34. Compression pad P34-1 is the #1 wash compression pad, compression pad P34-2 is the #2 wash compression pad, and compression pad P34-3 is the #3 wash compression pad.

Compression pad P34-4 is the #4 wash compression pad and aligns with the vertical section 42 of the wash reagent chamber C34.

Compression pad P34-5 is the #5 wash compression pad and aligns with the lower neck 40 of the wash reagent chamber C34. The #5 wash pad head P34-5 further includes parallel raised ribs P34-5a extending across the compression pad. Ribs P34-5a provide a tight compressive seal for closing off the neck portion 40 of receptacle 10 to prevent fluid flow from the upper portion 38 of the wash reagent chamber 34 into the vertical section 42 and lateral section 44 of chamber 34. Compression pads P36-1, P36-2 and P36-3 are aligned with the vertical inlet 48 of chamber C36. Note that compression pad P36-3 is wider than the compression pad P36-1 and P36-2 so that a portion of the compression pad P36-3 covers the neck 46 of chamber C36. Compression pad P36-1 is the #1 waste compression pad, compression pad P36-2 is the #2 waste compression pad, and pad P36-3 is the #3 waste compression pad.

Compression pad P72 is a clamp aligned with portal 72. Similarly, compression pad P70 is a clamp that aligns with portal 70, compression pad P62 is a clamp that aligns with portal 62, compression pad P58 is a clamp that aligns with portal 58, compression pad P60 is a clamp that aligns with portal 60, compression pad P66 is a clamp that aligns with portal 66, compression pad P68 is a clamp that aligns with portal 68, compression pad P56 is a clamp that aligns with portal 56, and compression pad P54 is a clamp that aligns with portal 54. Compression pad P64 is a clamp aligned with portal 64.

Compression pad heads may be formed from a black acetal resin sold under the brand name Delrin® by DuPont of Wilmington, Del.

Compression pad P26 is positioned so as to align with chamber C26. In a preferred embodiment, pad P26 is coupled to a screw actuator or other relatively slow-moving actuator. A screw actuator provides slow and steady compression, rather than the abruptly-applied compressive forces generated by pneumatically actuated compression pads. This controlled motion can provide several advantages. For example, a screw actuator allows the user to control the rate and extent to which the compression pad P26 moves, thereby making it possible to limit or prevent turbulence within a chamber being compressed. Avoiding turbulence is desirable when, for example, using detergent-based reagents that are prone to bubble under turbulent conditions or when removing wash reagent from a chamber during a magnetic separation wash procedure. While the wash reagent is being removed from a chamber containing immobilized, magnetically-responsive particles, turbulence within the chamber can cause the particles to become dislodged and, thus, to be washed away into a waste chamber. The controlled movement of the compression pad P26 can also help to prevent over-compressing a chamber, which can result in peeling apart or rupturing a wall of a chamber.

Figure 12A:
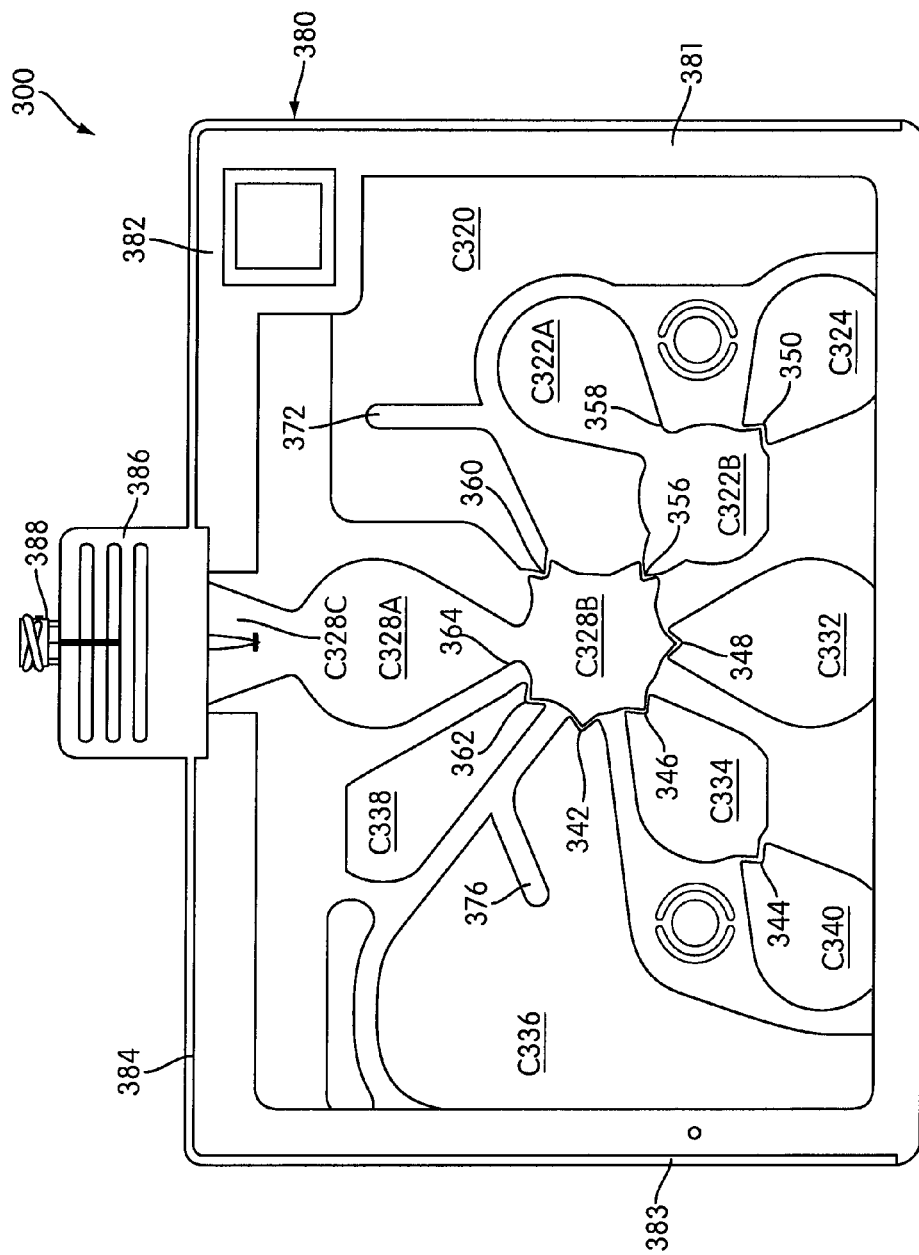
FIG. 12A is a plan view illustrating an alternative embodiment multi-chambered receptacle embodying aspects of the current invention.
Figure 12B:
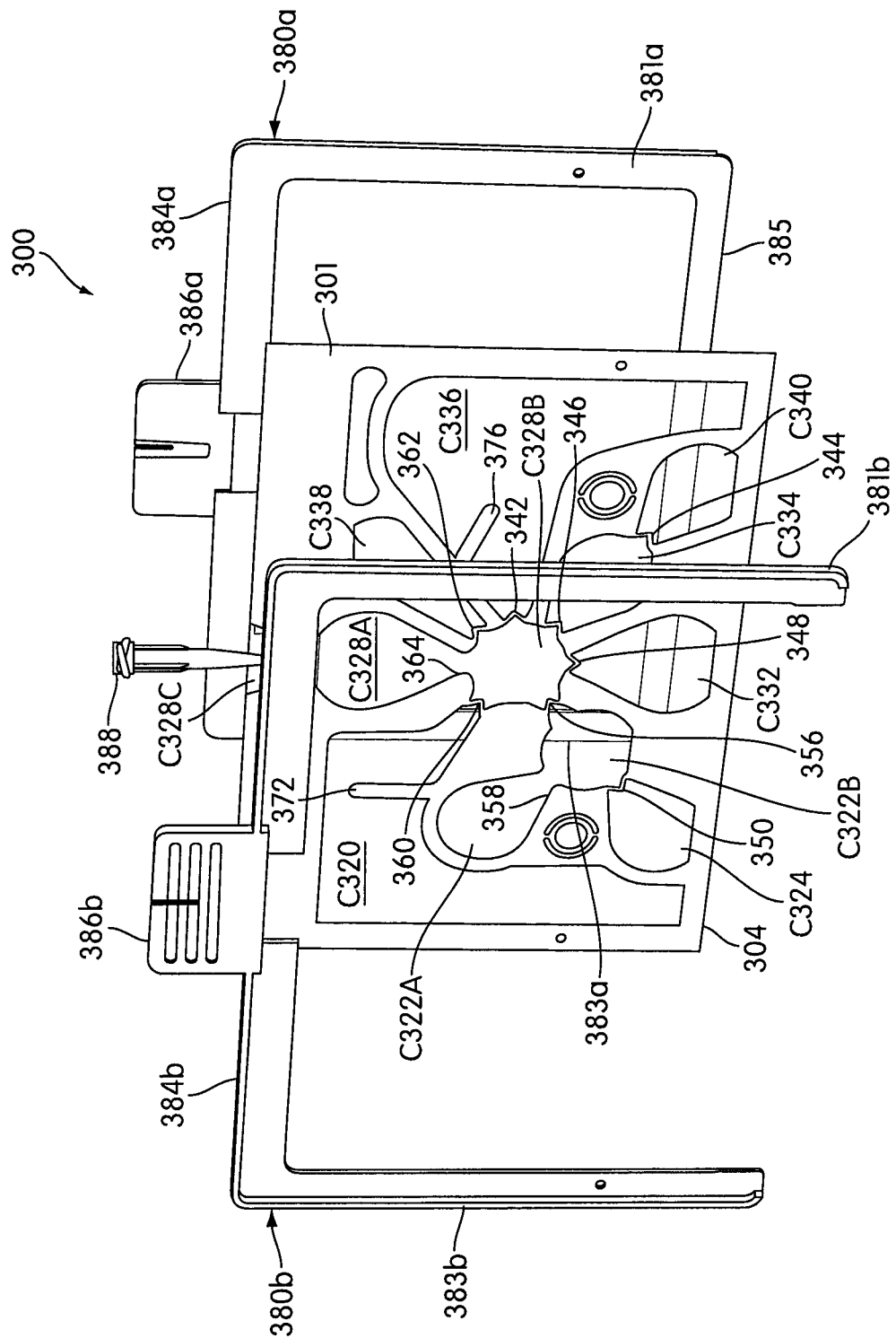
FIG. 12B is an exploded perspective view of the receptacle of FIG. 12A.

FIGS. 12A and 12B shows another receptacle 300 in accordance with the present invention. Like receptacle 10 described above, receptacle 300 includes a generally planar vessel having flexible top and bottom sheets formed from thin flexible materials, such as foils and/or plastics, and defining a pouch-like vessel. The receptacle 300 has an upper edge 302 and a lower edge 304 that indicate the preferred orientation of the receptacle during use and define an upper direction and a lower direction. An exemplary receptacle of the type shown in FIG. 12A has dimensions of about 5.5 inches by about 3.4-4.0 inches and is about 0.4 inches thick (when filled with sample and process materials), but may be of any dimensions suitable for manual manipulation or for use with an automated system, similar to the one described herein. Preferred materials for constructing receptacle 300 are the same as those described above for receptacle 10. Receptacle 300 includes an inlet port 306 for loading a sample material, or other substance, into the receptacle 300. Receptacle 300 includes nine chambers C320, C322, C324, C328, C332, C334, C336, C338, and C340.

As shown in FIG. 12A, the receptacle 300 may include a rigid frame 380 comprising vertical portions 381 and 383, a top horizontal portion 384, and a bottom horizontal portion 385. A panel 382 may receive an identifying label, such as a bar code or other human or machine readable indicia. The information carried on such label may include lot number, serial number, assay type, expiration date, etc.

A projecting tab 386 projects above the top portion 384 and provides an appendage for grasping the pouch 300 and inserting it into an instrument and removing it from the instrument. A port cover 388 (e.g., a one-way valve) is provided for introducing sample into the sample chamber C328A through inlet channel C328C. Frame 380, including the projecting tab 386 and sample cover 388, are preferably formed from a suitably rigid material such as plastic.

Further details of the receptacle 300 are shown in FIG. 12B, which is an exploded view of the receptacle. Frame 380 comprises rear frame component 380a and front frame component 380b between which is sandwiched a flexible pouch 301. Rear frame component 380a includes vertical portions 381a, 383a, a top horizontal portion 384a, a bottom horizontal portion 385, and projecting tab 386a. Front frame component 380b includes vertical portions 381b, 383b, top horizontal portion 384b, and projecting tab 386b, but does not include a bottom horizontal portion.

Each frame component 380a and 380b may be injection molded, and the two components may be connected to one another in a frame assembly by ultrasonic welding. The flexible pouch portion 301 of the receptacle 300 positioned and secured in the frame 380 by pins on the frame components 380a, 380b extending through holes formed in the periphery of the pouch.

In an exemplary use of the receptacle 300, the chambers can be filled with substances needed to perform a binding reaction. For example, sample material may be loaded into chamber C328 through inlet port 306. Chamber C328 consists of an upper region C328A and a lower region C328B connected by a restricted section 364 that can be closed by a pressure application mechanism so that the lower region is segregated from the upper region. Chamber C332 may be loaded with a sample processing reagent for binding and immobilizing an analyte present in the sample material on a solid support, the lower region C328B of chamber C328 may, in addition to receiving sample material, function as a sample processing region of chamber C328 for separating the immobilized analyte from other components of the sample material, chamber C334 may be loaded with a dried, first process material, chamber C340 may be loaded with a reagent for reconstituting the first process material, chamber C322 may be loaded with a dried, second process material, chamber C324 may be loaded with a reagent for reconstituting the second process material, chamber C336 may be loaded with a wash reagent, chamber C338 may be loaded with a rinse reagent for removing inhibitory components of the wash reagent, and chamber C320 may function as a waste chamber for receiving and storing waste substances in relative isolation from other aspects of the reaction. In addition to containing the second process material, a lower region C322B of chamber C322 may also function as a detection region of chamber C322 for detecting a signal or change in a reaction mixture that is indicative of the presence of at least one analyte of interest in the sample material.

Chamber C320 is configured to receive waste materials from chamber C328 and includes an initial, generally vertical inlet 370 extending from chamber C328, an upper neck 372, and a collection region 374. Vertical inlet 370 is positioned generally above the lower region C328B of chamber C328 and is connected to chamber C328 by means of portal 360 positioned near the top of the lower region C328B of chamber C328. The arrangement of chamber C320 relative to the chamber C328 allows for bubbles contained in chamber C328 to be transferred directly into chamber C320 when waste materials are moved from chamber C328 to chamber C320. Furthermore, because upper neck 372 is positioned above the collection region 374 of chamber C320, waste material can be retained within collection region 374 by force of gravity without the application of a clamp or other means for sealing the upper neck 372.

As illustrated in FIG. 12, in the interconnected chamber system of the receptacle 300, chamber C324 is connected to the lower region C322B of chamber C322 by portal 350, the lower region C322B of chamber C322 is connected to chamber C328 by portal 356, chamber C340 is connected to chamber C334 by portal 344, chamber C334 is connected to the lower region C328B of chamber C328 by portal 346, chamber C332 is connected to the lower region C328B of chamber C328 by portal 348, chamber C338 is connected to the lower region C328B of chamber C328 by portal 362, and chamber C336 is connected to the lower region C328B of chamber C328 by portal 342. A wall 376 projects obliquely into chamber C336 for preventing air bubbles that have collected in an upper portion of chamber C336 from being moved through portal 342 and into chamber C328 during a wash procedure. In one embodiment, each of the portals 342, 344, 346, 348, 350, 356, 360, and 362 is temporarily closed by an openable seal or other barrier to prevent fluid flow therethrough. Like receptacle 10, receptacle 300 defines a non-linear arrangement of chambers useful for performing complex procedures requiring or benefiting from non-sequential processing of samples.

Chamber C322 includes the lower region C322B discussed above and an upper region C322A which are connected by a restricted section 358. In the illustrated arrangement, the combined substances of chambers C324 and C322 (before or after being combined with substances from chamber C328) can be mixed in chamber C322 by moving the combined substances back-and-forth between the upper and lower regions C322A, C322B of chamber C322, while each of portals 350 and 356 is clamped by a pressure application mechanism to prevent substances from moving into chambers C324 and C328. Due to the relative orientations of the upper and lower regions C322A and C322B of chamber C322, gravity assists in moving the combined substances from the upper region C322A into the lower region C322B as pressure being applied to the lower region C322B is removed. Thus, in the embodiment shown, there is no need for an external pressure to move substances from the upper region C322A to the lower region C322B of chamber C322.

Receptacle 300 is processed in an instrument (not shown) having an arrangement of pressure application mechanisms—such as compression pads—and thermal zones sized, shaped, and positioned to conform to the chambers of the receptacle 300 for selectively moving substances between chambers and for selectively providing heating and/or cooling to one or more selected chambers.

Figure 13:
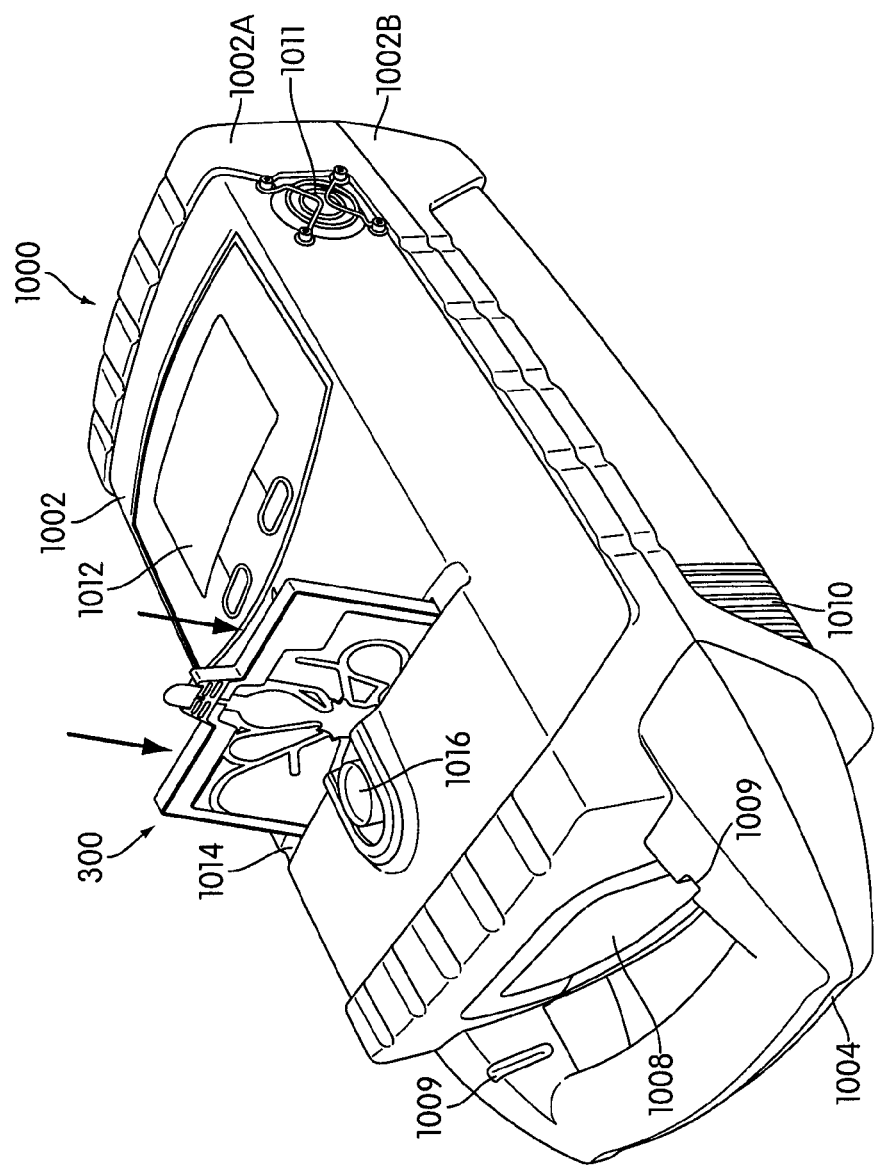
FIG. 13 is a front perspective view of an alternative embodiment of an automated instrument embodying aspects of the present invention.

A second embodiment of an instrument embodying aspects of the invention, and configured to process a receptacle 300, such as shown in FIGS. 12A and 12B, is designated by reference number 1000 in FIG. 13. Instrument 1000 includes a housing 1002 having a top portion 1002*a* and a bottom 1002*b*. Housing 1002 further includes a handle 1004. Handle 1004 includes opposed slots 1009 for holding a receptacle 300 during preparation. Instrument 1000 further includes an air intake 1008, preferably covered by a suitable filter material, and an exhaust vent 1010. A status screen 1012 displays status and other information useful to the operator, and operation buttons may be provided, for example below screen 1012, as shown. A receptacle insert slot 1014 in the top portion 1002*a* of the housing is configured to receive a receptacle 300, as shown in FIG. 13. Receptacle insert slot 1014 is preferably convex so that spilled liquid will run off the housing 1002, rather than into the slot. A slot cover slide 1016 can be manually manipulated after the receptacle 300 is inserted into the slot 1014 to provide a closure over the slot 1014 and may again be opened to permit removal of the receptacle 300. Fan 1011 provides cooling air for electronics and other components internal to the housing 1002.

Figure 14:
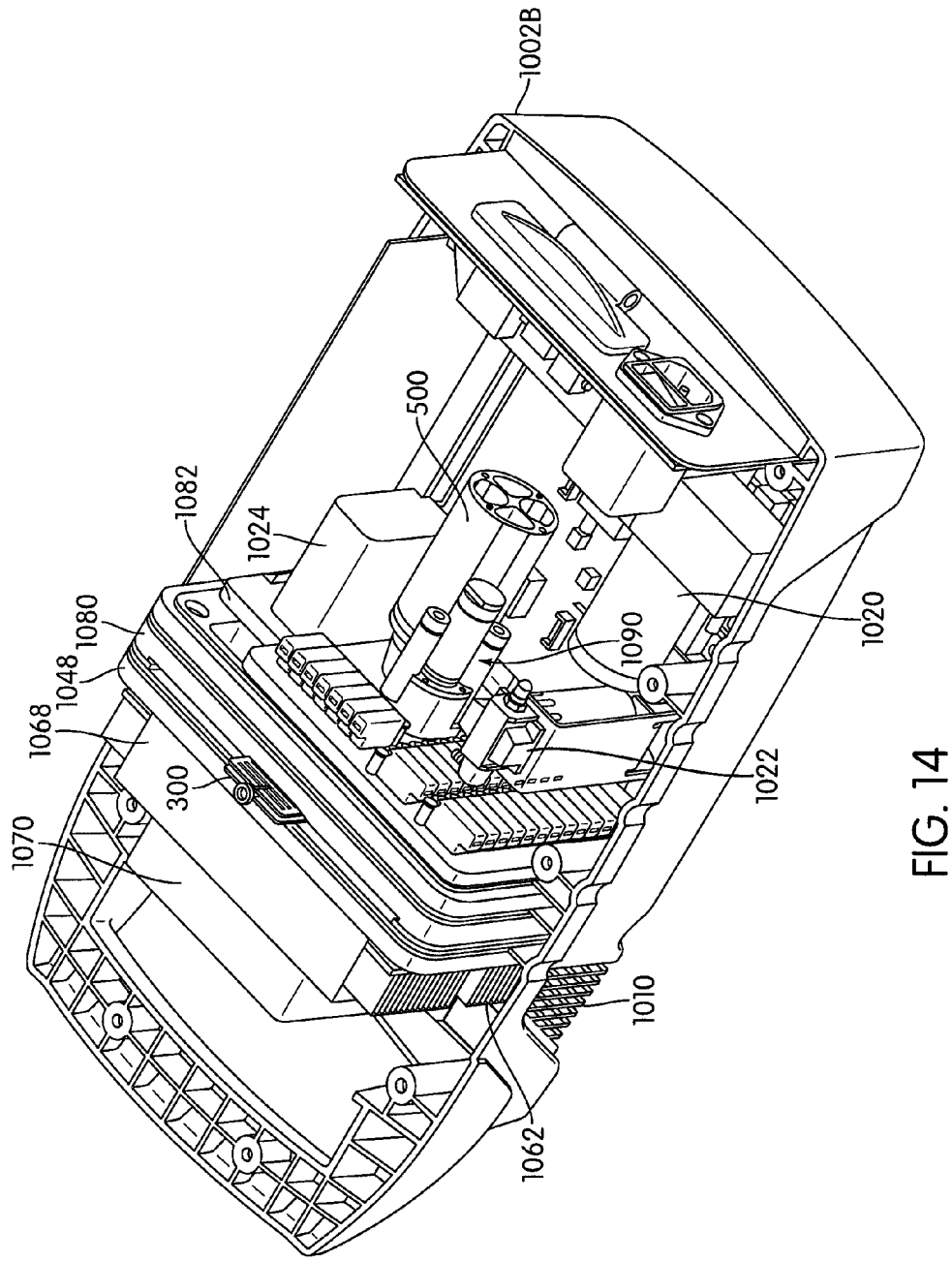
FIG. 14 is a rear perspective view of the instrument of FIG. 13, with a top portion of an exterior housing removed to show the interior of the housing.
Figure 15:
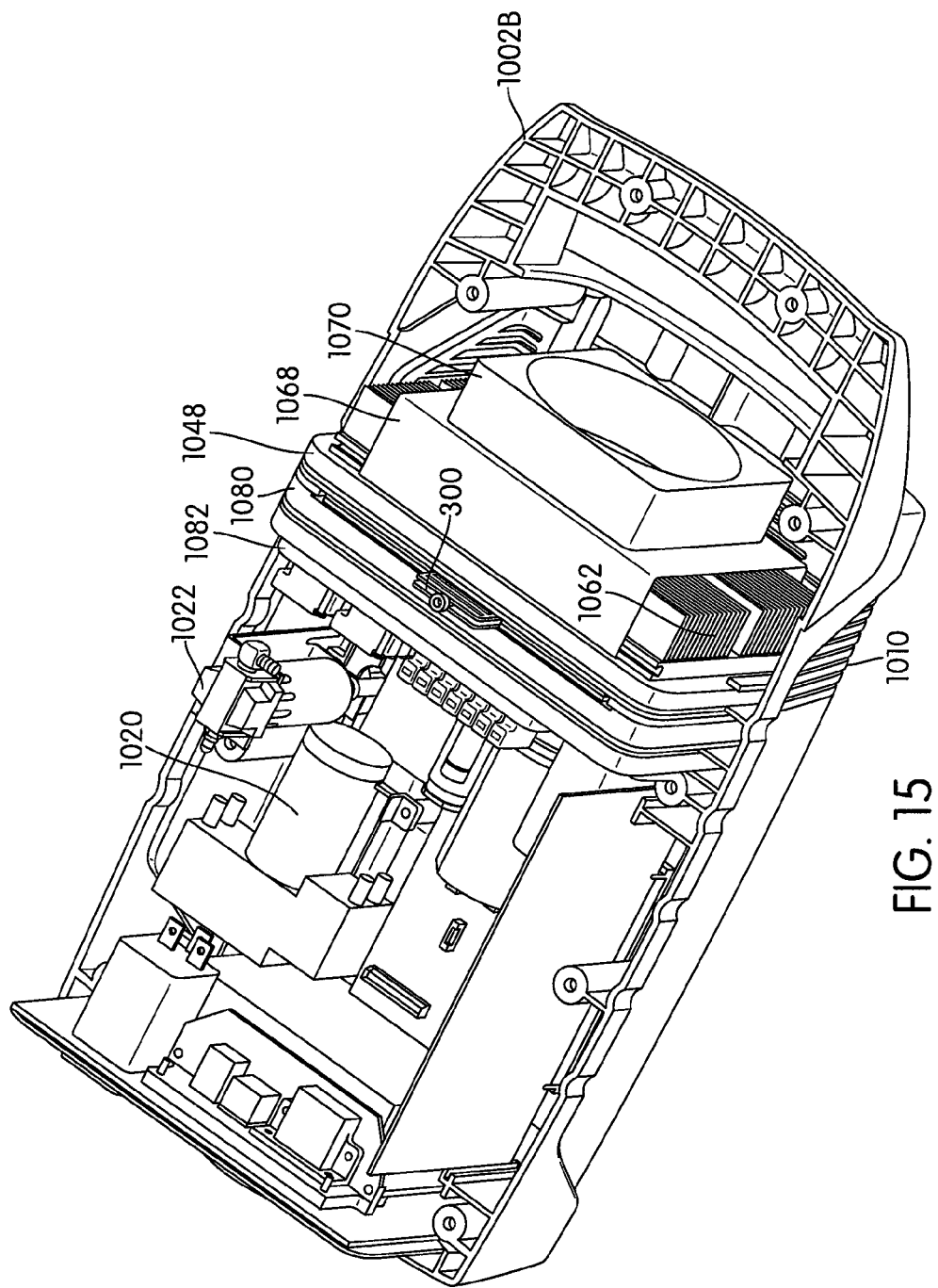
FIG. 15 is a front perspective view of the instrument of FIG. 13, with the top portion of the exterior housing removed.

Looking into the interior of the housing 1002 in FIGS. 14 and 15, the instrument 1000 includes an air compressor 1020 and an air reservoir 1024. The instrument further includes a detector, such as fluorometer 500 (described in more detail below), and a magnet actuator 1090 for selectively moving magnets into and out of operative position with respect to the receptacle. Instrument 1000 further includes an air manifold 1082 and an actuator plate 1080. Instrument 1000 may further include a coalescing air filter 1022. Aspects of the temperature control system are also shown and include a thermal isolating frame 1048 and a heat dissipating system, including a fan 1070, a shroud 1068, and heat sink 1064. Fan 1070 draws air into the instrument through the air intake 1008, and the heated air, after flowing over the heat sinks 1064, exits the housing 1002 through the exhaust vents 1010.

Figure 9A:
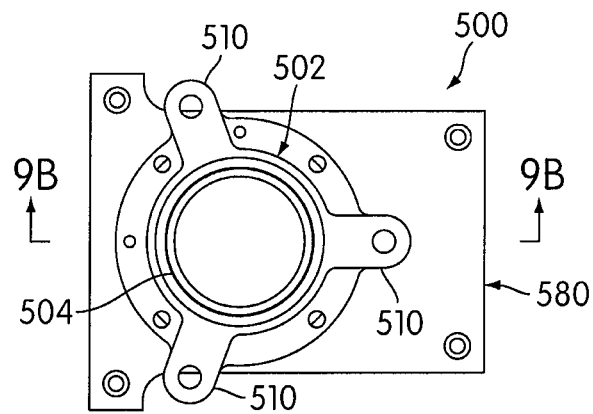
FIG. 9A is an end view of the fluorometer.
Figure 16:
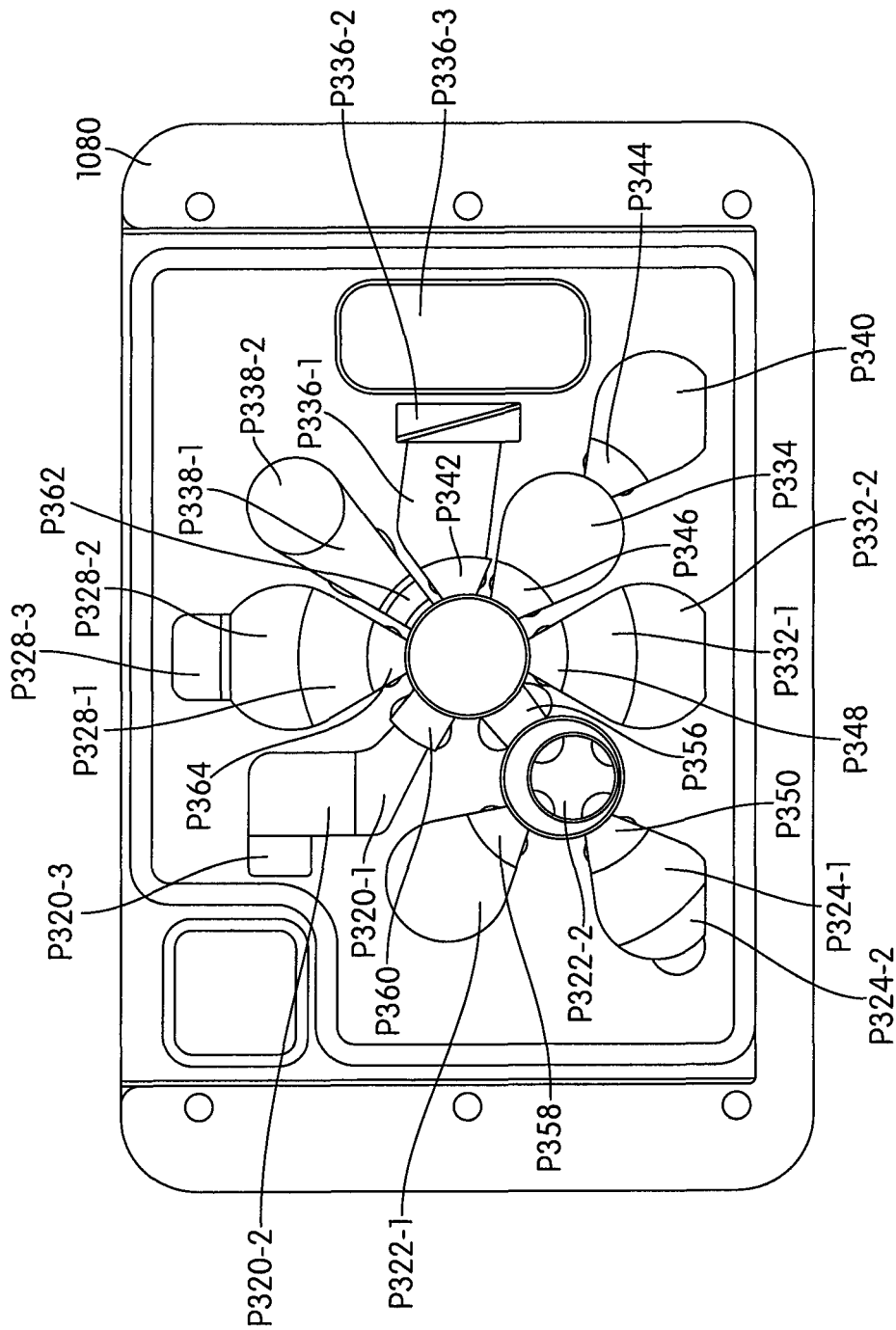
FIG. 16 is a front view illustrating an arrangement of compression pads of a pressure mechanism cluster of the instrument of FIG. 13.

A pressure mechanism cluster of the instrument 1000 for applying selective pressure to the receptacle 300 shown in FIG. 9 is shown in FIG. 16. The cluster is installed within the actuator plate 1080, which may be formed (e.g., machined) from Delrin® or aluminum, which may be coated with Teflon® (PTFE). As with cluster 180 described above, the cluster of FIG. 16 includes a plurality of individual compression pads constructed and arranged for reciprocal movement transversely to the actuator plate 1080 to selectively apply pressure to selected portions of the receptacle 300. The pressure mechanism cluster includes a plurality of compression pads sized and arranged to align with various chambers and portals of the receptacle 300. Each compression pad includes a head operatively attached to a reciprocating pneumatic actuator, a magnetic actuator, solenoid, or other suitable mechanical, electro-mechanical or other actuator (not shown) for moving the pad out into compressing engagement with a corresponding portion of the receptacle 300 and then back into its stowed position.

In one embodiment, each compression pad is coupled to an air conduit formed in the manifold 1082, which directs pressurized air to the pad to move the pad to an extended position. More specifically, each compression member is controlled by a solenoid valve which, when engaged, connects pressurized system air to a pathway that goes to a portal where a pressure regulator (not shown) is installed, and the output of this regulator is connected back into another portal on the manifold 1082, which feeds the now-regulated & pressurized air to the compression member. Pressure sensors may be provided for monitoring pressure within the system.

Compression pads P328-1 and P328-2 are aligned with lower and upper portions, respectively, of the sample chamber C328A of the receptacle 300. Compression pad P328-3 is aligned with an upper neck C328C. Compression pad P364 is aligned with the restricted area P364 between chamber C328A and chamber C328B and provides a means for selectively opening or closing the restriction 364 for controlling fluid flow between chambers C328A and C328B.

Compression pad P338-2 is a circular pad aligned with an upper portion of the rinse chamber C338, and compression pad P338-1 aligns with a lower portion of the chamber C338. Compression pad P362 aligns with the portal 362 connecting the rinse chamber with C338 with the magnetic separation chamber C328B and provides a means for selectively opening or closing the portal 362 (after an initially-closed burstable seal has been opened) for controlling fluid flow between the chambers.

Compression pads P320-1, P320-2, and P320-3 align with different portions of the waste chamber C320. Compression pads P320-1 and P320-2 align with lower and upper portions, respectively, of an inlet passage connecting chamber C328B to the waste chamber C320 and are adapted for moving fluid up the passage into the upper neck 372 of the chamber C320. Compression pad P320-3 controls movement of fluid through the upper neck 372 and, in particular, prevents fluid from flowing back from the waste chamber C320 toward the chamber C328B. Compression pad 360 is aligned with the portal 360 connecting the waste chamber C320 with chamber C328B and provides a means for selectively opening or closing the portal 360 to control fluid flow between the chambers.

Compression pad P356 is aligned with the portal 356 connecting chamber C322B and chamber C328B and provides a means for opening or closing the portal to control fluid flow between the chambers. Compression pad P322-1 is aligned with chamber C322A, and compression pad P358 is aligned with the restricted section 358 connecting regions C322A and C322B of chamber C322. Compression pad P358 provides a means for opening or closing the restricted section 358 for controlling fluid flow between the chambers.

Compression P322-2 is aligned with the chamber C322B. In one embodiment, lower region C322B of chamber C322 functions as a detection chamber for detecting a signal or change in a reaction mixture that is indicative of the presence of at least one analyte of interest in the sample material. Accordingly, in some embodiments, compression pad P322 is configured to allow optical transmission through the compression pad, thereby permitting the detection of an optical signal emitted by the contents of chamber region C322B.

Compression pads P324-1 and P324-2 are aligned with upper and lower portions, respectively of the chamber C324. Compression pad P350 is aligned with the portal 350 connecting chamber C324 and C322B and provides a means for opening or closing the portal to control fluid flow between the chambers.

Compression pads P332-1 and P332-2 are aligned with the upper end lower portions, respectively of the chamber C332. Compression P348 is aligned with the portal 348 connecting chamber C332 and chamber C328B and provides a means for selectively opening and closing the portal 348 to control fluid flow between the chambers.

Compression pad P340 is aligned with chamber C340, and compression pad P334 is aligned with chamber C334. Compression pad P344 is aligned with portal 344 connecting chambers C340 and C334 and provides a means for selectively opening or closing the portal 344 for controlling fluid flow between the chambers. Compression P346 is aligned with portal 346 connecting chamber C334 and C328B and provides a means for opening or closing portal 346 for controlling fluid flow between the chambers.

Compression pad P336-1 is aligned with a portion of the wash chamber C336 and compression pad P336-2 is aligned with another portion of the wash chamber P336. Compression pad P336-2 aligns with a portion of the wash chamber P336 extending from an end of the oblique wall 376 and a peripheral side wall of the chamber C336 and provides a means for dividing chamber C336 into two sub-chambers. Compression pad P342 aligns with the portal 342 connecting chamber C336 and chamber C328B and provides a means for selectively opening or closing the portal 342 to control fluid flow between the chambers.

Compression pad P336-3 is aligned with a portion of wash chamber C336 and is a bladder formed by a sheet of flexible, relatively non-porous material, secured at its edges to a recess formed in the actuator plate 1080. The bladder P336-3 is in communication with an air conduit formed in the manifold 1082 and may be controlled by a regulator. When filled with air, the bladder P336-3 inflates (expands) to apply pressure to a portion of chamber C336 to displace wash fluid from the chamber. The bladder P336-3 is preferred over a reciprocating compression pad for this location because inflation of the bladder can be controlled to provide a slow, steady displacement of chamber C336.

The function of the bladder P336-3 is to gently pressurize the wash chamber C336 enough to move an aliquot of wash buffer reagent into the channel area adjacent portal 342 The compress pad P336-2 has a single raised thin-surface to hold the wash aliquot in place until it is moved to the chamber C328B. The bladder P336-3 is actuated much like any of the other compression members, controlled by a solenoid valve which, when engaged, connects the pressurized system air to a pathway that goes to a portal where a pressure regulator is installed, and the output of this regulator is connected back into another portal on the manifold 1082 which feeds the now-regulated & pressurized air to the bladder. A suitable operating pressure for the bladder P336-3 is approximately 10 psi.

The pressure mechanism cluster may be covered by an elastomeric shield (See reference number 1081 in FIGS. 18 and 19) which stretches to permit the compression pads to operate and which covers and protects the compression pads, for example, from spilled fluids. The shield may include one opening through which a detector (e.g., fluorometer 500) may detect optical singles emitted from the contents of a chamber located adjacent the opening. The shield may be provided with non-stick properties (e.g, a non-stick coating) to facilitate insertion and removal of the receptacle 300 from the instrument 1000 after processing.

Figure 17A:
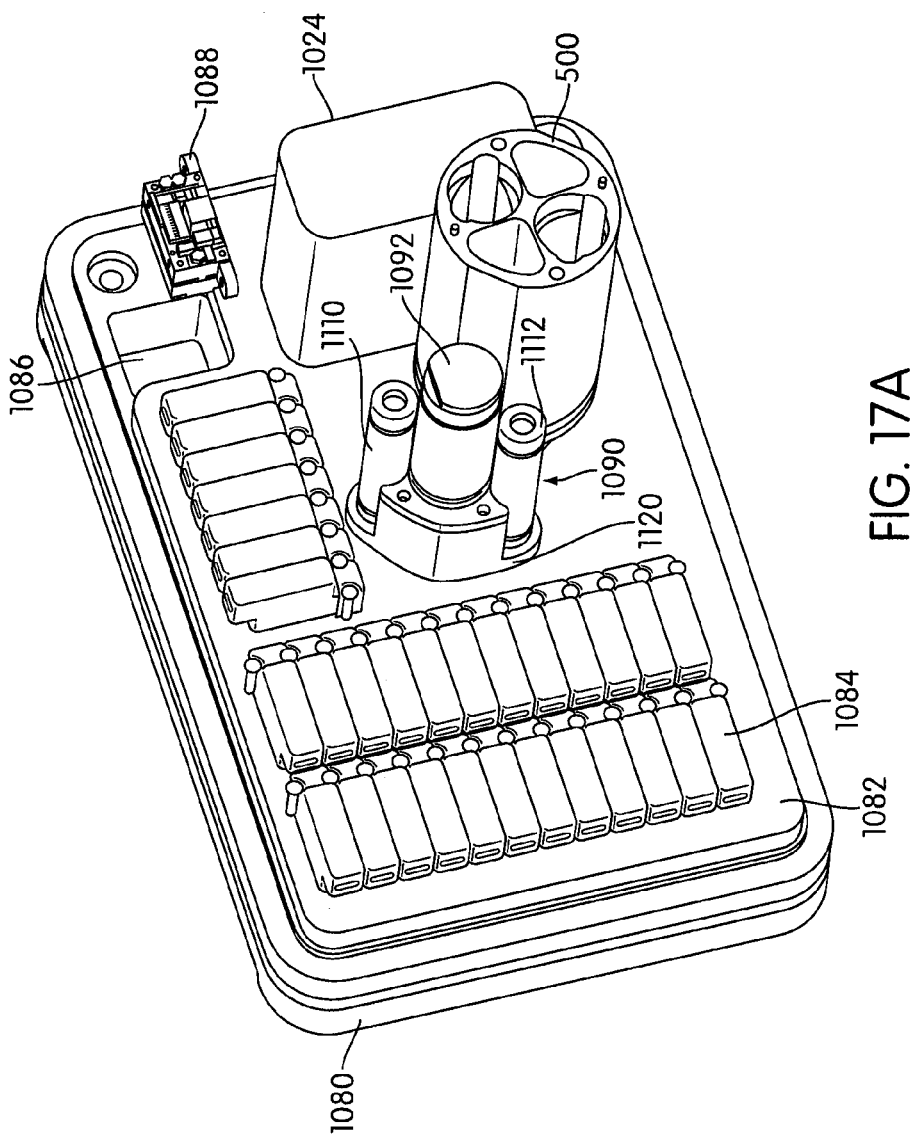
FIG. 17A is a rear perspective view of an air manifold and attached components of the instrument of FIG. 13.

As shown in FIG. 17A, the pneumatic manifold 1082 is attached to the actuator plate 1080. The air reservoir 1024 is connected to the manifold 1082 as is the magnet actuator 1090 and the detector 500. A window 1086 permits viewing of a bar code or other label provided on the panel 382 of the receptacle 300 (see FIG. 12A), and bar code reader 1088 is constructed and arranged to read a bar code on the receptacle. Valves 1084 (e.g., solenoid valves) control the pressure distribution to the various conduits of the manifold, each of which is connected to one of the pneumatic compression pads shown in FIG. 16.

Figure 17B:
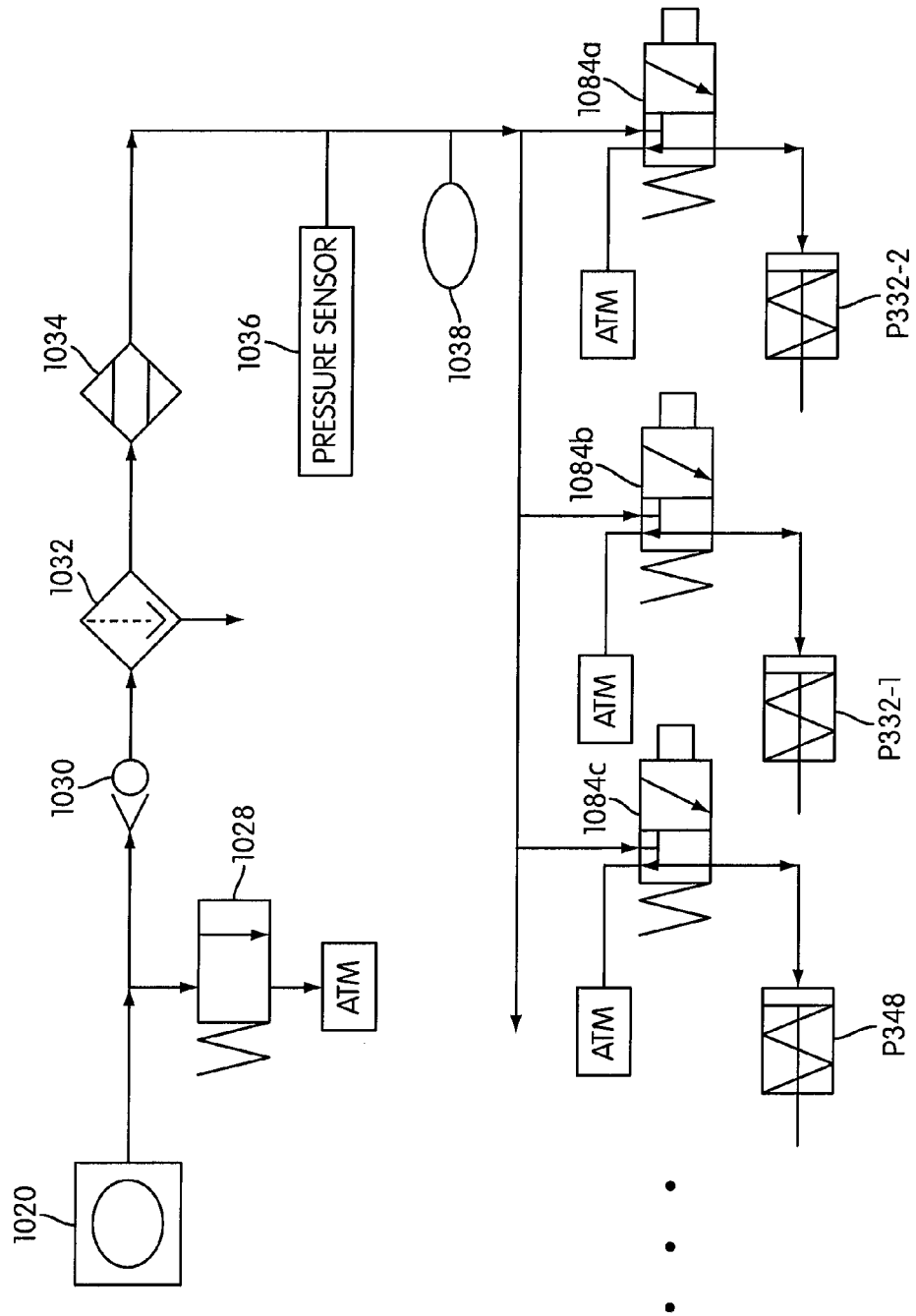
FIG. 17B is a circuit diagram of the pneumatic system of the instrument.

More specifically, FIG. 17B shows a circuit diagram of the pneumatic system of the instrument 1000. The system shown in FIG. 17B differs somewhat from the structure shown in FIG. 17A. For example, the system shown in FIG. 17B lacks an air reservoir. The pneumatic system includes pump 1020 connected to a check valve 1030, a water trap 1032, and an air dryer 1034 (e.g., a desiccant device for removing moisture from pressurized air). A valve 1028 (e.g., a solenoid valve) is constructed and arranged for selectively disconnecting the pump from the pneumatic system by venting the pump to atmosphere "ATM". A pressure sensor 1036 detects the pressure in the system and may communicate with the control and processing computer 730 (See FIG. 2). The system may also include an accumulator 1038. The system next includes the valves 1084 and the compression members (e.g., as shown in FIG. 16). In FIG. 17B, only three valves 1084*a*, 1084*b*, 1084*c* and three associated compression members P332-2, P332-1, and P348 are shown. As can be seen in the Figure, each valve 1084*a*, 1084*b*, 1084*c* can selectively connect the associated compression pad to the pressure source (pump 1020 or accumulator 1038), connect the associated compression pad atmosphere "ATM" to vent the compression pad (to remove pressure that might inhibit complete retraction of the compression pad), or block the compression member branch from the rest of the pneumatic circuit.

Figure 19:
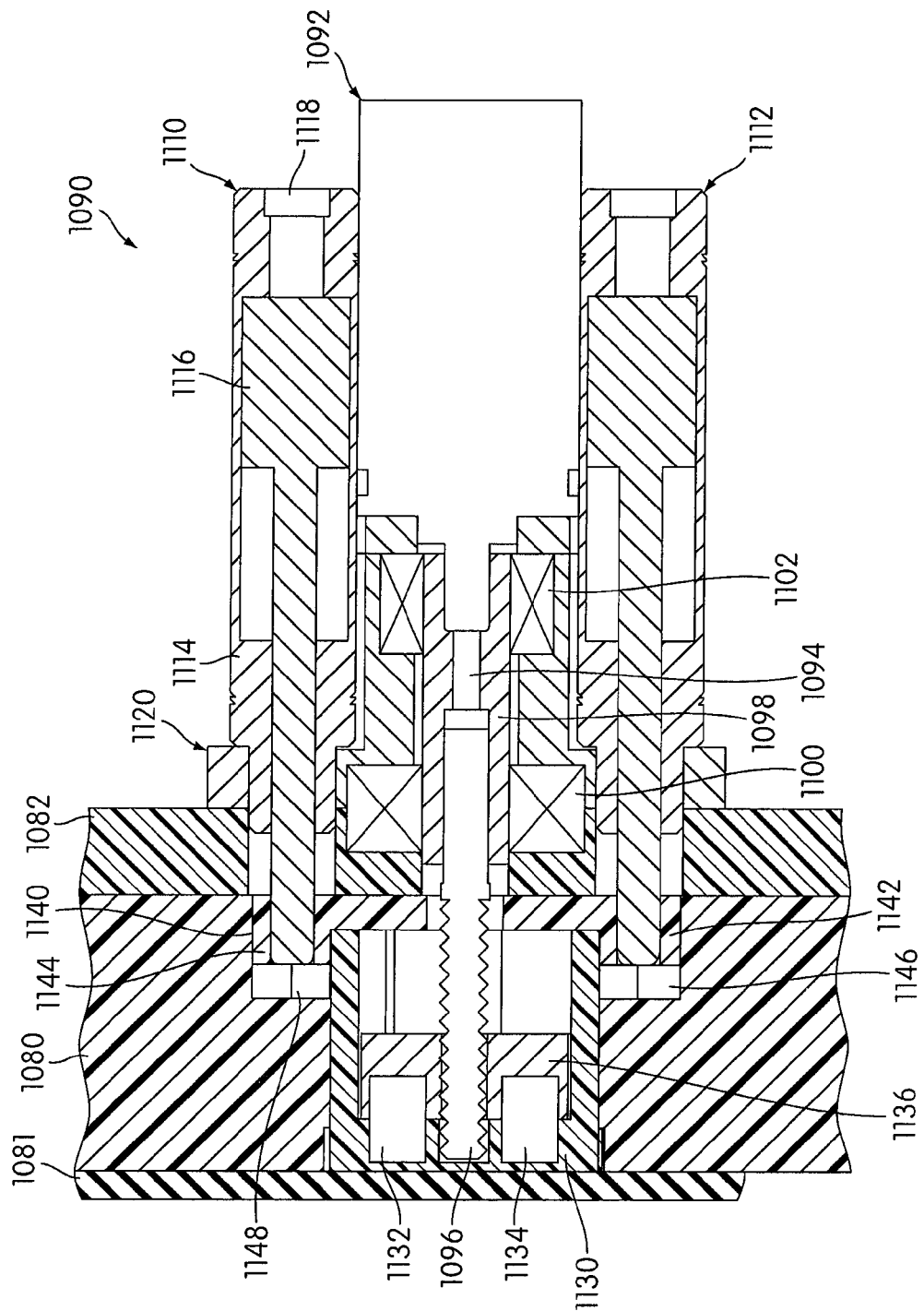
FIG. 19 is a cross-section of a compression pad integrated with a magnet actuator.

The magnet actuator 1090, shown in cross-section in FIG. 19, includes a motor 1092 which moves a magnet holder 1136 holding magnets 1132, 1134 via a shaft 1094 coupled to a lead screw 1096. Magnet actuator 1090 further includes cylinders 1110, 1112 which are coupled to an actuator fitting 1140 for reciprocally moving a compression cup 1130. Motor 1092 and cylinders 1110, 1112 are mounted atop a mounting block 1120 attached to the manifold 1082.

More specifically, motor 1092 includes a shaft 1094 coupled to lead screw 1096 by a coupler 1098 that is rotatably mounted within bearings 1100, 1102. Lead screw 1096 is able to slide axially within coupler 1098 and is threadably coupled to the magnet holder 1136 within which are held a number of magnets, including magnets 1132, 1134 shown in the figure. In a preferred embodiment, the magnet holder 1136 holds three such magnets. The magnet holder 1136 is disposed within a hollow portion of the compression cup 1130, which is disposed within a circular hole formed transversely through the actuator plate 1080. An end of the lead screw 1096 inserted into the coupler 1098 has a square or other shaped cross-section that will prevent the lead screw 1096 from rotating with respect to the coupler 1098. Furthermore, the magnet holder 1136 has projecting ridges or a non-circular peripheral shape that conforms to the inner wall of the hollow compression cup 1130 to prevent the magnet holder 1136 from rotating within the compression cup 1130. Thus rotation of the lead screw 1096 by the motor 1092 causes corresponding translation of the magnet holder 1136.

In addition simply moving the magnet holder 1136 between on and off positions, the motor 1092 can be controlled to vary the speed with which the magnet holder 1136 is moved from the on position to the off position and vice versa as well as to vary positions between on and off. Those skilled in the art could imagine how, using a combination of speed and position, the strength and rate of change of magnetic field strength can be optimized to maximize magnetic particle retention.

Each of the cylinders 1110, 1112 includes a cylinder housing 1114 within which is disposed a reciprocating piston 1116. (Note: Cylinders 1110 and 1112 are identical; accordingly, only the features of cylinder 1110 are numbered in the figure). A pneumatic port 1118 is provided for coupling the cylinder 1110 to a source of air pressure. The pistons of each of the cylinders 1110, 1112 are coupled to the actuator fitting 1140.

The actuator fitting 1140 includes a circular center portion which fits into a portion of the same hole into which the compression cup 1130 fits and two radial projections 1142, 1144 which fit into openings 1146, 1148, respectively, formed into the actuator plate 1080 adjacent the circular opening that receives the compression cup 1130. The pistons 1116 are attached to the radial projections 1142, 1144.

As shown in the figure, the magnets 1132, 1134 carried in the magnet holder 1136 are in an "on" position. That is, the magnets are in close proximity to the elastomeric shield 1081 covering the actuator plate 1080, and thus are in close proximity to the chamber of the receptacle within which a magnetic separation procedure is being performed. The magnets can be moved to an "off" position by rotating the lead screw 1096 via the motor 1092 to translate the magnet holder 1136 away from the shield 1081 (i.e., to the right in the figure) within the hollow portion of the compression cup 1130. Reversing the rotation of the motor 1092 and the lead screw 1096 extends the magnet holder 1136 back to the "on" position at the end of the compression cup 1130. Continued rotation of the lead screw 1096 will push the magnet holder 1136 and compression cup 1130 out (to the left in the figure) against elastomeric shield 1081 to apply a compressive force to a chamber adjacent the compression cup 1130. Thus, the chamber is compressed to displace liquid from the chamber while the magnets are in the "on" position to hold and retain magnetic particles within the chamber, for example during a rinse step of the magnetic separation procedure.

When the compression cup 1130 is extended by the lead screw 1096 and the magnet holder 1136, the actuator fitting 1140, which is rigidly attached to the compression cup (e.g., the two components are threaded together), also moves to an extended position (to the right in the figure). The pistons 1116 of the cylinders 1110, 1112 move passively along with the actuator fitting 1140. When the magnet holder 1136 is retracted by the lead screw 1096, springs (not shown) within the cylinders 1110, 1112 cause the actuator fitting 1140 and the compression cup 1130 to return to the retracted position shown in the figure.

The magnet actuator 1090 also functions as a compression pad for applying a compressive force to a chamber of the receptacle to force the fluid contents from the chamber when the magnets are in the "off" position. This is accomplished by turning the lead screw 1096 to withdraw the magnet holder 1136 to the "off" position (to the right in the figure) and then pressurizing the pistons 1116 of the cylinders 1110, 1112 to extend the pistons and thus extend the actuator fitting 1140 and the compression cup 1130 (to the left in the figure) against the shield 1081, which will stretch and deflect in response to the reciprocating projection of the cup 1130, to compress a chamber adjacent the compression cup 1130. As the actuator fitting 1140 is extended, the magnet holder 1136, which has been retracted back (to the right) into contact with the actuator fitting 1140, will also be moved in the direction of extension. To accommodate this movement of the magnet holder 1136, the end of the lead screw 1096 is able to slide with the coupler 1098 (i.e., the lead screw 1096 "floats" within coupler 1098). Springs within the cylinder 1110, 1112 retract the actuator fitting 1140 and compression cup 1130 when pressure is removed from the pistons 1116.

Figure 20:
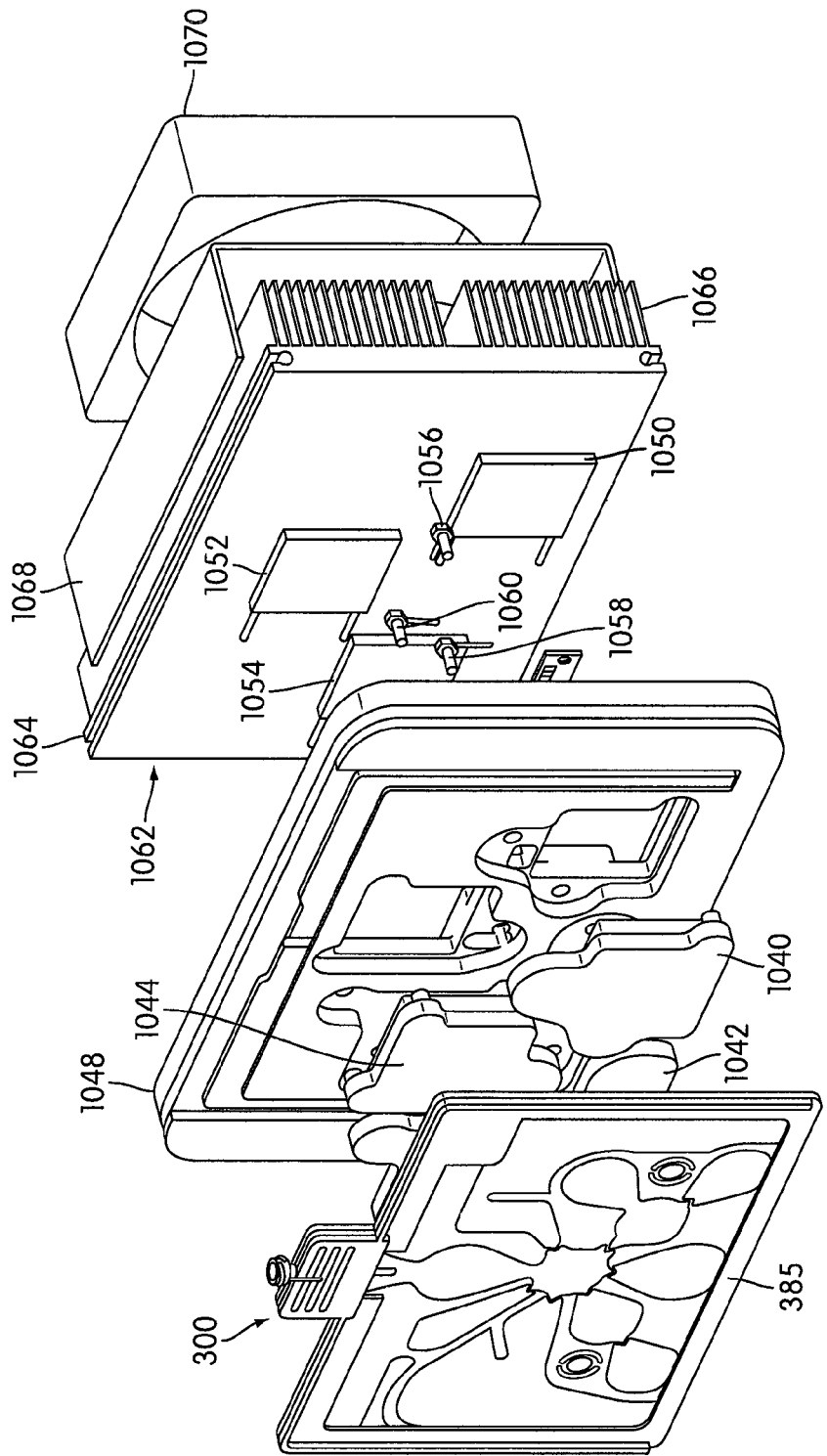
FIG. 20 is an exploded perspective view of a temperature control system of the instrument of FIG. 13.

The temperature control system of instrument 1000 is shown in FIG. 20 and includes thermal conductive elements 1040, 1042, 1044 disposed within a thermal isolating frame 1048. The thermal conductive elements are preferably made from a thermally conductive material, such copper or aluminum, and the isolating frame 1048 is preferably formed from a thermal insulating material, such as Ultem® or Delrin®. In the illustrated embodiment, ach of the conductive elements 1040, 1042, 1044 is sized and shaped so as to be in thermal communication with a region of the receptacle 300 encompassing more than one chamber. Furthermore, at least a portion of each conductive elements 1040, 1042, 1044 is in close proximity to at least a portion of an adjacent conductive element such that a chamber encompassed by one conductive element is closely adjacent to a chamber encompassed by the adjacent conductive element, and the two chambers are connected by a portal with no passageway extending between the two chambers. Such close proximity between adjacent conductive elements without thermal crosstalk between the adjacent conductive elements is facilitated by the insulation provided by the isolating frame 1048.

The receptacle 300 is held in an operative position within the instrument 1000 between the actuator plate 1080 and the isolating frame 1048 (See FIGS. 14 and 15). The arrangement of the isolating frame 1048 and the actuator plate 1080 within the instrument 1000 results in a receptacle-receiving gap therebetween, and that gap is dimensioned with respect to the receptacle 300 such that when a chamber of the receptacle that is adjacent one of the conductive elements 1040, 1042, 1044 is filled with fluid, the chamber expands to increase the thermal contact between the surface of the chamber and the adjacent conductive element.

Peltier' devices 1050, 1052, 1054 are positioned in thermal contact with conductive elements 1040, 1044, 1042, respectively. Temperature sensors 1056, 1058, 1060 are positioned in thermal contact with the conductive elements 1040, 1042, 1044, respectively, for sensing the temperature of the respective thermal conductive element. Sensors 1056, 1058, 1060 may comprise RTD sensors, and are coupled to a controller (e.g., temperature controller 722) for controlling operation of the Peltier devices. Heating elements other than Peltier devices, such as resistive foil heaters, can be used as well.

The Peltier' devices 1050, 1052, 1054 (or other heating or cooling elements), are preferably mounted onto a heat sink 1062 which may comprise an aluminum block having a first portion 1064 with a first planar side on which the Peltier' devices are mounted and heat dissipating fins 1066 projecting from the opposite side. A shroud 1068 partially covers the dissipating fins 1066 of the heat sink 1062, and a cooling fan mounted within a fan housing 1070 is positioned for drawing air into shroud 1068 and past the heat dissipating fins 1066.

The Peltier' devices 1050, 1052, 1054 can be selectively operated to heat or cool the conductive elements 1040, 1044, 1042 and thereby heat or cool the contents of any chambers and portions of chambers of the receptacle 300 that are in proximity to the respective conductive elements. The conductive elements 1040, 1042, 1044, as well as the isolating frame 1048, are in a fixed position with respect to the pouch 300. When the pouch 300 is inserted into the slot 1014 of the instrument 1000, the pouch 300 is disposed in close proximity to the conductive elements 1040, 1042, and 1044. When a chamber is filled with a substance, the chamber of a flexible pouch will expand into the conductive element, thereby providing more complete physical, as well as thermal, contact with the conducting element positioned adjacent that chamber.

The results of an analytical procedure performed with the receptacle 10 or 300 and instrument 100 or 1000 are determined by measuring an optical output of the sample, such as fluorescence or luminescence. Accordingly, an optical detector is provided with a lens projecting through opening 176 formed in the front portion 120 of the processing unit 102. In the illustrated embodiment, the optical detector is a fluorometer 500. Alternative detectors could be readily adapted for use with the illustrated instrument, including detectors that sense electrical changes or changes in physical characteristics, such as mass, color or turbidity.

Details of a fluorometer embodying aspects of the present invention are shown in FIGS. 6, 7, 8a-c, and 9a-c. The fluorometer 500 includes a front housing 502 and a rear housing 520 together mounted to a base 580.

Front housing 502 partially encloses an interior lens chamber 506 and includes an upper barrel 504 having a generally cylindrical shape. The upper barrel 504 extends into opening 176 formed in an actuator plate 124 (see FIG. 3) within the instrument 100, or onto an opening formed in the manifold 1082 of the instrument 3000 (see FIG. 14, 18). Front housing 502 further includes three mounting legs 510 for securing the fluorometer 500 to the actuator plate 124 within the instrument 100 or to the manifold 1082 of the instrument 1000.

The rear housing 520 is mounted, beneath the front housing 502, to the base 580 by mechanical fasteners or the like. In the illustrated embodiment, the rear housing 520 includes four light conduits extending from one end thereof to the opposite end thereof. In particular, the rear housing includes a first emission conduit 522, a second emission conduit 524, a first excitation conduit 526, and a second excitation conduit 528. Housing 520 is exemplary; the fluorometer 500 may include one or more emission conduits and one or more excitation conduits.

Further details of the rear housing 520 are shown in FIGS. 6 and 7a-c. Within housing 520, the two excitation conduits 526 and 528 are identical and the two emission conduits 522 and 524 are identical.

Each excitation conduit 526, 528 includes a first portion 532 having a cross-section in the general shape of a right triangle with rounded corners and a convexly rounded hypotenuse. The purpose of this shape is to limit the weight of the rear housing 520. The shape is merely preferred; other cross-sectional shapes can be used for the conduits—including circular or rectangular—so long as the features of the conduit do not interfere with the passage of light. The excitation conduits 526, 528 further include a second portion 534 that is generally cylindrical in shape. A circular passage 536 connects the first portion 532 with the second portion 534, and the diameter of passage 536 is smaller than that of second portion 534, thereby forming an annular lens shelf 540 within second portion 534. Finally, excitation conduits 526, 528 include an O-ring seat 538 formed at the end of second portion 534.

Each emission conduit 522, 524 includes a first portion 552 having a cross-section in the general shape of a right triangle with rounded corners and a convexly rounded hypotenuse. The emission conduits 522, 524 further include a second portion 554 that is generally cylindrical in shape. A circular passage 556 connects the first portion 552 with the second portion 554, and the diameter of passage 556 is smaller than that of second portion 554, thereby forming an annular lens shelf 560 within second portion 554. Emission conduits 522, 524 also include an O-ring seat 558 formed at the end of second portion 554. Finally, a circular photodiode seat 562 is superimposed within an end of the first portion 552 of each of the emission conduits 522, 524.

Front housing 502 and rear housing 520 are preferably machined from 6061 T6 aluminum and have a black anodized finish. Alternatively, the front and rear housings could be molded or cast—either separately or as a single, integrated unit, from any material that can withstand the temperature environment within the instrument and will provide uninterrupted light conduits.

Base 580 includes a front printed circuit board ("PCB") 582 and a rear printer circuit board ("PCB") 586. Front PCB 582 and rear PCB 586 are held together in a fixed, spaced-apart relation by mechanical fasteners (e.g., bolts, screws) extending through cylindrical spacer elements 584. Details of exemplary circuits for the PCB's 582, 584 are described below.

Figure 9B:
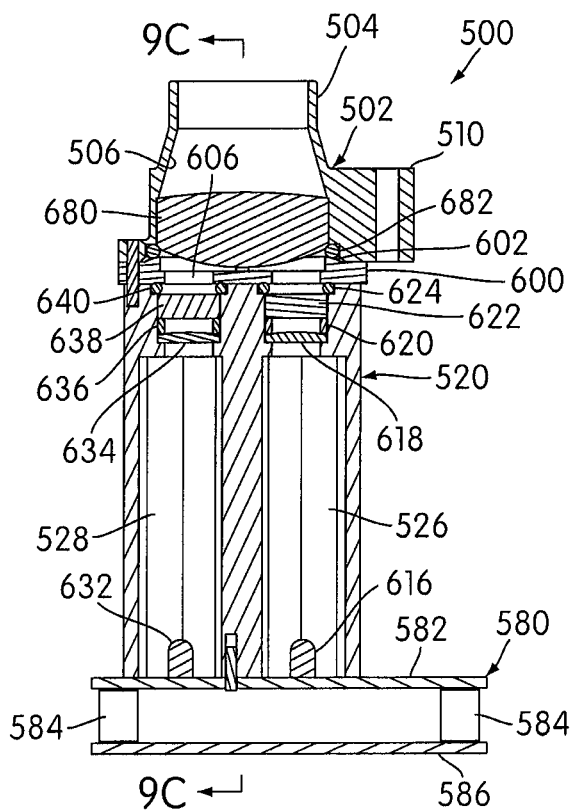
FIG. 9B is a cross-section of the fluorometer taken along the line 9B-9B of FIG. 9A.

With reference to FIG. 9b, installed within the first excitation conduit 526 of the rear housing 520 are first excitation optic elements. The first excitation optic elements include a first light emitting diode ("LED") 616 disposed at one end of the first portion 532 of the first excitation conduit 526 and mounted to the front PCB 582 of the base 580. A first excitation lens 618, which may be a collimating lens, is seated on the lens seat 540 within the second portion 534 of the first excitation conduit 526. A first excitation filter 622 is positioned at the end of the first excitation conduit 526 and is aligned in series with (i.e., along the optic axis of) the first excitation lens 618. The first excitation filter 622 and the first excitation lens 618 are separated from one another by a spacer 620, preferably made from aluminum with a black anodized finish. The first excitation conduit 526, along with the associated optics elements, are referred to collectively as the first excitation channel.

Similarly, second excitation optic elements are installed within the second excitation conduit 528 of the rear housing 520. The second excitation optic elements include a second LED 632 disposed at one end of the first portion 532 of the second excitation conduit 528 and mounted to the front PCB 582 of the base 580. A second excitation lens 634, which may be a collimating lens, is seated on the lens seat 540 of the second portion 534 of the second excitation conduit 528. A second excitation filter 638 is positioned at the end of the second excitation conduit 528 and is aligned in series with (i.e. along the optic axis of) the second excitation lens 634. The second excitation filter 638 and the second excitation lens 634 are separated from one another by a spacer 636, preferably made from aluminum with a black anodized finish. The second excitation conduit 528, along with the associated optics elements, are referred to collectively as the second excitation channel.

Figure 9C:
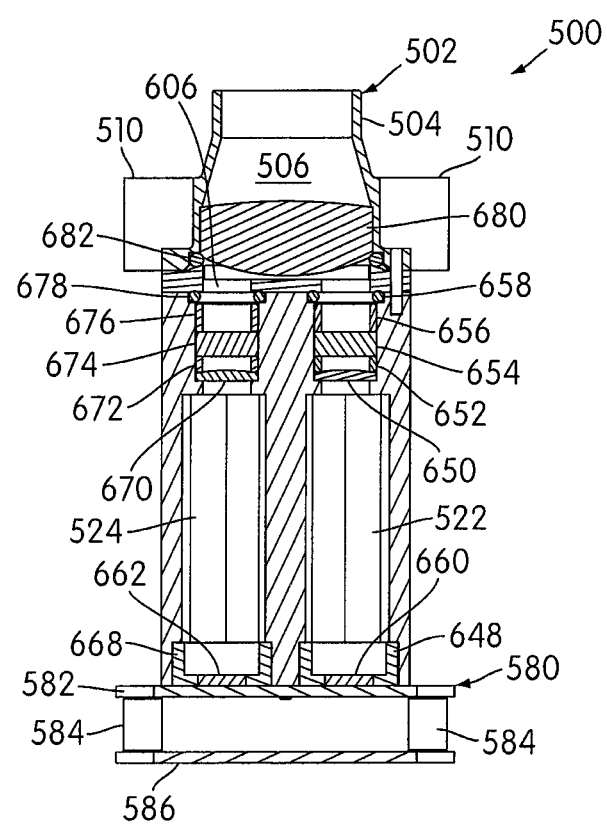
FIG. 9C is a cross-section of the fluorometer taken along the line 9C-9C of FIG. 9B.

With reference to FIG. 9c, first emission optic elements are installed within the first emission conduit 522 of the rear housing 520. The first emission optic elements include a first photodiode 660 mounted within a photodiode mount 648 disposed in the photodiode seat 562 within the first portion 552 of the first emission conduit 522 and mounted to the front PCB 582 of the base 580. A first emission lens 650, which may be a collimating lens, is seated on the lens seat 560 of the second portion 554 of the first emission conduit 522. A first emission filter 654 is positioned near the end of the first emission conduit 522 and is aligned in series with (i.e. along the optic axis of) the first emission lens 650. The first emission filter 654 and the first emission lens 650 are separated from one another by a spacer 652, preferably made from aluminum with a black anodized finish. Furthermore, the first emission filter 654 is separated from the end of the first emission conduit 522 by an additional spacer 656, also preferably made from aluminum with a black anodized finish. The first emission conduit 522, along with the associated optics elements, are referred to collectively as the first emission channel.

Similarly, second emission optic elements are installed within the second emission conduit 524 of the rear housing 520. The second emission optic elements include a second photodiode 662 mounted within a photodiode mount 668 disposed in the photodiode seat 562 within the first portion 552 of the second emission conduit 524 and mounted to the front PCB 582 of the base 580. A second emission lens 670, which may be a collimating lens, is seated on the lens seat 560 of the second portion 554 of the second emission conduit 524. A second emission filter 674 is positioned near the end of the first emission conduit 524 and is aligned in series with (i.e. along the optic axis of) the second emission lens 670. The second emission filter 674 and the second emission lens 670 are separated from one another by a spacer 672, preferably made from aluminum with a black anodized finish. Furthermore, the second emission filter 674 is separated from the end of the second emission conduit 524 by an additional spacer 676, also preferably made from aluminum with a black anodized finish. The second emission conduit 524, along with the associated optics elements, are referred to collectively as the second emission channel.

Figure 6:
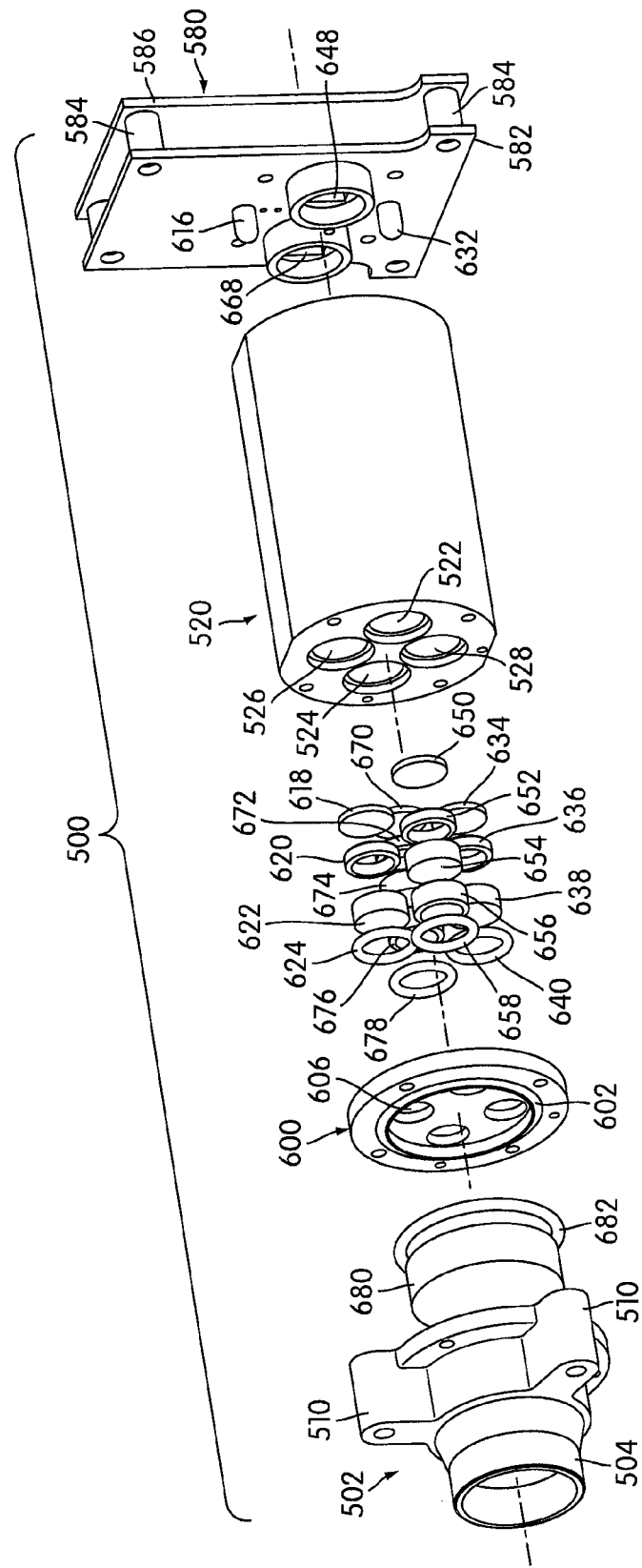
FIG. 6 is an exploded perspective view of a fluorometer embodying aspects of the present invention.
Figure 7:
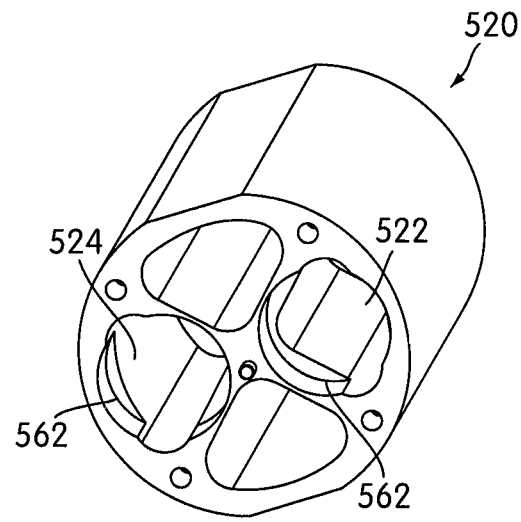
FIG. 7 is a perspective view of a rear housing of the fluorometer.
Figure 8A:
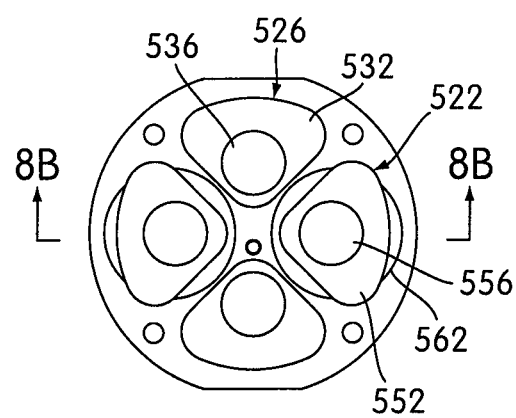
FIG. 8A is an end view of the rear housing of the fluorometer.
Figure 8B:
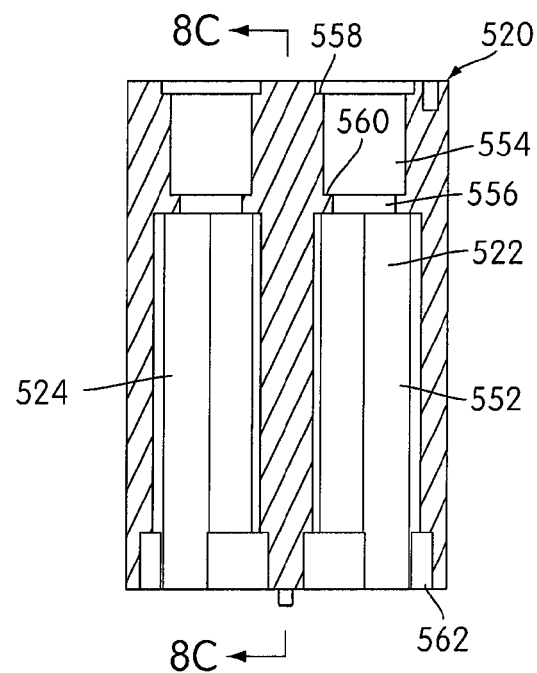
FIG. 8B is a cross-section of the rear housing taken along the line 8B-8B of FIG. 8A.
Figure 8C:
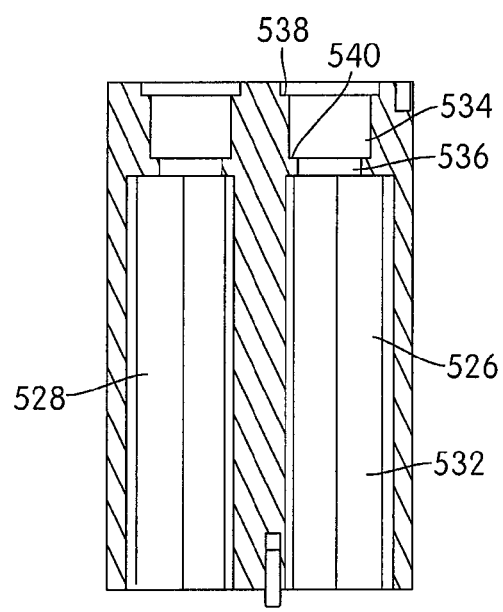
FIG. 8C is a cross-section of the rear housing taken along the line 8C-8C of FIG. 8B.

A front housing cover disc 600 is disposed between the front housing 502 and the rear housing 520 (see FIG. 6). The front housing cover disc 600 includes a raised circular ridge 602 projecting slightly within the lens chamber 506 of the upper housing 502 (see FIGS. 8b, 8c). The front housing cover disc 600 further includes four circular light openings 606, each being aligned with one of the light conduits 522, 524, 526, and 528 formed in the rear housing 520 when the cover disc 600 is installed.

A common lens 680 is housed within the lens chamber 506 of the front housing 502. In one embodiment, the fluorometer 500 includes only a single, undivided common lens 680 which comprises the only optic element of the fluorometer outside the excitation and emission conduits. In this context, "undivided" means the common lens is made exclusively from optically transmissive material (e.g., glass) and includes no structure for redirecting or impeding light, such as optically opaque structure embedded in and/or applied to the surface of the lens to physically and optically divide the lens into two or more sub-parts.

An O-ring 682 is seated at an end of the lens chamber 506, and the raised circular ridge 602 of the front housing cover disc 600 projects into the lens chamber 506, pressing against the O-ring 682 to ensure a light-tight connection between the front housing 502 and the front housing cover disc 600. An O-ring 624 is provided within the O-ring seat 538 at an end of the first excitation conduit 526 and compresses against a rear side of the front housing cover disc 600 to provide a light-tight connection. Similarly, an O-ring 640 is provided in the O-ring seat 538 of the second excitation conduit, an O-ring 658 is provided in the O-ring seat 558 of the first emission conduit 522, and an O-ring 678 is provided in the O-ring seat 558 of the second emission conduit 524. O-rings 624, 640, 658, 678 prevent light infiltration into the light conduits 526, 528, 522, 524, respectively. The O-rings prevent light infiltration by compensating for the dimensional variations of the machined parts within the specified tolerance and also by compensating for the deformations induced by thermal factors.

In operation, excitation light signals are emitted by the light-emitting diodes 616 and 632. The signals are preferably of a prescribed wavelength corresponding to a dye to be detected. Light from the diode 616 is transmitted through the first excitation conduit 526 and impinges upon lens 618 which focuses at least a portion of the light to the first excitation filter 622. The first excitation filter 622 passes light of only a prescribed wavelength (or a prescribed range of wavelengths) and removes undesirable wavelengths from the transmitted light. The filtered light progresses through the common lens 680, which focuses at least a portion of the light out through the upper barrel 504 of the front housing 502, where the excitation light impinges upon a chamber (for example, chamber C28) of a receptacle 10 within the instrument 100. Assuming the presence of a first analyte or group of analytes within that chamber, the dye of a first binding agent or group of binding agents mixed with the sample and adapted to detect the presence of the first analyte(s) will fluoresce. A portion of the fluorescent emission enters the upper barrel 504 and then travels through the common lens 680 which directs at least a portion of the fluorescent emission into first emission conduit 522. Light entering first emission conduit 522 passes through the first emission filter 654, which will filter undesired wavelengths of emission light. The filtered emission light then travels through the lens 650 and finally onto the photodiode 660, which will detect the presence of light at the prescribed wavelength.

Similarly, excitation light signals emitted by diode 632 are transmitted through the second excitation conduit 528 and impinges upon lens 634 which focuses at least a portion of the light to the second excitation filter 638. The second excitation filter 638 passes light of only a prescribed wavelength (or a prescribed range of wavelengths) and removes undesirable wavelengths from the transmitted light. The filtered light progresses through the common lens 680, which focuses at least a portion of the light out through the upper barrel 504 of the front housing 502, where the excitation light impinges upon a chamber (for example, chamber C28) of a receptacle 10 within the instrument 100. Assuming the presence of a second analyte or group of analytes within that chamber, the dye of a second binding agent or group of binding agents mixed with the sample and adapted to detect the presence of the analyte(s) will fluoresce. A portion of the fluorescent emission enters the upper barrel 504 and then travels through the common lens 680 which directs at least a portion of the fluorescent emission into second emission conduit 524. Light entering second emission conduit 524 passes through the second emission filter 674, which will filter undesired wavelengths of emission light. The filtered emission light then travels through the lens 670 and finally onto the photodiode 662, which will detect the presence of light at the prescribed wavelength.

Light emissions detected by the photodiodes are converted to signals that can provide qualitative or quantitative information about the presence or amount of an analyte or analytes in a sample using known algorithms. Examples of quantitation algorithms are identified in the "Uses" section hereinabove.

In the illustrated embodiment, the excitation conduits 526, 528 are located opposite each other, and the emission conduits 522, 524 are located opposite each other within the rear housing 520 to minimize background from excitation light passing through the emission filter. However, the excitation conduits 526, 528 and the emission conduits 522, 524 could be located next to each other.

Fluorometer 500 includes two excitation channels and two emission channels, which permit the fluorometer to differentially detect two dyes or reporter moieties that are excited at different wavelengths. Light emissions from these different dyes are generally quenched in the absence of target (e.g., an analyte, a control, or amplification product that is representative of the presence of either). Such dyes may include, for example, N,N,N'N'-tetramethyl-6-carboxyrhodamine ("TAMRA") and 6-carboxyfluorescein ("FAM") or 6-carboxy-X-rhodamine ("ROX") and 2'7'-dimethoxy-4'5-dichloro-6-carboxyfluorescein ("JOE"). DABCYL is useful quencher moiety for quenching light emissions from any of these dyes in the absence of target. Thus, the instrument is capable of distinguishing between two different analytes or groups of analytes or of distinguishing an analyte or group of analytes from an internal control. It is contemplated, however, that a fluorometer embodying aspects of the present invention may include more or less than two excitation and emission channels, with the number of excitation channels and the number of emission channels being equal.

The specific optical components selected for the excitation and emission channel(s) will depend on the wavelength of the dye fluorescence to be detected. For the dye FAM, for example, a suitable LED for the excitation channel is available from Kingbright Corporation of Brea, Calif. as Part No. L7113PBCH, and a suitable excitation filter for the same dye is available from Semrock of Rochester, N.Y. as Part No. FF01-485/20-9.0-D. For the same dye, a suitable photo-detector for the emission channel is available from OSI Optoelectronics, Inc. of Hawthorne, Calif. as Model No. PIN-44DI, and a suitable emission filter is available from Semrock as Part No. FF01-531/22-9.0-D. For the dye TAMRA, for example, a suitable LED for the excitation channel available from Nichia America Corporation of Torrance, Calif. as Model No. NSPG500S, and a suitable excitation filter is available from Semrock as Part No. FF01-543/22-9.0-D. For the same dye, a suitable photo-detector for the emission channel is available from OSI Optoelectronics as Model No. PIN-44DI, and a suitable emission filter is available from Semrock as Part No. FF01-587/11-9.0-D.

Accordingly, a fluorometer embodying aspects of the present invention is able to excite and detect multiple, different signals (such as different wavelengths) without moving with respect to the sample or without the different excitation and emission channels moving with respect to each other. Moreover, the arrangement of the fluorometer with respect to the actuator plate and the detection chamber of the receptacle carried within the instrument, enables the fluorometer to direct excitation signals at the detection chamber and detect emissions from the detection chamber without the use of fiber optics. Moreover, the optic channels (excitation and emission) defined by the fluorometer are parallel throughout there extents, and thus excitation light can be transmitted toward the sample and emissions from the sample can be detected without the use of reflective elements (e.g., mirrors) that redirect substantially all the light impinging on the element or light characteristic separating elements that redirect a portion of a light signal having a first optical characteristic (e.g., wavelength) and transmit another portion of the light signal having a second optical characteristic, such as a dichroic beam splitter.

FIGS. 21-26 illustrate one embodiment of suitable circuitry. This circuitry provides for local control of the fluorometer 500 with operating modes selected, measurements made, and results reported in response to macro commands communicated remotely via a serial interface.

Figure 21:
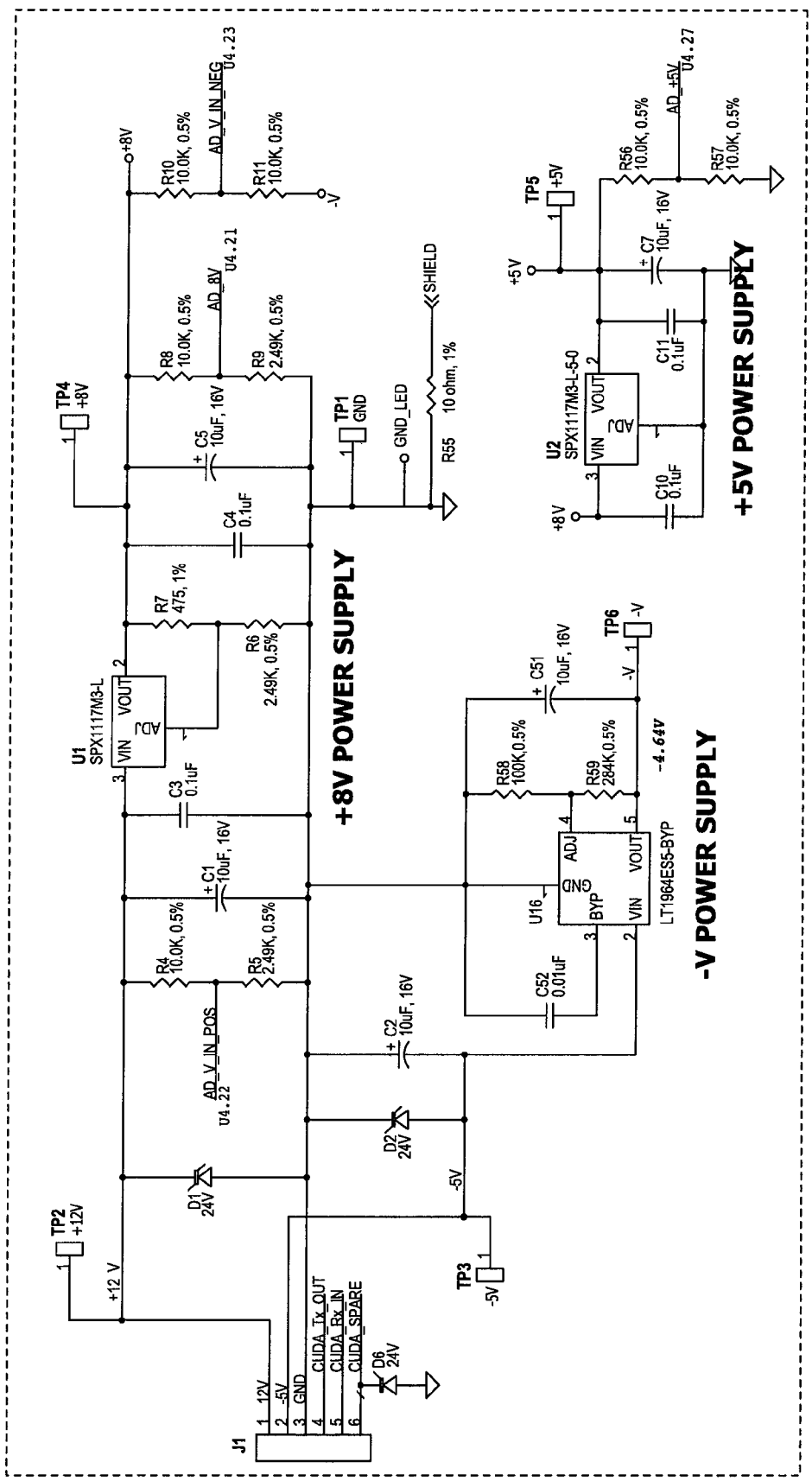
FIG. 21 is a schematic view of interconnection circuitry and power supplies for the fluorometer of FIGS. 6-9C.
Figure 22:
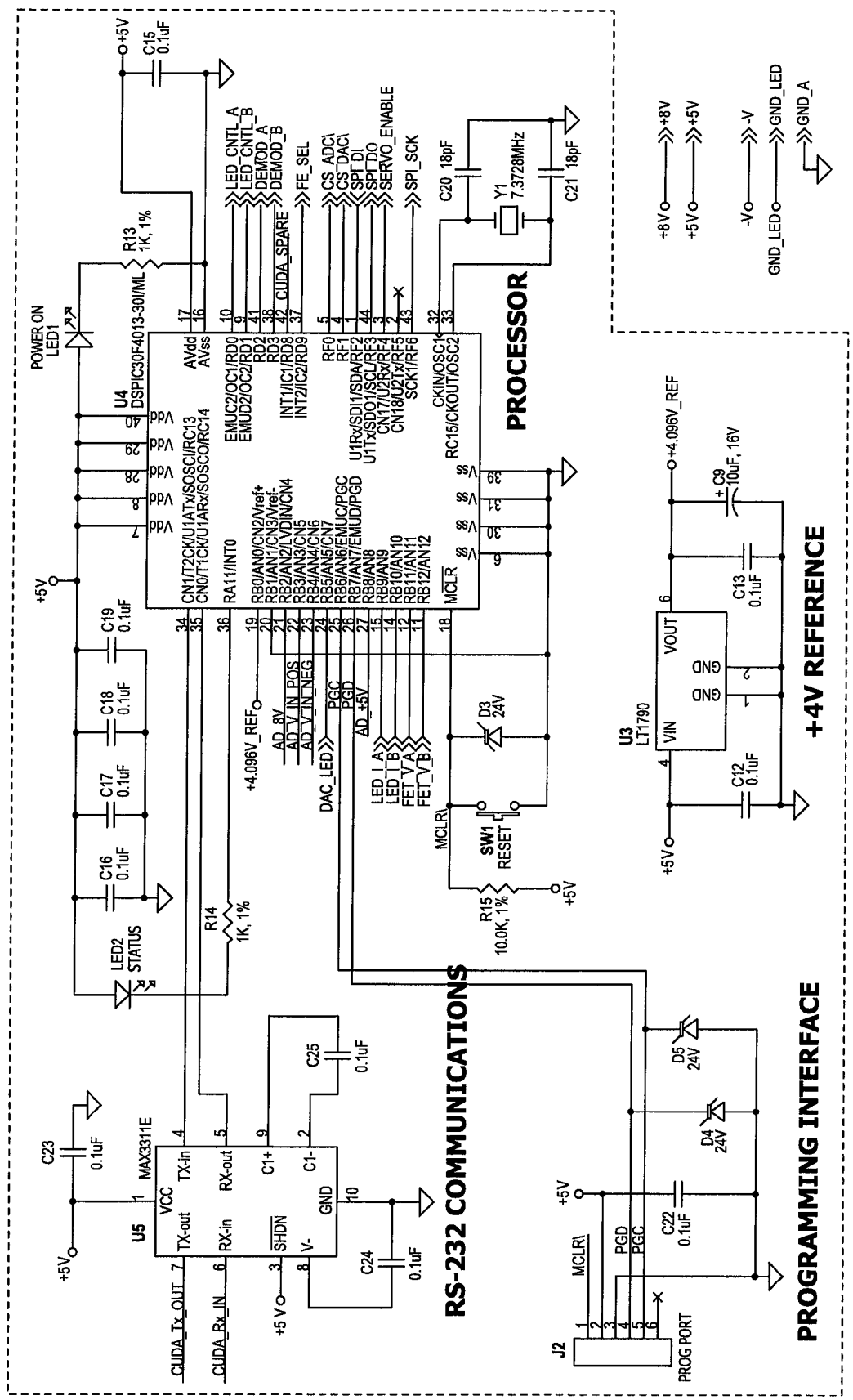
FIG. 22 is a schematic view of control, processing and communication circuitry for the fluorometer.
Figure 23:
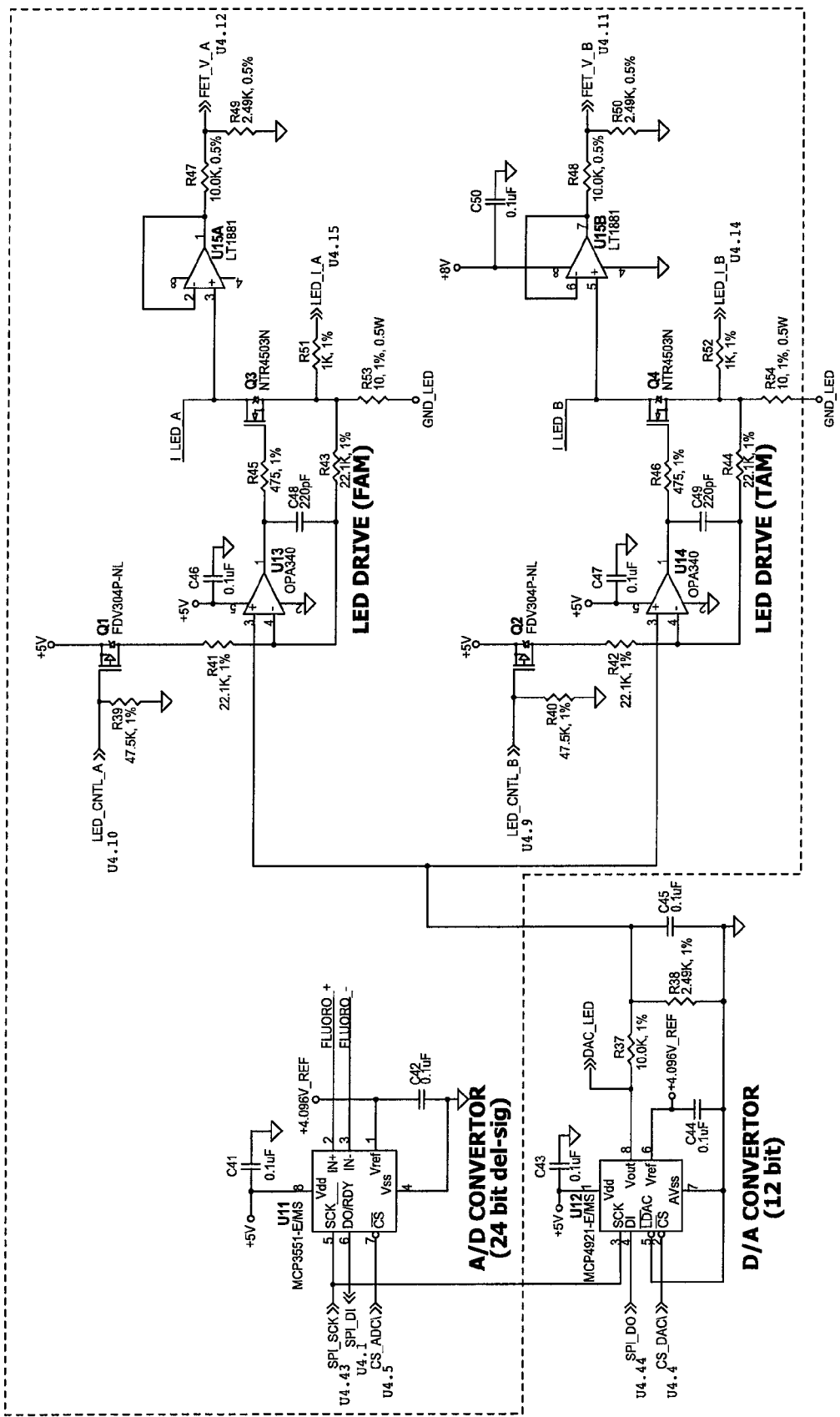
FIG. 23 is a schematic view of circuitry for voltage measurement and LED control for the fluorometer.
Figure 24:
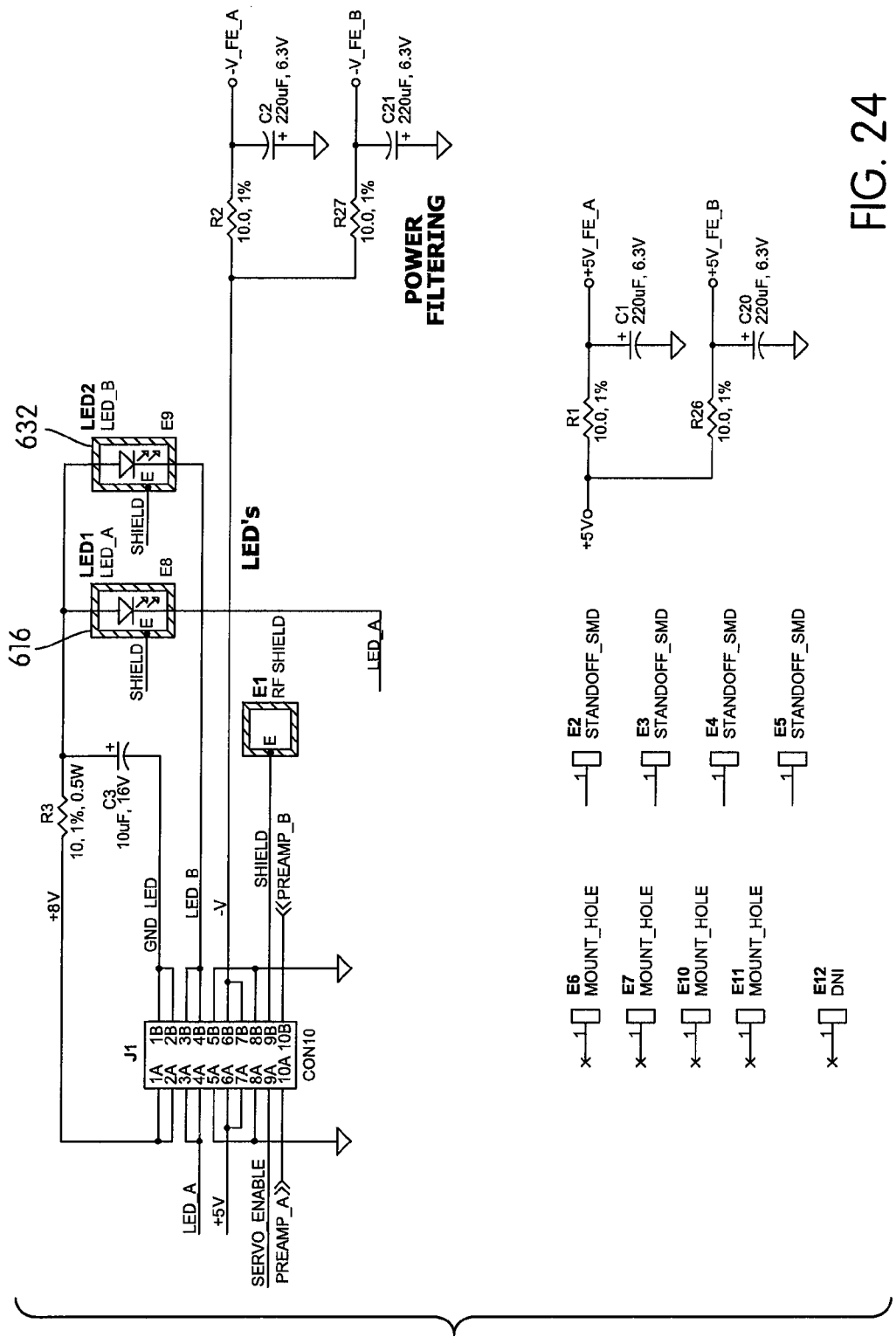
FIG. 24 is a schematic view of LEDs, RF shielding, and power filtering circuitry for the fluorometer.
Figure 25A:
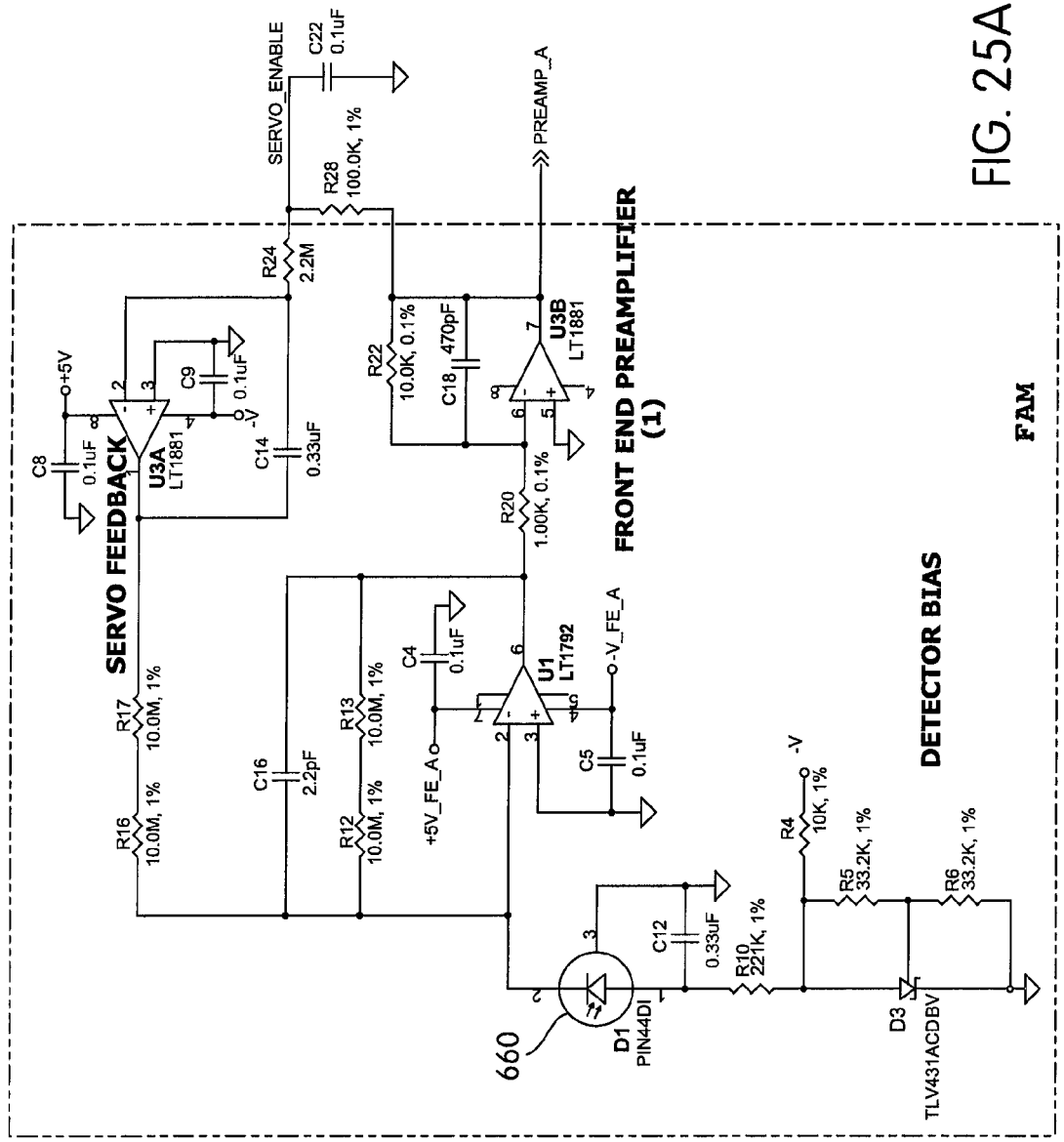
FIG. 25A is a schematic view of a first front-end amplifier circuit for the fluorometer.
Figure 25B:
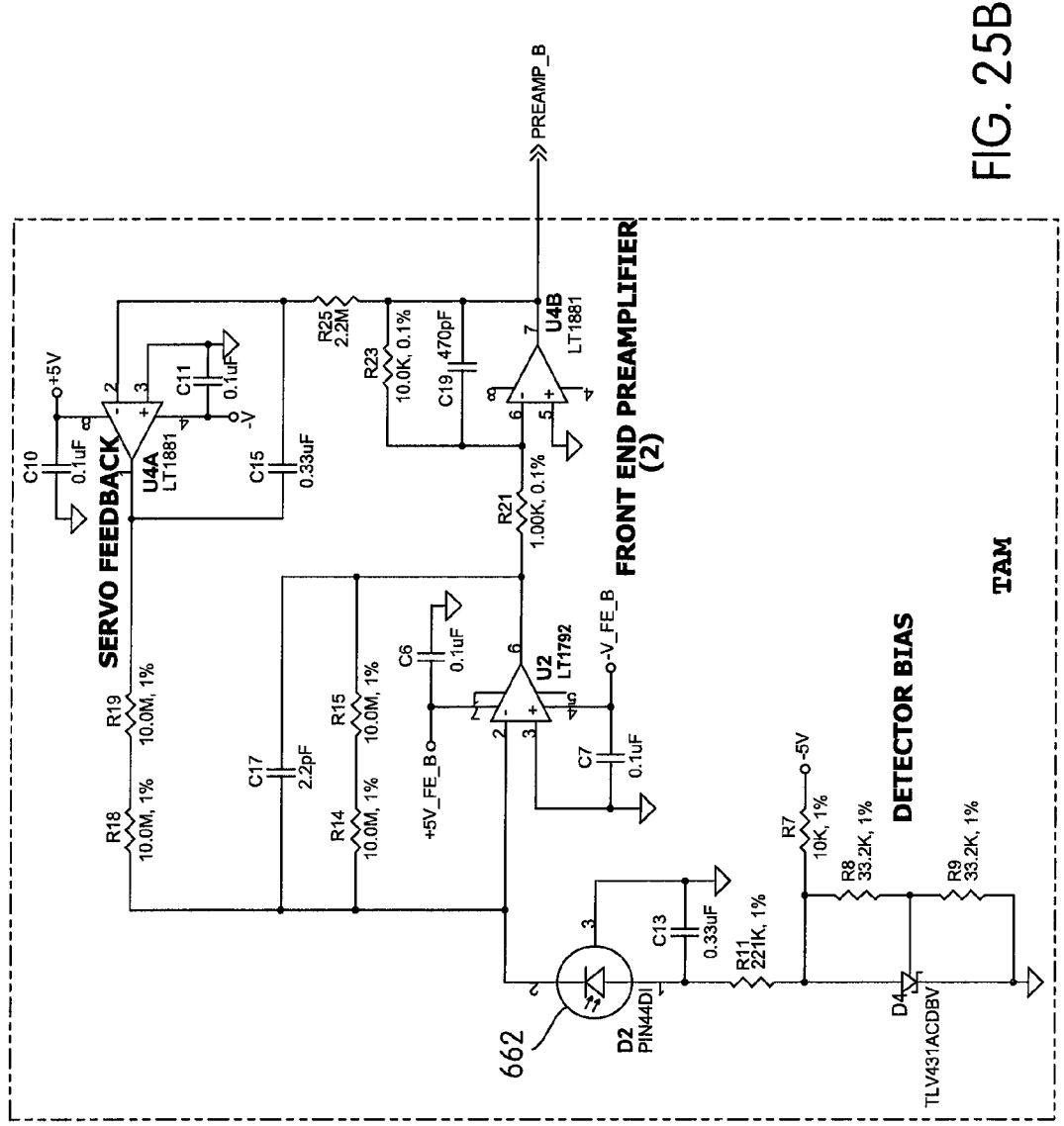
FIG. 25B is a schematic view of a second front-end amplifier circuit for the fluorometer.
Figure 26:
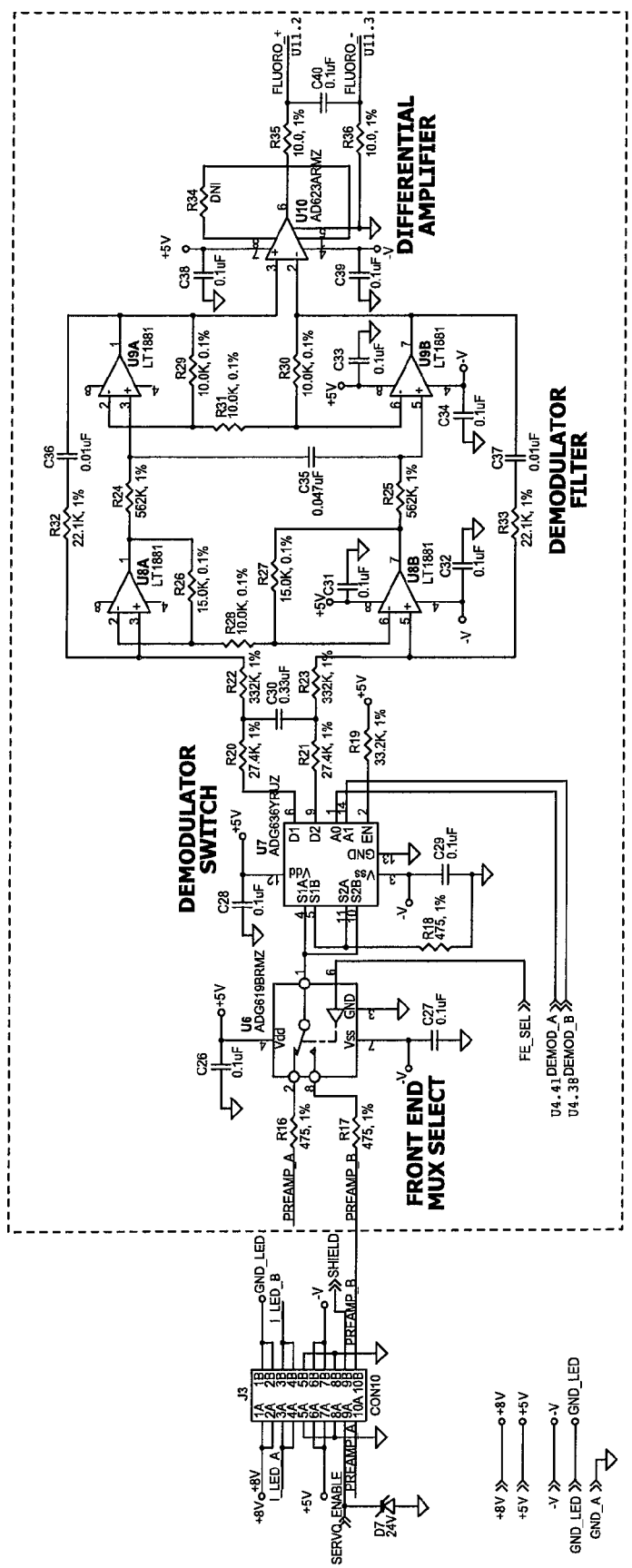
FIG. 26 is a schematic view of a demodulation circuit for the fluorometer.

FIG. 21 represents circuitry comprising interconnection means and a number of power supply circuits. FIG. 22 represents circuitry comprising control, processing and communication means, circuitry comprising means to program and debug the processor, and a circuit that provides a stable voltage reference. FIG. 23 represents circuitry comprising a voltage measurement circuit and a means to provide processor control of LED intensity and modulation. FIG. 24 represents circuitry comprising the excitation means (LEDs), an RF shield, and supplemental power filtering for sensitive preamplifier circuits (described in the next figures). FIG. 25A and FIG. 25B represent two similar embodiments of a front-end amplifier circuit (the differences of which are explained later) which convert the modulated optical signal from the contents of a chamber into a modulated electrical voltage. FIG. 26 represents a demodulation circuit that converts the modulated and amplified signal into an analog voltage proportional to the amplitude of the modulated optical signal.

This embodiment incorporates a modulation/demodulation scheme that allows the circuit to reject the effects of varying background ambient light whose wavelength falls within the band-pass range of the optical filters physically placed between the photodiodes D1 (660) (FIG. 25A) and D2 (662) (FIG. 25B) and the chamber being interrogated. Microprocessor U4 (FIG. 22) generates a clock (set at 275 Hz in this embodiment) that is used to alternately modulate LED1 (616) and LED2 (632) while controlling the polarity of the analog switch U7 (FIG. 26). By alternating the polarity of the analog switch U7 at the same frequency and in phase with the modulation of the LED (either LED1 (616) or LED2 (632)), a matched transmitter/receiver pair is created. Only those optical signals arriving at the same frequency and in phase with this clock will be amplified at full gain; all ambient light and other light signals modulated at a different frequency are suppressed.

In FIG. 21, J1 provides the main interconnection means to the circuit. Devices D1 and D6 protect the circuit by absorbing transient voltages that are applied to the circuit via this connection to external circuits. Integrated circuit U1 and associated components (C1, C3-C5, and R4-R7) form an adjustable voltage regulator that provides the positive analog power supply for this circuit. Integrated circuit U16 and associated components (C2, C51-C52, and R58-R59) form an adjustable voltage regulator that provides the negative analog power supply for this circuit. A separate +5V supply (U2 and associated components C7 and C10-C11) forms the digital power supply. Lastly, several resistor-divider pairs are provided (R4/R5, R8/R9, R10/R11, and R56/R57) to translate the voltage level out of each supply to a voltage within the conversion range of the A/D converter found in the microprocessor (U4).

In FIG. 22, microprocessor U4 provides the primary control and processing means for the circuit. A number of capacitors (C15-C19) provide power supply bypassing for this device. Power-on reset of the circuit is accomplished by circuitry incorporated within the microprocessor, however, the microprocessor can be manually reset by use of the pushbutton switch SW1 (in combination with pull-up resistor R15). A diode D3 is provided to protect the circuit from potential static discharge associated with ungrounded contact with the reset switch. Crystal Y1 and associated components (C20 and C21) provide a stable timebase and clock for the circuit. Communication between the microprocessor (U4) and external circuits is accomplished by use of integrated circuit U5 and associated components (C23-C25), converting TTL level serial signals in and out of the microprocessor to signals in compliance with the RS-232 standard. Programming and debugging of the circuit is accomplished by use of the PROGRAMMING INTERFACE (components J2, C22, and D4-D5). Visual indicators are provided to indicate "Power On" (components LED1 and R13) and "Status" (components LED2 and R14 with on/off control provided by the microprocessor U4). Lastly, a precision voltage reference circuit (components U3, C9, and C12-C13) is provided to establish a stable reference for the A/D converter (which is incorporated within the microprocessor U4) and to the external A/D converter U11 and D/A converter U12.

In FIG. 23, integrated circuits U11 and U12 provide an interface between the analog circuits of the device and the microprocessor U4. Both of these devices are controlled by and communicate with the microprocessor U4 via its Serial Peripheral Interface (SPI). A/D CONVERTER U11 converts the differential analog signal out of the DEMODULATOR FILTER (FIG. 26) into a digital result with 24-bit resolution (signed, with approximately 0.5 µA of resolution per bit). D/A CONVERTER U12 receives a digital setting from the microprocessor and sets a corresponding analog voltage on its output, a voltage which is then used to regulate LED current. The DAC output voltage is connected to a resistor divider with a low-pass filter (components C45 and R37-R38) which lowers this output control voltage, resulting in the circuit being capable of controlling LED current over the range of 0-80 mA with 20 µA/bit resolution. Two identical circuits follow, one for FAM LED DRIVE and the other for TAM LED DRIVE.

In FIGS. 23 and 24, circuits are provided that directly regulate and modulate the flow of current through the excitation LEDs (LED1 (616) and LED2 (632)). Power to the LEDs originates from the +12V supply. LED current flows first through resistor R3 that reduces the voltage potential of the supply and, in conjunction with capacitor C3, provides filtering of the switched current load to the modulated LED. Current then flows through the LED (LED 1 (616) or LED2 (632)) and then through the drain source channel of a FET transistor (Q3 or Q4). Finally, the LED current passes through a feedback resistor (R53 or R54) that generates a voltage proportional to the current through the LED.

Referring to FIG. 23, control of electrical current through the LED is achieved by use of a traditional feedback circuit comprised of an operational amplifier (U13 or U14), FET transistor (Q3 or Q4), and feedback resistor (R53 or R54). Control is achieved when the voltage potential is equal at both inputs of the operational amplifier. Should the voltage at the inverting input of the operational amplifier drop below the voltage at the non-inverting input, the voltage at the output of the operational amplifier increases. This increase in output voltage is incident on the gate of the FET transistor, which then starts to conduct more electrical current. An increase in electrical current through the feedback resistor results in an increase in voltage across that resistor and a corresponding increase in voltage on the inverting input of the operational amplifier, completing the feedback loop.

Additionally, to control switching (modulation or power on/off) of the LED, circuits are provided (Q1 or Q2 and associated components) that force the operational amplifier into and out of saturation, thereby switching the controlling FET transistors (Q3 or Q4) off and on, respectively. In order to "inhibit" LED current, the voltage potential at the gate of the FET transistor (Q1 or Q2) is taken several volts below the voltage at the source terminal of the FET. This in turn allows current to flow through the FET and into the circuit node formed at the inverting input of the operational amplifier, thereby causing the voltage to rise to approximately 2.5V at that node. The output voltage of the operational amplifier subsequently drops to zero volts and the FET transistor (Q3 or Q4) is turned off, along with the respective LED. To "enable" LED current, the voltage potential at the gate of the FET transistor (Q1 or Q2) is kept at a voltage equal to or slightly below the voltage at the source of the transistor. This keeps the transistor turned "off", with no current flowing through the FET into the circuit node at the inverting input of the amplifier. Voltage at the inverting input of the operational amplifier is now equivalent to the voltage across the feedback resistor (R53 or R54), and this voltage now tracks the voltage applied by the DAC circuit to the non-inverting input of the operational amplifier. LED current is controlled proportionally to this applied voltage.

In FIG. 23, LED health is monitored by the use of circuitry to probe the voltage across and current passing through the LED. Resistors R51 and R52 provide a low impedance path between the A/D converter of the microprocessor U4 (see FIG. 22) and the respective feedback resistors (R53 and R54); voltage measured by the A/D circuit across these resistors is proportional to LED current. In addition, LED voltage can be determined by use of the voltage buffering circuit formed by operational amplifier U15 and associated components. A resistor divider circuit (R47/R49 or R48/R50) follows the buffering amplifier to bring the voltage down to a level within the conversion range of the A/D converter. LED voltage is calculated by taking the reduced voltage out of the buffer amplifier plus the voltage measured across the respective feedback resistor (which equates to the voltage across the dropping resistor R3) and subtracting these from the measured value of the +12V supply (with specific weighting for each measurement).

In FIG. 23, additional features are illustrated that improve circuit rejection of transient stimuli (both internally and externally generated). An RF shield E1 is provided to protect the circuitry found in FIGS. 25A and 25B from electromagnetic and radio frequency interference. Two guard circuits (E8 and E9) are provided to prevent electrical leakage between the current carrying conductors to the LEDs (LED 1 (616) and LED2 (632)) and the sensitive circuits found in FIGS. 25A and 25B. These guard circuits are comprised of exposed ground traces on the outside layers of the board, adjacent to and encircling exposed pads and traces connected to the LEDs. Lastly, four low-pass filters (R1/C1, R2/C2, R26/C20, and R27/C21) are utilized to provide additional attenuation of power supply noise on the supplies used for the preamplifiers (U1 and U2, FIGS. 25A and 25B).

Referring now to FIGS. 25A and 25B, a photodiode (D1 (660) or D2 (662)) converts incident light (both background illumination and the modulated fluorescent signal from the contents of the chamber being interrogated) into an electrical current which is supplied into the circuit node connected to the inverting input of the operational amplifier (U1 or U2). Components D3 and R4-R6 (FIG. 25A; and D4 and R7-R9 in FIG. 25B) create a bias voltage on the anode of this photodiode; a higher bias voltage increases dark current through the diode while decreasing photodiode noise. Next, a compensation circuit is provided (U3A and U4A and associated components) that generates an offsetting current equivalent to the current out of the photodiode attributable to ambient light. This compensation is vital as ambient light can create current out of the photodiode that is many orders of magnitude greater than the electrical current attributable to the modulated fluorescent signal. Without correction, any variation in the level of ambient light can result in offsets to the measurement. In addition, without compensation, the current out of the photodiode associated with ambient light is likely to saturate the output of the preamplifier circuit. Lastly, a trans-impedance amplifier circuit is provided (U1 or U2 and associated components) that generates a voltage sufficient to source/sink any additional current out of the photodiode. The voltage out of this amplifier (U1 or U2) is proportional to current out of the photodiode that is attributable to the modulated optical signal from the contents of the chamber being interrogated. Additionally, there is a small amount of signal associated with change in ambient background lighting (which is filtered out by the subsequent demodulator circuit).

Due to the high gain of the trans-impedance preamplifier and the small signal being measured, the circuit described in the preceding paragraph can be highly susceptible to drift as a result of changes in temperature and humidity. To minimize these effects, a number of design and process provisions are implemented in preparing circuit boards 582, 586. First, all circuit traces and components are located as far as possible from other circuits. Second, the printed circuit solder mask has been eliminated from underneath components R12-R15 and C16-C17. This provides a greater clearance between the circuit board and the components, enabling wash and rinse reagents to pass through during sample processing procedures. Third, cylindrical resistors (MELF type) are selected for use at R12-R15 (again, maximizing clearance between components and the circuit board). Lastly, to minimize the amount of contaminants and residual flux remaining on the circuit board after assembly, the board is first washed with saponifiers appropriate for the solder/flux used in the soldering process, followed by a rinse with de-ionized water. Photodiodes D1 (660) and D2 (662) are preferably soldered to the circuit board (after the above assembly process is completed) with a "no-wash flux" core solder. Residual flux remaining on the circuit board after this last soldering process provides a protective barrier and, therefore, is preferably not removed.

Referring again to FIGS. 25A and 25B, amplifiers U3B and U4B (and associated components) provide additional amplification of the signal. In addition, feedback components R22 and C18 form a simple low-pass filter within that amplifier circuit (attenuating signals above 34 KHz). Concerning the compensation feedback circuit (identified in FIGS. 25A and 25B as "SERVO FEEDBACK"), operational amplifiers U3A and U3B (and associated components) are configured as integration amplifiers with a cut-off frequency of approximately 5 Hz. The output voltage of these amplifiers create a DC bias current that negates that portion of the electrical current from the photodiode (D1 (660) or D2 (662)) that is attributed to background ambient light and other natural DC offsets in the circuit. This results in an output signal (at U3B or U4B) that has a zero DC voltage component, i.e., the signal is centered around 0V.

In FIG. 25A, components R28 and C22 (in combination with digital control signal "SERVO_ENABLE" from the microprocessor) are used to disable the compensation amplifier (U3A only) from integrating at times when the TAM circuit (FIG. 25B) is being utilized. This is because the output spectra of LED2 (632) (TAM) overlaps the band-pass of the optical filters in front of photodiode D1 (660). Without this disable feature, the FAM detector/amplifier circuit (FIG. 25A) would integrate the excitation signal used for the TAM circuit (FIG. 25B), resulting in longer circuit settling times when the circuit is switched back to measure FAM response. Disabling of the integrating function in the FAM compensation circuit (U3A and associated components) is accomplished by setting the "SERVO_ENABLE" output from the microprocessor U4 to active ground. At other times, this digital signal from the microprocessor is tri-stated and components R28 and C22 have no effect on the operation of the circuit.

Referring to FIG. 26, the entire circuit takes an incoming AC signal, modulated at the same frequency as the respective LED, and converts this signal to a DC voltage (referenced to circuit ground) with amplitude six times that of the peak-to-peak AC voltage. The two signals "PREAMP_A" and "PREAMP_B" (the outputs from the circuits in FIGS. 25A and 25B, respectively) are connected to the two contacts of a solid-state, single-pole, double-throw analog switch (U6). "FE_SEL" is the logic signal that determines whether the signal "PREAMP_A" or "PREAMP_B" will be connected through switch U6 to the subsequent analog switch U7. Analog switch U7 acts as a sort of buffer/inverter, alternately switching its two inputs (the selected preamplifier output and circuit ground) to either of the positive and negative inputs of the demodulator filter (operational amplifiers U8, U9, and associated components). In this implementation, the DEMODULATOR SWITCH (U7) is switched in phase with the LED, such that when the LED is powered, the more positive signal out of the preamplifier is switched to the positive input of the demodulator filter (through R20) and the more negative signal is switched to the negative input of the demodulator filter (through R21). Connections to the DEMODULATOR FILTER are reversed when the LED is turned off. In this manner, the maximum positive gain is attained from the demodulator and filter circuit.

Continuing with FIG. 26, the output of the analog switch U7 is connected to a low-pass filter (comprised of components R20, R21, and C30) with a cut-off frequency of approximately 9 Hz. Capacitor C30 of this filter is charged to a DC voltage of amplitude approximately one-half that of the peak-to-peak amplitude of the modulated signal coming out of the preamplifier as a result of the switching of the preamplifier signal through analog switch U7. The subsequent active filter (operational amplifiers U8A/B and U9A/B and associated components) comprises a multi-pole, low-pass filter with gain of approximately 12. In the first part of this filter, operational amplifier U8A/B (and associated components) form a differential amplifier with a DC gain of 4. The output of this filter is passed through a low-pass filter (components R24, R25, and C35) with a cut-off frequency of approximately 3 Hz. The second active stage of this filter is comprised of operational amplifier U9A/B (and associated components) which forms a differential amplifier with a DC gain of 3. Components R32 and C36 form a feed-forward compensation path for the positive side of this filter while components R33 and C37 form a feed-forward compensation path for the negative side of this filter. This filter is used to attenuate any and all signals from the pre-amplifier that fall outside of a 10 Hz range around the operating frequency of the LEDs (275 Hz in this example).

Finally, in FIG. 26, the outputs of the DEMODULATOR FILTER are fed into a differential amplifier circuit (U10) with unity gain. Its function is to convert the voltage differential between the two signals out of the differential filter into a positive voltage referenced to circuit ground. The two output signals "FLUORO+" and "FLUORO−" connect to the A/D converter discussed above.

Figure 10A:
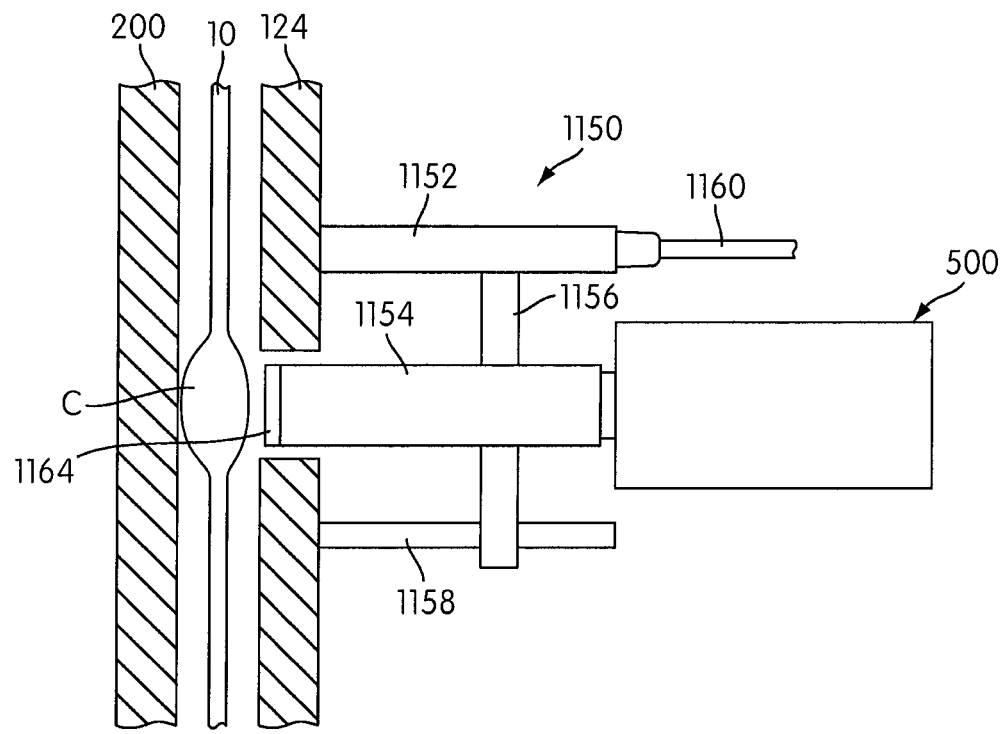
FIGS. 10A and 10B are a side and top view, respectively, of an embodiment of a compression pad integrated with a signal detector.
Figure 10B:
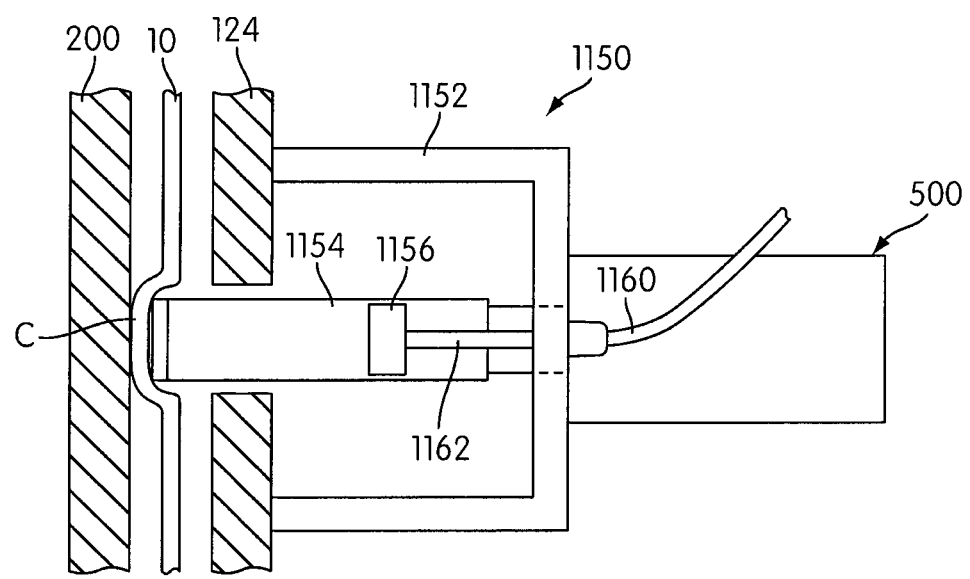

In certain circumstances, it is necessary or desirable to move substance out of a detection chamber of a receptacle. Under such circumstances, it may be necessary to incorporate a chamber compression member with a detector, such as the fluorometer 500 described above. One such embodiment of a compression member for incorporation with a detector is shown in FIGS. 10A and 10B. The compression mechanism, or detector actuator, is designated by reference number 1150 and includes a bracket 1152 connected to and projecting from the actuator plate 124. A compression tube 1154 is positioned in front of the lens of the detector 500 and extends through an opening in the actuator plate. Compression tube 1154 may have a transparent window 1164 mounted at its distal end relative to the detector 500. An actuating bar 1156 extends transversely in opposite directions from the compression tube 1154. An actuating mechanism, for example, a pneumatic piston represented by rod 1162 connected to a pressure source by pneumatic line 1160, is carried on the bracket 1152 and engages the actuating bar 1156 to move the compression tube 1154. A guide rod 1158 extends from the actuator plate 124 through an opening in a bottom end of the actuating bar 1156.

Extending the actuating mechanism 1162 against the actuating bar 1156 moves the compression tube 1154 to an extended position (to the left as shown in FIG. 10*b*) to compress the chamber C against the door assembly 200. The guide rod 1158 extending through the actuating bar 1156 helps keep the compression tube 1154 in a straight orientation and helps prevent skewing of the compression tube 1154 during movement of the tube by the actuating mechanism 1162. Guide rod 1158 may be omitted if skewing of the compression tube 1154 is not a concern.

Figure 11:
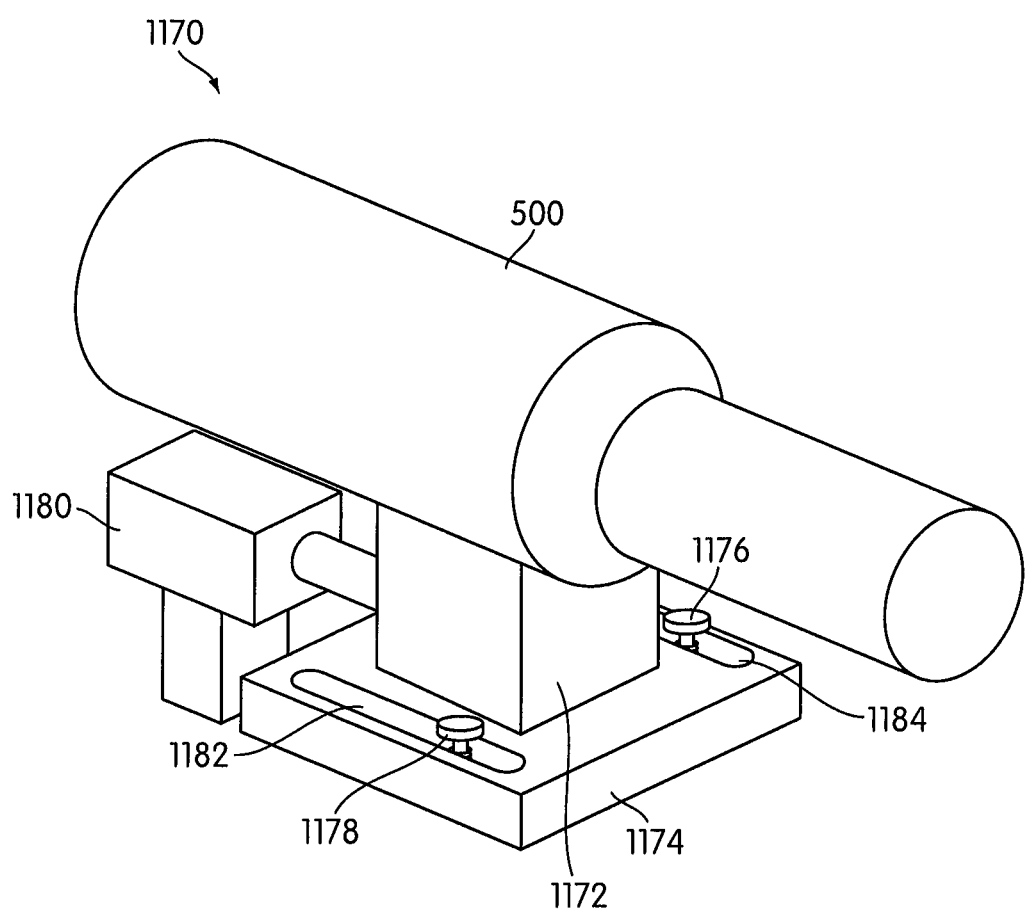
FIG. 11 is a perspective view of an alternative embodiment of a compression pad integrated with a signal detector.

An alternative mechanism for incorporating a compression member with a detector is shown in FIG. 11. In FIG. 11, detector 500 is mounted on a translating mounting platform or sled 1172 having a base 1174 with guide pins 1176 and 1178 extending through longitudinal slots 1184 and 1182, respectively. A piston (for example, a pneumatic piston) 1180 causes reciprocal movement of the sled 1172 and the detector 500 and thus provides a means for moving the entire detector into and out of engagement with a receptacle chamber.

Figure 18:
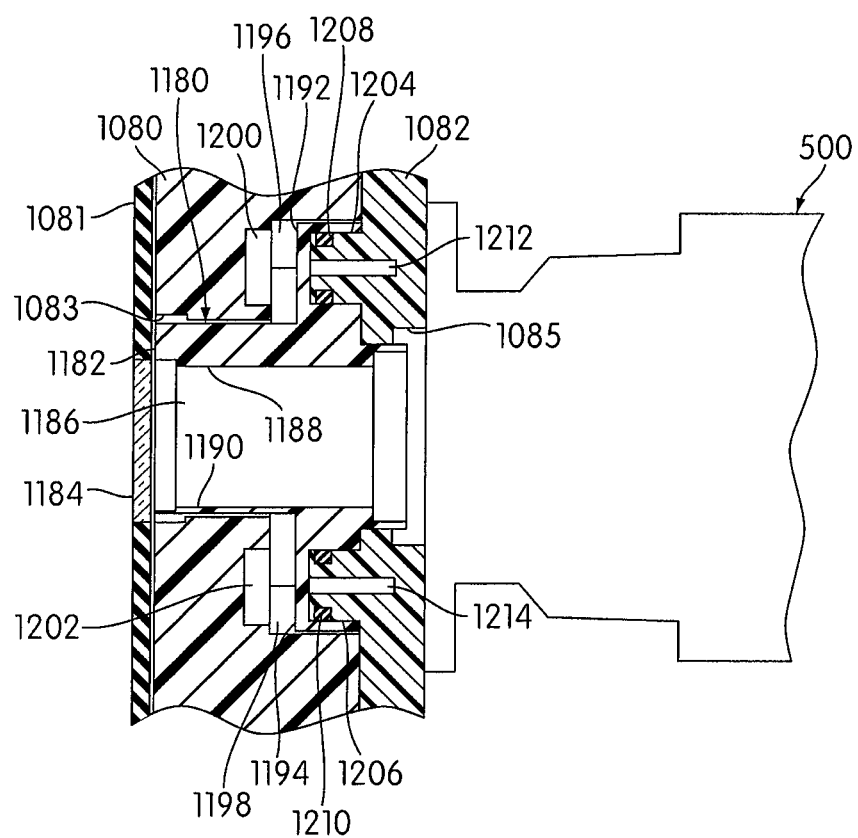
FIG. 18 is a cross-section of an alternative embodiment of a compression pad integrated with a signal detector

FIG. 18 shows a transverse cross section of an alternative embodiment of a compression pad 1180 integrated with the signal detector 500. The compression pad 1180 comprises an actuator cup 1182 disposed within an opening 1083 formed through the actuator plate 1080. A transparent window, or detection lens, 1184 is positioned in front of the actuator 1182 within an opening formed in the elastomeric shield 1081. A generally circular through bore 1186 is formed through the cup 1182 at an off center position with respect to an axis of symmetry of the actuator cup 1182, thus forming an upper portion 1188 of the actuator cup 1182 that is thicker than a lower portion 1190 of the cup 1182. A reason for the off-center location is that there may be extra air in the detection chamber during the detection process to help ensure better thermal contact between the chamber and a heater element disposed adjacent the chamber and also helps with the fluidics transfer from the chamber of lower volumes of liquid. Because the extra air will cause the liquid to pool down towards the bottom of the "actuator area" (air rises to the top), the off-center detection lens and focal point of the fluorometer 500 are configured to read fluorescence in the lower portion of the detection area, where there will be more liquid (and therefore more fluorescence). In an alternate implementation, for example, when the detection chamber if fully full of liquid, the bore 1186 may be formed through the center of the actuator cup 1182.

The actuator cup 1182 further includes a first radial lug 1192 and a second radial lug 1194 extending from diametrically opposed positions on the actuator cup 1182. Radial lug 1192 resides within a radial opening 1196 extending from the opening 1083, and radial lug 1194 resides within a radial opening 1198 extending from the opening 1083. A circular blind hole 1200 extends from the radial opening 1196, and a circular blind hole 1202 extends from the radial opening 1198. Blind holes 1200 and 1202 hold coil compression springs (not shown) which press against the radial lugs 1192 and 1194 to bias the cup 1182 in the retracted position, as shown.

Detector 500 is mounted to the manifold 1082 over an opening 1085 formed through the manifold. First and second cylindrical projections 1204 and 1206 extend from the manifold 1082 on opposite sides of the opening 1085. An O ring 1208 is positioned on the cylindrical projection 1204, and an O ring 1210 is positioned on the cylindrical projection 1206. Cylindrical projection 1204 extends in to a cup-like blind hole formed in the radial lug 1192, and the cylindrical projection 1206 extends into a cup-like blind hole formed in the radial lug 1194. An air pressure conduit 1212 extends into the cylindrical projection 1204 and exits at the top of the projection. Similarly, an air conduit 1214 extends into the cylindrical projection 1206 and exits from the top of the projection. The actuator cup 1182 is moved from the retracted position shown in FIG. 18 to an extended position (to the left as shown in the figure), by applying pressure at the conduits 1212 and 1214, thus pushing the radial projections 1192 and 1194 up into the radial openings 1196 and 1198, respectively, and moving the actuator 1182 to the left. The depth of the circular blind holes 1200 and 1202 accommodate the length of the compressed springs (not shown) thereby permitting the radial lugs 1192, 1194 to move completely to the ends of the radial openings 1196, 1198.

EXAMPLES

Examples are provided below illustrating some of the uses of the receptacles and systems provided herein. Skilled artisans will appreciate that these examples are not intended to limit the invention to the particular uses described therein. Additionally, those skilled in the art could readily adapt the receptacles and systems provided herein for use in performing other kinds of reactions, processes or tests.

The following examples provides a number of experiments that were conducted to compare the sensitivity of a manual, real-time transcription-mediated amplification ("TMA") reaction with that of automated real-time TMA reactions using either liquid or dried amplification and enzyme reagents. TMA reactions are two enzyme, transcription-based amplification reactions that rely upon a reverse transcriptase to provide an RNase H activity for digesting the RNA template after producing a complementary DNA extension product with an antisense primer or promoter-primer. Examples of TMA reactions are disclosed in McDonough et al., U.S. Pat. No. 5,766,849; Kacian et al., U.S. Pat. No. 5,824,518; and Becker et al., U.S. Pat. No. 7,374,885. The target for this experiment was *Chlamydia trachomatis* 23S ribosomal RNA, referred to hereinafter as "the target nucleic acid."

In each experiment, a "wobble" capture probe was used to non-specifically bind the target nucleic acid in the test samples. The wobble capture probe consisted of a 3' region having a random arrangement of 18 2'-methoxyguanine and 2'-methoxyuridine residues (poly(K)$_{18}$) joined to a 5' tail having 30 deoxyadenine residues (poly(dA)$_{30}$). Complexes comprising the wobble capture probe and bound target nucleic acid were immobilized on magnetically-responsive particles having oligonucleotide tails consisting of 14 deoxythymine residues (poly(dT)$_{14}$) derivatized thereon and then subjected to a wash procedure to remove interfering substances from the test samples.

After the wash procedure, the target nucleic acid was exposed to TMA reagents and conditions and the resulting amplification product was detected in real-time using a fluorescently labeled, molecular beacon probe. See Kacian et al., U.S. Pat. No. 5,824,518; see also Tyagi et al., U.S. Pat. No. 5,925,517. The primers used for amplification included an antisense promoter-primer having a 3' target binding sequence and a 5' T7 promoter sequencer and a sense primer. The molecular beacon probe was comprised of 2'-O-methyl ribonucleotides and had an internal sequence for binding to the target nucleic acid sequence. The molecular beacon probe was synthesized to include interacting FAM and DABCYL reporter and quencher moieties using fluorescein phosphoramidite (BioGenex, San Ramon, Calif.; Cat. No. BTX-3008) and 3'-DABCYL CPG (Prime Synthesis, Inc., Aston, Pa.; Cat. No. CPG 100 2N12DABXS). The probes and primers of this experiment were synthesized using standard phosphoramidite chemistry, various methods of which are well known in the art, using an Expedite™ 8909 DNA Synthesizer (PerSeptive Biosystems, Framingham, Mass.). See, e.g., Carruthers, et al., 154 Methods in Enzymology, 287 (1987).

Example 1

Manual Amplification Reactions

For this experiment, manual TMA reactions were set up in 12×75 mm polypropylene reaction tubes (Gen-Probe Incorporated, San Diego, Calif.; Cat. No. 2440), and each reaction tube was provided with 125 μL of a Target Capture Reagent containing 160 μg/mL 1 micron magnetic particles Sera-Mag™ MG-CM Carboxylate Modified (Seradyn, Inc.; Indianapolis, Ind.; Cat. No. 24152105-050450) derivatized with poly(dT)$_{14}$ and suspended in a solution containing 250 mM HEPES, 310 mM LiOH, 1.88 M LiCl, 100 mM EDTA, adjusted to pH 7.5, and 10 μmol/reaction of the wobble capture probe. Each reaction tube was then provided with 500 FL of a mixture containing a Sample Transport Medium (150 mM HEPES, 294 mM lithium lauryl sulfate (LLS) and 100 mM ammonium sulfate, adjusted to pH 7.5) and water in a 1-to-1 ratio. The mixtures contained either $10^5$ copies of the target nucleic acid (test samples) or no target nucleic acid (negative control samples). The reaction tubes were covered with a sealing card and their contents mixed by vortexing for 15 seconds, and then incubated at 25° C. for 5 minutes in a water bath to facilitate binding of the wobble capture probes to the target nucleic acid. (The wobble capture probes bind to the derivatized poly(dT)$_{14}$ when the Target Capture Reagent is prepared.)

To purify bound target nucleic acid, a DTS® 400 Target Capture System (Gen-Probe; Cat. No. 5210) was used to isolate and wash the magnetic particles. The DTS 400 Target Capture System has a test tube bay for positioning the reaction tubes and applying a magnetic field thereto. The reaction tubes were placed in the test tube bay for about 3 minutes in the presence of the magnetic field to isolate the magnetic particles within the reaction tubes, after which the supernatants were aspirated. Each reaction tube was then provided with 1 mL of a Wash Buffer (10 mM HEPES, 6.5 mM NaOH, 1 mM EDTA, 0.3% (v/v) ethanol, 0.02% (w/v) methylparaben, 0.01% (w/v) propylparaben, 150 mM NaCl, and 0.1% (w/v) sodium lauryl sulfate, adjusted to pH 7.5), covered with a sealing card and vortexed for 15 seconds to resuspend the magnetic particles. The reaction tubes were returned to the test tube bay and allowed to stand at room temperature for 3 minutes before the Wash Buffer was aspirated. The wash steps were repeated once.

Following purification of the target nucleic acid, 75 FL of an Amplification/Detection Reagent (44.1 mM HEPES, 2.82% (w/v) trehalose, 33 mM KCl, 0.01% (v/v) TRITON® X-100 detergent, 30.6 mM MgCl$_2$, 0.3% (v/v) ethanol, 0.1% methylparaben, 0.02% (w/v) propylparaben, 0.47 mM each of dATP, dCTP, dGTP and dTTP, 1.76 mM each of rCTP and UTP, 9.41 mM rATP and 11.76 mM rGTP, adjusted to pH 7.7 at 23° C.) containing 11.9 μmol/reaction of the T7 promoter-primer, 9.35 μmol/reaction of the non-T7 primer, and 10 μmol/reaction of the molecular beacon probe was added to each reaction tube. The reaction tubes were covered with a sealing card and mixed by vortexing for 15 seconds. After mixing, the contents of the reaction tubes were transferred to separate reaction wells of a white, 96-well microplate (Thermo Electron Corporation, Waltham, Mass.; Product No. 9502887), each reaction well containing 75 μL of an Oil Reagent (silicone oil (United Chemical Technologies, Inc., Bristol, Pa.; Cat. No. PS038)). The microplate was covered with a ThermalSeal film (Sigma-Aldrich Co., St. Louis, Mo.; Cat. No. Z369675) and incubated in a Solo HT Microplate Incubator (Thermo Electron; Cat. No. 5161580) at 60° C. for 5 minutes, and then in a Solo Microplate Incubator (Thermo Electron; Cat. No. WI036) at 42° C. for 5 minutes. While in the second incubator, the sealing card was removed from the microtiter plate and 25 μL of an Enzyme Reagent (58 mM HEPES, 50 mM N-acetyl-L-cysteine, 1.0 mM EDTA, 10% (v/v) TRITON® X-100 detergent, 3% (w/v) trehalose, 120 mM KCl, 20% (w/v) glycerol, 120 RTU/4 Moloney murine leukemia virus reverse transcriptase ("MMLV-RT"), and 80 U/4 T7 RNA polymerase, adjusted to pH 7.0) was added to each reaction well. (One reverse transcriptase unit ("RTU") of activity for MMLV-RT is defined as the incorporation of 1 nmol dTMP into DE81 filter-bound product in 20 minutes at 37° C. using (poly(rA)-p(dT)$_{12-18}$) as the substrate; and for T7 RNA polymerase, one unit ("U") of activity is defined as the production of 5.0 fmol RNA transcript in 20 minutes at 37° C.) Immediately following addition of the Enzyme Reagent, the contents of the reaction wells were mixed by stirring with standard 200 μL pipette tips engaged by an 8-channel multi-pipettor and used to transfer the Enzyme Reagent to the microtiter plates. The microtiter plate was then re-sealed with a clear sealing card.

Figure 27:
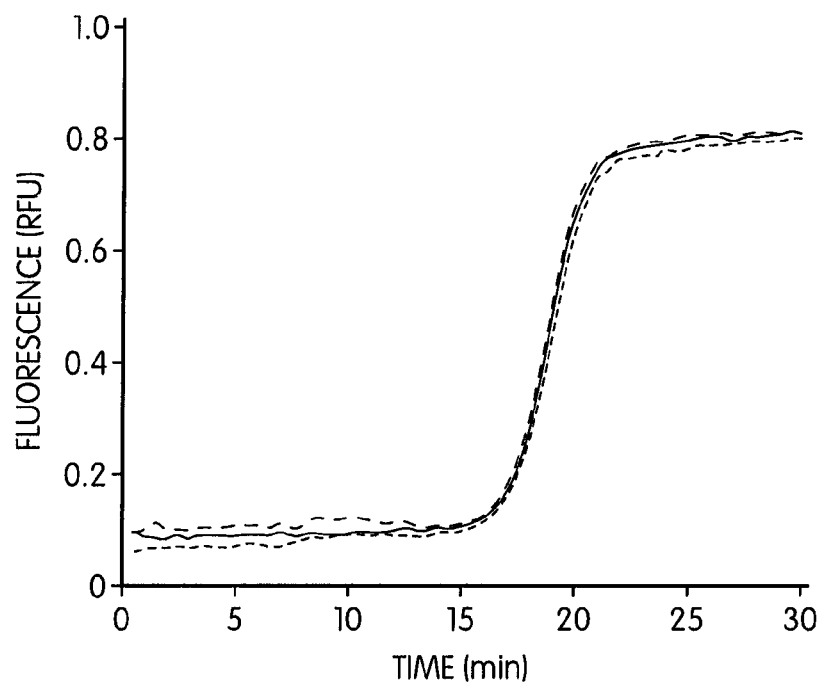
FIG. 27 is a graph showing relative fluorescent units detected versus time for a set of manually performed real-time amplification reactions.

To detect the presence of amplification product in the reaction wells, the sealed plate was placed in a Fluoroskan Ascent® 100 Microplate Fluorometer (Thermo Electron; Product No. 5210480) pre-warmed to 42° C. and fluorescent readings were taken at 30-second intervals over a 50 minute period. Detection depended upon a conformational change in the molecular beacon probes as they hybridized to amplification products, thereby resulting in the emission of detectable fluorescent signals. As long as the molecular beacon probes maintained a hairpin configuration, i.e., they were not hybridized to an amplification product of the target nucleic acid, fluorescent emissions from the fluorescein reporter moieties were generally quenched by the DABCYL quencher moieties. But as more of the molecular beacon probes hybridized to amplicon in the reaction wells, there was increase in detectable fluorescent signals. Thus, fluorescent emissions that increased over time provided an indication of active amplification of the target region of the target nucleic acid. The results of this experiment are shown in FIG. 27, where raw data from the fluorometer are plotted as fluorescent units (y-axis) versus time in minutes (x-axis) for each reaction well. Samples containing the target nucleic acid yielded strong fluorescent signals that emerged from background approximately 15 minutes into the reaction, while control samples yielded no significant signal above background.

Example 2

Automated Amplification Reactions in a Multi-Chambered, Flexible Receptacle Using Liquid Reagents In this experiment, the TMA reaction of Section 1 of this example was performed using the receptacle 10 and instrument 100 illustrated in FIGS. 1A and 3. The receptacle 10 illustrated in FIG. 1B was pre-loaded with reagents in the following manner: (i) 125 μL of the Target Capture Reagent was added to chamber C18; (ii) 3 mL of the Wash Buffer was added to chamber C34; (iii) 25 μL of the Oil Reagent, followed by 85 μL of the Amplification/Detection Reagent, was added to chamber C20; and (iv) 35 μL of the Oil Reagent, followed by 25 μL of the Enzyme Reagent, was added to chamber C32. After reagent loading, all of the chambers of the receptacle 10 except chamber C16 were closed by heat sealing. A 500 μL test sample having $10^5$ copies of the target nucleic acid, as described in Example 1 above, was then pipetted into chamber C16, the sample chamber, which was then closed by heat sealing.

For the initial set-up, the sealed receptacle 10 was mounted on the front portion 120 of the housing 104 and the door assembly 200 was closed, sandwiching the chambers of the receptacle 10 between the pressure mechanism cluster 180 and the thermal zones 260, 262, 264, 266, and 268 in the door assembly 200. The thermal zones were set to heat adjacent chambers at 30° C. The movement of materials between chambers of the receptacle 10 was controlled by the compression pads making up the pressure mechanism cluster 180 described infra. Prior to starting the test, compression pads P72, P70, P62, P51-1, P56, P58, P60, P64, P66 and P68 were all activated to clamp and protect corresponding seals associated with portals (or neck) 72, 70, 62, 51, 56, 58, 60, 64, 66 and 68, respectively, from prematurely opening or leaking Wash Buffer and air bubbles were removed from the vertical and lateral sections 42, 44 of chamber C34, the wash buffer chamber, and the vertical inlet 48 of chamber C36, the waster chamber, was concurrently closed by engaging the following compression pads in the indicated order: (i) compression pads P34-1 and P36-1; (ii) compression pads P34-2 and P36-2; (iii) compression pads P34-3 and P36-3; (iv) compression pad P34-4; and (v) compression pad P34-5.

After the initial set-up, compression pad P68 was refracted and compression pads P32 and P68 were sequentially activated to press chamber C32 and portal 68, thereby forcing open sealed portal 68 and moving the Enzyme and Oil Reagents from chamber C32 to chamber C30. At the same time, compression pad P56 was retracted and compression pads P20 and P56 were sequentially activated to press chamber C20 and portal 56, thereby forcing open sealed portal 56 and moving the Amplification/Detection and Oil Reagents from chamber C20 to chamber C22. Compression pads P68 and P56 remained activated to clamp portals 68 and 56, respectively, thereby preventing a backflow of the Enzyme and Amplification/Detection Reagents into chambers C32 and C20.

After moving the Enzyme and Amplification/Detection Reagents, compression pads P18-1, P18-2 and P54 were sequentially activated to press chamber C18 and portal 54, thereby forcing open sealed portal 54 and moving the Target Capture Reagent ("TCR") from chamber C18 to chamber C16. The TCR and sample were mixed by twice moving the combined contents back-and-forth between chambers C16 and C18 using compression pads associated with these chambers. Once mixing was completed, compression pad P54 was activated to clamp portal 54, thereby maintaining the TCR/sample mixture in chamber C16, where it was incubated by heating thermal zone 260 at 30° C. for 5 minutes. This incubation step was carried out to facilitate non-specific binding of the target nucleic acid to the wobble capture probes and immobilization of the wobble capture probes on the magnetically-responsive particles present in the TCR.

To separate the target nucleic acid from other material in the test sample, the magnet translation mechanism 208 was activated to move the magnet into position adjacent chamber C26 (referred to herein as the "on" position), the magnetic separation chamber 102 during the initial set-up. Compression pad P62 was retracted and compression pads P16-3, P16-4 and P62 were sequentially activated to press a portion of chamber C16, thereby forcing open sealed portal 62 and moving a first aliquot of the TCR/sample mixture from chamber C16 to chamber C26. After moving the first aliquot of the TCR/sample mixture to chamber C26, compression pad P62 remained activated to clamp portal 62, thereby preventing the movement of material between chambers C16 and C26, and compression pads P16-3 and P16-4 were sequentially retracted. In chamber C26, the magnetically-responsive particles were subjected to the magnetic fields of the magnet for 1 minute at a temperature of 30° C. provided by thermal zone 268. While the magnet remained in the "on" position, compression pads P26, P70, P36-1, P36-2 and P36-3 were sequentially activated to press chamber C26, portal 70 and the vertical inlet 48 of chamber C36, the waste chamber, and to move liquid from chamber C26 into chamber C36.

By activating different arrangements of the compression pads associated with chambers C16 and C18, three additional aliquots of the TCR/sample mixture were moved from chambers C16 and C18 to chamber C26. For the second aliquot of TCR/sample mixture moved to chamber C26, the sequential operation of the compression pads was as follows: P18-1 (+), P18-2 (+), P18-2 (−), P62 (−), P16-3 (+), P16-4 (+), P62 (+), P16-3 (−) and P16-4 (−). For the third aliquot of TCR/sample mixture moved to chamber C26, the sequential operation of the compression pads was as follows: P51-2 (+), P18-1 (−), P16-4 (+), P16-3 (+), P16-2 (+), P16-1 (+), P16-1 (−), P16-2 (−), P16-3 (−), P16-4 (−), P18-1 (+), P18-2 (+), P54 (+), P62 (−), P16-3 (+), P16-4 (+), P62 (+), P16-3 (−) and P16-4 (−). And for the fourth aliquot of TCR/sample mixture moved to chamber C26, the sequential operation of the compression pads was as follows: P16-2 (+), P16-1 (+), P62 (−), P16-3 (+), P16-4 (+), P16-3 (−) and P16-4 (−). The (+) designation indicates that the referred to compression pad was activated to press a corresponding portal or portion of a chamber, and the (−) designation indicates that the referred to compression pad was retracted from corresponding portal or portion of a chamber. The immobilization and liquid waste removal steps were repeated for each additional aliquot until all of the TCR/sample mixture had been processed and the sample reduced to a manageable size for further processing in the receptacle 10.

A wash procedure was then initiated to remove unwanted and potentially interfering material from the immobilized nucleic acids, during which the magnet remained in the on position. At the start of the wash procedure, compression pads P34-5, P34-4, P34-3, P34-2 and P34-1 were operated to prime the vertical and lateral sections 42, 44 (the "neck region") of chamber C34 and, after retracting compression pad P72, to press on the neck region of chamber 34, thereby opening sealed portal 72 and moving about 200 μL of Wash Buffer from chamber C34 to chamber C26. Compression pad P72 then clamped portal 72 and the Wash Buffer was moved back-and-forth three times between chamber C26 and the area covered by compression pads P62 and P16-4 of chamber C16 by the action of compression pads P62, P16-4 and P26 to remove any residual TCR/sample mixture material lodged in opened portal 62 and to purify bound nucleic acids. In this step, P26 was only partially activated to prevent overfilling the areas of chamber C16 covered by compression pads P62 and P16-4 and to minimize foaming. All of the liquid was finally collected in chamber C26 and exposed to the magnetic fields of the magnet for 1 minute at a temperature of about 30° C. to immobilize any magnetically-responsive particles. The Wash Buffer was then moved from chamber C26 into chamber C36 by the action of compression pads P26, P70, P36-1, P36-2 and P36-3. Another aliquot of about 200 μL, of Wash Buffer was then moved from chamber C34 to chamber C26 by the operation of compression pads associated with the neck region of chamber C34, compression pad P72 was activated to clamp opened portal 72, and the washing process was repeated, except that the Wash Buffer was only moved into that portion of chamber C16 covered by compression pad P62, and the movement between chamber C26 and chamber C16 was only performed twice. Finally, a third aliquot of about 200 μL of Wash Buffer was moved from chamber C34 to chamber C26 by the operation of compression pads associated with the neck region of chamber C34, compression pad P72 was activated to clamp opened portal 72, and the magnetically-responsive particles were exposed to the magnetic fields of the magnet for 1 minute at a temperature of 30° C. to immobilize any dislodged magnetically-responsive particles. Afterwards, the liquid was moved from chamber C26 to chamber C34 by the action of compression pads P70, P36-1, P36-2 and P36-3. After the wash procedure was completed, the magnet was moved out of alignment with chamber C26 (the "off" position) and thermal zone 268 was moved into alignment with chamber C26.

Following separation of the target nucleic acid, compression pads P22 and P58 were sequentially activated to press on chamber C22 and portal 58, thereby forcing open sealed portal 58 and moving the Amplification/Detection Reagent from chamber C22 to chamber C26. To ensure that the magnetic particles were fully suspended in the Amplification/Detection Reagent, the Amplification/Detection Reagent was moved between chambers C22 and C26 two times by operation of compression pads P26, P58 and P22. In chamber C26, the Amplification/Detection Reagent was incubated with thermal zone 268 at 62° C. (with a tolerance of, e.g., ±1.5° C.) for 5 minutes to facilitate binding of the promoter-primer to target nucleic acids. At the same time, thermal zones 264 and 266 brought the temperature of chambers C28 and C30 to 42° C. (with a tolerance of, e.g., ±0.45° C.), an optimal temperature for TMA. Following the 62° C. incubation, the contents of chamber C26 were incubated at 42° C. for another 5 minutes, after which compression pads P26 and P64 were sequentially activated to press on chamber C26 and portal 64, thereby forcing open sealed portal 64 and moving the heated Amplification/Detection Reagent and magnetic particle mixture from chamber C26 to chamber C28. Once in chamber C28, compression pads P30 and P66 were sequentially activated to press on chamber C30 and portal 66, thereby forcing open sealed portal 66 and moving the heated Enzyme Reagent from chamber C30 to chamber C28. After the Enzyme Reagent was moved to chamber C28, the temperature of thermal zone 266 was adjusted to 38° C.±1° C. To mix the Amplification/Detection Reagent, Enzyme Reagent and magnetic particles, gravity assisted in draining the contents of chamber C28 into chamber C30 through opened portal 66 and then moved back into chamber C28 by sequentially pressing on chamber C30 and portal 66 with compression pads P30 and P66. This process was repeated three times to ensure adequate mixing of the reagents for amplification of the target sequence, after which mixing compression pad P66 was activated to clamp opened portal 66 and to move any residual reagents from opened portal 66 to chamber C28.

Figure 28:
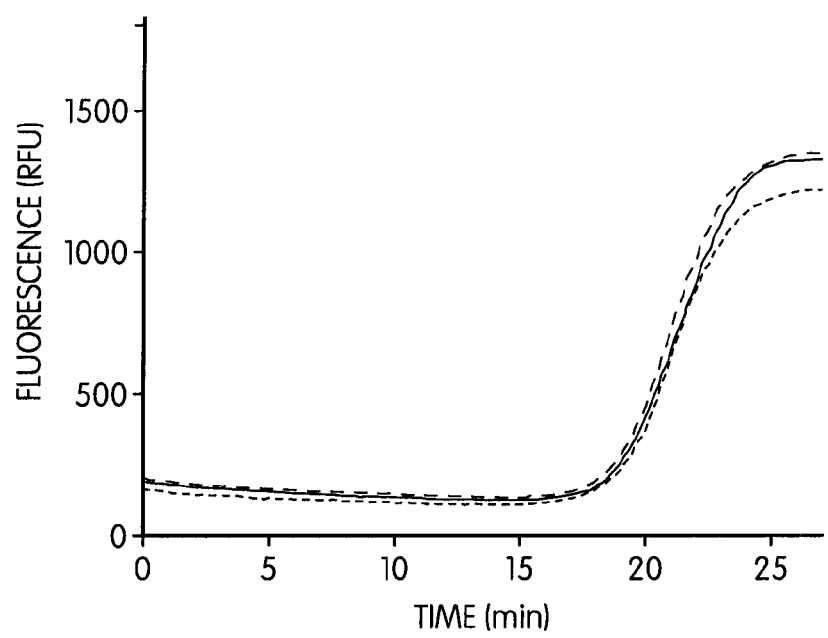
FIG. 28 is a graph showing relative fluorescent units detected versus time for a set of real-time amplification reactions carried out using liquid reagents and receptacles and instruments embodying aspects of the invention.

To detect amplification products generated in this mixture, the fluorometer 500 positioned adjacent a transparent window of chamber C28 took fluorescent readings at 5-second intervals, each reading averaging just over 4 seconds, during a 27 minute period. The results of this experiment are represented in FIG. 28, which is a graph showing fluorescence units detected from chamber C28 on the y-axis versus the time in minutes on the x-axis. These results demonstrate that the real-time TMA reaction performed using the instrument 100 and receptacle 10 described herein gave equivalent results to the manually formatted real-time TMA reaction of Example 1 above.

Example 3

Figure 29:
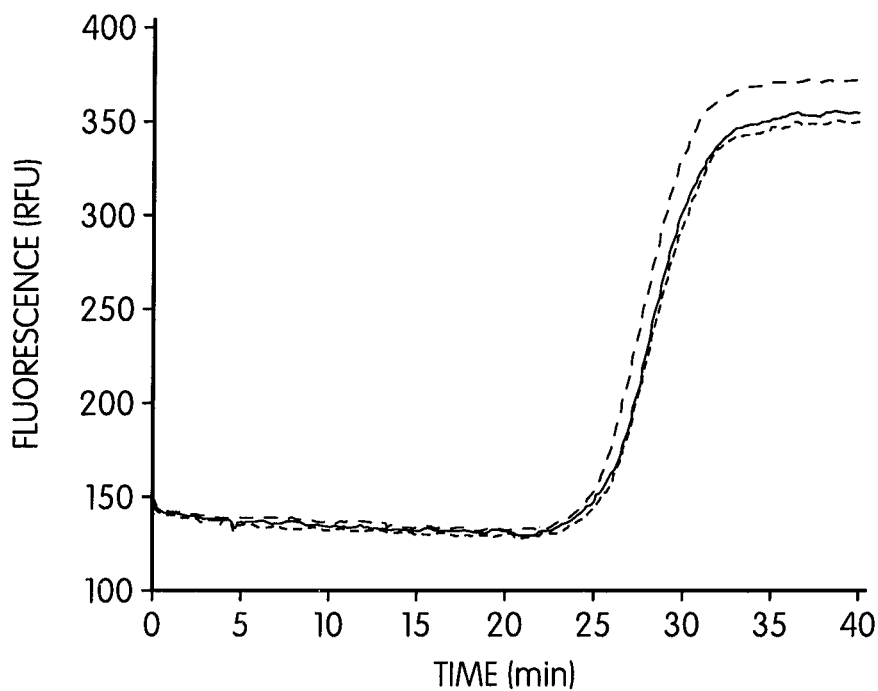
FIG. 29 is a graph showing relative fluorescent units detected versus time for a set of real-time amplification reactions carried out using a urine sample, liquid reagents and receptacles and instruments embodying aspects of the invention.

Automated Amplification Reactions in a Multi-Chambered, Flexible Receptacle Using Liquid Reagents and a Urine Samples This experiment was designed to evaluate a real-time TMA reaction using a urine sample spiked with $10^5$ copies of target nucleic acid. The materials and methods of this experiment were the same as those of the real-time TMA reaction described in Example 2, with the following exceptions: (i) chamber C18 was loaded with 150 µL of the Target Capture Reagent containing 10 µmol of the wobble capture probe in combination with 100 µL of water; (ii) chamber C34 was loaded with 2 mL of the Wash Buffer; (iii) the Oil Reagent was not loaded into chamber C20 or chamber C32 prior to loading the Amplification/Detection and Enzyme Reagents into these chambers; (iv) the test sample included 250 µL of urine from a healthy donor and 250 µL of the Sample Transport Medium; and (v) the steps of moving the TCR/sample mixture from chamber C16 to chamber C26, subjecting the magnetic particles contained within chamber C26 to the magnetic fields of the magnet, and moving liquid from chamber C26 to chamber C36 while the magnetic particles were immobilized was repeated only two times. The results of this experiment are illustrated in FIG. 29, which is a graph showing fluorescence units detected from chamber C28 on the y-axis versus time in minutes on the x-axis. These results of this experiment demonstrate that the real-time TMA reaction detected the target nucleic acid provided in the urine sample using the instrument 100 and receptacle 10 described herein.

Example 4

Automated Amplifications Reaction in a Multi-Chambered, Flexible Receptacle Using Dried Reagents The purpose of this experiment was to evaluate the automated, real-time TMA reaction of Example 2 using dried forms of the Amplification and Enzyme/Probe Reagents. The receptacle 10 was pre-loaded with the following reagents: (i) 125 µL of the Target Capture Reagent was added to chamber C18; (ii) 3 mL of the Wash Buffer was added to chamber C34; (iii) 25 µL of the Oil Reagent, followed by 85 µL of an Amplification Reconstitution Reagent (0.4% (v/v) ethyl alcohol (absolute), 0.10% (w/v) methyl paraben, 0.02% (w/v) propyl paraben, 33 mM KCl, 30.6 mM $MgCl_2$, and 0.003% phenol red), was added to C-20; (iv) an Amplification Reagent Pellet (formed from a 14 µL droplet containing 250 mM HEPES, 16% (w/v) trehalose, 53.4 mM ATP, 10 mM CTP, 66.6 mM GTP, 10 mM UTP, 2.66 mM of each of dATP, dCTP, dGTP and dTTP, adjusted to pH 7.0, 0.6 nmol/L of the antisense T7 promoter-primer and 0.47 nmol/L of the sense non-T7 primer, where the droplet was dispensed into liquid nitrogen and the resulting frozen pellet was lyophilized) was added to chamber C22; (v) 35 µL of the Oil Reagent, followed by 25 µL of an Enzyme/Probe Reconstitution Reagent (50 mM HEPES, 1 mM EDTA, 10% (v/v) TRITON® X-100 detergent, and 120 mM KCl, adjusted to pH 7.0), was added to chamber C32; and (vi) an Enzyme/Probe Reagent Pellet (formed from a 7.28 µL droplet containing 20 mM HEPES, 125 mM N-acetyl-L-cysteine, 0.1 mM EDTA, 0.01% (v/v) TRITON® X-100 detergent, 20% (w/v) Trehalose, 412 MR/L MMLV-RT (dialyzed), 687 MU/L T7 RNA polymerase (dialyzed), where "M" represents one million, and 2.20 nmol/L of the molecular beacon probe) was added to chamber C30. After reagent loading, all of the chambers of the receptacle 10 except chamber C16 were closed by heat sealing. A 500 µL test sample having $10^5$ copies of the target nucleic acid, as described in Example 1 above, was then pipetted into chamber C16, which was then closed by heat sealing. The initial set-up was the same as Example 2 above.

Following the initial set-up, compression pads P32 and P68 were sequentially activated to press on chamber C32 and portal 68, thereby forcing open sealed portal 68 and moving the Enzyme/Probe Reconstitution Reagent and Oil Reagent combination from chamber C32 to chamber C30, where the Enzyme/Probe Reagent Pellet was allowed to dissolve in the Enzyme/Probe Reconstitution Reagent for two minutes. Compression pads P20 and P56 were then sequentially activated to press on chamber C20 and portal P20, thereby forcing open sealed portal 56 and moving the Amplification Reconstitution Reagent and Oil Reagent combination from chamber C20 to chamber C22, and compression pads P20 and P22 were activated to move the contents of chamber C22 back-and-forth four times between chambers C20 and C22 to fully reconstitute the Amplification Reagent, after which compression pad P56 was activated to clamp portal 56. Following a two minute dwell period in chamber C30, the compression pads P30 and P32 were activated to move the contents of chamber C30 back-and-forth two times between the chambers C30 and C32 to fully reconstitute the Enzyme/Probe Reagent, after which compression pad P68 was activated to clamp portal 68. The remainder of the steps were the same as those Example 2.

Figure 30:
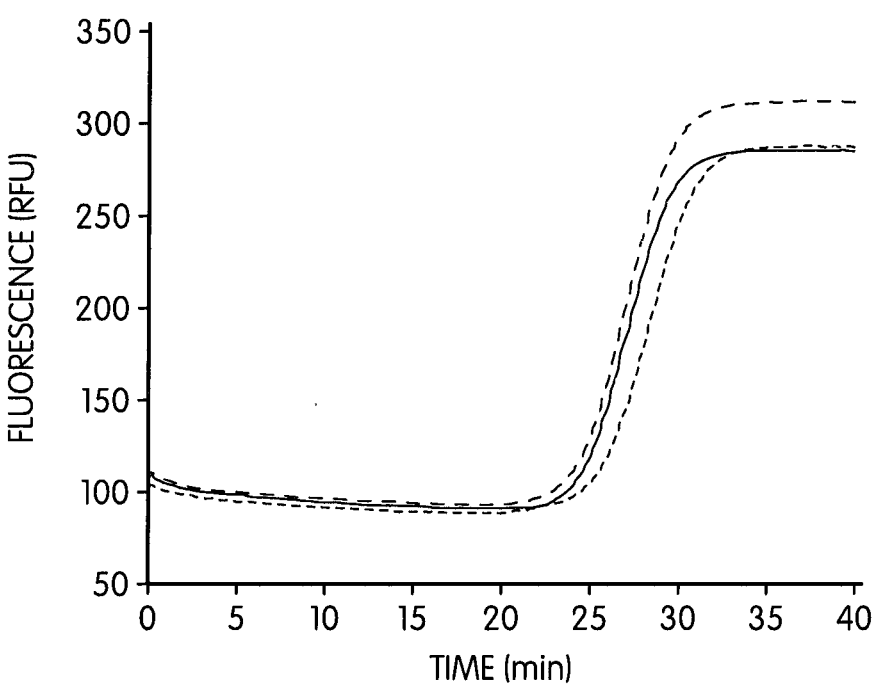
FIG. 30 is a graph showing relative fluorescent units detected versus time for a set of real-time amplification reactions carried out using dried reagents and receptacles and instruments embodying aspects of the invention.

The results of this experiment are illustrated in FIG. 30, which is a graph showing fluorescence units detected from chamber C28 on the y-axis versus the number of time in minutes on the x-axis. These results show that this real-time TMA reaction, using pelleted amplification and enzyme/probe reagents that are reconstituted on-board, detected the targeted transcript using the instrument 100 and receptacle 10 described herein.

Example 5

Figure 31:
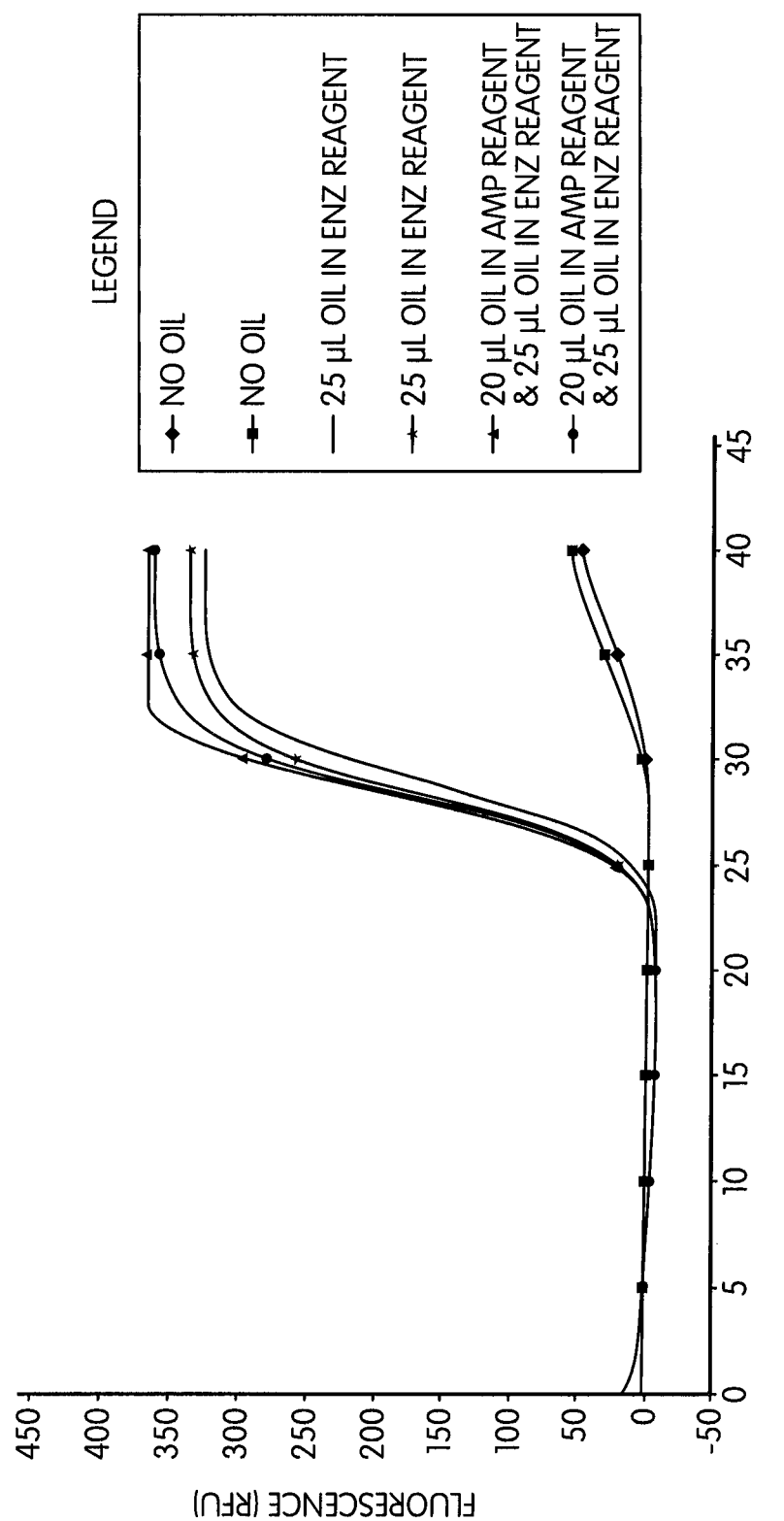
FIG. 31 is a graph showing relative fluorescent units detected versus time for a set of real-time amplification reactions carried out with and without oil in the amplification and/or enzyme reagents.

Automated Amplification Reactions Using Liquid Reagents in the Presence or Absence of an Oil Reagent This experiment was designed to evaluate the benefits of providing an immiscible liquid to open chambers of a multichambered receptacle prior to loading liquid reagents for performing TMA reactions. For this experiment, receptacles of the type illustrated in FIG. 4 were prepared in replicates of two as follows: (i) in the controls, no Oil Reagent was added to chambers containing the Amplification/Detection Reagent (chamber C20) or the Enzyme Reagent (chamber C32); (ii) 25 µL Oil Reagent was added to chamber C32 prior to adding the Enzyme Reagent and no oil was added to chamber C20; and (iii) 25 µL Oil Reagent was added to each of chambers C20 and C32 prior to adding the Amplification/Detection and Enzyme Reagents. Chamber C18 was loaded with 250 µL of the Target Capture Reagent containing 10 µmol of the wobble capture probe and 100 µL of water. The materials and methods of this experiment were otherwise substantially the same as those of the reactions described in Example 2, except that the amplification reaction was conducted at about 40° C. for 40 minutes. FIG. 31 is a graph illustrating the results of this experiment, showing the fluorescence units detected from chamber C28 on the y-axis versus time in minutes on the x-axis. The results show that the real-time TMA reactions of this experiment performed noticeably better when at least one of the Amplification/Detection and Enzyme Reagents was combined with the Oil Reagent.

While the present invention has been described and shown in considerable detail with reference to certain illustrative embodiments, those skilled in the art will readily appreciate other embodiments of the present invention. Accordingly, the present invention is deemed to include all modifications and variations encompassed within the spirit and scope of the following appended claims.

The invention claimed is:

1. An instrument for processing a sample in a receptacle having a plurality of interconnected chambers, the instrument comprising:
   a receptacle-receiving area for receiving the receptacle;
   a detector having components positioned to detect a light signal from the contents of a detection chamber of the receptacle when the receptacle is placed in an operative position in said receptacle-receiving area, said components comprising a light source and a signal detecting element disposed on the same side of the receptacle-receiving area;
   at least one movable compression element disposed to be adjacent the detection chamber and situated between the receptacle and said light source and said signal detecting element of said detector when the receptacle is placed in the operative position in said receptacle-receiving area, wherein said compression element is configured to move relative to the detector and to transmit light from said light source to said detection chamber and to transmit light signals from said detection chamber to said signal detecting element;
   an actuator constructed and arranged to move the compression element; and
   a controller programmed to activate the actuator to move said compression element into engagement with a flexible portion of the detection chamber to thereby depress the flexible portion to agitate the contents of the detection chamber or to move the contents of the detection chamber into an adjacently connected chamber of the receptacle.

2. The instrument of claim 1, wherein the actuator is a pneumatic actuator.

3. The instrument of claim 1, wherein the compression element includes a window that permits the light signal to pass to the lens of the detector.

4. The instrument of claim 1, wherein the detector is fixed in the instrument.

5. The instrument of claim 1, wherein the compression element has a tubular body in sliding engagement with a light-directing conduit of the detector.

6. The instrument of claim 1, wherein an end surface of the compression element generally conforms to the shape of the detection chamber.

7. The instrument of claim 1, wherein the compression element is one of a plurality of compression elements arranged to engage a plurality of the chambers of the receptacle.

8. The instrument of claim 1, wherein the compression element has a tubular body in sliding engagement with a light-directing conduit of the detector, the receptacle is carried adjacent to an actuator plate disposed between the receptacle and the detector, and the compression element is in alignment with an opening formed through the actuator plate with the detection chamber disposed adjacent the opening, and wherein the instrument further includes:
   a bracket extending from the actuator plate;
   an actuator carried on the bracket and controlled by the controller for selective reciprocal movement; and
   an actuating bar extending from the compression element to the actuator and adapted to translate movement of the actuator to the compression element such that reciprocal movement of the actuator causes corresponding reciprocal movement of the compression tube between a retracted position and an extended position engaged with the detection chamber.

9. The instrument of claim 8, further comprising a guide rod extending from the actuator plate and into engagement with a portion of the actuating bar and adapted to guide the compression tube during movement of the compression tube.

10. The instrument of claim 8, wherein the compression element includes a window that permits the light signal to pass to the light-directing conduit of the detector.

11. The instrument of claim 8, wherein the actuator comprises a pneumatic piston.

12. The instrument of claim 1, further comprising a thermal element including at least a portion thereof disposed to be adjacent the detection chamber on a side of the receptacle-receiving area opposite the compression element.

\* \* \* \* \*